US007890267B2

(12) United States Patent
Glinsky

(10) Patent No.: US 7,890,267 B2
(45) Date of Patent: Feb. 15, 2011

(54) PROGNOSTIC AND DIAGNOSTIC METHOD FOR CANCER THERAPY

(75) Inventor: Gennadi V. Glinsky, Loudonville, NY (US)

(73) Assignee: Ordway Research Institute, Albany, NY (US)

( * ) Notice: Subject to any disclaimer, the term of this patent is extended or adjusted under 35 U.S.C. 154(b) by 714 days.

(21) Appl. No.: 11/732,442

(22) Filed: Apr. 2, 2007

(65) Prior Publication Data
US 2009/0170715 A1 Jul. 2, 2009

Related U.S. Application Data

(60) Provisional application No. 60/875,061, filed on Dec. 15, 2006, provisional application No. 60/823,577, filed on Aug. 25, 2006, provisional application No. 60/822,705, filed on Aug. 17, 2006, provisional application No. 60/787,818, filed on Mar. 31, 2006.

(51) Int. Cl.
*G06F 7/00* (2006.01)

(52) U.S. Cl. ............................ 702/19; 702/20; 703/11; 703/13; 435/6; 436/501; 536/24.5

(58) Field of Classification Search ...................... None
See application file for complete search history.

(56) References Cited

U.S. PATENT DOCUMENTS

| 2006/0073479 A1 | 4/2006 | Frudakis | 435/6 |
| 2009/0098538 A1* | 4/2009 | Glinsky | 435/6 |

FOREIGN PATENT DOCUMENTS

| WO | WO 01/53834 | * | 7/2001 |
| WO | WO 2004/011625 A2 | | 2/2004 |
| WO | WO 07/114896 | * | 10/2007 |
| WO | WO 08/021483 | * | 2/2010 |
| WO | WO 03/060164 | * | 7/2010 |

OTHER PUBLICATIONS

Mimori et al. 2005, EJSO 31 : 376-380.*
Hamer et al. 2002, Hybridoma and Hybridomics).*
Berezovska, Olga P. et al. (2006) "Essential role for activation of the polycomb group (PcG) protein chromatin silencing pathway in metastatic prostate cancer", Cell Cycle 5(16): 1886-1901.*
Bild, Andrea H. et al. (2006) "Oncogenic pathway signatures in human cancers as a guide to targeted therapies", Nature, 439(7074): 353-357.*
Cao, R. et al. (2005) "Role of Bmi-1 and Ring1A in H2A ubiquitylation and hox gene silencing", Molecular Cell 20(6): 845-854.*
Glinsky, G.V. et al. (2004) "Classification of human breast cancer using gene expression profiling as a component of the survival predictor algorithm", Clinical Cancer Research, 10(7): 2272-2283.*
Glinsky, G.V. et al. (2005) "Death-from- cancer signatures and stem cell contribution to metastatic cancer", Cell Cycle, 4(9): 1171-1175.*
Glinsky, G.V. et al. (2006) "Integrative genomics and proteomics analysis reveals engagement of cooperating oncogenic pathways driven by the Polycomb Group (PcG) proteins BMI1 and Ezh2:...", Proceedings of the American Association for Cancer Research Annual Meeting, 47:984-985. (Abstract only).*
Raaphorst, F. M. et al. (2000) "Coexpression of BMI-1 and EZH2 polycomb group genes in Reed- Sternberg cells of Hodgkin's disease", American J. Pathology, 157(3): 709-715.*
Veer, Van T L J et al. (2002) "Gene expression profiling predicts clinical outcome of breast cancer", Nature, 415(6871): 530-536.*
Affymetrix: "GeneChip human genome U95 set", Data Sheet, [Online] 2003, XP002504985, retrieved from the Internet: URL:http://www.affymetrix.com/support/technical/datasheets/hgu95_datasheet.pdf>.
Cheung et al., "Mapping determinants of human gene expression by regional and genome-wide association", *Nature*, 437:1365-1369 (2005).
Glinsky et al., "Gene expression profiling predicts clinical outcome of prostate cancer", *J. Clin. Invest.*, 113(6):913-923 (2004).
Glinsky et al., "Microarray analysis identifies a death-from-cancer signature predicting therapy failure in patients with multiple types of cancer", *J. Clin. Invest.*, 115(6):1503-1521 (2005).
Imai et al., "C421A polymorphism in the human breast cancer resistance protein gene is associated with low expression of Q141K protein and low-level drug resistance", *Mol. Cancer Ther.*, 1(8):611-616 (2002).
Spielman et al., "Common genetic variants account for differences in gene expression among ethnic groups", *Nat. Genetics*, 39(2):226-231 (2007).
Varambally et al., "Integrative genomic and proteomic analysis of prostate cancer reveals signature of metastatic progression", *Cancer Cell*, 8(5):393-406 (2005).

* cited by examiner

*Primary Examiner*—Mary K Zeman
(74) *Attorney, Agent, or Firm*—Ivor R. Elrifi; Mintz Levin Cohn Ferris Glovsky and Popeo PC

(57) ABSTRACT

The present invention provides novel methods and kits for diagnosing the presence of cancer within a patient, and for determining whether a subject who has cancer is susceptible to different types of treatment regimens. The cancers to be tested include, but are not limited to, prostate, breast, lung, gastric, ovarian, bladder, lymphoma, mesothelioma, medulloblastoma, glioma, and AML. Identification of therapy-resistant patients early in their treatment regimen can lead to a change in therapy in order to achieve a more successful outcome. One embodiment of the present invention is directed to a method for diagnosing cancer or predicting cancer-therapy outcome by detecting the expression levels of multiple markers in the same cell at the same time, and scoring their expression as being above a certain threshold, wherein the markers are from a particular pathway related to cancer, with the score being indicative or a cancer diagnosis or a prognosis for cancer-therapy failure. This method can be used to diagnose cancer or predict cancer-therapy outcomes for a variety of cancers. The markers can come from any pathway involved in the regulation of cancer, including specifically the PcG pathway and the "stemness" pathway. The markers can be mRNA, microRNA, DNA, or protein.

2 Claims, 218 Drawing Sheets

Metastasis-free survival of 97 breast cancer patients with distinct expression profiles of the 6-gene signature from 100 most variable loci Relapse-free survival of prostate cancer patients with distinct expression profiles of the 14-gene signature from 100 most variable loci Metastasis-free survival of 97 early stagebreast cancer patients with distinct expression profiles of the 10-gene SNP-based signature Relapse-free survival of 79 prostate cancer patients with distinct expression profiles of the 17-gene SNP-based signature Metastasis-free survival of 97 early stage breast cancer patients with distinct expression profiles of the SNP-based 11-gene signature Relapse-free survival of 79 prostate cancer patients with distinct expression profiles of the SNP-based 10-gene signature RT-PCR analysis of the BMI1 siRNA-mediated gene silencing in PC-3-32 cells. B, BMI1 & L, luciferase siRNA RT-PCR analysis of the Ezh2 siRNA-mediated gene silencing in PC-3-32 cells. E, Ezh2 siRNA; L, luciferase siRNA.

| Percentile rank | 1-20% | 21-40% | 41-60% | 61-80% | 81-100% |
|---|---|---|---|---|---|
| Number of censored subjects | 3 | 5 | 8 | 10 | 16 |
| Number od deaths/events | 12 | 11 | 8 | 6 | 0 |
| 5-year survival | 20% | 44% | 61% | 63% | 100% |
| Median survival | 18 | 43.2 | 67.4 | Undefined | Undefined |

Breast cancer data set of 286 patients with early-stage LN negative disease

Breast Cancer CTOP Signatures (Affymetrix Chip-Based Algorithm)
11-gene BMI1-pathway signature
11-gene MYC-pathway signature
14-gene Her2/neu-pathway signature
7-gene 14q32-locus signature
7-gene SNP-based signature (BrCa_97_Table9_8_Genes)
27-gene SNP-based signature (Cheung_Nature_2005)
5-gene Suz12-pathway signature
27-gene SNP-based signature (Table_9 Nature_2005)
6-gene 100-Variable loci signature
18-gene SNP-based signature (Table_10 Nature_2005)
24-gene proteomics-based signature
25-gene Beta-catenin-pathway signature
14-gene Src-pathway signature
20-gene Ras-pathway signature
34(25)-gene cell line-based signature
32-gene CCND1-pathway signature
27-gene E2F3-pathway signature 7-gene SNP-based signature (BrCa_97_Table9_8_Genes)
|         |            | Coeff.BrCa_286 |
|---------|------------|----------------|
| RAGE    | 205130_at  | -1.7499        |
| BRF1    | 215676_at  | 0.8222         |
| IGHG3   | 211430_s_  | -0.3997        |
| COLEC11 | 219873_at  | 0.3786         |
| EDAR    | 220048_at  | 1.3155         |
| ERCC6   | 207347_at  | -2.3444        |
| CEACAM1 | 206576_s_  | -0.7468        |

6-gene 100-Variable loci signature
|          |            | Coeff.BrCa_286 |
|----------|------------|----------------|
| KIAA0449 | 204411_at  | -0.1919        |
| RNF5     | 209111_at  | 2.1163         |
| RPP30    | 203436_at  | -1.2727        |
| GNAS1    | 200780_x_  | -0.052         |
| EPB41L2  | 201719_s_  | 0.6852         |
| SLC25A16 | 209910_at  | 0.5759         |

27-gene SNP-based signature (Cheung_Nature_2005)
|         |            | Coeff.BrCa_286 |
|---------|------------|----------------|
| DDX17   | 208151_x_  | -0.7691        |
| ICAP-1A | 203337_x_  | 0.3413         |
| IL16    | 209827_s_  | -0.6075        |
| S100A13 | 202598_at  | 0.2455         |
| SMARCB1 | 206532_at  | -0.2408        |
| VAMP8   | 202546_at  | -1.3839        |
| TM7SF3  | 217974_at  | -0.1247        |
| ZNF85   | 206572_x_  | -1.7358        |

Fig. 27-1

| | | |
|---|---|---|
| CGI-96 | 217276_x_ | 0.3412 |
| CGI-96 | 202938_x_ | 0.1377 |
| CGI-96 | 214243_s_ | -0.9617 |
| CGI-96 | 217284_x_ | 0.3492 |
| CGI-96 | 202937_x_ | 0.518 |
| EIF3S8 | 200647_x_ | -0.3886 |
| CTBP1 | 203392_s_ | -0.6149 |
| RPS26 | 217753_s_ | -0.3595 |
| CTSH | 202295_s_ | -0.5336 |
| GSTM2 | 204418_x_ | -0.7323 |
| GSTM1 | 204550_x_ | 0.2581 |
| CPNE1 | 206918_s_ | 0.0047 |
| AA827892 | 65588_at | 0.2572 |
| CSTB | 201201_at | -2.0975 |
| LRAP (LOC641 | 219759_at | 0.0842 |
| HLA-DRB2 | 209480_at | 0.1356 |
| PSPHL | 205048_s_ | -0.0519 |
| POMZP3 | 204148_s_ | -0.316 |
| IRF5 | 205469_s_ | -0.5652 |

18-gene SNP-based signature (Table_10 Nature_2005)
Coeff.BrCa_286

| | | |
|---|---|---|
| LCT | 206945_at | -0.2548 |
| CDH12 | 219656_at | 0.4552 |
| PMCHL1 | 217123_x_ | 0.2418 |
| CD36 | 209554_at | -0.1737 |
| CD36 | 206488_s_ | -0.3618 |
| CD36 | 209555_s_ | 0.2745 |
| PMS2L5 | 214757_at | -0.0757 |
| WBSCR16 | 221247_s_ | -0.03 |
| ARNT2 | 202986_at | 0.0478 |
| ITGAE | 205055_at | 0.6221 |
| HSA277841 | 218896_s_ | 0.808 |
| CAMKK | 207359_at | 0.5355 |
| CAMKK | 210787_s_ | 0.4013 |
| P2RX1 | 210401_at | -0.2664 |
| LARGE | 204414_at | -0.1886 |
| HEPH | 203903_s_ | 0.6079 |
| HEPH | 203902_at | -0.3033 |
| MAOB | 204041_at | -0.1906 |

27-gene SNP-based signature (Table_9 Nature_2005)
Coeff.BrCa_286

| | | |
|---|---|---|
| THEA | 214763_at | 1.3178 |
| THEA | 216103_at | -0.6966 |
| FY | 204997_at | -0.0208 |
| COLEC11 | 219873_at | 0.3336 |
| ALMS1 | 214707_x_ | -0.738 |
| ALMS1 | 214221_at | 0.1192 |
| ALMS1 | 214220_s_ | -0.6032 |

Fig. 27-2

| | | |
|---|---|---|
| EDAR | 220048_at | 1.9277 |
| FXR1 | 201637_s_ | 1.0058 |
| MCF2L2 | 215112_x_ | 0.2093 |
| SLC30A9 | 202614_at | 0.701 |
| ADH1B | 209612_s_ | -0.4537 |
| ADH1B | 209613_s_ | 0.1297 |
| SLC39A4 | 219215_s_ | 0.6118 |
| ERCC6 | 207347_at | 0.155 |
| NEUROG3 | 207965_at | -0.399 |
| F2 | 205754_at | -0.1212 |
| HERC1 | 218306_s_ | 0.2901 |
| ZNF646 | 204876_at | -1.4154 |
| ZNF646 | 214226_at | 0.9969 |
| FUT6 | 211885_x_ | -0.0897 |
| FUT6 | 211882_x_ | 0.4409 |
| FUT6 | 210399_x_ | 0.7802 |
| FUT6 | 211465_x_ | -1.8658 |
| CEACAM1 | 206576_s_ | -0.7197 |
| GNB1L | 220762_s_ | 0.5006 |
| EDA2R | 221399_at | -0.4436 |

5-gene Suz12-pathway signature

| | | Coeff.BrCa_286 |
|---|---|---|
| SMARCA4 | 213720_s_ | 1.8143 |
| SMARCA4 | 212520_s_ | -1.5726 |
| FLJ10350 | 217943_s_ | 0.5446 |
| PIG7 | 200704_at | -1.8815 |
| KIAA0794 | 217100_s_ | -1.1788 |

11-gene MYC-pathway signature

| | Coeff.BrCa_286 |
|---|---|
| 201257_x_at | -0.5513 |
| 202614_at | -0.044 |
| 203560_at | 0.7248 |
| 218215_s_at | -0.5977 |
| 203728_at | -0.2553 |
| 201939_at | -0.3067 |
| 202645_s_at | -0.5774 |
| 204687_at | -1.3927 |
| 201463_s_at | -0.5314 |
| 208822_s_at | 0.5336 |
| 201493_s_at | -0.3513 |

11-gene MYC-pathway signature

| | HG-U133A | | Log10_FC | Log10_FC_MYC_PrCa |
|---|---|---|---|---|
| RPS3A | 201257_x_ | 93480_at | 1.727812 | 0.761176 |
| SLC30A9 | 202614_at | 97920_at | 1.01219 | 0.498311 |

```
GGH              203560_at 93575_at   0.686355   0.320146
NR1H2            218215_s_ 101981_at  0.632576   0.385606
BAK1             203728_at 104710_at  0.317336   0.222716
PLK2             201939_at 92310_at   0.289402   0.193125
MEN1             202645_s_ 102783_at  0.182033   0.184691
DKFZP564O08      204687_at 100547_at  -0.50616   -0.24304
TALDO1           201463_s_ 95120_at   -0.54782   -0.29667
DAP3             208822_s_ 103999_at  -0.57915   -0.24797
PUM2             201493_s_ 103833_at  -1.11837   -0.50786
PUM2             216221_s_ 103833_at  -1.11837   -0.50786
```

Relapse-free survival of 286 breast cancer patients with early stage LN negative disease and distinct expression profiles of the 11-gene *MYC*-pathway signature

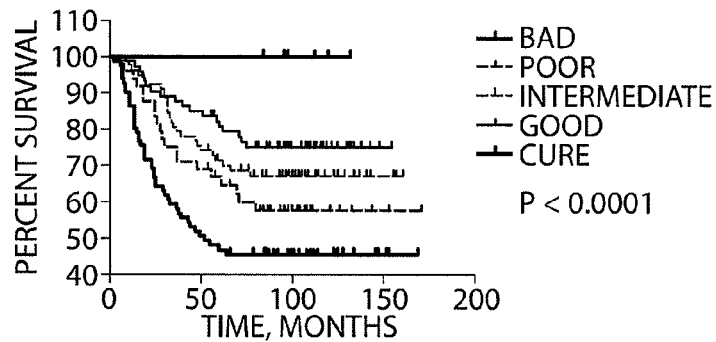

$p < 0.0001$

BAD
POOR
INTERMEDIATE
GOOD
CURE 32-gene CCND1-pathway signature

```
           HG_U133/ Coeff.BrCa_286
HSPG2      201654_s_   -0.1094
HSPG2      201655_s_    2.1647
RPS6KA1    203379_at   -1.9011
AXIN1      212849_at   -0.5451
EVX1       207914_x_    0.3491
MT2A       212185_x_    0.1073
MT2A       212859_x_   -0.3585
LOR        207720_at    0.1258
GNAI2      201040_at   -0.1148
KIF22      216969_s_    0.3857
KIF22      202183_s_   -0.1592
HADH2      202282_at    0.9952
RAB31      217764_s_    2.5208
RAB31      217762_s_   -0.7709
RAB31      217763_s_   -1.1503
LTBR       203005_at    1.3203
HSPA1B     202581_at    0.3912
HSPH1      206976_s_    1.9668
HSPH1      208744_x_   -0.4138
HSPA1A     200799_at    0.2274
HSPA1A     200800_s_   -0.0017
ASNS       205047_s_    1.4163
```

| | | |
|---|---|---|
| LGALS3BP | 200923_at | -0.3446 |
| PPID | 204185_x_ | 0.9434 |
| PPID | 204186_s_ | -0.5779 |
| EFNA1 | 202023_at | 0.2104 |
| HEXA | 201765_s_ | -1.3534 |
| HEXA | 215155_at | -0.4056 |
| TGFB1 | 203084_at | -0.5546 |
| TGFB1 | 203085_s_ | 0.6784 |
| MADH3 | 205397_x_ | 0.7286 |
| MADH3 | 205398_s_ | -0.319 |

Relapse-free survival of 286 early-stage LN negative breast cancer patients with distinct expression profiles of the 32-gene *CCND1*-pathway signature

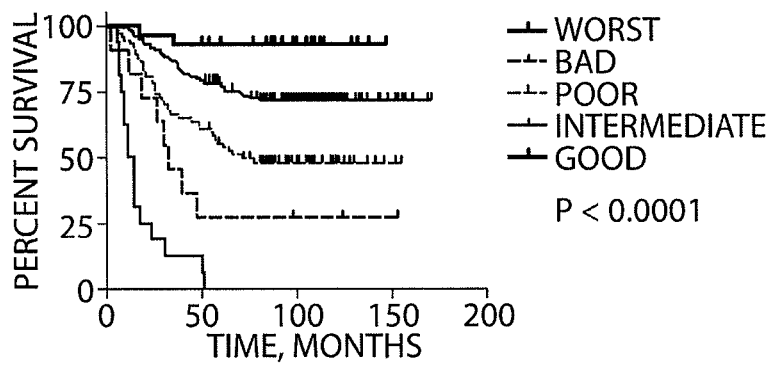

$P < 0.0001$

34(25)-gene cell line-based signature

| | | Coeff.BrCa_286 |
|---|---|---|
| AP2B1 | 200612_s_ | -1.0816 |
| AP2B1 | 200615_s_ | 1.6081 |
| MCM6 | 201930_at | 0.3501 |
| EXT1 | 201995_at | -1.3101 |
| GSTM3 | 202554_s_ | -0.2405 |
| AKAP2 | 202760_s_ | -1.1881 |
| OXCT | 202780_at | 0.2495 |
| DCK | 203302_at | 0.6672 |
| ALDH4A1 | 203722_at | 0.372 |
| CDC42BPA | 203794_at | 0.1411 |
| KNTC2 | 204162_at | -1.2649 |
| FLT1 | 204406_at | -0.0036 |
| MELK | 204825_at | 1.4495 |
| CCNE2 | 205034_at | 1.6436 |
| FGF18 | 206986_at | -0.0909 |
| FGF18 | 206987_x_ | 0.4006 |
| TGFB3 | 209747_at | -0.4338 |
| FLT1 | 210287_s_ | -0.1881 |
| FGF18 | 211029_x_ | -0.1789 |
| FGF18 | 211485_s_ | 0.0139 |

Fig. 27-5

| | | |
|---|---|---|
| ALDH4A1 | 211552_s_ | -0.1629 |
| BBC3 | 211692_s_ | 0.0438 |
| CCNE2 | 211814_s_ | 0.1238 |
| CDC42BPA | 213595_s_ | 0.1262 |
| FGF18 | 214284_s_ | 0.0294 |
| GMPS | 214431_at | 0.1271 |
| CDC42BPA | 214464_at | 0.6559 |
| CDC42BPA | 215296_at | 0.4751 |
| DC13 | 218447_at | 1.2131 |
| SCUBE2 | 219197_s_ | 0.3124 |
| ECT2 | 219787_s_ | -0.9872 |
| C20orf46 | 219958_at | 0.5044 |
| DIAPH3 | 220997_s_ | 0.2623 |
| FLT1 | 222033_s_ | 1.313 |

Relapse-free survival of 286 early-stage LN negative breast cancer patients with distinct expression profiles of the 34-gene cell line-based signature

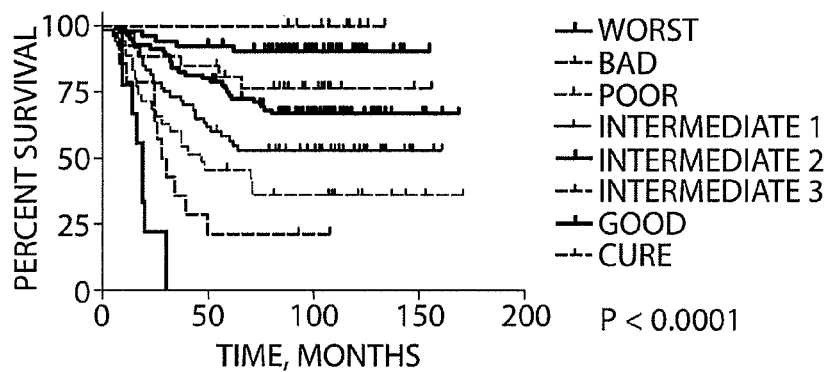

$P < 0.0001$ 25-gene Beta-catenin-pathway signature

| | | Coeff.BrCa_286 |
|---|---|---|
| CBX3 | 200037_s_ | 1.7813 |
| EPRS | 200842_s_ | 1.8719 |
| AI432196 | 201865_x_ | -0.241 |
| NR3C1 | 201866_s_ | 1.2031 |
| TRIM14 | 203147_s_ | -1.5688 |
| C6orf56 | 204047_s_ | -0.694 |
| FUSIP1 | 206095_s_ | 0.3975 |
| SFRS6 | 206108_s_ | 0.6177 |
| NRD1 | 208709_s_ | 0.6567 |
| KIAA0217 | 208953_at | -0.5185 |
| CSPG6 | 209259_s_ | 1.0769 |
| SMG1 | 210057_at | 0.4366 |
| COL13A1 | 211343_s_ | 1.1768 |
| KIAA0323 | 212356_at | 0.6172 |

Fig. 27-6

| | | |
|---|---|---|
| JMJD2B | 212495_at | 0.203 |
| KIAA1033 | 212794_s_ | -1.3719 |
| KIAA1033 | 212795_at | 0.7128 |
| NEK1 | 213331_s_ | -0.7198 |
| KIAA0779 | 213349_at | -0.3565 |
| RPS11 | 213350_at | -1.0971 |
| FUSIP1 | 213594_x_ | 0.5765 |
| BE503392 | 213637_at | 0.2659 |
| RPESP | 214725_at | 0.1129 |
| C20orf42 | 218796_at | -0.1837 |
| THOC2 | 222122_s_ | -0.2331 |

Relapse-free survival of 286 early-stage LN negative breast cancer patients with distinct expression profiles of the 25-gene Wnt/β-catenin pathway signature 14-gene Src-pathway signature

| | | Coeff.BrCa_286 |
|---|---|---|
| TEB4 | 201736_s_ | 0.8939 |
| DMTF1 | 203301_s_ | 1.6743 |
| ZNF-U69274 | 204847_at | 2.1594 |
| FLJ21940 | 205836_s_ | -1.4425 |
| RRM2 | 209773_s_ | 0.6683 |
| RRM2 | 201890_at | 0.3395 |
| MARK3 | 202569_s_ | -2.1484 |
| TRRAP | 202642_s_ | 0.2057 |
| TNFAIP3 | 202644_s_ | -1.0438 |
| HSPH1 | 206976_s_ | 1.0417 |
| JMJD2B | 212495_at | -0.16 |
| MRPS6 | 213167_s_ | 0.3007 |
| RPS19 | 213414_s_ | -1.2665 |
| FANCL | 218397_at | 0.3961 |

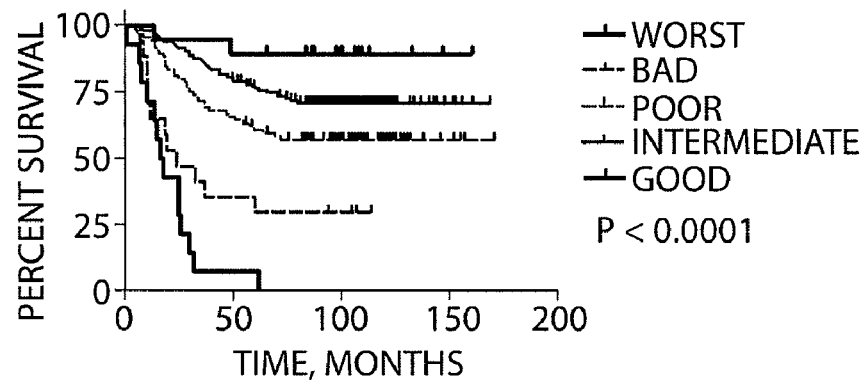

Relapse-free survival of 286 early-stage LN negative breast cancer patients with distinct expression profiles of the 20-gene *Ras*-pathway signature 24-gene proteomics-based signature

| Gene | Probe | Coeff.BrCa_286 |
|---|---|---|
| RAN | 200749_at | 2.2157 |
| STMN1 | 200783_s_ | -1.4252 |
| PRSS8 | 202525_at | -0.5833 |
| AMACR | 209424_s_ | 1.4373 |
| SMARCC2 | 201321_s_ | 3.2232 |
| ITGA5 | 201389_at | 2.0463 |
| STK6 | 208079_s_ | 1.8921 |
| AMACR | 209425_at | -2.7739 |
| CDKN2A | 209644_x_ | 1.2597 |
| NEXN | 212847_at | 2.3007 |
| TRAF3IP2 | 215411_s_ | 0.6156 |
| AMACR | 217113_at | -1.0155 |
| UBE2I | 208760_at | 1.2075 |
| UBE2I | 211008_s_ | 0.4531 |
| UBE2I | 213536_s_ | -0.7147 |
| PDLIM5 | 213684_s_ | -0.4287 |
| TGFB1I1 | 209651_at | 2.5214 |
| MAPKAPK3 | 202788_at | -1.62 |
| PDLIM5 | 203243_s_ | 0.9864 |
| EZH2 | 203358_s_ | 0.635 |
| ACTA1 | 203872_at | -0.5586 |
| MMP23A | 207118_s_ | -0.241 |
| CASP7 | 207181_s_ | -1.9609 |
| NEXN | 214093_s_ | -1.9885 |

Fig. 27-9

| 11-gene BMI1-pathway signature | | 11-gene BMI1-pathway signature | |
|---|---|---|---|
| | Coeff.Brca_286 | | |
| 210560_at | 0.0092 | Gbx2 | 210560_at |
| 212022_s_at | 1.088 | KI67 | 212022_s_at |
| 214710_s_at | 1.5138 | Cyclin B1 | 214710_s_at |
| 216277_at | 0.2118 | BUB1 | 216277_at |
| 204162_at | -0.7901 | HEC | 204162_at |
| 216964_at | -0.3928 | KIAA1063 | 216964_at |
| 202473_x_at | -1.3438 | HCFC1 | 202473_x_at |
| 205215_at | 0.4783 | RNF2 | 205215_at |
| 209442_x_at | 0.0465 | ANK3 | 209442_x_at |
| 203638_s_at | 0.5148 | FGFR2 | 203638_s_at |
| 208228_s_at | -0.0694 | FGFR2 | 208228_s_at |
| 209616_s_at | 0.1831 | CES | 209616_s_at |

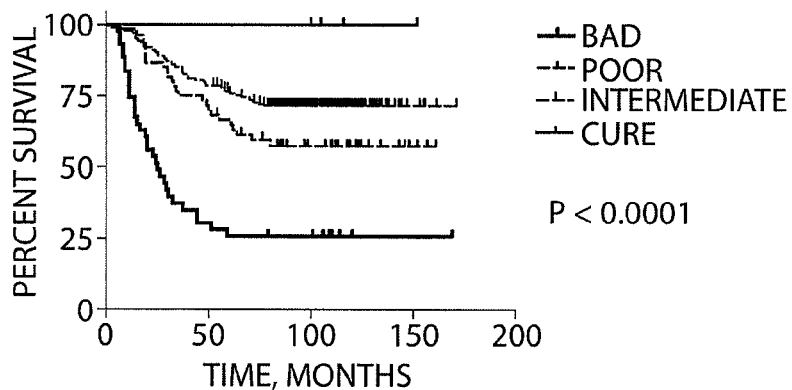

Relapse-free survival of 286 breast cancer patients WITH early stage LN negative disease and distinct expression profiles of the 11-gene *BMI1*-pathway signature

| 14-gene Her2/neu-pathway signature | | 14-gene Her2/neu-pathway signature | |
|---|---|---|---|
| | Coeff.BrCa_286 | | |
| 203373_at | -0.8698 | STATI2 | 203373_at |
| 202677_at | 0.6695 | RASA1 | 202677_at |
| 201063_at | -0.3836 | RCN1 | 201063_at |
| 220286_at | 0.1774 | FLJ20313 | 220286_at |
| 212211_at | -0.6679 | KIAA0697 | 212211_at |
| 218859_s_at | -0.6124 | HDCMC28 | 218859_s_at |
| 205420_at | 0.8886 | PEX7 | 205420_at |
| 204485_s_at | 0.4887 | TOM1L1 | 204485_s_at |
| 204010_s_at | -0.3749 | KRAS2 | 204010_s_at |
| 204256_at | 1.5795 | MGC5487 | 204256_at |
| 210868_s_at | -0.696 | MGC5487 | 210868_s_at |
| 213457_at | 0.9886 | MASL1 | 213457_at |
| 219534_x_at | 0.3154 | CDKN1C | 219534_x_at |
| 219533_at | -0.2943 | CDKN1C | 219533_at |

Fig. 27-10

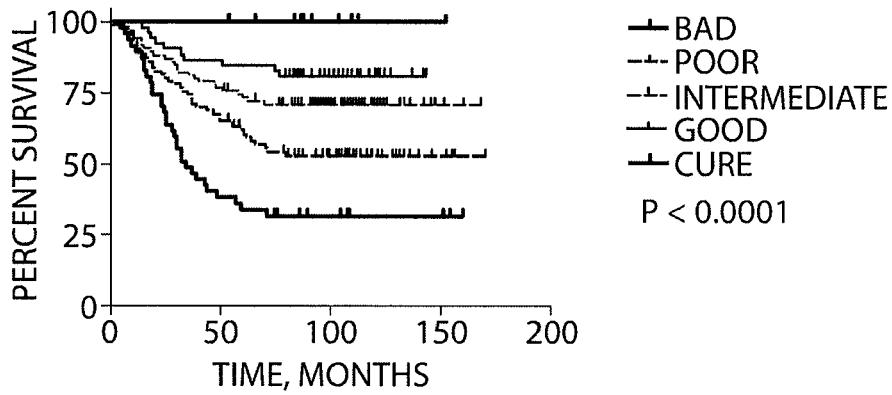

Relapse-free survival of 286 breast cancer patients with early-stage LN negative disease and distinct expression profiles of the 14-gene Her2/neu-pathway signature 7-gene 14q32-locus signature

|  |  | Coeff.BrCa_286 |
|---|---|---|
| IGBP1 | 202105_at | -2.261 |
| PLAA | 209532_at | 0.7378 |
| XPC | 209375_at | -1.2898 |
| NDUFB2 | 222090_at | -0.0686 |
| SNRPB2 | 208821_at | 0.6476 |
| NDUFB2 | 221894_at | 0.1476 |
| SNRPB2 | 213175_s_ | -0.9471 |

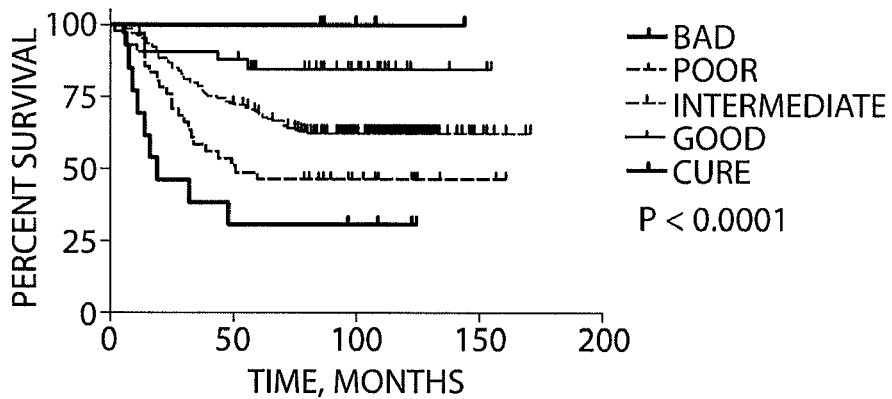

Survival of 286 breast cancer patients with early stage LN negative disease and distinct expression profiles of the 7-gene 14q32 locus signature

Fig. 27-11

| 27-gene E2F3-pathway signature | |
|---|---|
| | Coeff.BrCa_286 |
| 201608_s_at | 1.7994 |
| 202464_s_at | 0.8056 |
| 203300_x_at | 2.3186 |
| 204540_at | 0.786 |
| 205067_at | -1.6671 |
| 205344_at | -1.2533 |
| 206102_at | 1.3152 |
| 206756_at | -0.4094 |
| 208545_x_at | 1.7697 |
| 209525_at | 1.4971 |
| 209890_at | -0.7937 |
| 211706_s_at | 1.011 |
| 212279_at | -2.2112 |
| 212956_at | 0.6362 |
| 212960_at | -1.82 |
| 213309_at | -1.0867 |
| 213457_at | 0.3075 |
| 213485_s_at | 1.3659 |
| 213885_at | -0.3661 |
| 217673_x_at | -2.5037 |
| 218782_s_at | 1.4726 |
| 218888_s_at | -0.0618 |
| 219701_at | -0.5083 |
| 220076_at | 0.4382 |
| 221306_at | -1.6274 |
| 221677_s_at | 1.236 |
| 39966_at | 1.1221 |

Relapse-free survival of 286 breast cancer patients with early stage LN negative disease and distinct expression profiles of the 27-gene E2F3-pathway signature Breast cancer data set of 97 patients with early-stage LN negative disease Breast Cancer CTOP Signatures (Rosetta/Agilent Chip-Based Algorithm)
5-gene 14q32-locus signature
6-gene 100-Variable loci signature
11-gene BMI1-pathway signature
11-gene MYC-pathway signature
14-gene Her2/neu-pathway signature
27-gene SNP-based signature (Cheung_Nature_2005)
11-gene SNP-based signature (BrCa_97_Table9_8_Genes)
10-gene Suz12-pathway signature
10-gene SNP-based signature (Table_9 Nature_2005)
4-gene SNP-based signature (Table_10 Nature_2005)
19-gene proteomics-based signature
21-gene Beta-catenin-pathway signature
16-gene Src-pathway signature
19-gene Ras-pathway signature
25-gene cell line-based signature
22-gene CCND1-pathway signature
11-gene E2F3-pathway signature 4-gene SNP-based signature (Table_10 Nature_2005)

|           |        | Coeff.BrCa_97 |
|-----------|--------|---------------|
| D38501    | PMS2L5 | -0.4276       |
| NM_002208 | ITGAE  | 2.7145        |
| NM_002558 | P2RX1  | 3.5123        |
| NM_014799 | HEPH   | 1.5033        |

10-gene SNP-based signature (Table_9 Nature_2005)

|              |           | Coeff.BrCa_97 |
|--------------|-----------|---------------|
| Contig42949_RC | MGC3279 | 0.6548        |
| AB002326     | KIAA0328  | 3.1316        |
| NM_005087    | FXR1      | 1.8077        |
| AB020668     | KIAA0861  | 1.3299        |
| NM_017767    | FLJ20327  | 1.6596        |
| NM_000124    | ERCC6     | -1.3295       |
| NM_014699    | KIAA0296  | -3.3696       |
| AL117635     | DKFZP434( | 0.917         |
| NM_000150    | FUT6      | 0.6706        |
| NM_001712    | CEACAM1   | 1.6036        |

Fig. 28-1

10-gene Suz12-pathway signature
                    Coeff.BrCa_97
NM_003072    SMARCA4    -1.4044
NM_014764    DAZAP2     -4.052
NM_006002    UCHL3       0.0817
NM_018067    FLJ10350    2.0965
NM_003343    UBE2G2      3.4353
NM_001681    ATP2A2      1.1407
NM_004862    PIG7       -0.0255
NM_014292    CBX6       -7.4662
Contig51822_RC CBX6      5.9117
AB018337     KIAA0794    4.5379

27-gene SNP-based signature (Cheung_Nature_2005)
                    Coeff.BrCa_97
AF131750     DDX17      -0.5882
NM_006386    DDX17      -0.2402
Z34893       ICAP-1A     0.1409
NM_004763    ICAP-1A     3.1999
NM_004513    IL16       -1.1249
NM_005979    S100A13     0.0291
NM_003073    SMARCB1     1.4373
NM_003761    VAMP8       2.3634
NM_016551    TM7SF3      2.5578
NM_003429    ZNF85      -2.951
AL157851     CGI-96     -0.8825
NM_015703    CGI-96      0.8036
NM_003752    EIF3S8      1.1903
AL137653     CTBP1      -0.7029
NM_001328    CTBP1       1.6308
NM_001029    RPS26      -1.9464
NM_004390    CTSH        0.2159
NM_000848    GSTM2      -2.9156
J03817       GSTM1       2.086
AK001936     GSTM1      -0.4866
NM_000561    GSTM1      -2.7089
NM_003915    CPNE1      -1.3906
NM_000100    CSTB       -0.6272
NM_003832    PSPHL       0.4715
NM_012230    POMZP3     -0.3209
NM_002200    IRF5        3.7037
NM_002703    PPAT        2.9092
NM_006756    TCEA1      -1.5255

11-gene SNP-based signature (BrCa_97_Table9_8_Genes)
                    Coeff.BrCa_97
NM_005432    XRCC3      -2.343
NM_014226    RAGE       -0.9131
NM_005552    KNS2        1.1569
NM_004926    BRF1        2.9384
NM_013312    HOOK2      -0.4838
NM_001362    DIO3       -0.9229

Fig. 28-2

| | | |
|---|---|---|
| Y14737 | IGHG3 | -0.0902 |
| NM_001055 | SULT1A1 | 0.5909 |
| AF130988 | EDAR | -0.367 |
| NM_000124 | ERCC6 | 2.863 |
| NM_001712 | CEACAM1 | 1.3358 |

11-gene MYC-pathway signature

| | Coeff.BrCa_97 |
|---|---|
| RPS3A | -1.3781 |
| C4orf1 | -0.3003 |
| GGH | 1.1687 |
| NR1H2 | -2.5135 |
| BAK1 | -0.1897 |
| SNK | -0.6042 |
| MEN1 | -3.0972 |
| DKFZP564O0823 | 0.9638 |
| TALDO1 | 1.7318 |
| DAP3 | 1.1146 |
| PUM2 | -1.3637 |

| 14-gene Her2/neu-pathway signature | | UP_NSC_ | AveCTRL | AveWK22r | Ratio | Log10 |
|---|---|---|---|---|---|---|
| NM_003877 | STAT12 | 99475_at | 7.600963 | 11.62454 | 1.52935 | 0.184507 |
| AJ252060 | TRABID | 160979_at | 6.036688 | 8.33408 | 1.380572 | 0.140059 |
| NM_002890 | RASA1 | 99467_at | 5.574146 | 7.517028 | 1.348552 | 0.129868 |
| NM_002901 | RCN1 | 160896_at | 6.690012 | 8.870105 | 1.325873 | 0.122502 |
| NM_017762 | FLJ20313 | 93235_at | 5.265068 | 6.966518 | 1.323158 | 0.121612 |
| AB014597 | KIAA0697 | 99031_at | 5.118872 | 6.611757 | 1.291643 | 0.111143 |
| NM_016649 | HDCMC28P | 103312_f_ | 5.347814 | 6.852053 | 1.281281 | 0.107644 |
| NM_000288 | PEX7 | 104706_at | 5.517225 | 7.052318 | 1.278236 | 0.106611 |
| NM_005486 | TOM1L1 | 104063_at | 6.614922 | 8.325303 | 1.258564 | 0.099875 |
| NM_004985 | KRAS2 | 97991_at | 6.533402 | 8.156472 | 1.248426 | 0.096363 |
| Contig29528 | MGC5487 | 103665_at | 9.276984 | 7.912785 | 0.852948 | -0.06908 |
| NM_004225 | MASL1 | 93195_at | 8.433986 | 6.667934 | 0.790603 | -0.10204 |
| Contig47045_RC | | 96134_at | 7.739964 | 6.000587 | 0.775273 | -0.11055 |
| NM_000076 | CDKN1C | 95471_at | 7.025674 | 5.169845 | 0.73585 | -0.13321 |

11-gene BMI1-pathway signature

| Systematic name | Gene name | Coeff.BrCa_97 |
|---|---|---|
| NM_001485 | GBX2 | 0.7854 |
| NM_002417 | MKI67 | 0.3956 |
| Contig56843_RC | CCNB1 | -0.3115 |
| NM_004336 | BUB1 | 0.438 |
| NM_006101 | HEC | 1.6793 |
| Contig32377_RC | KIAA1063 | 0.1231 |
| NM_005334 | HCFC1 | 0.4043 |
| NM_007212 | RNF2 | 0.4445 |
| NM_020987 | ANK3 | -1.3653 |
| NM_000141 | FGFR2 | 0.367 |
| NM_001266 | CES1 | -0.3061 |

Fig. 28-3

25-gene cell line-based signature

| | | Coeff.BrCa_97 |
|---|---|---|
| AF201951 | MS4A7 | -2.0269 |
| NM_003239 | TGFB3 | 0.5238 |
| U82987 | BBC3 | 1.539 |
| NM_001282 | AP2B1 | -0.5815 |
| NM_003748 | ALDH4A1 | -0.6614 |
| NM_018354 | FLJ11190 | 1.5464 |
| NM_020188 | DC13 | 0.8018 |
| NM_003875 | GMPS | -3.7032 |
| Contig57258_RC | AKAP2 | -0.3621 |
| NM_000788 | DCK | 2.0026 |
| Contig25991 | ECT2 | 4.6314 |
| Contig38288_RC | | 2.6992 |
| NM_000436 | OXCT | 0.8278 |
| NM_000127 | EXT1 | 1.4377 |
| NM_020974 | CEGP1 | -1.2327 |
| NM_003862 | FGF18 | -1.2188 |
| NM_000849 | GSTM3 | 0.8379 |
| Contig55377_RC | | -0.6924 |
| NM_004702 | CCNE2 | 1.2498 |
| NM_014791 | KIAA0175 | -1.9596 |
| Contig46218_RC | | 0.8741 |
| NM_003607 | PK428 | 0.6626 |
| NM_002019 | FLT1 | 2.5929 |
| NM_006101 | HEC | -4.2436 |
| NM_005915 | MCM6 | 2.5502 |

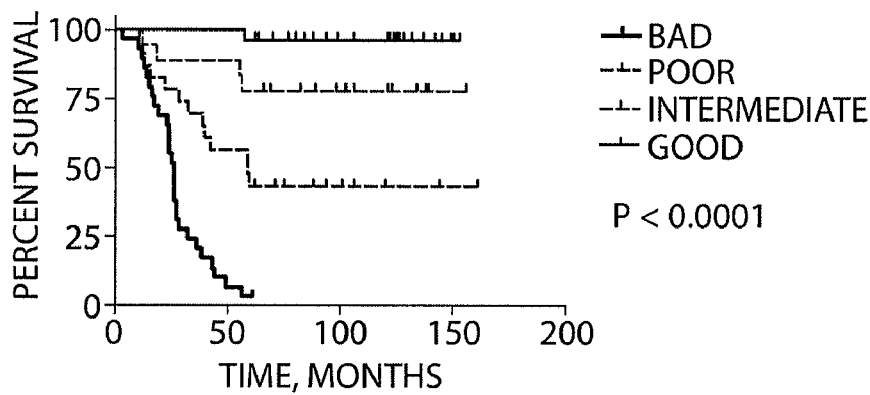

Metastasis-free survival of 97 early-stage LN negative breast cancer patients with distinct expression profiles of the 25-gene cell line-based signature

— BAD
--- POOR
-·- INTERMEDIATE
— GOOD $P < 0.0001$

Fig. 28-4

21-gene Beta-catenin-pathway signature

| | | Coeff.Brca_97 |
|---|---|---|
| NM_007276 | CBX3 | -2.9021 |
| NM_004446 | EPRS | 2.927 |
| NM_000176 | NR3C1 | 0.3742 |
| Contig1352_RC | KIAA0129 | -0.8521 |
| NM_014721 | KIAA0680 | -0.6975 |
| NM_006625 | TASR1 | 3.2573 |
| AL110214 | SFRS6 | 2.2709 |
| NM_002525 | NRD1 | 1.6321 |
| D86971 | KIAA0217 | 2.1861 |
| NM_005445 | CSPG6 | -0.2718 |
| Contig55397_RC | CSPG6 | 1.3787 |
| AB007881 | KIAA0421 | 2.6904 |
| NM_005203 | COL13A1 | -6.4778 |
| AB002321 | KIAA0323 | -0.7072 |
| AL133622 | KIAA0876 | -0.9227 |
| AL137753 | KIAA1033 | -0.2574 |
| AL050385 | NEK1 | -2.4488 |
| AB018322 | KIAA0779 | -1.9218 |
| NM_001015 | RPS11 | -4.1403 |
| AK001652 | ROK1 | -0.5307 |
| NM_017671 | FLJ20116 | -1.3101 |

Metastasis-free survival of 97 early-stage LN negative breast cancer patients with distinct expression profiles of the 21-gene Wnt/β-catenin pathway signature

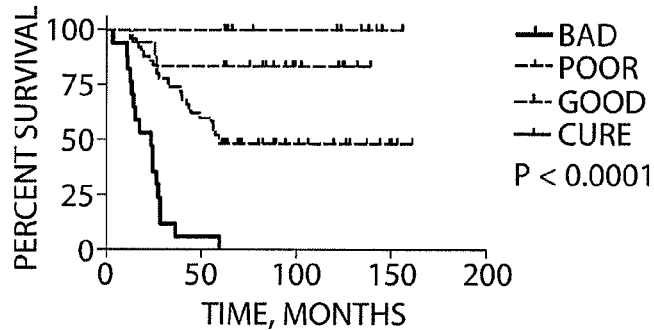

16-gene Src-pathway signature

| | | Coeff.BrCa_97 |
|---|---|---|
| NM_005885 | TEB4 | 1.9026 |
| AF084530 | DMTF1 | 0.9089 |
| NM_021145 | DMTF1 | -1.6623 |
| NM_014415 | ZNF-U6927 | 3.0055 |
| Contig38905_RC | ZNF-U6927 | 0.3042 |
| AK000915 | FLJ21940 | -1.8007 |
| Contig41413_RC | RRM2 | 1.7668 |
| NM_001034 | RRM2 | -0.7002 |
| NM_002376 | MARK3 | -0.9909 |
| U64205 | MARK3 | -1.1443 |

Fig. 28-5

| | | |
|---|---|---|
| NM_003496 | TRRAP | 3.9636 |
| NM_006290 | TNFAIP3 | -0.5859 |
| NM_006644 | HSP105B | -0.1893 |
| AL133622 | KIAA0876 | -1.5241 |
| NM_001022 | RPS19 | -0.6498 |
| NM_018062 | FLJ10335 | 0.1412 |

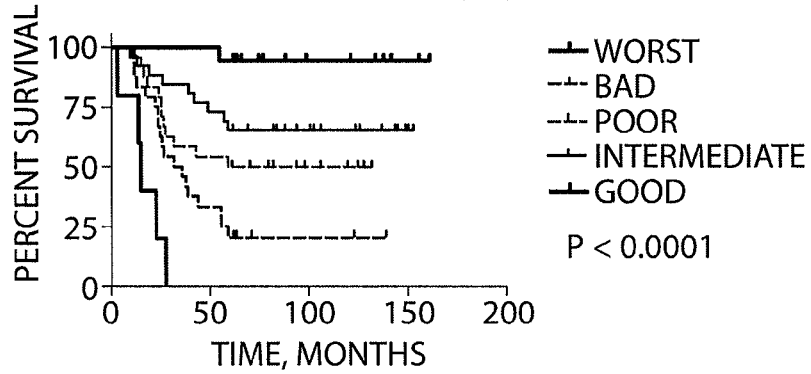

Metastasis-free survival of 97 early-stage LN negative breast cancer patients with distinct expression profiles of the 16-gene *Src*-pathway signature 19-gene Ras-pathway signature

| | | Coeff.Brca_97 |
|---|---|---|
| NM_005917 | MDH1 | -1.0586 |
| NM_002224 | ITPR3 | 1.9646 |
| NM_000311 | PRNP | -0.5071 |
| M77142 | TIA1 | 0.963 |
| M30142 | DAF | 1.512 |
| NM_000574 | DAF | -0.6722 |
| NM_002999 | SDC4 | -0.9125 |
| NM_000104 | CYP1B1 | 0.3447 |
| NM_005983 | SKP2 | 3.0706 |
| NM_001945 | DTR | 2.3327 |
| NM_014787 | DNAJC6 | -0.2076 |
| NM_005757 | MBLL | 1.5948 |
| Contig39759_RC | MBLL | -1.7108 |
| NM_004503 | HOXC6 | 1.7288 |
| NM_006499 | LGALS8 | 1.6179 |
| NM_005520 | HNRPH1 | 1.8855 |
| D38503 | PMS2L6 | 0.3245 |
| X78932 | ZNF273 | -2.4531 |
| AF052692 | GJB3 | 0.0172 |

Fig. 28-6

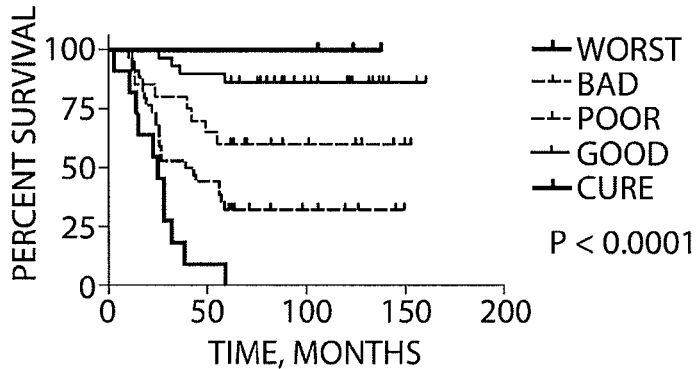

Metastasis-free survival of 97 early-stage LN negative breast cancer patients with distinct expression profiles of the 19-gene *Ras*-pathway signature $p < 0.0001$ 19-gene proteomics-based signature

|  |  | Coeff.BrCa_97 |
|---|---|---|
| NM_006325 | RAN | -3.1722 |
| NM_005563 | STMN1 | -0.464 |
| NM_002773 | PRSS8 | -0.1021 |
| NM_014324 | AMACR | 5.1678 |
| NM_003075 | SMARCC2 | -0.7444 |
| NM_002205 | ITGA5 | -0.1622 |
| NM_003158 | STK6 | 1.768 |
| NM_000077 | CDKN2A | -0.1366 |
| AF136408 | C6orf4 | -0.2259 |
| NM_015524 | C6orf5 | 0.5966 |
| NM_003345 | UBE2I | -4.4034 |
| Contig48019_RC | LIM | -1.2439 |
| NM_015927 | TGFB1I1 | -5.0553 |
| NM_004635 | MAPKAPK3 | -0.8388 |
| NM_006457 | LIM | 0.3877 |
| NM_004456 | EZH2 | 2.1229 |
| NM_001100 | ACTA1 | 2.4729 |
| NM_004659 | MMP23A | -2.6567 |
| NM_001227 | CASP7 | -0.7146 |

6-gene 100-Variable loci signature

|  |  | Coeff.BrCa_ Coeff.BrCa_97 |
|---|---|---|
| NM_017596 | KIAA0449 | 1.5604 |
| NM_006913 | RNF5 | -5.0342 |
| NM_006413 | RPP30 | 3.6697 |
| NM_000516 | GNAS1 | 3.737 |
| NM_001431 | EPB41L2 | -4.387 |
| M31659 | SLC25A16 | -4.6038 |

Fig. 28-7

5-gene 14q32-locus signature

| | | Coeff.BrCa_97 |
|---|---|---|
| NM_001551 | IGBP1 | -2.3887 |
| NM_004253 | PLAA | 1.5589 |
| NM_004628 | XPC | -3.6128 |
| NM_004546 | NDUFB2 | 1.5526 |
| NM_003092 | SNRPB2 | -1.4112 |

22-gene CCND1-pathway signature

| | | Coeff.BrCa_97 |
|---|---|---|
| NM_005529 | HSPG2 | -2.5732 |
| NM_002953 | RPS6KA1 | -0.0556 |
| AF009674 | AXIN1 | 1.2508 |
| NM_005953 | MT2A | 0.1906 |
| NM_000427 | LOR | 0.6552 |
| NM_002070 | GNAI2 | -0.8646 |
| NM_007317 | KNSL4 | 0.7156 |
| NM_004493 | HADH2 | -0.9365 |
| NM_006868 | RAB31 | -0.617 |
| NM_002342 | LTBR | -0.9308 |
| NM_005346 | HSPA1B | -0.6366 |
| NM_005345 | HSPA1A | 0.8066 |
| NM_001673 | ASNS | 2.6545 |
| NM_005567 | LGALS3BP | -0.3262 |
| NM_005038 | PPID | -1.4838 |
| Contig49938_RC | PPID | -5.5328 |
| NM_004428 | EFNA1 | -0.0973 |
| J04178 | HEXA | -1.9174 |
| NM_000520 | HEXA | 1.8262 |
| X02812 | TGFB1 | -0.0641 |
| NM_000660 | TGFB1 | -5.9344 |
| NM_005902 | MADH3 | 1.0596 |

Metastasis-free survival of 97 early-stage LN negative breast cancer patients with distinct expression profiles of the 22-gene *CCND1*-pathway signature

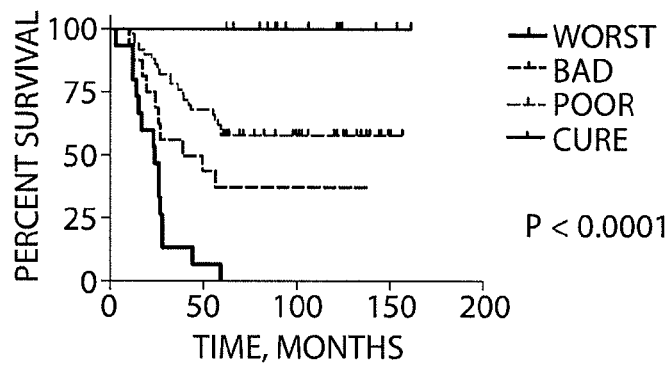

Fig. 28-8

11-gene E2F3-pathway signature

| | | Coeff.BrCa_97 |
|---|---|---|
| NM_003916 | AP1S2 | 2.1266 |
| NM_006574 | CSPG5 | 2.9253 |
| NM_019886 | CHST7 | 3.6788 |
| AW139198_RC | MAC30 | 0.6555 |
| AB020689 | KIAA0882 | -1.8367 |
| AB029015 | PLCE2 | -0.7477 |
| NM_004225 | MASL1 | -1.9235 |
| NM_000516 | GNAS1 | 4.2321 |
| AJ251759 | GNAS1 | -1.4337 |
| NM_014548 | TMOD2 | 1.1155 |
| NM_018971 | GPR27 | -1.2291 |

Metastasis-free survival of 97 breast cancer patients with early-stage LN negative disease with distinct expression profiles of the 11-gene *E2F3*-pathway signature

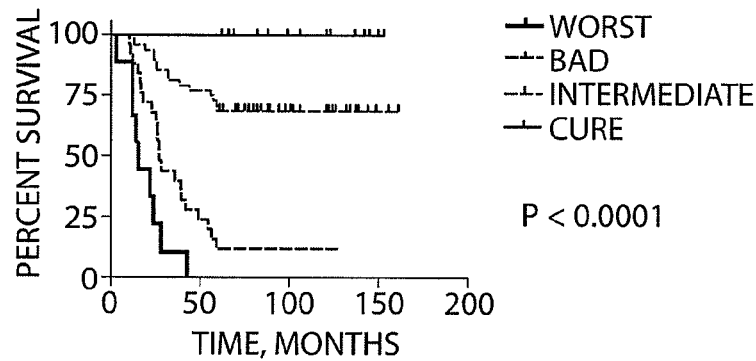

$P < 0.0001$ 24-gene E2F3-pathway signature

| | | Coeff.BrCa_97 |
|---|---|---|
| NM_007062 | PWP1 | 2.1593 |
| NM_004566 | PFKFB3 | -0.045 |
| NM_003916 | AP1S2 | 3.5316 |
| NM_001958 | EEF1A2 | -0.3 |
| NM_000576 | IL1B | 0.1339 |
| NM_006574 | CSPG5 | 9.5689 |
| D80008 | KIAA0186 | 0.2914 |
| NM_019886 | CHST7 | 2.9178 |
| NM_003185 | TAF2C1 | 1.6822 |
| NM_005723 | TSPAN-5 | -0.3677 |
| AL122055 | KIAA1028 | 1.0924 |
| AW139198_RC | MAC30 | 1.8741 |
| AB020689 | KIAA0882 | -1.648 |
| AB029015 | PLCE2 | -2.2059 |
| NM_004225 | MASL1 | -2.1117 |
| NM_006458 | RNF22 | 0.0874 |
| NM_000516 | GNAS1 | 4.0703 |
| AJ251759 | GNAS1 | -1.1788 |
| NM_014109 | PRO2000 | 0.4442 |

Fig. 28-9

Prostate cancer data set of 79 patients

Prostate Cancer CTOP Signatures (Affymetrix Chip-Based Algorithm)
11-gene BMI1-pathway signature
11-gene MYC-pathway signature
14-gene Her2/neu-pathway signature
14-gene 100-Variable loci signature
14-gene Suz12-pathway signature
8-gene 14q32-locus signature
10-gene SNP-based signature (BrCa_97_Table9_8_Genes)
32-gene proteomics-based signature          100% samples were correctly stratified
17-gene SNP-based signature (Table_9 Nature_2005)
27-gene SNP-based signature (Cheung_Nature_2005)
4-gene SNP-based signature (Table_10 Nature_2005)
25-gene Beta-catenin-pathway signature
26-gene Src-pathway signature
20-gene Ras-pathway signature
32-gene CCND1-pathway signature
16-gene xenograft/cell line-based signature
29-gene E2F3-pathway signature 27-gene SNP-based signature (Cheung_Nature_2005)
                       Coeff. MSKCC_79
| Gene | Probe | Coeff. |
|---|---|---|
| DDX17 | 208151_x_ | 1.7183 |
| ICAP-1A | 203337_x_ | 0.3116 |
| IL16 | 209827_s_ | 0.749 |
| S100A13 | 202598_at | -4.9848 |
| SMARCB1 | 206532_at | 0.2689 |
| VAMP8 | 202546_at | 2.3804 |
| TM7SF3 | 217974_at | -1.9625 |
| ZNF85 | 206572_x_ | 1.6251 |
| CGI-96 | 217276_x_ | -0.1655 |
| CGI-96 | 202938_x_ | 2.3483 |
| CGI-96 | 214243_s_ | 1.9064 |
| CGI-96 | 217284_x_ | -0.4586 |
| CGI-96 | 202937_x_ | 1.5771 |
| EIF3S8 | 200647_x_ | -1.4703 |
| CTBP1 | 203392_s_ | 1.6951 |
| RPS26 | 217753_s_ | -3.2413 |
| CTSH | 202295_s_ | 3.0892 |
| GSTM2 | 204418_x_ | -3.9871 |
| GSTM1 | 204550_x_ | 0.5737 |
| CPNE1 | 206918_s_ | 4.2553 |
| AA827892 | 65588_at | 7.1215 |
| CSTB | 201201_at | -9.453 |
| LRAP (LO( | 219759_at | 0.981 |
| HLA-DRB2 | 209480_at | 0.4147 |
| PSPHL | 205048_s_ | -0.1712 |
| POMZP3 | 204148_s_ | 1.3422 |
| IRF5 | 205469_s_ | -6.8191 |

Fig. 29-1

17-gene SNP-based signature (Table_9 Nature_2005)
                    Coeff.MSKCC_79
THEA      214763_at    -3.7999
THEA      216103_at     1.7271
FY        204997_at    -2.6346
EDAR      220048_at     1.0374
FXR1      201637_s_     6.1842
MCF2L2    215112_x_    -0.3272
SLC30A9   202614_at     3.0752
ADH1B     209612_s_    -1.4724
SLC39A4   219215_s_     0.9661
ERCC6     207347_at     3.0411
NEUROG3   207965_at     1.2535
F2        205754_at     2.239
HERC1     218306_s_    -3.5042
ZNF646    214226_at     2.6201
FUT6      211882_x_    -1.149
CEACAM1   206576_s_     1.6976
EDA2R     221399_at    -1.658

4-gene SNP-based signature (Table_10 Nature_2005)
                    Coeff.MSKCC_79
CD36      206488_s_     1.2619
ARNT2     202986_at     1.2959
ITGAE     205055_at     5.8529
MAOB      204041_at    -1.1239

10-gene SNP-based signature (BrCa_97_Table9_8_Genes)
                    Coeff.ProCa
203930_s_ MAPT_Log    -0.5929
218954_s_ BRF1_Log     1.197
216299_s_ XRCC3_L     -0.1836
205130_at RAGE_Log     1.6177
205999_x_ CYP3A4_L    -1.588
218780_at HOOK2_L     -3.0175
219873_at COLEC11      0.6188
220048_at EDAR        -0.5216
207347_at ERCC6        4.0099
206576_s_ CEACAM1      0.7804

Fig. 29-2

14-gene Suz12-pathway signature
         Coeff.MSKCC_79
hnRNPM    200072_s_   24.2905
MFN2      201155_s_  -13.4978
TRIP-Br2  202656_s_   -5.8398
SMARCA4   213720_s_    7.0918
SMARCA4   212520_s_   -4.2775
DAZAP2    200794_x_   -9.4075
UCHL3     204616_at   -7.7347
FLJ10350  217943_s_  -12.8083
UBE2G2    209042_s_    5.279
UBE2G2    209041_s_   -7.5201
ATP2A2    212361_s_    5.0805
PIG7      200704_at  -10.5556
CBX6      202048_s_   -2.9146
KIAA0794  217100_s_    4.6126

14-gene Her2/neu-pathway signature
         Coeff.MSKCC_79
STATI2    203373_at   -2.7502
RASA1     202677_at   -0.0752
RCN1      201063_at    1.5017
FLJ20313  220286_at    0.7351
KIAA0697  212211_at    2.0673
HDCMC28   218859_s_    2.9991
PEX7      205420_at   -0.5167
TOM1L1    204485_s_    3.2103
KRAS2     204010_s_    0.0941
MGC5487   204256_at   -0.549
MGC5487   210868_s_    0.8717
MASL1     213457_at   -0.6354
CDKN1C    219534_x_    0.8179
CDKN1C    219533_at   -0.843

11-gene MYC-pathway signature
         Coeff.MSKCC_79
RPS3A     201257_x_   -0.7533
SLC30A9   202614_at   -1.5304
GGH       203560_at    0.8976
NR1H2     218215_s_   -1.4173
BAK1      203728_at    0.1124
PLK2      201939_at    0.4513
MEN1      202645_s_    1.2905
DKFZP564  204687_at   -1.0023
TALDO1    201463_s_   -0.5993
DAP3      208822_s_    1.6965
PUM2      201493_s_    0.9185

Fig. 29-3

11-gene BMI1-pathway signature

| Gene | Probe | Coeff.MSKCC_79 |
|---|---|---|
| Gbx2 | 210560_at | -0.403 |
| KI67 | 212022_s_ | 1.2494 |
| Cyclin B1 | 214710_s_ | -0.3105 |
| BUB1 | 216277_at | -0.1226 |
| HEC | 204162_at | 0.0077 |
| KIAA1063 | 216964_at | 0.0369 |
| HCFC1 | 202473_x_ | -1.7493 |
| RNF2 | 205215_at | -1.1853 |
| ANK3 | 209442_x_ | 1.5242 |
| FGFR2 | 203638_s_ | -0.5628 |
| FGFR2 | 208228_s_ | -0.5628 |
| CES | 209616_s_ | -0.4333 |

32-gene CCND1-pathway signature

| Gene | HG_U133/ | Coeff.MSKCC_79 |
|---|---|---|
| HSPG2 | 201654_s_ | -0.52 |
| HSPG2 | 201655_s_ | 2.4716 |
| RPS6KA1 | 203379_at | -3.7732 |
| AXIN1 | 212849_at | -4.4648 |
| EVX1 | 207914_x_ | 0.6812 |
| MT2A | 212185_x_ | -4.1153 |
| MT2A | 212859_x_ | 2.0253 |
| LOR | 207720_at | -1.3093 |
| GNAI2 | 201040_at | 0.333 |
| KIF22 | 216969_s_ | -2.0419 |
| KIF22 | 202183_s_ | -1.2243 |
| HADH2 | 202282_at | 8.4434 |
| RAB31 | 217764_s_ | 0.5606 |
| RAB31 | 217762_s_ | 2.4785 |
| RAB31 | 217763_s_ | -4.0779 |
| LTBR | 203005_at | 1.4705 |
| HSPA1B | 202581_at | -0.8748 |
| HSPH1 | 206976_s_ | 1.8783 |
| HSPH1 | 208744_x_ | -2.2173 |
| HSPA1A | 200799_at | -4.8672 |
| HSPA1A | 200800_s_ | 6.6829 |
| ASNS | 205047_s_ | 3.5647 |
| LGALS3BF | 200923_at | -2.3166 |
| PPID | 204185_x_ | -2.0068 |
| PPID | 204186_s_ | 2.6827 |
| EFNA1 | 202023_at | -0.3473 |
| HEXA | 201765_s_ | -4.7409 |
| HEXA | 215155_at | 1.4595 |
| TGFB1 | 203084_at | -0.3616 |
| TGFB1 | 203085_s_ | 1.1399 |
| MADH3 | 205397_x_ | -0.7573 |
| MADH3 | 205398_s_ | -1.7769 |

Fig. 29-4

Relapse-free survival of prostate cancer patients with distinct expression profiles of the 32-gene *CCND1*-pathway signature

— WORST
-▲- POOR
-▲- CURE

P < 0.0001

25-gene Beta-catenin-pathway signature

| Gene | Probe | Coeff.MSKCC_79 |
|---|---|---|
| CBX3 | 200037_s_ | -0.5011 |
| EPRS | 200842_s_ | 3.563 |
| AI432196 | 201865_x_ | 1.352 |
| NR3C1 | 201866_s_ | 4.8462 |
| TRIM14 | 203147_s_ | -5.1958 |
| C6orf56 | 204047_s_ | 1.19 |
| FUSIP1 | 206095_s_ | -8.4031 |
| SFRS6 | 206108_s_ | 1.5428 |
| NRD1 | 208709_s_ | 3.7079 |
| KIAA0217 | 208953_at | -6.6364 |
| CSPG6 | 209259_s_ | 1.6003 |
| SMG1 | 210057_at | -0.2281 |
| COL13A1 | 211343_s_ | 0.3588 |
| KIAA0323 | 212356_at | 5.4587 |
| JMJD2B | 212495_at | 1.3045 |
| KIAA1033 | 212794_s_ | 3.503 |
| KIAA1033 | 212795_at | -11.7494 |
| NEK1 | 213331_s_ | 3.0624 |
| KIAA0779 | 213349_at | 13.4742 |
| RPS11 | 213350_at | -4.7344 |
| FUSIP1 | 213594_x_ | 8.5252 |
| BE503392 | 213637_at | 15.5957 |
| RPESP | 214725_at | 0.0759 |
| C20orf42 | 218796_at | 0.0232 |
| THOC2 | 222122_s_ | 7.01 |

| | | |
|---|---|---|
| RRM2 | 209773_s_ | 0.4602 |
| ACLY | 210337_s_ | -1.5782 |
| KIAA0779 | 213349_at | 3.9713 |
| ESDN | 213865_at | -1.1191 |
| TEB4 | 215512_at | 2.0729 |
| TIA1 | 217164_at | 6.2582 |
| RPLP2 | 217670_at | -1.1281 |
| C20orf42 | 218796_at | 1.8268 |
| SRC | 221284_s_ | 1.7416 |
| C20orf42 | 60474_at | -4.3812 |

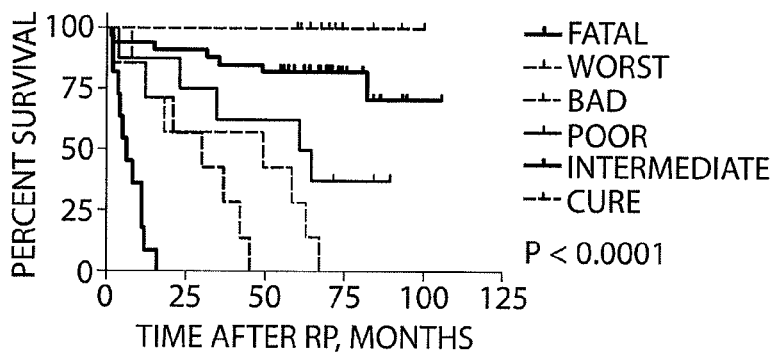

Relapse-free survival of prostate cancer patients with distinct expression profiles of the 26-gene Src-pathway signature $p < 0.0001$

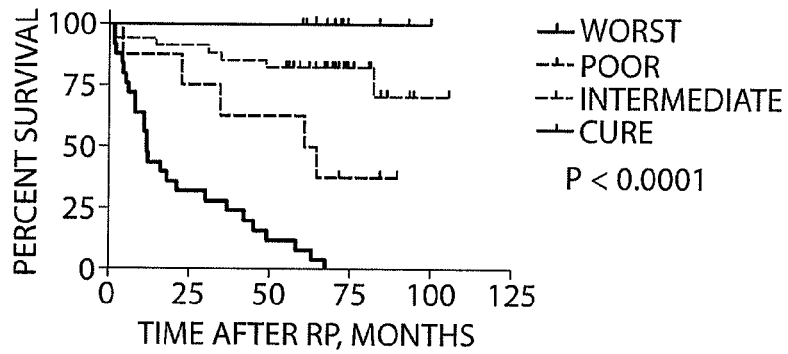

Relapse-free survival of prostate cancer patients with distinct expression profiles of the 26-gene Src-pathway signature $p < 0.0001$ 20-gene Ras-pathway signature

| | | Coeff.MSKCC_79 |
|---|---|---|
| MDH1 | 200978_at | -9.3748 |
| ITPR3 | 201188_s_ | -3.7615 |
| PRNP | 201300_s_ | -5.7913 |
| TIA1 | 201446_s_ | 7.3328 |
| DAF | 201925_s_ | 1.0738 |
| SDC4 | 202071_at | 2.6924 |

Fig. 29-7

| | | |
|---|---|---|
| CYP1B1 | 202437_s_ | -0.9151 |
| SKP2 | 203626_s_ | 2.7371 |
| DTR | 203821_at | 0.4029 |
| DNAJC6 | 204721_s_ | -0.4982 |
| MBNL2 | 205017_s_ | -1.6876 |
| HOXC6 | 206858_s_ | 2.355 |
| LGALS8 | 210732_s_ | 2.28 |
| DIPA | 213250_at | -2.2794 |
| HNRPH1 | 213472_at | 1.4919 |
| PMS2L6 | 214756_x_ | 2.0622 |
| MGC1251! | 215239_x_ | 6.9853 |
| GJB3 | 215243_s_ | -4.129 |
| PMS2L6 | 215667_x_ | -4.6702 |
| TIA1 | 217164_at | 2.6394 |

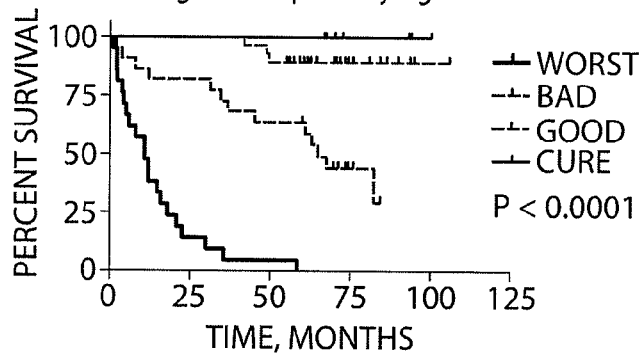

Relapse-free survival of prostate cancer patients with distinct expression profiles of the 20-gene *Ras*-pathway signature 32-gene proteomics-based signature

| | | Coeff.MSKCCP_79 |
|---|---|---|
| ERBB2IP | 209754_s_ | 1.9376 |
| UBE2I | 208760_at | -17.2525 |
| UBE2I | 211008_s_ | 1.8841 |
| UBE2I | 213536_s_ | 5.6111 |
| XPO1 | 208775_at | 10.3901 |
| CDKN2A | 207039_at | -2.2044 |
| VTI1B | 209452_s_ | 22.0481 |
| UBA2 | 201177_s_ | -20.1756 |
| TRIM28 | 200990_at | -9.392 |
| OCLN | 209925_at | -12.1465 |
| RAN | 200749_at | 6.3728 |
| STMN1 | 200783_s_ | -6.8369 |
| KPNA2 | 201088_at | 3.6356 |
| MCM2 | 202107_s_ | -3.4931 |
| RAB27A | 210951_x_ | 42.2657 |
| RAB27A | 209514_s_ | -38.7311 |
| RAB27A | 209515_s_ | -22.9889 |
| KLK3 | 204582_s_ | 2.9217 |

Fig. 29-8

| | | |
|---|---|---|
| PRSS8 | 202525_at | -6.2904 |
| TRAF3IP2 | 202987_at | -6.9908 |
| PPP1R12/ | 201604_s_ | -14.4325 |
| PDLIM5 | 221994_at | 7.318 |
| PDLIM5 | 213684_s_ | -3.5972 |
| PDLIM5 | 203242_s_ | 8.028 |
| CSRP1 | 200621_at | -5.4397 |
| FLNA | 200859_x_ | -10.0321 |
| DLGAP1 | 206490_at | 1.1934 |
| BIRC2 | 202076_at | 32.3308 |
| CAV2 | 203324_s_ | 1.5603 |
| TGFB1I1 | 209651_at | 15.1056 |
| AMACR | 209424_s_ | -14.9004 |
| AMACR | 209426_s_ | 13.3569 |

8-gene 14q32-locus signature
                              Coeff.MSKCC_79

| | | |
|---|---|---|
| RPN2 | 213399_x_ | -3.7072 |
| TOP1 | 202789_at | 3.1065 |
| TIMM17A | 201821_s_ | 6.333 |
| STC2 | 203438_at | 1.2414 |
| NDUFB2 | 222090_at | 2.8596 |
| PLAA | 209532_at | -1.6749 |
| SNRPB | 208821_at | -5.4384 |
| SNRPB | 213175_s_ | 6.0506 |

14-gene 100-Variable loci signature
                              Coeff. MSKCC_79

| | | |
|---|---|---|
| DHFR | 202534_x_ | 8.7024 |
| GK | 207387_s_ | 8.8939 |
| HMG17 | 208347_at | -2.4414 |
| PFDN4 | 205360_at | -2.7279 |
| RNF5 | 209111_at | -14.9637 |
| WASF1 | 204165_at | -6.7075 |
| RRP4 | 214507_s_ | 2.1056 |
| PRKX | 204061_at | 5.8494 |
| TNFSF7 | 206508_at | -1.926 |
| SLC15A1 | 207254_at | 2.0415 |
| FN1 | 212464_s_ | 6.4321 |
| CYP3A4 | 205999_x_ | -3.7402 |
| EPB41L2 | 201719_s_ | -11.0229 |
| CLDN4 | 201428_at | -5.5909 |

Fig. 29-9

16-gene xenograft/cell line-based signature
                    Coeff.MSKCC_79
JUNB      201473_at    -2.7524
ZFP36     201531_at    -1.3776
IER3      201631_s_    -1.0662
KIAA0476  202860_at    -2.7505
ITPR1     203710_at     0.053
CHAF1A    203976_s_    -1.4013
TCF2      208135_at    -1.7968
COPEB     208960_s_    -3.2701
COPEB     208961_s_     4.9706
FOS       209189_at     1.6428
ITPR1     211323_s_    -0.7199
MGC5466   212129_at     2.3723
CDS2      212862_at    -0.7569
Wnt5A     213425_at    -1.3157
PPFIA3    215280_s_     0.2566
ITPR1     216944_s_     0.4734

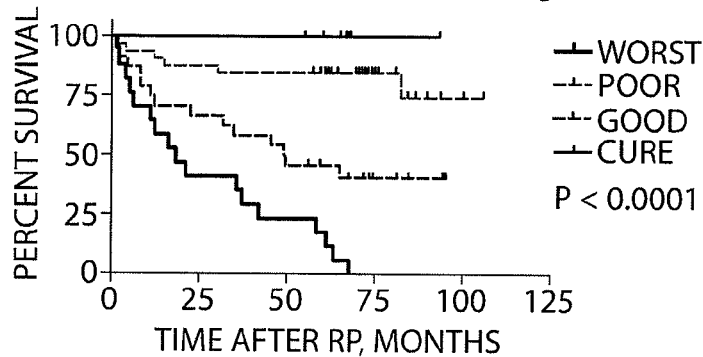

Relapse-free survival of prostate cancer patients with distinct expression profiles of the 16-gene xenograft/cell line model-based signature 29-gene E2F3_Signature Prostate Cancer
221306_at    10.3043   GPR27
214291_at     8.5007   RPL17
36829_at      7.1543   PER1
209473_at     6.4699   ENTPD1
218585_s_     5.6482   RAMP
205567_at     4.7317   CHST1
209478_at     1.537    STRA13
204380_s_     1.2472   FGFR3
205909_at     1.1533   POLE2
213812_s_     0.7429   CAMKK2
206233_at     0.353    B4GALT6
205344_at    -0.2093   CSPG5
214071_at    -0.5022   GNAL
209320_at    -0.7693   ADCY3
207138_at    -1.5709   PHF2

Fig. 29-10

PI3K Pathway CTOP Signatures 35-gene PI3K pathway prostate cancer CTOP signature

| | Coeff.ProCa79 |
|---|---|
| 200799_at | -30.0065 |
| 200800_s_at | 69.7629 |
| 201473_at | 27.3417 |
| 201555_at | -33.1266 |
| 201697_s_at | -39.3919 |
| 201890_at | 14.723 |
| 201930_at | 72.5277 |
| 201970_s_at | -34.6765 |
| 201997_s_at | 61.1862 |
| 202581_at | -41.2771 |
| 203968_s_at | 35.7443 |
| 204767_s_at | -30.4871 |
| 204946_s_at | -54.3903 |
| 205393_s_at | 9.2755 |
| 208937_s_at | 34.1472 |
| 209305_s_at | 6.9651 |
| 209421_at | -15.6777 |
| 209777_s_at | 43.3196 |
| 209980_s_at | -13.7291 |
| 210053_at | 18.3871 |
| 212099_at | -54.2362 |
| 213281_at | -41.6134 |
| 213560_at | 23.8903 |
| 215165_x_at | -34.837 |
| 217099_s_at | -49.7603 |
| 218719_s_at | 18.3019 |
| 219004_s_at | 97.3456 |
| 219286_s_at | 56.1173 |
| 219490_s_at | 16.6766 |
| 221558_s_at | 7.5823 |
| 222028_at | -16.8786 |
| 205707_at | -31.3466 |
| 209057_x_at | -33.6678 |
| 209055_s_at | 41.8885 |
| 221306_at | 84.7638 |

Logrank Test
  Chi square        70.93
  P value           P<0.0001
Median survival
  Data 1:Data Set-A    18
  Data 1:Data Set-B    Undefined Hazard Ratio
  Ratio             36.43
  95% CI of ratio   10.66 to 44.80

Fig. 30-1

38-gene PI3K pathway breast cancer CTOP signature

| Probe | Coeff.BrCa286 |
|---|---|
| 1053_at | -0.9253 |
| 200799_at | 2.1468 |
| 200875_s_at | 1.161 |
| 201465_s_at | 1.3283 |
| 201693_s_at | -1.4468 |
| 201697_s_at | -2.002 |
| 201890_at | 1.2237 |
| 201930_at | 1.3924 |
| 201970_s_at | -2.8104 |
| 201997_s_at | 3.3397 |
| 202309_at | -3.9652 |
| 203244_at | 3.8455 |
| 204126_s_at | -1.0222 |
| 204128_s_at | 1.6324 |
| 204441_s_at | 2.1669 |
| 204798_at | -0.6034 |
| 204946_s_at | 1.327 |
| 205345_at | 3.0416 |
| 205393_s_at | 0.7357 |
| 205436_s_at | -3.6927 |
| 207574_s_at | 3.5383 |
| 209304_x_at | -1.7727 |
| 209507_at | 1.0932 |
| 209773_s_at | 1.6176 |
| 209980_s_at | -0.8773 |
| 212141_at | 0.7238 |
| 212281_s_at | -1.6824 |
| 212898_at | 1.5665 |
| 213124_at | 1.4952 |
| 213523_at | -1.2462 |
| 218719_s_at | -0.9244 |
| 218889_at | -2.8499 |
| 219258_at | 0.7278 |
| 222028_at | -2.2254 |
| 222201_s_at | 2.5435 |
| 39966_at | 2.1615 |
| 203362_s_at | 1.4845 |
| 221306_at | -1.971 |

Logrank Test
  Chi square      87.87
  P value         P<0.0001

Median survival
  Data 1:Data Set-A      47
  Data 1: Data Set-B     Undefined

Hazard Ratio
  Ratio             8.178
  95% CI of ratio   4.372 to 9.537

Fig. 30-2

Table 1 Thirty-five genes with greater than twofold difference in mean expression between CEU and CHB+JPT samples

| Gene symbol | Gene Name |
|---|---|
| UGT2B17 | UDP glucuronosyltransferase 2 family, polypeptide B17 |
| ROBO1 | Roundabout, axon guidance receptor, homolog 1 |
| ATP8B1 | ATPase, class I, type 8B, member 1 |
| ARPC4 | Actin-related protein 2/3 complex, subunit 4, 20 kDa |
| DPYSL2 | Dihydropyrimidinase-like 2 |
| RGS20 | Regulator of G-protein signaling 20 |
| FCER2 | FC fragment of IGE, low affinity II, receptor for CD23A |
| FCER2 | FC fragment of IGE, low affinity II, receptor for CD23A |
| MEIS2 | MEIS1, myeloid ecotropic viral integration site 1 homolog 2 |
| COPG | Coatomer protein complex, subunit gamma |
| HSPB1 | Heat shock protein 1 |
| TCF7 | Transcription factor 7 |
| HDGFRP3 | Hepatoma-derived growth factor, related protein 3 |
| STXBP2 | Syntaxin binding protein 2 |
| D21S2056E | EST |
| MAN2A1 | Mannosidase, alpha, class 2A, member 1 |
| STS | Steroid sulfatase, arylsulfatase C, isozyme S |
| STS | Steroid sulfatase, arylsulfatase C, isozyme S |
| STS | Steroid sulfatase, arylsulfatase C, isozyme S |
| STS | Steroid sulfatase, arylsulfatase C, Isozyme S |
| CTSS | Cathepsin S |
| PDE4B | Phosphodiesterase 4B, CAMP-specific |
| OCIL | C-type lectin domain family 2, member D |
| TMPRSS3 | Serine protease TADG12 |
| NFIL3 | Nuclear factor, interleukin 3-regulated |
| LEF1 | Lymphoid enhancer-binding factor 1 |
| LEF1 | Lymphoid enhancer-binding factor 1 |
| DNAJB9 | DNAJ (HSP40) homolog, subfamily B, member 9 |
| DNAJB9 | DNAJ (HSP40) homolog, subfamily B, member 9 |
| ARL7 | ADP-ribosylation factor-like 4C |
| PTPRO | Protein tyrosine phosphatase, receptor type, O |
| PTPRO | Protein tyrosine phosphatase, receptor type, O |
| ADM | Adrenomedullin |
| IGF1 | Insulin-like growth factor 1 (somatomedin C) |
| IGF1 | Insulin-like growth factor 1 (somatomedin C) |
| PSPHL | Phosphoserine phosphatase |
| CD38 | CD38 antigen (P45) |
| SEC10L1 | Exocyst complex component 5 |
| WFDC2 | WAP four-disulfide core domain 2 |
| P2RY5 | Purinergic receptor P2Y, G protein-coupled, 5 |
| SLC2A5 | Solute carrier family 2, member 5 |
| NK4 | Interleukin 32 |
| CLECSF2 | C-type lectin domain family 2, member b |

35-gene parent signature (Nature Genetics, 2007; Cheung lab paper)

| Affymetrix Probe Sets | Gene symbol |
|---|---|
| 207245_at | UGT2B17 |
| 213194_at | ROBO1 |

Fig. 31-1

| | |
|---|---|
| 214594_x_at | ATP8B1 |
| 217818_s_at | ARPC4 |
| 200762_at | DPYSL2 |
| 210138_at | RGS20 |
| 206759_at | FCER2 |
| 206760_s_at | FCER2 |
| 207480_s_at | MEIS2 |
| COPG | COPG |
| 201841_s_at | HSPB1 |
| 205255_x_at | TCF7 |
| HDGFRP3 | HDGFRP3 |
| 209367_at | STXBP2 |
| 218758_s_at | D21S2056E |
| 205105_at | MAN2A1 |
| 203767_s_at | STS |
| 203769_s_at | STS |
| 203768_s_at | STS |
| 203770_s_at | STS |
| 202902_s_at | CTSS |
| 203708_at | PDE4B |
| OCIL | OCIL |
| 220177_s_at | TMPRSS3 |
| 203574_at | NFIL3 |
| 221558_s_at | LEF1 |
| 210948_s_at | LEF1 |
| 202842_s_at | DNAJB9 |
| 202843_at | DNAJB9 |
| ARL7 | ARL7 |
| 208121_s_at | PTPRO |
| 211320_s_at | PTPRO |
| 202912_at | ADM |
| 209542_x_at | IGF1 |
| 211577_s_at | IGF1 |
| 205048_s_at | PSPHL |
| 205692_s_at | CD38 |
| 218748_s_at | SEC10L1 |
| WFDC2 | WFDC2 |
| P2RY5 | P2RY5 |
| 204430_s_at | SLC2A5 |
| 203828_s_at | NK4 |
| CLECSF2 | CLECSF2 |

Fig. 31-2

36-transcripts SNP-based prostate cancer CTOP signature

| | Coeff.ProCa79 |
|---|---|
| 207245_at | 1.4368 |
| 213194_at | -1.7874 |
| 214594_x_at | 5.8051 |
| 217818_s_at | 0.8995 |
| 200762_at | -0.046 |
| 210138_at | -3.3957 |
| 206759_at | -1.7081 |

| | | |
|---|---|---|
| 206760_s_at | | -0.1977 |
| 207480_s_at | | -1.8535 |
| 201841_s_at | | 1.2535 |
| 205255_x_at | | 5.2765 |
| 209367_at | | -1.129 |
| 218758_s_at | | -12.031 |
| 205105_at | | 7.2618 |
| 203767_s_at | | 5.9338 |
| 203769_s_at | | -3.3143 |
| 203768_s_at | | -0.8474 |
| 203770_s_at | | -0.7451 |
| 202902_s_at | | -6.6198 |
| 203708_at | | 7.9722 |
| 220177_s_at | | -0.28 |
| 203574_at | | 0.7137 |
| 221558_s_at | | 6.1743 |
| 210948_s_at | | 6.7553 |
| 202842_s_at | | 8.527 |
| 202843_at | | -10.2605 |
| 208121_s_at | | 1.3941 |
| 211320_s_at | | 21.3275 |
| 202912_at | | -1.6646 |
| 209542_x_at | | -6.9566 |
| 211577_s_at | | 3.3754 |
| 205048_s_at | | -0.0688 |
| 205692_s_at | | 1.3062 |
| 218748_s_at | | -2.2824 |
| 204430_s_at | | -4.5932 |
| 203828_s_at | | -0.6254 |
| | | |
| Logrank Test | | |
| Chi square | | 61.97 |
| P valve | P<0.0001 | |
| Median survival | | |
| Data 1:Data Set-A | | 21 |
| Data 1:Data Set-B | Undefined | |
| | | |
| Hazard Ratio | | |
| Ratio | | 22.73 |
| 95% Cl of ratio | 8.546 to 35.45 | |

49-transcripts SNP-based breast cancer CTOP signature
Coeff.BrCa286

| | |
|---|---|
| 200762_at | 0.8962 |
| 200818_at | 1.2005 |
| 201201_at | -2.3888 |
| 201841_s_at | 0.8999 |
| 202399_s_at | -3.5515 |
| 202842_s_at | 0.6883 |
| 202843_at | 0.0262 |
| 202902_s_at | -0.5663 |

Fig. 31-3

| | |
|---|---|
| 202912_at | 0.4513 |
| 203375_s_at | -0.497 |
| 203574_at | 0.0336 |
| 203708_at | -0.0388 |
| 203767_s_at | -0.6972 |
| 203768_s_at | -0.4283 |
| 203769_s_at | -0.3031 |
| 203770_s_at | 0.5702 |
| 203828_s_at | 0.2822 |
| 204148_s_at | -0.457 |
| 204430_s_at | 0.398 |
| 204545_at | -0.1789 |
| 205045_at | -0.3019 |
| 205048_s_at | -0.0452 |
| 205105_at | -0.2581 |
| 205255_x_at | -1.1577 |
| 205692_s_at | -0.2604 |
| 206759_at | -0.6837 |
| 206760_s_at | -0.0578 |
| 207245_at | -0.3658 |
| 207480_s_at | 0.3669 |
| 208121_s_at | 0.8094 |
| 209367_at | 0.2642 |
| 209542_x_at | -0.5628 |
| 210138_at | -0.1283 |
| 210948_s_at | -0.2603 |
| 211320_s_at | 0.4586 |
| 211577_s_at | 0.6257 |
| 213194_at | 0.2504 |
| 213520_at | 0.9612 |
| 214594_x_at | 2.2749 |
| 217818_s_at | 0.1107 |
| 218022_at | 0.5454 |
| 218227_at | -0.2727 |
| 218680_x_at | -0.2867 |
| 218748_s_at | 0.4177 |
| 218758_s_at | 0.0568 |
| 220177_s_at | -1.0593 |
| 221558_s_at | 0.5897 |
| 221998_s_at | 0.1414 |
| 221999_at | -3.4944 |

| Logrank Test | | |
|---|---|---|
| Chi square | | 62.97 |
| P value | P<0.0001 | |
| Median survival | | |
| Data 1:Data Set-A | | 51 |
| Data 1:Data Set-B | Undefined | |
| Hazard Ratio | | |
| Ratio | | 5.344 |
| 95% CI of ratio | 3.262 to 7.086 | |

Fig. 31-4

Table S2. Parent Methylation Signature
Supplementary Table 4
Genes marked with polycomb reported to be hypermethylated in cancer
Gene Name TP73
TNFRSF25
RBP7
PAX7
POU3F1
CDKN2C
JUN
ALX3
RASSF5
GATA4
DLC1
EGR3
NKX3-1
SFRP1
CEBPD
NDRG1
PAX5
APBA1
NTRK2
GADD45G
FOXE1
KLF4
CXCL12
PRKG1
RBP4
SLIT1
SFRP5
KCNQ1
CALCA
MYOD1
PAX6
WT1
WIT-1
CD44
FLJ33790
PGR
FEZ1
PTHLH
VDR
CYP27B1
DUSP6
TBX3
HRK
PXMP2
GJB2
CDX2
CCNA1

Fig. 32-1

RIPK3
NKX2-8
LGALS3
AMN
PPP1R13B
CRIP1
FBN1
ETFA
NR2F2
HBA1
ASC
MT3
MT1A
CDH13
HIC1
PMP22
ACCN1
RARA
HOXB13
CACNA1G
LGICZ
NPTX1
LAMA3
DSC3
DCC
BCL2
GPR54
TNFSF9
ABHD9
FOXA2
THBD
TFAP2C
GNAS
CDH4
GATA5
C21orf63\
TBX1
PCDH11X
TCEAL1
CHRDL1
GPC3

Prostate cancer CTOP methylation signature
Gene Name          Coeff.ProCa79
LGALS3    200923_at   -7.0582
JUN       201464_x_   29.9796
JUN       201473_at  -24.9571
FBN1      202766_s_   10.909
BCL2      203684_s_   7.7394
BCL2      203685_at  -16.0174

Fig. 32-2

| | | |
|---|---|---|
| LAMA3 | 203726_s_ | -3.9206 |
| RARA | 203750_s_ | -21.9307 |
| JUN | 203752_s_ | -48.3963 |
| THBD | 203887_s_ | 28.7886 |
| CRIP1 | 205081_at | 9.8068 |
| CYP27B1 | 205676_at | 16.5633 |
| CCNA1 | 205899_at | 7.6005 |
| MT3 | 205970_at | -10.8464 |
| EGR3 | 206115_at | 7.1541 |
| HRK | 206863_x_ | -3.8294 |
| HRK | 206865_at | 6.6457 |
| CDH4 | 206866_at | -9.2355 |
| FOXE1 | 206912_at | -7.7479 |
| BCL2 | 207005_s_ | -6.2994 |
| NTRK2 | 207152_at | 11.1465 |
| NKX2-8 | 207451_at | 8.6249 |
| TBX1 | 207662_at | -9.3868 |
| ALX3 | 207690_at | -2.8331 |
| CACNA1G | 207869_s_ | 10.3238 |
| PAX7 | 208060_at | 16.4496 |
| PCDH11X | 208366_at | 2.778 |
| NR2F2 | 209121_x_ | 26.2422 |
| NKX3-1 | 209706_at | -29.9142 |
| CD44 | 209835_x_ | -49.7958 |
| PCDH11X | 211227_s_ | 13.7622 |
| CD44 | 212014_x_ | 28.5387 |
| TBX3 | 219682_s_ | 9.8665 |
| KLF4 | 220266_s_ | 6.2996 |
| FEZ1 | 221719_s_ | -15.2149 |

Chi Square= 135.6101; df=35; p= 0.0000

Breast cancer methylation signature
Coeff.BrCa286

| | | |
|---|---|---|
| 200632_s_at | 0.5946 | NDRG1 |
| 200780_x_at | -1.7738 | GNAS |
| 200923_at | -0.6029 | LGALS3 |
| 201465_s_at | 0.6063 | JUN |
| 203562_at | 1.0509 | FEZ1 |
| 203684_s_at | -0.7341 | BCL2 |
| 204490_s_at | -4.5825 | CD44 |
| 204726_at | 0.7473 | CDH13 |
| 205646_s_at | 0.6856 | PAX6 |
| 206067_s_at | 0.5233 | WT1 |
| 206865_at | 0.9028 | HRK |
| 206954_at | -0.8852 | WIT-1 |
| 207119_at | 0.6989 | PRKG1 |
| 208060_at | 1.2431 | PAX7 |
| 208305_at | -0.3927 | PGR |
| 209706_at | -0.6818 | NKX3-1 |
| 211227_s_at | -0.6063 | PCDH11X |
| 211802_x_at | -1.7214 | CACNA1G |

Fig. 32-3

| | | |
|---|---|---|
| 216953_s_at | 0.9716 | WT1 |
| 219140_s_at | -0.5219 | RBP4 |
| 220804_s_at | -1.6418 | TP73 |
| 221721_s_at | 1.04 | FEZ1 |

Chi Square= 132.6873; df=22; p= 0.0000

Breast cancer methylation signature (Agilent)
Coeff.BrCa97

| | | |
|---|---|---|
| NM_002228 | JUN | 7.1196 |
| NM_006167 | NKX3A | -5.5294 |
| NM_005195 | CEBPD | 2.1314 |
| NM_006180 | NTRK2 | 1.8774 |
| NM_006744 | RBP4 | -4.309 |
| NM_003061 | SLIT1 | -18.3141 |
| NM_000218 | KCNQ1 | 3.556 |
| NM_002478 | MYOD1 | -6.8676 |
| NM_000280 | PAX6 | -11.5534 |
| X51630 | WT1 | 1.7146 |
| NM_015855 | WIT-1 | 2.6366 |
| AF098641 | CD44 | -18.4003 |
| NM_000610 | CD44 | 10.3727 |
| NM_005103 | FEZ | 10.1825 |
| NM_002820 | PTHLH | -4.6079 |
| NM_000376 | VDR | 6.0321 |
| NM_003806 | HRK | 4.1321 |
| NM_000138 | FBN1 | -10.0173 |
| M64497 | NR2F2 | -2.9014 |
| NM_013258 | ASC | -2.4327 |
| NM_018896 | CACNA1G | -7.8966 |
| NM_000227 | LAMA3 | -18.9565 |
| NM_001941 | DSC3 | 4.0569 |
| NM_005215 | DCC | 2.1193 |
| NM_000633 | BCL2 | -2.7638 |
| NM_000657 | BCL2 | 12.3807 |
| NM_003811 | TNFSF9 | -9.8688 |
| NM_000516 | GNAS1 | 3.1351 |
| NM_014522 | PCDH11 | 1.8382 |

Chi Square= 141.0866; df=29; p= 0.0000

Fig. 32-4

Table S3. Histones H3 and H2A CTOP signatures
Prostate cancer

| | Coeff.ProCa79 |
|---|---|
| 208583_x_ | 1.2943 |
| 214644_at | -1.3298 |
| 212524_x_ | 2.0518 |
| 213344_s_ | -4.3968 |
| 218280_x_ | 4.76 |
| 214500_at | -8.6386 |
| 214290_s_ | -13.482 |
| 214469_at | 2.8115 |
| 214542_x_ | 3.6864 |
| 207156_at | -0.5515 |
| 213911_s_ | -11.3613 |
| 200853_at | 5.7792 |
| 215071_s_ | -0.5738 |
| 214554_at | -3.4244 |
| 211999_at | -1.7676 |
| 211997_x_ | 5.0102 |
| 211998_at | -1.2153 |
| 208577_at | 2.194 |
| 200080_s_ | 3.7312 |
| 214646_at | -1.3311 |
| 214472_at | 2.5982 |
| 211940_x_ | 4.9932 |
| 213826_s_ | -6.5189 |
| 213828_x_ | -10.3003 |
| 208572_at | 2.5584 |
| 208575_at | -3.6907 |
| 208496_x_ | 3.5378 |

Chi Square= 78.5927; df=27; p= 0.0000

Breast cancer (Agilent)

| | Coeff.BrCa97 |
|---|---|
| Contig506H3F3B | 2.6014 |
| NM_00349H3FT | 8.7025 |
| NM_00352H3FA | -0.2338 |
| NM_00353H3FB | -6.5779 |
| NM_00353H3FC | 11.9774 |
| NM_00353H3FD | -0.1029 |
| NM_00353H3FF | -3.1392 |
| NM_00353H3FH | -8.4709 |
| NM_00353H3FJ | 15.4178 |
| NM_00353H3FK | -1.2235 |
| NM_00353H3FL | 0.9435 |
| NM_02101H3FI | -21.9658 |
| NM_00532H3F3B | -1.5539 |
| NM_00210H3F3A | 1.7716 |
| NM_00351H2AFD | -12.1397 |

Fig. 33-1

| | |
|---|---|
| NM_00351H2AFL | 0.2418 |
| NM_00351H2AFM | -0.4121 |
| NM_00351H2AFN | 1.088 |
| NM_00351H2AFO | 0.2493 |
| NM_02105H2AFA | 2.4053 |
| NM_02106H2AFP | 5.6892 |
| NM_02106H2AFG | 15.0926 |
| Contig439H2AFA | -1.2748 |
| NM_00489H2AFY | 1.5876 |
| Contig440 H2AFL | 0.2538 |
| NM_01864MACROH2 | 0.4571 |
| L19778   H2AFP | 0.2862 |
| NM_00210H2AFX | -1.9364 |
| NM_00210H2AFZ | 3.7693 |

Chi Square= 54.0014; df=29; p= 0.0032

Breast cancer (Affimetrix)
Coeff.BrCa286

| | |
|---|---|
| 211999_at | 2.4079 |
| 211997_x_ | 2.2277 |
| 211998_at | -0.5456 |
| 206110_at | -0.1476 |
| 214616_at | -2.4671 |
| 208576_s_ | 0.4233 |
| 208577_at | -0.2196 |
| 200080_s_ | -2.4972 |
| 208506_at | -0.3869 |
| 214646_at | 0.5179 |
| 214472_at | 0.184 |
| 208755_x_ | -8.3994 |
| 211940_x_ | 5.8136 |
| 213826_s_ | 3.1317 |
| 209069_s_ | -4.9488 |
| 213828_x_ | 2.8209 |
| 208572_at | 0.3432 |
| 214509_at | -0.1111 |
| 208575_at | -0.0155 |
| 208496_x_ | 0.1068 |
| 214522_x_ | 0.9503 |
| 208583_x_ | -0.5991 |
| 214644_at | -0.5086 |
| 212524_x_ | 0.3414 |
| 218279_s_ | 0.1195 |
| 208569_at | -0.2809 |
| 212525_s_ | -0.9717 |
| 218445_at | -0.109 |
| 213344_s_ | 0.1121 |
| 218280_x_ | -2.126 |
| 214500_at | -0.4795 |

Chi Square= 78.1539;  df=44;  p= 0.0012

Fig. 33-3

Table 4. CTOP gene expression signatures for prostate cancer
36_Genes EED_ESC_Signature

|  |  | Coeff.MSKCC79 |
|---|---|---|
| Pax8 | 121_at | 19.1405 |
| Yy1 | 200047_s_at | -18.6412 |
| Pcna | 201202_at | -12.0663 |
| Igf2 | 202410_x_at | -2.703 |
| Hprt1 | 202854_at | 12.0642 |
| Sox9 | 202936_s_at | 2.722 |
| Pdgfra | 203131_at | -2.712 |
| Ezh2 | 203358_s_at | -1.1031 |
| Fgfr3 | 204379_s_at | -1.1875 |
| Hoxb7 | 204779_s_at | -1.6233 |
| Bmpr1a | 204832_s_at | -11.3731 |
| Tcf21 | 204931_at | 7.1003 |
| Tal1 | 205339_at | 20.235 |
| Crabp1 | 205350_at | -1.0333 |
| Hoxb2 | 205453_at | 9.8517 |
| Gata4 | 205517_at | 3.7254 |
| Fgf7 | 205782_at | -3.0097 |
| Bmp6 | 206176_at | 4.2866 |
| HoxA4 | 206289_at | 7.4911 |
| Cbx4 | 206724_at | -0.6047 |
| Hoxc5 | 206739_at | -11.5152 |
| Hoxc6 | 206858_s_at | 3.8716 |
| Dlx2 | 207147_at | 0.5777 |
| Foxh1 | 207644_at | -3.7847 |
| Sox21 | 208468_at | 0.3689 |
| Neurog1 | 208497_x_at | -0.0015 |
| Eed | 209572_s_at | 11.2603 |
| Gata3 | 209602_s_at | -0.0046 |
| Gata1 | 210446_at | -2.377 |
| Myst4 | 212452_x_at | -9.6539 |
| Yy1 | 213494_s_at | 3.3719 |
| Hoxa2 | 214457_at | 0.8382 |
| Pax8 | 214528_s_at | -0.6819 |
| Pdgfra | 215305_at | -3.1419 |
| Tal1 | 216928_at | 1.365 |
| Dkk2 | 219908_at | 2.2393 |

28_Genes NANOG_Sox2_Oct4_Signature

|  |  | Coeff.MSKCC79 |
|---|---|---|
| JUP | 201015_s_at | 11.2302 |
|  | 201049_s_at | 7.0988 |
|  | 201292_at | 1.3184 |
|  | 201431_s_at | 7.8837 |
| BUB3 | 201457_x_at | 16.8188 |
|  | 201499_s_at | -2.7861 |
| ICMT | 201611_s_at | -14.7461 |
|  | 201667_at | -0.8042 |
| GNG10 | 201921_at | -15.2391 |

Fig. 34-1

|  |  |  |
|---|---|---|
|  | 202724_s_at | -3.1493 |
|  | 203100_s_at | -0.892 |
|  | 204101_at | -0.0183 |
|  | 204335_at | -4.9135 |
|  | 204391_x_at | 1.0964 |
|  | 209590_at | 0.4761 |
|  | 213540_at | -4.7824 |
|  | 220398_at | -1.7874 |
|  | 222039_at | 3.7961 |
|  | 202884_s_at | 8.8512 |
|  | 204536_s_at | 3.2012 |
|  | 213047_x_at | 2.1026 |
| SET | 213048_s_at | -10.5865 |
|  | 213870_at | 4.2788 |
| PPAP2A | 214693_x_at | 11.5778 |
| LARGE | 215543_s_at | -17.7795 |
|  | 216928_at | 7.1312 |
| FUS | 217370_x_at | -19.9505 |
| NUCKS | 217802_s_at | 17.1103 |

26_Genes Suz12_NoPOLII_Signature

|  | Coeff.MSKCC79 |
|---|---|
| 204197_s_at | -7.3396 |
| 206307_s_at | 2.9093 |
| 206424_at | 5.9775 |
| 206461_x_at | -2.0264 |
| 206893_at | -1.2388 |
| 207152_at | -13.347 |
| 207890_s_at | -9.4097 |
| 208493_at | 2.964 |
| 208536_s_at | 3.8839 |
| 209120_at | -11.1846 |
| 209347_s_at | -2.5947 |
| 209602_s_at | -4.4431 |
| 209603_at | 6.8789 |
| 209604_s_at | 15.7739 |
| 209897_s_at | 7.4749 |
| 210273_at | -23.7153 |
| 211529_x_at | -42.337 |
| 211958_at | 27.0153 |
| 211959_at | -8.3799 |
| 213943_at | 3.8193 |
| 214639_s_at | -7.1451 |
| 214961_at | -2.717 |
| 217436_x_at | 24.5186 |
| 217762_s_at | 5.9211 |
| 217763_s_at | -8.5441 |
| 218723_s_at | 4.4378 |

Fig. 34-2

22_Genes Suz12_RNAPII_Bound_Signature

| | | Coeff._MSKCC_79 |
|---|---|---|
| PAK1 | 209615_s_at | -0.6761 |
| ING1 | 208415_x_at | -3.0356 |
| POLR3K | 218866_s_at | 3.0449 |
| | 204483_at | 1.5619 |
| PLD1 | 215723_s_at | 0.9152 |
| BAIAP2 | 207832_at | -1.3529 |
| BDNF | 206382_s_at | -1.8394 |
| EGFR | 211551_at | -2.0166 |
| FBN2 | 203184_at | 2.8178 |
| KIAA0427 | 204303_s_at | -6.9953 |
| CAST | 207467_x_at | -2.5533 |
| GADD45B | 209305_s_at | 2.709 |
| GADD45B | 209304_x_at | -0.7771 |
| PRKCH | 206099_at | -4.5776 |
| CYP1B1 | 202437_s_at | 0.0863 |
| JUN | 201473_at | -1.767 |
| | 214326_x_at | 0.6099 |
| | 213281_at | -0.8828 |
| | 201373_at | 2.4154 |
| | 209596_at | -2.3978 |
| | 205409_at | -2.0167 |
| | 207172_s_at | 1.3363 |

21_Genes PcG_TF_Signature

| | | Coeff._MSKCC_79 |
|---|---|---|
| JUNB | 201473_at | -1.6686 |
| HOXB2 | 205453_at | 4.0579 |
| NPAS2 | 205460_at | -2.2701 |
| IRF5 | 205469_s_at | -5.3543 |
| PAX6 | 205646_s_at | 7.9705 |
| SIX1 | 205817_at | 3.3184 |
| WT1 | 206067_s_at | -0.9522 |
| HOXA4 | 206289_at | 4.375 |
| HOXC6 | 206858_s_at | 3.9631 |
| NKX2B | 206915_at | 1.8103 |
| HOXD13 | 207398_at | 1.9003 |
| HOXB1 | 208224_at | -3.1035 |
| NEUROG1 | 208497_x_at | -3.2926 |
| FOXB1 | 208513_at | 3.7144 |
| GATA6 | 210002_at | 2.322 |
| BARX2 | 210419_at | 1.878 |
| LEF1 | 210948_s_at | 5.0275 |
| NHLH2 | 214497_s_at | -4.3598 |
| TAL1 | 216928_at | 4.219 |
| TBR1 | 220025_at | -5.7199 |
| BACH2 | 221234_s_at | -2.1589 |

Fig. 34-3

32_Genes TEX_Signature

| | | Coeff.MSKCC79 |
|---|---|---|
| | 200916_at | 0.4687 |
| | 201921_at | -6.2342 |
| | 202265_at | 4.8514 |
| | 202308_at | -1.416 |
| | 202410_x_at | 4.1373 |
| | 203222_s_at | 0.826 |
| | 203637_s_at | -2.0001 |
| | 203685_at | -0.7066 |
| | 203744_at | 5.4714 |
| | 204358_s_at | -2.3164 |
| | 205266_at | 0.0629 |
| | 205918_at | -2.6063 |
| | 205935_at | 1.2403 |
| | 206140_at | -0.5393 |
| | 206289_at | 2.2274 |
| | 206739_at | -0.644 |
| | 206858_s_at | 3.0929 |
| | 206915_at | 1.2723 |
| | 206940_s_at | -0.2292 |
| | 207676_at | 2.6427 |
| | 208482_at | 0.6752 |
| | 208563_x_at | -0.9707 |
| | 209357_at | 0.1177 |
| | 209897_s_at | -4.0996 |
| | 210273_at | -1.71 |
| | 211802_x_at | -1.7655 |
| | 213943_at | 2.1129 |
| | 218150_at | 1.3299 |
| | 219738_s_at | -0.95 |
| | 219920_s_at | -0.7677 |
| | 220025_at | -0.2186 |
| | 221366_at | -0.5651 |

31_Genes Wound_Signature

| | | Coeff.MSKCC79 |
|---|---|---|
| | 210987_x_at | 13.5838 |
| APP | 211277_x_at | 33.5031 |
| | 211320_s_at | 25.2384 |
| | 211458_s_at | -31.2917 |
| | 211697_x_at | -14.5805 |
| | 211760_s_at | 28.6615 |
| | 211921_x_at | -18.7556 |
| | 212289_at | -16.0408 |
| | 212779_at | -12.3353 |
| | 213805_at | 7.7972 |

Fig. 34-4

|  |  |  |
|---|---|---|
|  | 214040_s_at | 13.0537 |
| PDLIM7 | 214121_x_at | -40.3494 |
|  | 214285_at | -19.2546 |
|  | 214727_at | 25.305 |
|  | 216870_x_at | 22.0628 |
|  | 216894_x_at | 22.0419 |
|  | 217005_at | 17.8487 |
|  | 217230_at | -14.3123 |
|  | 217234_s_at | 27.8897 |
| ARPC4 | 217817_at | 60.6616 |
|  | 217824_at | -15.7607 |
| MRPS16 | 218046_s_at | 52.6516 |
| FLJ10726 | 218314_s_at | 52.2607 |
|  | 218603_at | -31.5345 |
|  | 218680_x_at | -41.577 |
| RNF138 | 218738_s_at | 48.1554 |
| ABHD5 | 218739_at | -75.748 |
|  | 219314_s_at | -32.6966 |
|  | 220326_s_at | -14.0576 |
|  | 221058_s_at | -34.1186 |
| CCNL2 | 221427_s_at | 33.6271 |

Bivalent Chromatin Domain
31_Genes BCD_TF signature

|  |  | Coeff.MSKCC_79 |
|---|---|---|
| Satb1 | 203408_s_at | 9.5095 |
| Hoxd9 | 205605_at | 8.1893 |
| Pax6 | 205646_s_at | 24.517 |
| Lmo4 | 209204_at | 11.3872 |
| Lmo4 | 209205_s_at | -16.0559 |
| Ebf1 | 202308_at | -25.0391 |
| Foxa1 | 204667_at | -23.0121 |
| Foxd3 | 208500_x_at | 7.5805 |
| Hoxa | 206847_s_at | -12.8474 |
| Hoxa | 206289_at | 22.4161 |
| Hoxa | 208493_at | 6.2193 |
| Hoxa | 214457_at | 3.872 |
| Hoxa | 206848_at | -13.5149 |
| Hoxa | 214651_s_at | 27.0627 |
| Hoxa | 208557_at | -28.9179 |
| Hoxa | 208604_s_at | -16.0551 |
| Hoxb | 205366_s_at | -7.1201 |
| Hoxb | 209844_at | 6.5797 |
| Hoxb | 208414_s_at | 6.8766 |
| Hoxb | 208224_at | -7.7611 |
| Hoxb | 205601_s_at | -17.7954 |
| Hoxc | 218959_at | 13.9442 |
| Hoxc | 206858_s_at | 17.2883 |
| Hoxd | 221411_at | 7.9524 |
| Hoxd | 205522_at | 4.7793 |

Fig. 34-5

| | | |
|---|---|---|
| Irx4 | 220225_at | 4.6682 |
| Maf | 206363_at | -7.6507 |
| Maf | 209348_s_at | 14.8545 |
| Mrg1 | 209357_at | 27.3768 |
| Nkx2-2 | 206915_at | 3.6777 |
| Nkx6-2 | 221366_at | 3.8212 |

18_CAN_Mutations_Signature    From 38

| U133A_18 | MSKCC79 | Gene_18 |
|---|---|---|
| 221337_s_at | 4.9487 | ADAM29 |
| 202204_s_at | -11.6791 | AMFR |
| 220115_s_at | -4.4055 | CDH10 |
| 202806_at | 10.4901 | DBN1 |
| 204718_at | -6.0125 | EPHB6 |
| 207347_at | 12.195 | ERCC6 |
| 203867_s_at | 2.96 | FLJ10458 |
| 206927_s_at | 6.3309 | GUCY1A2 |
| 204303_s_at | -8.345 | KIAA0427 |
| 205951_at | 1.6725 | MYH1 |
| 210631_at | 3.4909 | NF1 |
| 204323_x_at | -17.9289 | NF1 |
| 204105_s_at | 4.1281 | NRCAM |
| 206380_s_at | -6.954 | PFC |
| 204723_at | 2.9879 | SCN3B |
| 205464_at | 2.473 | SCNN1B |
| 203557_s_at | -9.2141 | TCF1 |
| 201746_at | -10.9725 | TP53 |

29_CAN_Mutations_Signature    From 40

| U133A_29 | MSKCC79 | Gene_29 |
|---|---|---|
| 203505_at | -34.3447 | ABCA1 |
| 203504_s_at | 42.4378 | ABCA1 |
| 202502_at | -42.0413 | ACADM |
| 202204_s_at | -13.6856 | AMFR |
| 203527_s_at | -11.2844 | APC |
| 203526_s_at | 15.9674 | APC |
| 204608_at | -26.0256 | ASL |
| 204320_at | 5.3928 | COL11A1 |
| 204136_at | -16.1068 | COL7A1 |
| 202806_at | 45.8877 | DBN1 |
| 207327_at | 7.004 | EYA4 |
| 203867_s_at | 12.2292 | FLJ10458 |
| 206927_s_at | 14.5518 | GUCY1A2 |
| 204225_at | -16.0677 | HDAC4 |
| 200643_at | 23.5956 | HDLBP |
| 204303_s_at | -22.4678 | KIAA0427 |
| 204009_s_at | 18.7654 | KRAS |
| 202674_s_at | -10.8445 | LMO7 |
| 204325_s_at | 6.8034 | NF1 |

Fig. 34-6

```
204323_x_at    -50.0309 NF1
204105_s_at      6.2136 NRCAM
202155_s_at     16.7047 NUP214
208447_s_at      8.2166 PRPS1
205503_at        5.853  PTPN14
208031_s_at     -1.9818 RFX2
204723_at        6.4669 SCN3B
204722_at       -5.6916 SCN3B
201802_at      -16.4745 SLC29A1
201746_at      -19.1304 TP53

19_CAN_Mutations_Signature              From 62
U133A_128   MSKCC79      Gene_19
221337_s_at      5.7151 ADAM29
202204_s_at    -10.864  AMFR
204531_s_at      2.6136 BRCA1
204136_at      -10.8338 COL7A1
217312_s_at      3.8765 COL7A1
205749_at        2.926  CYP1A1
202806_at        4.9093 DBN1
206070_s_at     -2.7925 EPHA3
204718_at       -6.0188 EPHB6
207347_at       10.3305 ERCC6
207327_at        3.3041 EYA4
203867_s_at      3.0243 FLJ10458
206927_s_at      5.0721 GUCY1A2
204303_s_at     -6.1784 KIAA0427
212504_at       -3.666  KIAA0934
204323_x_at    -10.4882 NF1
211095_at       -3.5357 NF1
204722_at       -2.5701 SCN3B
209561_at        8.8579 THBS3

38_CAN_Mutations_Signature
U133A_38    MSKCC79      Gene_38
221337_s_at      4.6151 ADAM29
202204_s_at    -15.7737 AMFR
220115_s_at     -7.9402 CDH10
204320_at       -0.7397 COL11A1
37892_at         2.2591 COL11A1
217312_s_at      0.5726 COL7A1
205749_at        1.4185 CYP1A1
202806_at       15.8081 DBN1
205554_s_at      4.0271 DNASE1L3
204718_at       -9.9508 EPHB6
207347_at       10.7914 ERCC6
203867_s_at      3.803  FLJ10458
200696_s_at     -4.6271 GSN
206927_s_at     10.4819 GUCY1A2
204225_at        3.2216 HDAC4
```

Fig. 34-7

| | | |
|---|---:|---|
| 204303_s_at | -8.1551 | KIAA0427 |
| 212503_s_at | 4.4668 | KIAA0934 |
| 212504_at | -3.7296 | KIAA0934 |
| 204155_s_at | -8.6045 | KIAA0999 |
| 205951_at | 2.9813 | MYH1 |
| 204323_x_at | -28.3965 | NF1 |
| 204325_s_at | 1.1586 | NF1 |
| 210631_at | 3.5752 | NF1 |
| 211095_at | -3.2043 | NF1 |
| 204105_s_at | 6.0565 | NRCAM |
| 220492_s_at | -2.5118 | OTOF |
| 206380_s_at | -7.2525 | PFC |
| 204196_x_at | -0.5635 | PKNOX1 |
| 205503_at | -2.9156 | PTPN14 |
| 203911_at | 2.9621 | RAP1GA1 |
| 211421_s_at | 1.1949 | RET |
| 204723_at | 5.8734 | SCN3B |
| 205464_at | 3.4865 | SCNN1B |
| 206108_s_at | -0.9646 | SFRS6 |
| 203557_s_at | -11.0862 | TCF1 |
| 207334_s_at | 0.9824 | TGFBR2 |
| 209561_at | 3.6056 | THBS3 |
| 201746_at | -15.1228 | TP53 |

40_CAN_Mutations_Signature

| U133A_40 | ProCa79 | Gene_40 |
|---|---:|---|
| 203504_s_at | 69.4359 | ABCA1 |
| 203505_at | -64.0864 | ABCA1 |
| 206317_s_at | -7.317 | ABCB8 |
| 202502_at | -111.9505 | ACADM |
| 202203_s_at | -6.3422 | AMFR |
| 202204_s_at | -29.75 | AMFR |
| 203526_s_at | 36.811 | APC |
| 203527_s_at | -35.2176 | APC |
| 204608_at | -57.547 | ASL |
| 204531_s_at | -2.8038 | BRCA1 |
| 204320_at | 11.0698 | COL11A1 |
| 204136_at | -51.5234 | COL7A1 |
| 202806_at | 116.3381 | DBN1 |
| 204977_at | 26.4931 | DDX10 |
| 206070_s_at | 18.8966 | EPHA3 |
| 207347_at | 5.0236 | ERCC6 |
| 207327_at | 17.1612 | EYA4 |
| 203867_s_at | 36.1505 | FLJ10458 |
| 206927_s_at | 43.1106 | GUCY1A2 |
| 204225_at | -25.8742 | HDAC4 |
| 200643_at | 59.0386 | HDLBP |
| 206906_at | -12.0304 | ICAM5 |
| 204303_s_at | -48.264 | KIAA0427 |
| 204155_s_at | -38.4086 | KIAA0999 |
| 204009_s_at | 57.2173 | KRAS |

Fig. 34-8

| | | |
|---|---|---|
| 204010_s_at | -9.6185 | KRAS |
| 202674_s_at | -16.1931 | LMO7 |
| 205395_s_at | 7.5895 | MRE11A |
| 204323_x_at | -95.5463 | NF1 |
| 204325_s_at | 7.9677 | NF1 |
| 204105_s_at | 15.1042 | NRCAM |
| 202155_s_at | 64.4907 | NUP214 |
| 208447_s_at | 18.6744 | PRPS1 |
| 205503_at | 25.3474 | PTPN14 |
| 208031_s_at | -4.7727 | RFX2 |
| 204722_at | -3.9878 | SCN3B |
| 204723_at | 16.4948 | SCN3B |
| 201802_at | -40.2418 | SLC29A1 |
| 203557_s_at | -11.2827 | TCF1 |
| 201746_at | -63.4453 | TP53 |

Fig. 34-9

Table 5. CTOP gene expression signatures for breast cancer

20_Genes EED_ESC_Signature Affymetrix

| Gene | Probe | Coeff.BrCa_286 |
|---|---|---|
| Ccnd2 | 200953_s_at | -0.4078 |
| Yy1 | 201901_s_at | -1.1799 |
| Sox9 | 202936_s_at | -0.5824 |
| Pdgfra | 203131_at | 0.5106 |
| Ezh2 | 203358_s_at | 0.7626 |
| Kit | 205051_s_at | -0.4873 |
| Pax6 | 205646_s_at | 0.6064 |
| Dicer1 | 206061_s_at | 1.8227 |
| Lhx2 | 206140_at | 0.1183 |
| Bmp6 | 206176_at | -1.0691 |
| Hoxc6 | 206858_s_at | 1.1216 |
| Pax9 | 207059_at | -0.9552 |
| Sox5 | 207336_at | 0.5262 |
| Wnt8b | 207612_at | -1.3226 |
| Esrrb | 207726_at | -0.5097 |
| Foxi1 | 208006_at | -0.1918 |
| Eed | 210656_at | 0.6201 |
| Yy1 | 213494_s_at | -0.7752 |
| Ckap2 | 218252_at | 2.1124 |
| Cbx8 | 219755_at | 0.5625 |

41_Genes NANOG_Sox2_Oct4_Signature

| Gene | Probe | Coeff.BrCa286 |
|---|---|---|
| RPS3A | 200099_s_at | -0.0871 |
| TOP2A | 201292_at | 1.3134 |
| BUB3 | 201456_s_at | 2.3139 |
| TALDO1 | 201463_s_at | 0.0358 |
| USP7 | 201498_at | -0.9829 |
| SNRPN | 201522_x_at | 0.0738 |
| ZFP36L1 | 201531_at | -03.759 |
| GNG10 | 201921_at | 0.491 |
| SFRP1 | 202037_s_at | -0.3732 |
| LAMA4 | 202202_s_at | 2.4384 |
| FEZ1 | 203562_at | 2.3905 |
| BUB1B | 203755_at | 0.9993 |
| MTM1 | 204101_at | 0.9752 |
| TIF1 | 204390_at | -0.7148 |
| NFE2L3 | 204702_s_at | -0.0642 |
| DTNA | 205741_s_at | 0.2477 |
| CA4 | 206208_at | -0.8146 |
| TDGF1 | 206286_s_at | -0.6072 |
| IFI16 | 206332_s_at | 2.6763 |
| TLE3 | 206472_s_at | 0.2683 |
| SPAG9 | 206748_s_at | -0.6428 |
| ZIC3 | 207197_at | 0.6293 |
| FGFR2 | 208234_x_at | 0.4479 |
| IFI16 | 208966_x_at | -2.0482 |

Fig. 35-1

| | | |
|---|---|---|
| STAT3 | 208991_at | -1.5833 |
| PPAP2A | 209147_s_at | 1.8536 |
| PPAP2A | 210946_at | -1.0985 |
| FGFR2 | 211401_s_at | 0.1129 |
| PHF8 | 212916_at | 0.0924 |
| LARGE | 215538_at | -2.0299 |
| RPS18 | 216065_at | -0.3371 |
| FUS | 217370_x_at | -0.6977 |
| FLJ10769 | 217940_s_at | 1.176 |
| DUSP12 | 218576_s_at | 2.3896 |
| FLJ10652 | 218614_at | -3.0236 |
| FLJ11029 | 219392_x_at | 2.6902 |
| RAD54B | 219494_at | 0.1818 |
| NANOG | 220184_at | 0.6938 |
| FEZ1 | 221721_s_at | 0.4697 |
| FEZ1 | 221722_x_at | 0.8917 |
| MTM1 | 36920_at | 1.5261 |

22_Genes NANOG_Sox2_Oct4_Signature

| | | Coeff.BrCa286 |
|---|---|---|
| TOP2A | 201292_at | 1.7447 |
| BUB3 | 201456_s_at | 2.3444 |
| SFRP1 | 202037_s_at | -0.3569 |
| LAMA4 | 202202_s_at | 1.8144 |
| FEZ1 | 203562_at | 2.5855 |
| MTM1 | 204101_at | 0.9351 |
| CA4 | 206208_at | -0.9975 |
| TDGF1 | 206286_s_at | -0.6928 |
| IFI16 | 206332_s_at | 2.3195 |
| SPAG9 | 206748_s_at | -0.7225 |
| ZIC3 | 207197_at | 0.9719 |
| IFI16 | 208966_x_at | -1.7671 |
| STAT3 | 208991_at | -2.1773 |
| PPAP2A | 209147_s_at | 1.2729 |
| LARGE | 215538_at | -1.8773 |
| FLJ10769 | 217940_s_at | 0.9433 |
| DUSP12 | 218576_s_at | 2.463 |
| FLJ10652 | 218614_at | -3.29 |
| FLJ11029 | 219392_x_at | 2.7464 |
| NANOG | 220184_at | 0.4874 |
| FEZ1 | 221722_x_at | 0.7185 |
| MTM1 | 36920_at | 1.6754 |

Fig. 35-2

25_Genes Suz12_NoPOLII_Signature

| Suz12_NoPOLII | | Coeff.BrCa286 |
|---|---|---|
| SFRP1 | 202037_s_at | -0.6435 |
| COL15A1 | 203477_at | 0.8597 |
| DFNA5 | 203695_s_at | 0.7031 |
| THBD | 203888_at | -0.3906 |

| | | |
|---|---|---|
| PSMB9 | 204279_at | -0.8116 |
| MYO5A | 204527_at | 1.0914 |
| MN1 | 205330_at | -2.0047 |
| RASGRP1 | 205590_at | -0.5264 |
| SYNGR3 | 205691_at | 0.5135 |
| RELN | 205923_at | 1.2882 |
| SALL1 | 206893_at | 0.2605 |
| MMP25 | 207890_s_at | -1.3599 |
| RASGRP2 | 208206_s_at | -0.244 |
| GATA3 | 209602_s_at | -0.566 |
| GATA6 | 210002_at | -0.3213 |
| PCDH7 | 210273_at | 2.007 |
| HLA-G | 211529_x_at | -0.6397 |
| TFAP2B | 214451_at | -0.2602 |
| FLJ10159 | 218974_at | 0.6687 |
| DLL3 | 219537_x_at | 0.5433 |
| GNA14 | 220108_at | 0.4024 |
| TGFB2 | 220406_at | -1.091 |
| TGFB2 | 220407_s_at | -1.1468 |
| WNT5B | 221029_s_at | 0.224 |
| BACH2 | 221234_s_at | -0.2467 |

20_Genes Suz12_RNAPII_Bound_Signature
Coeff.BrCa_286

| | | |
|---|---|---|
| CXCR4 | 211919_s_at | -0.3766 |
| KIAA0368 | 212427_at | 0.5784 |
| PLD1 | 215723_s_at | 0.731 |
| PLD1 | 205203_at | -1.2774 |
| NID2 | 204114_at | 0.2637 |
| ATF3 | 202672_s_at | -1.4834 |
| KIAA0427 | 204302_s_at | -0.3753 |
| DUSP4 | 204014_at | -0.7839 |
| SMTN | 207390_s_at | 0.7635 |
| GADD45B | 207574_s_at | 5.3821 |
| GADD45B | 209304_x_at | -5.7651 |
| PRKCH | 206099_at | -0.9562 |
| JUN | 201466_s_at | 1.6983 |
| JUN | 201473_at | -0.9137 |
| PCDH17 | 205656_at | 2.2209 |
| TIMP3 | 201150_s_at | -1.1872 |
| PLEC1 | 201373_at | 0.9565 |
| LIF | 205266_at | -0.8349 |
| SOX9 | 202936_s_at | -0.9101 |
| CDH11 | 207172_s_at | 1.5839 |

30_Genes PcG_TF_Signature
Coeff.BrCa_286

| | | |
|---|---|---|
| Nr2e1 | 200067_x_at | 2.0406 |

| Gene | Probe | Coeff |
|---|---|---|
| Atf3 | 202672_s_at | -0.9872 |
| Sox9 | 202936_s_at | -0.902 |
| Zfhx1b | 203603_s_at | 0.3674 |
| Jun | 203752_s_at | -0.8539 |
| Cebpa | 204039_at | -0.3315 |
| Npas2 | 205459_s_at | -0.2993 |
| Npas2 | 205460_at | -0.4384 |
| Dach1 | 205471_s_at | 0.4471 |
| Six1 | 205817_at | 0.3229 |
| Egr3 | 206115_at | -0.0461 |
| Foxf2 | 206377_at | 0.5292 |
| Cart1 | 206837_at | -0.8559 |
| Hoxc6 | 206858_s_at | 0.7224 |
| Pax9 | 207059_at | -0.2872 |
| Dlx2 | 207147_at | -0.3413 |
| Six6 | 207250_at | 1.4882 |
| Alx3 | 207690_at | -0.9141 |
| Hoxb3 | 208414_s_at | -0.5386 |
| Pou4f3 | 208554_at | -0.1844 |
| Pou3f3 | 208563_x_at | 0.3186 |
| Nr2f2 | 209120_at | -0.3312 |
| Mafa | 210288_at | -1.4236 |
| Pax1 | 214401_at | -0.3852 |
| Gsh1 | 216497_at | -1.0376 |
| Wt1 | 216953_s_at | 0.4053 |
| Sox18 | 219568_x_at | -0.6512 |
| Lhx6 | 219884_at | 0.2084 |
| Tbr1 | 220025_at | 1.2469 |
| En1 | 220559_at | 0.8794 |

36_Genes TEZ_Signature

| GENE | | Coeff.BrCa286 |
|---|---|---|
| Gng10 | 201921_at | 1.1993 |
| Sox9 | 202936_s_at | -0.8358 |
| Bcl2 | 203684_s_at | -0.9332 |
| Pura | 204020_at | 0.5856 |
| Lif | 205266_at | 0.2635 |
| Mn1 | 205330_at | -1.2293 |
| Hoxd | 205522_at | -0.24 |
| Bai3 | 205638_at | -1.1858 |
| Gfra2 | 205722_s_at | -2.1487 |
| Six1 | 205817_at | 0.216 |
| Cacna1 | 206399_x_at | -0.7765 |
| Six2 | 206510_at | 0.8464 |
| Smarca2 | 206543_at | 0.2751 |
| Smarca2 | 206544_x_at | -0.4955 |

| | | |
|---|---|---|
| Gad1 | 206669_at | 0.2828 |
| Adcy8 | 206811_at | -0.5813 |
| Hoxa | 206847_s_at | -0.3569 |
| Hoxc | 206858_s_at | 0.572 |
| Pax9 | 207059_at | -1.4496 |
| Zic3 | 207197_at | 1.1007 |
| Hoxb | 208414_s_at | -0.2052 |
| Pou3f3 | 208563_x_at | 0.2542 |
| Hoxb | 209844_at | 1.0774 |
| Slit2 | 209897_s_at | -1.4691 |
| Pcdh7 | 210273_at | 3.1706 |
| Cacna1g | 210380_s_at | -0.3109 |
| Cdh8 | 210518_at | -1.0806 |
| Cacna1g | 211802_x_at | -0.4659 |
| Cnr1 | 213436_at | -0.325 |
| Hoxa | 214639_s_at | 0.6397 |
| Hoxd | 217076_s_at | 0.3247 |
| Rreb1 | 217411_s_at | 0.6625 |
| Arl5 | 218150_at | 4.1618 |
| Chchd7 | 218642_s_at | 0.8752 |
| Tbr1 | 220025_at | 0.7043 |
| A2bp1 | 221217_s_at | 0.9554 |

51_Genes Wound_Signature

| Best_BrCa286 | Coeff.BrCa286 |
|---|---|
| 201277_s_at | 1.1028 |
| 201525_at | -0.1284 |
| 202731_at | -1.1428 |
| 203316_s_at | 1.4747 |
| 203670_at | 0.7619 |
| 203979_at | -0.4433 |
| 204435_at | 1.0825 |
| 204521_at | 1.2116 |
| 204863_s_at | -0.5041 |
| 205027_s_at | -0.5544 |
| 205547_s_at | 0.8929 |
| 205738_s_at | -0.5295 |
| 205822_s_at | -0.5384 |
| 205909_at | 0.1097 |
| 205925_s_at | 0.6811 |
| 207115_x_at | 0.8816 |
| 207323_s_at | -2.1391 |
| 209238_at | 1.2321 |
| 209320_at | -0.6429 |
| 209716_at | -0.1845 |
| 209737_at | 0.5184 |
| 210050_at | 0.9047 |
| 210285_x_at | -0.182 |
| 210986_s_at | -0.0801 |
| 211574_s_at | 0.3902 |

Fig. 35-5

| | |
|---|---|
| 211930_at | 1.2594 |
| 212594_at | 0.2761 |
| 213011_s_at | -0.2674 |
| 213088_s_at | -0.3264 |
| 213092_x_at | 0.6939 |
| 213253_at | 0.3206 |
| 214953_s_at | -0.2175 |
| 217995_at | -0.3279 |
| 218675_at | 0.6931 |
| 201919_at | -3.5616 |
| 201999_s_at | -2.5803 |
| 202590_s_at | -0.4652 |
| 202998_s_at | 0.7878 |
| 207001_x_at | 1.5277 |
| 208070_s_at | 2.2309 |
| 208765_s_at | -1.9033 |
| 208828_at | 1.2965 |
| 208881_x_at | 1.4229 |
| 209034_at | -1.3097 |
| 209183_s_at | -0.1788 |
| 211760_s_at | 1.1584 |
| 212289_at | -1.3928 |
| 216783_at | 1.5336 |
| 217824_at | -0.087 |
| 218739_at | -1.5989 |
| 219314_s_at | -2.2533 |

19_Genes Wound_Signature

| | Coeff.BrCa286 |
|---|---|
| 201919_at | -3.2317 |
| 201999_s_at | -1.9807 |
| 202590_s_at | -1.2269 |
| 202998_s_at | 1.046 |
| 207001_x_at | 1.0968 |
| 208070_s_at | 2.3544 |
| 208765_s_at | -1.6538 |
| 208828_at | 1.5547 |
| 208881_x_at | 1.1116 |
| 209034_at | -1.8662 |
| 211760_s_at | 1.2843 |
| 216783_at | 1.1375 |
| 217824_at | -1.7977 |
| 218739_at | -2.0663 |
| 219314_s_at | -2.3737 |
| 202731_at | -1.1447 |
| 203979_at | -0.6907 |
| 207115_x_at | 1.1838 |
| 207323_s_at | -1.9264 |

Fig. 35-6

Bivalent Chromatin Domain
26_Genes BCD_TF_Signature

| | Coeff.BrCa286 |
|---|---|
| 205646_s_at | 0.7741 |
| 210560_at | -0.6541 |
| 214639_s_at | 0.7464 |
| 209204_at | 0.7737 |
| 209205_s_at | -1.2642 |
| 208468_at | 0.3575 |
| 207147_at | -0.2219 |
| 207914_x_at | -0.9349 |
| 206847_s_at | -0.817 |
| 206848_at | 0.7047 |
| 209844_at | 0.6194 |
| 221278_at | -1.0114 |
| 208414_s_at | -0.9915 |
| 208224_at | -0.6805 |
| 206739_at | -0.6928 |
| 219832_s_at | -0.2817 |
| 206858_s_at | 1.8118 |
| 217076_s_at | 0.7682 |
| 207397_s_at | -0.4929 |
| 220225_at | -0.4145 |
| 208434_at | 1.0664 |
| 215073_s_at | -0.5597 |
| 207059_at | -0.8167 |
| 206511_s_at | 1.9172 |
| 208574_at | -0.4387 |
| 203603_s_at | 0.9182 |

18_CAN_Mutations_Signature

| U133A_18 BrCa286 | | Gene_18 From 30 |
|---|---|---|
| 202502_at | 1.2871 | ACADM |
| 37892_at | 0.7505 | COL11A1 |
| 219454_at | -1.4133 | EGFL6 |
| 206071_s_ | -0.5314 | EPHA3 |
| 206335_at | 1.9253 | GALNS |
| 200643_at | -1.2482 | HDLBP |
| 204302_s_ | -0.72 | KIAA0427 |
| 204155_s_ | 2.4747 | KIAA0999 |
| 213034_at | -2.4061 | KIAA0999 |
| 204009_s_ | 4.075 | KRAS |
| 214352_s_ | -2.0016 | KRAS |
| 205395_s_ | 0.9058 | MRE11A |
| 204325_s_ | 1.9228 | NF1 |
| 211094_s_ | 0.5878 | NF1 |
| 204196_x_ | -1.0697 | PKNOX1 |
| 205879_x_ | -0.9761 | RET |
| 205464_at | 0.6861 | SCNN1B |
| 200883_at | -2.0171 | UQCRC2 |

Fig. 35-7

17_CAN_Mutations_Signature
U133A_17 BrCa286      Gene_17   From 27
221300_at      1.5961 C15orf2
204320_at     -2.5543 COL11A1
37892_at       3.0196 COL11A1
219454_at     -1.396 EGFL6
206335_at      1.59 GALNS
204302_s_    -0.6918 KIAA0427
204155_s_     1.1717 KIAA0999
204009_s_     3.0585 KRAS
205395_s_     0.925 MRE11A
204325_s_     1.5782 NF1
207091_at    -0.7716 P2RX7
204196_x_    -0.9369 PKNOX1
205879_x_    -1.0592 RET
208031_s_     0.6711 RFX2
208039_at    -1.7754 SLC9A2
203509_at    -0.9391 SORL1
200883_at    -1.7327 UQCRC2

20_CAN_Mutations_Signature
U133A_20 BrCa286      Gene_20   From 38
202502_at      1.7101 ACADM
204531_s_     0.7527 BRCA1
221300_at     1.3471 C15orf2
204320_at    -3.2301 COL11A1
37892_at      3.8595 COL11A1
219454_at    -1.1527 EGFL6
206071_s_    -0.6253 EPHA3
206335_at     1.7055 GALNS
204155_s_     3.0112 KIAA0999
213034_at    -2.4022 KIAA0999
204009_s_     2.5968 KRAS
205395_s_     1.233 MRE11A
204325_s_     2.2481 NF1
211094_s_     0.5143 NF1
204196_x_    -0.9991 PKNOX1
205879_x_    -0.8938 RET
204723_at    -0.5892 SCN3B
205464_at     0.9106 SCNN1B
208039_at    -1.6216 SLC9A2
200883_at    -2.6071 UQCRC2

30_CAN_Mutations_Signature
U133A_30 BrCa286      Gene_30
202502_at      1.2634 ACADM
202952_s_     1.1954 ADAM12
203527_s_    -0.8157 APC

Fig. 35-8

| | | |
|---|---|---|
| 204531_s_ | 0.5003 | BRCA1 |
| 37892_at | 0.4585 | COL11A1 |
| 219454_at | -1.0868 | EGFL6 |
| 206071_s_ | -0.5922 | EPHA3 |
| 206335_at | 2.129 | GALNS |
| 207036_x_ | -0.4199 | GRIN2D |
| 200643_at | -1.3861 | HDLBP |
| 204302_s_ | -0.6645 | KIAA0427 |
| 204155_s_ | 2.5925 | KIAA0999 |
| 204157_s_ | -0.5402 | KIAA0999 |
| 213034_at | -2.2362 | KIAA0999 |
| 204009_s_ | 4.0903 | KRAS |
| 214352_s_ | -2.0214 | KRAS |
| 201862_s_ | 1.2101 | LRRFIP1 |
| 201069_at | -0.9366 | MMP2 |
| 205395_s_ | 1.132 | MRE11A |
| 204325_s_ | 2.1266 | NF1 |
| 211094_s_ | 0.5324 | NF1 |
| 207091_at | -0.7242 | P2RX7 |
| 204196_x_ | -0.8055 | PKNOX1 |
| 205879_x_ | -0.7654 | RET |
| 208031_s_ | 0.5489 | RFX2 |
| 204723_at | -0.6138 | SCN3B |
| 205464_at | 0.8713 | SCNN1B |
| 204893_s_ | 0.9516 | SMAD3 |
| 221296_at | -0.5532 | TECTA |
| 200883_at | -2.5445 | UQCRC2 |

27_CAN_Mutations_Signature

| U133A_27 BrCa286 | | Gene_27 |
|---|---|---|
| 202952_s_ | 1.4019 | ADAM12 |
| 219498_s_ | 0.2643 | BCL11A |
| 204531_s_ | 0.6638 | BRCA1 |
| 221300_at | 1.0466 | C15orf2 |
| 204320_at | -3.2109 | COL11A1 |
| 37892_at | 3.4614 | COL11A1 |
| 219454_at | -1.5605 | EGFL6 |
| 206071_s_ | -0.5186 | EPHA3 |
| 206335_at | 2.4155 | GALNS |
| 204302_s_ | -0.6138 | KIAA0427 |
| 204155_s_ | 1.732 | KIAA0999 |
| 204156_at | -0.4723 | KIAA0999 |
| 204009_s_ | 2.6039 | KRAS |
| 200915_x_ | 1.1398 | KTN1 |
| 201862_s_ | 1.0442 | LRRFIP1 |
| 201069_at | -0.7928 | MMP2 |
| 205395_s_ | 1.1373 | MRE11A |
| 204325_s_ | 1.713 | NF1 |
| 207091_at | -0.8076 | P2RX7 |
| 204196_x_ | -1.025 | PKNOX1 |
| 205879_x_ | -0.958 | RET |

Fig. 35-9

| | | |
|---|---|---|
| 208031_s_ | 0.6518 | RFX2 |
| 205464_at | 0.3975 | SCNN1B |
| 201802_at | 0.8553 | SLC29A1 |
| 208039_at | -1.4172 | SLC9A2 |
| 203509_at | -1.1567 | SORL1 |
| 200883_at | -2.1977 | UQCRC2 |

38_CAN_Mutations_Signature

| U133A_38 | Gene_38 | | Coeff.BrCa286 |
|---|---|---|---|
| 200643_at | HDLBP | 200643_at | -0.6084 |
| 200883_at | UQCRC2 | 200883_at | -3.0985 |
| 200915_x_ | KTN1 | 200915_x_ | 1.0098 |
| 201069_at | MMP2 | 201069_at | -0.9204 |
| 201802_at | SLC29A1 | 201802_at | 0.6831 |
| 201862_s_ | LRRFIP1 | 201862_s_ | 1.1762 |
| 202502_at | ACADM | 202502_at | 1.1282 |
| 202952_s_ | ADAM12 | 202952_s_ | 1.4952 |
| 203509_at | SORL1 | 203509_at | -0.2642 |
| 203527_s_ | APC | 203527_s_ | -0.9618 |
| 204009_s_ | KRAS | 204009_s_ | 3.6976 |
| 204155_s_ | KIAA0999 | 204155_s_ | 3.2438 |
| 204156_at | KIAA0999 | 204156_at | -0.403 |
| 204157_s_ | KIAA0999 | 204157_s_ | -0.4489 |
| 204196_x_ | PKNOX1 | 204196_x_ | -0.9139 |
| 204302_s_ | KIAA0427 | 204302_s_ | -0.5995 |
| 204320_at | COL11A1 | 204320_at | -2.8926 |
| 204325_s_ | NF1 | 204325_s_ | 2.221 |
| 204531_s_ | BRCA1 | 204531_s_ | 0.6197 |
| 204723_at | SCN3B | 204723_at | -0.7521 |
| 204893_s_ | SMAD3 | 204893_s_ | 0.7025 |
| 205395_s_ | MRE11A | 205395_s_ | 1.3253 |
| 205464_at | SCNN1B | 205464_at | 0.9067 |
| 205879_x_ | RET | 205879_x_ | -0.8062 |
| 206071_s_ | EPHA3 | 206071_s_ | -0.5798 |
| 206335_at | GALNS | 206335_at | 2.3463 |
| 207036_x_ | GRIN2D | 207036_x_ | -0.3046 |
| 207091_at | P2RX7 | 207091_at | -0.809 |
| 208031_s_ | RFX2 | 208031_s_ | 0.4903 |
| 208039_at | SLC9A2 | 208039_at | -1.0354 |
| 211094_s_ | NF1 | 211094_s_ | 0.5305 |
| 213034_at | KIAA0999 | 213034_at | -2.1093 |
| 214352_s_ | KRAS | 214352_s_ | -1.4327 |
| 219454_at | EGFL6 | 219454_at | -1.3024 |
| 219498_s_ | BCL11A | 219498_s_ | 0.3361 |
| 221296_at | TECTA | 221296_at | -0.4371 |
| 221300_at | C15orf2 | 221300_at | 1.35 |
| 37892_at | COL11A1 | 37892_at | 3.2528 |

35 genes ESC pattern3 signature
AffyProbe Coeff. BrCa286 SYMBOL

Fig. 35-10

| | | |
|---|---|---|
| 200635_s_ | -2.0926 | Ptprf |
| 200644_at | -1.3797 | Marcks |
| 200859_x_ | 1.7715 | Flna |
| 201207_at | -3.0804 | Tnfaip1 |
| 201215_at | 1.1348 | Pls3 |
| 201587_s_ | -4.0919 | Irak1 |
| 201668_x_ | -0.4378 | Marcks |
| 202148_s_ | 3.3676 | Pycr1 |
| 202242_at | 1.2227 | Tm4sf2 |
| 202608_s_ | -0.6243 | Ndst1 |
| 202806_at | 1.9195 | Dbn1 |
| 203269_at | 1.6018 | Nsmaf |
| 203706_s_ | -1.5781 | Fzd7 |
| 203747_at | 1.1729 | Aqp3 |
| 203787_at | -0.9869 | Ssbp2 |
| 204239_s_ | 0.757 | Nnat |
| 204759_at | 0.9679 | Chc1l |
| 204948_s_ | -0.4431 | Fst |
| 205439_at | 0.953 | Gstt2 |
| 205709_s_ | -1.4063 | Cds1 |
| 205723_at | -0.7046 | Cntfr |
| 207131_x_ | 4.1841 | Ggt1 |
| 207345_at | -1.2907 | Fst |
| 208284_x_ | -3.1769 | Ggt1 |
| 209368_at | -0.1914 | Ephx2 |
| 209644_x_ | 0.8904 | Cdkn2a |
| 209772_s_ | 0.4476 | Cd24a |
| 210880_s_ | -0.9745 | Efs |
| 211946_s_ | 0.646 | Bat2 |
| 213201_s_ | 0.4744 | Tnnt1 |
| 216565_x_ | -1.4888 | Ifitm3 |
| 218329_at | 0.8554 | Prdm4 |
| 219568_x_ | -0.5618 | Sox18 |
| 220750_s_ | 1.2391 | Lepre1  GROS1, MGC117314, P3H1 |
| 221866_at | -1.6115 | Mdfi |

56 genes ESC pattern3 signature
Coeff.BrCa286

| | |
|---|---|
| 200619_at | 0.4438 |
| 200635_s_ | -1.9959 |
| 200644_at | -1.7406 |
| 200859_x_ | 1.4797 |
| 201102_s_ | 0.5265 |
| 201207_at | -2.5422 |
| 201215_at | 1.2466 |
| 201587_s_ | -3.8509 |
| 201668_x_ | -0.5002 |
| 202148_s_ | 2.9737 |
| 202242_at | -1.1708 |
| 202531_at | -0.7809 |
| 202608_s_ | -0.7082 |

Fig. 35-11

| | |
|---|---:|
| 202806_at | 1.9549 |
| 202869_at | -0.4785 |
| 203269_at | 2.2866 |
| 203287_at | 0.0402 |
| 203706_s_ | -1.6891 |
| 203747_at | 0.8251 |
| 203787_at | -0.8356 |
| 203973_s_ | -0.13 |
| 204239_s_ | 0.7278 |
| 204759_at | 1.138 |
| 204948_s_ | -0.8105 |
| 205439_at | 0.7343 |
| 205552_s_ | 0.5615 |
| 205709_s_ | -1.4932 |
| 205710_at | -0.0069 |
| 205723_at | -0.8657 |
| 207039_at | -0.1683 |
| 207131_x_ | 3.7275 |
| 207345_at | -0.8511 |
| 207521_s_ | -0.1571 |
| 207558_s_ | 0.2774 |
| 208284_x_ | -2.6438 |
| 208711_s_ | -0.2376 |
| 208712_at | 0.7566 |
| 209220_at | 0.3599 |
| 209368_at | -0.4372 |
| 209644_x_ | 1.4036 |
| 209772_s_ | 0.7769 |
| 210880_s_ | -0.8806 |
| 211703_s_ | 0.4235 |
| 211946_s_ | 1.528 |
| 213201_s_ | 0.3056 |
| 214435_x_ | -0.1301 |
| 214712_at | -0.2494 |
| 216565_x_ | -1.5276 |
| 218329_at | 1.3454 |
| 219568_x_ | -0.7731 |
| 219735_s_ | 0.5608 |
| 219966_x_ | 0.1222 |
| 220750_s_ | 1.4515 |
| 221866_at | -1.7243 |
| 266_s_at | -0.6114 |
| 39249_at | 0.4093 |

Fig. 35-12

Table 6. CTOP gene expression signatures for lung cancer
20_Genes EED_ESC_Signature

| Log10 | Coeff.LungCa91_log 10cox | RMA | Coeff.LungCa91_20_EED_ESC |
|---|---|---|---|
| 200953_s_ | -3.4753 | 200953_s_ | -0.1738 |
| 201901_s_ | 15.432 | 201901_s_ | 0.7683 |
| 202936_s_ | 2.4782 | 202936_s_ | 0.1189 |
| 203131_at | 6.7438 | 203131_at | 0.3616 |
| 203358_s_ | -2.2988 | 203358_s_ | -0.1611 |
| 205051_s_ | -3.3541 | 205051_s_ | -0.2163 |
| 205646_s_ | -10.7446 | 205646_s_ | -0.6573 |
| 206061_s_ | -1.4025 | 206061_s_ | -0.1475 |
| 206140_at | 2.9812 | 206140_at | 0.2603 |
| 206176_at | -2.394 | 206176_at | -0.1064 |
| 206858_s_ | 0.5956 | 206858_s_ | 0.0441 |
| 207059_at | 7.1331 | 207059_at | 0.443 |
| 207336_at | -30.686 | 207336_at | -2.9335 |
| 207612_at | 4.2563 | 207612_at | 0.2396 |
| 207726_at | 10.9799 | 207726_at | 0.7819 |
| 208006_at | 7.5936 | 208006_at | 0.6372 |
| 210656_at | 4.4204 | 210656_at | 0.4849 |
| 213494_s_ | -24.8241 | 213494_s_ | -1.6183 |
| 218252_at | -0.4717 | 218252_at | -0.0636 |
| 219755_at | -9.8559 | 219755_at | -0.5786 |

Survival of 91 lung cancer patients with distinct expression profiles of the 20-gene EED/ESC signature $P = 0.0002$ 41_Genes NANOG_Sox2_Oct4_Signature

| Log10 | Coeff.LungCa91 | RMA | Coeff.RMA_LungCa91 |
|---|---|---|---|
| 200099_s_ | 32.8415 | 200099_s_ | 1.4047 |
| 201292_at | -13.1206 | 201292_at | -0.967 |
| 201456_s_ | 9.8948 | 201456_s_ | 0.644 |
| 201463_s_ | 15.9534 | 201463_s_ | 0.7291 |
| 201498_at | -25.9862 | 201498_at | -1.4283 |
| 201522_x_ | -13.1076 | 201522_x_ | -0.8301 |
| 201531_at | 22.3469 | 201531_at | 0.9159 |
| 201921_at | -5.291 | 201921_at | -0.3868 |
| 202037_s_ | 7.2357 | 202037_s_ | 0.4075 |
| 202202_s_ | 2.5435 | 202202_s_ | 0.2283 |
| 203562_at | -14.0444 | 203562_at | -0.956 |
| 203755_at | 22.2016 | 203755_at | 1.3799 |
| 204101_at | -2.0284 | 204101_at | 0.5534 |
| 204390_at | 24.2723 | 204390_at | 2.3452 |
| 204702_s_ | 0.2286 | 204702_s_ | 0.0081 |
| 205741_s_ | -8.9197 | 205741_s_ | -0.7882 |
| 206208_at | 2.1184 | 206208_at | 0.3196 |
| 206286_s_ | -35.3483 | 206286_s_ | -2.4243 |
| 206332_s_ | 97.6612 | 206332_s_ | 5.2821 |
| 206472_s_ | 9.9114 | 206472_s_ | 0.7326 |
| 206748_s_ | 24.4308 | 206748_s_ | 1.6787 |
| 207197_at | -11.6269 | 207197_at | -1.4425 |
| 208234_x_ | -7.3157 | 208234_x_ | -0.1109 |
| 208966_x_ | -100.309 | 208966_x_ | -5.49 |
| 208991_at | -31.7876 | 208991_at | -1.2829 |
| 209147_s_ | -30.653 | 209147_s_ | -1.4572 |
| 210946_at | 18.5774 | 210946_at | 0.8934 |
| 211401_s_ | -41.1166 | 211401_s_ | -3.1266 |
| 212916_at | 3.9668 | 212916_at | 0.2071 |
| 215538_at | 21.0379 | 215538_at | 1.5107 |
| 216065_at | -8.3332 | 216065_at | -0.9852 |
| 217370_x_ | -9.6031 | 217370_x_ | -0.5745 |
| 217940_s_ | 31.6788 | 217940_s_ | 1.535 |
| 218576_s_ | -38.8332 | 218576_s_ | -2.179 |
| 218614_at | -9.0352 | 218614_at | -0.5856 |
| 219392_x_ | 10.3794 | 219392_x_ | 0.7916 |
| 219494_at | 13.6747 | 219494_at | 0.9674 |
| 220184_at | 20.2124 | 220184_at | 1.4763 |
| 221721_s_ | -19.1942 | 221721_s_ | -2.1373 |
| 221722_x_ | 4.8095 | 221722_x_ | -0.0129 |
| 36920_at | -4.5077 | 36920_at | -0.8804 |

Fig. 36-2

Survival of 91 lung cancer patients with distinct expression profiles of the 41-gene Nanog/Oct4/Sox2 signature — Bottom 50%
— Top 50%
P < 0.0001

25_Genes Suz12_NoPOLII_Signature

| Probe | Coeff.25Suz12NoPOLII_RMA_LungCa91 | Probe | Coeff.25Suz12NoPOLII_Log10 |
|---|---|---|---|
| 202037_s_ | -0.1122 | 202037_s_ | -1.1984 |
| 203477_at | 0.1694 | 203477_at | 2.7848 |
| 203695_s_ | 0.0042 | 203695_s_ | -1.604 |
| 203888_at | -0.0736 | 203888_at | -0.6411 |
| 204279_at | 0.0478 | 204279_at | 0.9518 |
| 204527_at | -0.0606 | 204527_at | -0.1244 |
| 205330_at | -0.0696 | 205330_at | -0.1704 |
| 205590_at | -0.2697 | 205590_at | -3.4879 |
| 205691_at | -0.567 | 205691_at | -5.5439 |
| 205923_at | -0.3127 | 205923_at | -1.2455 |
| 206893_at | 0.5954 | 206893_at | 3.4607 |
| 207890_s_ | -1.4405 | 207890_s_ | -21.4444 |
| 208206_s_ | 1.0127 | 208206_s_ | 12.7845 |
| 209602_s_ | 0.2624 | 209602_s_ | 3.7264 |
| 210002_at | 0.2438 | 210002_at | 3.148 |
| 210273_at | 0.3917 | 210273_at | 6.6809 |
| 211529_x_ | -0.5798 | 211529_x_ | -15.0066 |
| 214451_at | 1.4233 | 214451_at | 12.2799 |
| 218974_at | -0.0574 | 218974_at | -2.2739 |
| 219537_x_ | 0.3639 | 219537_x_ | 5.1016 |
| 220108_at | -0.105 | 220108_at | -1.3876 |
| 220406_at | 0.592 | 220406_at | 4.3304 |
| 220407_s_ | 0.3991 | 220407_s_ | 5.1581 |
| 221029_s_ | 0.4778 | 221029_s_ | 6.6218 |
| 221234_s_ | -0.8282 | 221234_s_ | -10.1445 |

Survival of 91 lung cancer patients with distinct expression profiles of the 25-gene Suz12/RNAPII (-) signature 20_Genes Suz12_RNAPII_Bound_Signature

| Probe | Coeff.20Suz12POLII_RMA_LungCa91 | Probe | Coeff.20Suz12POLIIboundLog10 |
|---|---|---|---|
| 211919_s_ | -0.171 | 211919_s_ | -4.455 |
| 212427_at | -0.3301 | 212427_at | -3.0585 |
| 215723_s_ | -0.3762 | 215723_s_ | -3.2707 |
| 205203_at | -0.1604 | 205203_at | -5.4014 |
| 204114_at | 0.6662 | 204114_at | 8.1058 |
| 202672_s_ | 0.0389 | 202672_s_ | 0.7665 |
| 204302_s_ | -1.8191 | 204302_s_ | -29.9654 |
| 204014_at | -0.0523 | 204014_at | -0.784 |
| 207390_s_ | 0.5696 | 207390_s_ | 8.947 |
| 207574_s_ | 0.7019 | 207574_s_ | 9.0523 |
| 209304_x_ | -0.4334 | 209304_x_ | -2.7547 |
| 206099_at | -1.5096 | 206099_at | -20.136 |
| 201466_s_ | -0.5765 | 201466_s_ | -9.9752 |
| 201473_at | 0.1651 | 201473_at | 3.6196 |
| 205656_at | 0.1793 | 205656_at | 3.5035 |
| 201150_s_ | 0.0279 | 201150_s_ | 0.5462 |
| 201373_at | 0.1184 | 201373_at | -0.207 |
| 205266_at | -0.6072 | 205266_at | -10.7432 |
| 202936_s_ | 0.1472 | 202936_s_ | 3.3705 |
| 207172_s_ | -0.2719 | 207172_s_ | -3.7381 |

Survival of 91 lung cancer patients with distinct expression profiles of the 20-gene Suz12/RNAPII (+) signature 30_Gene PcG_TF_Signature

| Coeff.30PcG_TF_RMA_LungCa91 | | LungCa91 Coeff.30_PcGTF_Log10 | |
|---|---|---|---|
| 200067_x_ | -0.372 | 200067_x_ | -5.4256 |
| 202672_s_ | 0.4472 | 202672_s_ | 7.3263 |
| 202936_s_ | 0.2001 | 202936_s_ | 3.6972 |
| 203603_s_ | 1.2822 | 203603_s_ | 14.6123 |
| 203752_s_ | -0.7113 | 203752_s_ | -18.9013 |
| 204039_at | 0.0026 | 204039_at | 0.6939 |
| 205459_s_ | 0.2979 | 205459_s_ | 3.3022 |
| 205460_at | 0.6471 | 205460_at | 5.9381 |
| 205471_s_ | -1.0642 | 205471_s_ | -13.3029 |
| 205817_at | -0.5265 | 205817_at | -9.9447 |
| 206115_at | -0.7414 | 206115_at | -10.264 |
| 206377_at | -0.452 | 206377_at | -7.5659 |
| 206837_at | -0.2269 | 206837_at | -4.3209 |
| 206858_s_ | -0.1631 | 206858_s_ | -3.237 |
| 207059_at | 0.3089 | 207059_at | 5.9681 |
| 207147_at | 2.7993 | 207147_at | 23.5478 |
| 207250_at | 0.1535 | 207250_at | 5.642 |
| 207690_at | 2.6833 | 207690_at | 33.5702 |
| 208414_s_ | 0.0516 | 208414_s_ | 2.0088 |
| 208554_at | -0.9812 | 208554_at | -9.5233 |
| 208563_x_ | -1.2833 | 208563_x_ | -13.4403 |
| 209120_at | 0.6227 | 209120_at | 10.9605 |
| 210288_at | -3.4201 | 210288_at | -43.397 |
| 214401_at | 0.4906 | 214401_at | 8.257 |
| 216497_at | 2.4887 | 216497_at | 24.5687 |
| 216953_s_ | -1.4904 | 216953_s_ | -13.4531 |

| | | | |
|---|---|---|---|
| 219568_x_ | 0.3779 | 219568_x_ | 3.1813 |
| 219884_at | -0.3938 | 219884_at | -5.0909 |
| 220025_at | 3.0713 | 220025_at | 30.1056 |
| 220559_at | -0.2841 | 220559_at | -2.7459 |

Survival of 91 lung cancer patients with distinct expression profiles of the 30-gene PcG/TF signature 36_Genes TEZ_Signature

| | Coeff.LungCa91_36TEZ | | Coeff.Log10_36_TEZ_LungCa191 |
|---|---|---|---|
| 201921_at | -0.0843 | 201921_at | -2.2419 |
| 202936_s_ | -0.342 | 202936_s_ | -5.5901 |
| 203684_s_ | -2.3148 | 203684_s_ | -30.2836 |
| 204020_at | 0.1288 | 204020_at | 4.944 |
| 205266_at | 0.97 | 205266_at | 16.2248 |
| 205330_at | 0.3109 | 205330_at | 5.5462 |
| 205522_at | 0.4398 | 205522_at | 6.0642 |
| 205638_at | -0.8636 | 205638_at | -7.2722 |
| 205722_s_ | 0.7804 | 205722_s_ | 11.7295 |
| 205817_at | -2.1759 | 205817_at | -31.3344 |
| 206399_x_ | 1.2752 | 206399_x_ | 14.3884 |
| 206510_at | -0.2873 | 206510_at | -5.4443 |
| 206543_at | -4.7577 | 206543_at | -39.0773 |
| 206544_x_ | 0.1363 | 206544_x_ | 2.4925 |
| 206669_at | 0.7889 | 206669_at | 10.8197 |
| 206811_at | -0.0947 | 206811_at | 0.2474 |
| 206847_s_ | -1.7438 | 206847_s_ | -17.6178 |
| 206858_s_ | -0.4431 | 206858_s_ | -7.0474 |
| 207059_at | 1.0878 | 207059_at | 15.3444 |
| 207197_at | -0.8984 | 207197_at | -4.1445 |
| 208414_s_ | -3.0264 | 208414_s_ | -52.2391 |
| 208563_x_ | 0.7767 | 208563_x_ | 5.4429 |

| | | | |
|---|---|---|---|
| 209844_at | 0.6203 | 209844_at | 2.9155 |
| 209897_s_ | -0.8347 | 209897_s_ | -13.1221 |
| 210273_at | 0.6454 | 210273_at | 8.4311 |
| 210380_s_ | 6.4444 | 210380_s_ | 77.8432 |
| 210518_at | 1.7758 | 210518_at | 20.3788 |
| 211802_x_ | -9.1736 | 211802_x_ | -134.917 |
| 213436_at | -2.604 | 213436_at | -22.0041 |
| 214639_s_ | 0.1734 | 214639_s_ | 2.9357 |
| 217076_s_ | 1.7153 | 217076_s_ | 12.6534 |
| 217411_s_ | -4.4753 | 217411_s_ | -53.4754 |
| 218150_at | -0.4941 | 218150_at | -12.2361 |
| 218642_s_ | -0.3585 | 218642_s_ | -4.9839 |
| 220025_at | 3.9445 | 220025_at | 32.6065 |
| 221217_s_ | -2.8638 | 221217_s_ | -26.7501 |

Survival of 91 lung cancer patients with distinct expression profiles of the 36-gene TEZ signature — Bottom 50%
— Top 50%
$P < 0.0001$ 19_Genes Wound_Signature
Coeff.19wound_RMA_LungCa91

| | |
|---|---|
| 201919_at | -0.3137 |
| 201999_s_ | 0.7085 |
| 202590_s_ | -0.3855 |
| 202998_s_ | 0.7668 |
| 207001_x_ | -1.0612 |
| 208070_s_ | 0.4876 |
| 208765_s_ | -0.107 |
| 208828_at | -0.1693 |
| 208881_x_ | -0.417 |
| 209034_at | -0.5469 |
| 211760_s_ | -0.3153 |
| 216783_at | -0.1818 |

| | |
|---|---|
| 217824_at | -0.6206 |
| 218739_at | -1.095 |
| 219314_s_ | -0.4551 |
| 202731_at | 0.67 |
| 203979_at | 0.6092 |
| 207115_x_ | 1.3414 |
| 207323_s_ | 0.0002 |

Survival of 91 lung cancer patients with distinct expression profiles of the 19-gene wound signature Bivalent Chromatin Domain
26_Genes BCD_TF_Signature

| Coeff.RMA_26BCD_TF_LungCa91 | | Coeff.26BCD_TF_Log10 | |
|---|---|---|---|
| 205646_s_ | 0.0597 | 205646_s_ | -0.1496 |
| 210560_at | -0.2414 | 210560_at | 2.2004 |
| 214639_s_ | -0.2373 | 214639_s_ | -2.8544 |
| 209204_at | 0.1726 | 209204_at | -1.2963 |
| 209205_s_ | -0.3053 | 209205_s_ | -2.4842 |
| 208468_at | -0.1574 | 208468_at | -2.2018 |
| 207147_at | 1.401 | 207147_at | 12.8453 |
| 207914_x_ | 0.3879 | 207914_x_ | 6.3229 |
| 206847_s_ | -0.6754 | 206847_s_ | -6.7412 |
| 206848_at | -0.0481 | 206848_at | -0.15 |
| 209844_at | 0.8464 | 209844_at | 8.6682 |
| 221278_at | -0.4801 | 221278_at | -4.4814 |
| 208414_s_ | 0.9052 | 208414_s_ | 10.23 |
| 208224_at | -2.9603 | 208224_at | -37.0692 |
| 206739_at | -0.0442 | 206739_at | -2.5922 |
| 219832_s_ | 0.9164 | 219832_s_ | 15.1048 |
| 206858_s_ | 0.0714 | 206858_s_ | 0.9205 |

| | |
|---|---|
| 217076_s_ | -0.2981 |
| 207397_s_ | -0.9523 |
| 220225_at | 0.1008 |
| 208434_at | 0.3945 |
| 215073_s_ | 0.148 |
| 207059_at | 0.8198 |
| 206511_s_ | 0.4062 |
| 208574_at | 1.0647 |
| 203603_s_ | 0.6092 |

| | |
|---|---|
| 217076_s_ | -1.4769 |
| 207397_s_ | -9.3026 |
| 220225_at | 2.3349 |
| 208434_at | 5.1324 |
| 215073_s_ | 2.7161 |
| 207059_at | 10.6936 |
| 206511_s_ | 5.2951 |
| 208574_at | 11.7734 |
| 203603_s_ | 5.9587 |

Survival of 91 lung cancer patients with distinct expression profiles of the 26-gene BCD/TF signature 42-gene CAN mutations signature

| | Coeff.LungCa91 |
|---|---|
| 200643_at | -1.6285 |
| 200915_x_ | 0.0163 |
| 201141_at | -0.5335 |
| 201802_at | 2.1928 |
| 202203_s_ | 0.9054 |
| 202204_s_ | -3.9588 |
| 202806_at | 0.6381 |
| 203557_s_ | 1.5909 |
| 203867_s_ | 1.5071 |
| 203911_at | -0.2776 |
| 204136_at | 1.4026 |
| 204155_s_ | 1.862 |
| 204343_at | 0.1486 |
| 204608_at | 0.4373 |
| 204977_at | 0.1875 |
| 205712_at | 0.5536 |

| | |
|---|---|
| 205879_x_ | -2.2225 |
| 205951_at | 1.7014 |
| 206071_s_ | -7.7729 |
| 206241_at | 1.3764 |
| 206317_s_ | 1.5157 |
| 206380_s_ | -0.4099 |
| 206657_s_ | -0.4941 |
| 206775_at | 5.8316 |
| 206836_at | -1.4866 |
| 206927_s_ | 1.5009 |
| 207036_x_ | 0.7731 |
| 207091_at | 0.2287 |
| 207112_s_ | -1.3589 |
| 207334_s_ | 0.2644 |
| 207549_x_ | -0.8002 |
| 208804_s_ | -0.0226 |
| 210345_s_ | .3.5943 |
| 210913_at | -2.3303 |
| 211095_at | 3.9135 |
| 211421_s_ | 1.7699 |
| 214352_s_ | 0.1992 |
| 215292_s_ | 0.9767 |
| 219497_s_ | 1.8124 |
| 219498_s_ | -4.0421 |
| 220062_s_ | -0.592 |
| 220492_s_ | -3.4079 |

Survival of 91 lung cancer patients with distinct expression profiles of the 42-gene CAN mutations signature 211930_at    0.2113
213092_x_   0.4802
217995_at  -0.4055
218675_at  -0.1536
207001_x_  -1.4574
209034_at   0.3785
217824_at  -0.8104
218739_at  -1.1615

Survival of 91 lung cancer patients with distinct expression profiles of the 18-gene "wound" signature --*-- Good prognosis
—*— Poor prognosis
—+— Worst prognosis $P < 0.0001$

| 35pattern3 | Coeff.LungCa91 | | Coeff.35pattern3_Log10 |
|---|---|---|---|
| 200635_s_ | 0.4984 | 200635_s_ | 14.8424 |
| 200644_at | -0.0984 | 200644_at | -0.3271 |
| 200859_x_ | 1.1189 | 200859_x_ | 25.0357 |
| 201207_at | 0.621 | 201207_at | 7.3065 |
| 201215_at | -0.5487 | 201215_at | -17.4317 |
| 201587_s_ | -1.3634 | 201587_s_ | -34.5052 |
| 201668_x_ | -1.1516 | 201668_x_ | -19.9338 |
| 202148_s_ | 0.0493 | 202148_s_ | -1.8415 |
| 202242_at | -0.3998 | 202242_at | -6.9997 |
| 202608_s_ | 2.3671 | 202608_s_ | 27.4071 |
| 202806_at | -0.2097 | 202806_at | -5.2605 |
| 203269_at | 1.5102 | 203269_at | 28.2159 |
| 203706_s_ | 0.1844 | 203706_s_ | 3.9662 |
| 203747_at | 0.2834 | 203747_at | 6.2866 |
| 203787_at | -0.4386 | 203787_at | -5.7484 |
| 204239_s_ | -0.7894 | 204239_s_ | -8.2447 |
| 204759_at | -0.9478 | 204759_at | -13.8381 |

| | | | |
|---|---|---|---|
| 204948_s_ | -0.5616 | 204948_s_ | -5.5427 |
| 205439_at | -0.3635 | 205439_at | -2.8386 |
| 205709_s_ | -0.1461 | 205709_s_ | -1.727 |
| 205723_at | -0.6675 | 205723_at | -7.628 |
| 207131_x_ | -0.7519 | 207131_x_ | -6.7172 |
| 207345_at | -0.3248 | 207345_at | -10.2961 |
| 208284_x_ | 0.1189 | 208284_x_ | -3.1357 |
| 209368_at | -0.9308 | 209368_at | -9.9188 |
| 209644_x_ | 0.2708 | 209644_x_ | 6.0016 |
| 209772_s_ | 0.2388 | 209772_s_ | 2.7124 |
| 210880_s_ | -0.3793 | 210880_s_ | -10.0583 |
| 211946_s_ | -0.6214 | 211946_s_ | -13.7541 |
| 213201_s_ | 0.27 | 213201_s_ | 4.1525 |
| 216565_x_ | -1.1739 | 216565_x_ | -25.4107 |
| 218329_at | 0.7644 | 218329_at | 16.1678 |
| 219568_x_ | 1.0013 | 219568_x_ | 11.3815 |
| 220750_s_ | 0.8583 | 220750_s_ | 13.0992 |
| 221866_at | -0.321 | 221866_at | -13.4007 |

Fig. 36-14

Table7. CTOP gene expression signatures for ovarian cancer
50 genes CAN mutations signature
Gene_128 U133A_12 Coeff.OvaCa133

| Gene | Probe | Coeff |
|---|---|---|
| HDLBP | 200643_at | -1.2 |
| GNAS | 200780_x_ | -2.0963 |
| UQCRC2 | 200883_at | -0.3422 |
| LRRFIP1 | 201862_s_ | -0.073 |
| MTMR3 | 202197_at | -0.4202 |
| AMFR | 202204_s_ | -0.0296 |
| DBN1 | 202806_at | 1.2232 |
| ADAM12 | 202952_s_ | -0.8456 |
| APC | 203527_s_ | 0.6925 |
| FLJ10458 | 203867_s_ | 0.5307 |
| RAP1GA1 | 203911_at | 1.0279 |
| KRAS | 204009_s_ | 1.0766 |
| KRAS | 204010_s_ | -3.2079 |
| KIAA0999 | 204155_s_ | -1.5895 |
| KIAA0999 | 204156_at | 2.0628 |
| PKNOX1 | 204196_x_ | 1.8339 |
| HDAC4 | 204225_at | -0.1483 |
| KIAA0427 | 204302_s_ | 5.648 |
| COL11A1 | 204320_at | 0.7124 |
| NF1 | 204323_x_ | 0.1514 |
| BRCA1 | 204531_s_ | 0.4278 |
| ADAM12 | 204943_at | 2.7553 |
| DNASE1L | 205554_s_ | 1.008 |
| LRP2 | 205710_at | -1.6498 |
| RET | 205879_x_ | -0.829 |
| EPHA3 | 206070_s_ | 1.4191 |
| EPHA3 | 206071_s_ | -5.2929 |
| MKRN3 | 206585_at | -0.5731 |
| CUBN | 206775_at | 1.4131 |
| ICAM5 | 206906_at | 0.6811 |
| GAB1 | 207112_s_ | -2.7209 |
| TGFBR2 | 207334_s_ | 1.034 |
| ERCC6 | 207347_at | -1.989 |
| RFX2 | 208031_s_ | -3.612 |
| SLC9A2 | 208039_at | 0.8692 |
| THBS3 | 209561_at | -0.2702 |
| SP110 | 209762_x_ | -0.3733 |
| CDH20 | 210913_at | -3.026 |
| NF1 | 211095_at | 2.2352 |
| EPHA3 | 211164_at | -4.51 |
| TP53 | 211300_s_ | 0.3501 |
| BRCA1 | 211851_x_ | 2.7203 |
| KIAA0934 | 212503_s_ | -0.2093 |
| COL7A1 | 217312_s_ | 1.2264 |
| SIX4 | 217661_x_ | 1.576 |
| APC2 | 218555_at | -1.2916 |
| MAP3K6 | 219278_at | 0.4023 |
| TECTA | 221296_at | 1.132 |
| C15orf2 | 221300_at | 4.5083 |

Fig. 37-1

COL11A1  37892_at    -0.2113

25-gene CAN mutations signature
Gene_128 U133A_12 Coeff.OvaCa133
HDLBP    200643_at   -1.4248
GNAS     200780_x_   -1.8047
DBN1     202806_at    1.035
ADAM12   202952_s_   -0.4179
RAP1GA1  203911_at    1.0064
KRAS     204009_s_    0.9987
KRAS     204010_s_   -3.0238
KIAA0999 204156_at    0.8732
KIAA0427 204302_s_    4.2489
ADAM12   204943_at    2.1794
LRP2     205710_at   -1.0405
EPHA3    206070_s_    1.4343
EPHA3    206071_s_   -3.9055
CUBN     206775_at    2.2893
ICAM5    206906_at    1.3975
GAB1     207112_s_   -2.641
TGFBR2   207334_s_    1.3335
ERCC6    207347_at   -2.1171
RFX2     208031_s_   -3.3056
CDH20    210913_at   -2.8469
BRCA1    211851_x_    3.0348
COL7A1   217312_s_    1.2426
SIX4     217661_x-    2.149
APC2     218555_at   -0.748
C15orf2  221300_at    3.9102

51 genes Wound signature
            Coeff.OvaCa133
201277_s_   -0.5399
201525_at   -0.8815
202731_at   -0.1632
203316_s_    0.7943
203670_at    0.9565
203979_at   -1.5038
204435_at    1.3045
204521_at   -0.5146
204863_s_    0.5412
205027_s_   -0.0633
205547_s_    0.3856
205738_s_   -0.7695
205822_s_    0.4066
205909_at   -0.568
205925_s_    2.5628
207115_x_    0.4653
207323_s_    2.2601
209238_at    0.3044

Fig. 37-2

| | | |
|---|---|---|
| 209320_at | -0.6222 | |
| 209716_at | 0.5874 | |
| 209737_at | -0.9785 | |
| 210050_at | -0.7104 | |
| 210285_x_ | 0.0431 | |
| 210986_s_ | -0.0737 | |
| 211574_s_ | -0.11 | |
| 211930_at | -0.0015 | |
| 212594_at | 0.0073 | |
| 213011_s_ | -0.8662 | |
| 213088_s_ | -0.0878 | |
| 213092_x_ | 0.2805 | |
| 213253_at | -1.2739 | |
| 214953_s_ | 0.5644 | |
| 217995_at | -0.6497 | |
| 218675_at | -0.2845 | |
| 201919_at | 0.5403 | |
| 201999_s_ | 0.4747 | |
| 202590_s- | 2.6075 | |
| 202998_s_ | -0.0308 | |
| 207001_x_ | -0.7694 | |
| 208070_s_ | -1.1442 | |
| 208765_s_ | 0.1287 | |
| 208828_at | -0.0655 | |
| 208881_x_ | -0.3183 | |
| 209034_at | -1.2599 | |
| 209183_s_ | 1.5408 | |
| 211760_s_ | 1.4771 | |
| 212289_at | -1.3015 | |
| 216783_at | 1.988 | |
| 217824_at | -0.3132 | |
| 218739_at | -2.2733 | |
| 219314_s_ | 0.7701 | |

11 genes BMI1 signature    RMA Coeff.OvaCa133

| | | |
|---|---|---|
| Gbx2 | 210560_at | 0.4004 |
| KI67 | 212022_s_ | -0.7457 |
| Cyclin B1 | 214710_s_ | 0.6989 |
| BUB1 | 216277_at | -1.1926 |
| HEC | 204162_at | -0.1735 |
| KIAA1063 | 216964_at | 1.9494 |
| HCFC1 | 202473_x_ | 1.0812 |
| RNF2 | 205215_at | -0.5817 |
| ANK3 | 209442_x_ | -0.2472 |
| FGFR2 | 203638_s_ | 0.4818 |
| FGFR2 | 208228_s_ | -0.1813 |
| CES1 | 209616_s_ | -0.176 |

11 genes BMI1 signature    Log10

Fig. 37-3

|  |  | Coeff.OvaCa133 |
|---|---|---|
| Gbx2 | 210560_at | 4.975 |
| KI67 | 212022_s_ | -11.4517 |
| Cyclin B1 | 214710_s_ | 11.3134 |
| BUB1 | 216277_at | -12.9451 |
| HEC | 204162_at | -2.1857 |
| KIAA1063 | 216964_at | 23.6975 |
| HCFC1 | 202473_x_ | 16.5245 |
| RNF2 | 205215_at | -6.8201 |
| ANK3 | 209442_x_ | -4.1185 |
| FGFR2 | 203638_s_ | 7.8887 |
| FGFR2 | 208228_s_ | -2.1974 |
| CES1 | 209616_s_ | -2.9093 |

41 genes NanogSox2Oct4

| | Coeff.OvaCa133 | | OvaCa133Log10 | Coeff.41NanOct4Sox2 |
|---|---|---|---|---|
| 200099_s_ | -0.2138 | | 200099_s_at | -4.6789 |
| 201292_at | -0.3739 | | 201292_at | -5.3654 |
| 201456_s_ | -0.0518 | | 201456_s_at | -2.5759 |
| 201463_s_ | -0.8017 | | 201463_s_at | -16.0833 |
| 201498_at | -0.609 | | 201498_at | -10.2117 |
| 201522_x_ | -0.0241 | | 201522_x_at | -0.7134 |
| 201531_at | 0.391 | | 201531_at | 8.9138 |
| 201921_at | -0.1848 | | 201921_at | -0.1385 |
| 202037_s_ | -0.4652 | | 202037_s_at | -6.3856 |
| 202202_s_ | -0.0313 | | 202202_s_at | -2.7149 |
| 203562_at | 0.914 | | 203562_at | 11.5644 |
| 203755_at | 1.0754 | | 203755_at | 17.3325 |
| 204101_at | 1.3043 | | 204101_at | 11.6967 |
| 204390_at | 2.2054 | | 204390_at | 25.5936 |
| 204702_s_ | 0.0596 | | 204702_s_at | 2.9505 |
| 205741_s_ | 0.0149 | | 205741_s_at | 0.5965 |
| 206208_at | 2.2776 | | 206208_at | 29.5515 |
| 206286_s_ | 0.7139 | | 206286_s_at | 8.404 |
| 206332_s_ | -0.7135 | | 206332_s_at | -9.4794 |
| 206472_s_ | -0.3812 | | 206472_s_at | -4.0585 |
| 206748_s_ | -0.8282 | | 206748_s_at | -12.797 |
| 207197_at | -0.8873 | | 207197_at | -12.26 |
| 208234_x_ | 1.6853 | | 208234_x_at | 28.6909 |
| 208966_x_ | 0.3518 | | 208966_x_at | 3.5563 |
| 208991_at | 0.7131 | | 208991_at | 15.855 |
| 209147_s_ | 0.1765 | | 209147_s_at | 4.2789 |
| 210946_at | -0.7124 | | 210946_at | -9.1628 |
| 211401_s_ | -0.318 | | 211401_s_at | -5.195 |
| 212916_at | -0.6257 | | 212916_at | -10.5513 |
| 215538_at | -1.5233 | | 215538_at | -17.6569 |
| 216065_at | -2.2165 | | 216065_at | -24.7141 |
| 217370_x_ | -0.2956 | | 217370_x_at | -5.6695 |
| 217940_s_ | 0.5979 | | 217940_s_at | 11.4505 |
| 218576_s_ | 1.9102 | | 218576_s_at | 27.8012 |
| 218614_at | 0.1157 | | 218614_at | 2.2713 |

Fig. 37-4

| | | | |
|---|---|---|---|
| 219392_x_ | -0.4529 | 219392_x_at | -10.3669 |
| 219494_at | -1.0609 | 219494_at | -13.4546 |
| 220184_at | 0.5657 | 220184_at | 8.1439 |
| 221721_s_ | 0.6276 | 221721_s_at | 4.1312 |
| 221722_x_ | 0.2286 | 221722_x_at | 3.9234 |
| 36920_at | -0.988 | 36920_at | -8.0338 |

36 genes TEZ signature

| | Coeff.OvaCa133 | | OvaCa133Log10Coeff.36TEZ |
|---|---|---|---|
| 201921_at | 0.1995 | 201921_at | 3.6359 |
| 202936_s_ | 0.1614 | 202936_s_at | 3.8468 |
| 203684_s_ | 0.46 | 203684_s_at | 6.0541 |
| 204020_at | -0.0506 | 204020_at | -0.5503 |
| 205266_at | 0.0506 | 205266_at | 0.6431 |
| 205330_at | 0.04 | 205330_at | 0.8339 |
| 205522_at | -0.0432 | 205522_at | -0.0653 |
| 205638_at | 0.758 | 205638_at | 4.9942 |
| 205722_s_ | -0.0666 | 205722_s_at | -1.0049 |
| 205817_at | -0.3516 | 205817_at | -4.6659 |
| 206399_x_ | 1.3081 | 206399_x_at | 17.0437 |
| 206510_at | 0.413 | 206510_at | 4.6025 |
| 206543_at | -0.0518 | 206543_at | -2.3447 |
| 206544_x_ | -0.7222 | 206544_x_at | -11.6962 |
| 206669_at | -0.455 | 206669_at | -5.1863 |
| 206811_at | 0.0453 | 206811_at | 0.7261 |
| 206847_s_ | -1.8319 | 206847_s_at | -19.2425 |
| 206858_s_ | -0.036 | 206858_s_at | -0.7329 |
| 207059_at | 0.1048 | 207059_at | 2.402 |
| 207197_at | -0.3133 | 207197_at | -3.7882 |
| 208414_s_ | 0.4086 | 208414_s_at | 5.1969 |
| 208563_x_ | 0.9151 | 208563_x_at | 10.7358 |
| 209844_at | 0.6096 | 209844_at | 8.5493 |
| 209897_s_ | 0.5179 | 209897_s_at | 8.7179 |
| 210273_at | 0.6531 | 210273_at | 11.7799 |
| 210380_s_ | 0.1148 | 210380_s_at | 1.9311 |
| 210518_at | -0.0937 | 210518_at | -0.5486 |
| 211802_x_ | 0.3304 | 211802_x_at | 5.5155 |
| 213436_at | 0.7814 | 213436_at | 6.8744 |
| 214639_s_ | 0.6139 | 214639_s_at | 9.5249 |
| 217076_s_ | 0.3884 | 217076_s_at | 4.0575 |
| 217411_s_ | 1.8875 | 217411_s_at | 24.812 |
| 218150_at | -0.0775 | 218150_at | -2.8352 |
| 218642_s_ | -0.4246 | 218642_s_at | -6.6993 |
| 220025_at | -2.1843 | 220025_at | -24.7157 |
| 221217_s_ | 0.4442 | 221217_s_at | 4.8849 |

30 genes PcG-TF signature

| | Coeff.OvaCa133 | | OvaCa133Log10Coeff.30PcGTFlog10 |
|---|---|---|---|
| 200067_x_ | -0.3699 | 200067_x_at | -5.7576 |
| 202672_s_ | -0.2472 | 202672_s_at | -6.2757 |

Fig. 37-5

| | | | |
|---|---|---|---|
| 202936_s_ | 0.4394 | 202936_s_at | 10.0708 |
| 203603_s_ | 0.9235 | 203603_s_at | 8.7405 |
| 203752_s_ | 0.3177 | 203752_s_at | 8.494 |
| 204039_at | -0.2999 | 204039_at | -6.9238 |
| 205459_s_ | -1.5781 | 205459_s_at | -27.6149 |
| 205460_at | 1.1213 | 205460_at | 16.6129 |
| 205471_s_ | -0.199 | 205471_s_at | -2.7432 |
| 205817_at | 0.5004 | 205817_at | 8.5064 |
| 206115_at | 0.0093 | 206115_at | 0.8538 |
| 206377_at | 0.4348 | 206377_at | 5.2862 |
| 206837_at | 0.2358 | 206837_at | 3.9895 |
| 206858_s_ | -0.1239 | 206858_s_at | -2.4139 |
| 207059_at | -1.5641 | 207059_at | -19.7726 |
| 207147_at | 0.6173 | 207147_at | 5.6087 |
| 207250_at | 0.7973 | 207250_at | 11.2462 |
| 207690_at | -1.5403 | 207690_at | -27.4111 |
| 208414_s_ | 0.9459 | 208414_s_at | 14.796 |
| 208554_at | -2.1115 | 208554_at | -24.1698 |
| 208563_x_ | 0.2058 | 208563_x_at | 0.3962 |
| 209120_at | -0.9593 | 209120_at | -15.8852 |
| 210288_at | -0.6625 | 210288_at | -12.0107 |
| 214401_at | 4.6824 | 214401_at | 73.7881 |
| 216497_at | 0.5184 | 216497_at | 7.6211 |
| 216953_s_ | 0.0646 | 216953_s_at | 1.2596 |
| 219568_x_ | 0.1136 | 219568_x_at | 2.0262 |
| 219884_at | 1.2063 | 219884_at | 21.7908 |
| 220025_at | 0.4701 | 220025_at | 7.6812 |
| 220559_at | -3.0479 | 220559_at | -33.8278 |

26 genes BCD-TF signature
Coeff.OvaCa133          OvaCa133log10 Coeff.26BCD_TF

| | | | |
|---|---|---|---|
| 205646_s_ | -0.0588 | 205646_s_at | -1.1292 |
| 210560_at | -0.4666 | 210560_at | -4.4163 |
| 214639_s_ | 0.0474 | 214639_s_at | 1.4901 |
| 209204_at | 0.1173 | 209204_at | 0.945 |
| 209205_s_ | -0.2599 | 209205_s_at | -3.7742 |
| 208468_at | -0.1565 | 208468_at | -0.968 |
| 207147_at | -0.3317 | 207147_at | -2.2984 |
| 207914_x_ | 0.7347 | 207914_x_at | 13.4567 |
| 206847_s_ | -1.8198 | 206847_s_at | -19.0821 |
| 206848_at | -0.0963 | 206848_at | -1.7852 |
| 209844_at | 1.1901 | 209844_at | 13.6236 |
| 221278_at | -0.5324 | 221278_at | -6.5046 |
| 208414_s_ | 0.5844 | 208414_s_at | 8.929 |
| 208224_at | 1.2127 | 208224_at | 18.5131 |
| 206739_at | 1.1633 | 206739_at | 20.9836 |
| 219832_s_ | -1.2374 | 219832_s_at | -16.8683 |
| 206858_s_ | -0.1245 | 206858_s_at | -1.7521 |
| 217076_s_ | -0.1305 | 217076_s_at | -1.8557 |
| 207397_s_ | 0.0731 | 207397_s_at | 0.7034 |
| 220225_at | -0.5454 | 220225_at | -7.7494 |

Fig. 37-6

| | | | |
|---|---|---|---|
| 208434_at | 0.2207 | 208434_at | 3.0434 |
| 215073_s_ | -0.8415 | 215073_s_at | -10.4457 |
| 207059_at | -0.4039 | 207059_at | -4.4144 |
| 206511_s_ | 0.4935 | 206511_s_at | 8.0223 |
| 208574_at | 1.1099 | 208574_at | 10.8391 |
| 203603_s_ | 0.2961 | 203603_s_at | 2.4689 |

25 genes Suz12 NoPolII signature
Coeff.OvaCa133                    OvaCa133log10 Coeff.25Suz12NoPOLII

| | | | |
|---|---|---|---|
| 202037_s_ | -0.043 | 202037_s_at | -0.7489 |
| 203477_at | -0.245 | 203477_at | -3.9976 |
| 203695_s_ | 0.6256 | 203695_s_at | 10.1881 |
| 203888_at | -0.5836 | 203888_at | -9.4447 |
| 204279_at | -0.3962 | 204279_at | -8.2726 |
| 204527_at | -0.1919 | 204527_at | -0.1438 |
| 205330_at | 0.5617 | 205330_at | 6.9354 |
| 205590_at | -0.3095 | 205590_at | -4.1273 |
| 205691_at | 0.2868 | 205691_at | 4.0824 |
| 205923_at | -0.0598 | 205923_at | -0.5131 |
| 206893_at | -0.4561 | 206893_at | -6.0638 |
| 207890_s_ | 0.184 | 207890_s_at | 4.1847 |
| 208206_s_ | 1.692 | 208206_s_at | 21.5417 |
| 209602_s_ | -0.7985 | 209602_s_at | -8.7651 |
| 210002_at | 0.0022 | 210002_at | 0.0058 |
| 210273_at | 0.5505 | 210273_at | 10.2089 |
| 211529_x_ | 0.193 | 211529_x_at | 6.2732 |
| 214451_at | -0.8709 | 214451_at | -7.4981 |
| 218974_at | -0.3887 | 218974_at | -5.644 |
| 219537_x_ | 0.6337 | 219537_x_at | 7.6641 |
| 220108_at | 0.0186 | 220108_at | -0.5397 |
| 220406_at | -0.2633 | 220406_at | -5.788 |
| 220407_s_ | 0.1732 | 220407_s_at | 3.4373 |
| 221029_s_ | -0.3701 | 221029_s_at | -4.6784 |
| 221234_s_ | -0.5992 | 221234_s_at | -6.042 |

20 genes Suz12 PolII Bound signature
Coeff.OvaCa133                    OvaCa133log10 Coeff.20Suz12POLIIbound

| | | | |
|---|---|---|---|
| 211919_s_ | -0.2469 | 211919_s_at | -5.161 |
| 212427_at | 0.9594 | 212427_at | 10.1373 |
| 215723_s_ | 0.4273 | 215723_s_at | 5.5232 |
| 205203_at | -0.305 | 205203_at | -6.148 |
| 204114_at | -0.5636 | 204114_at | -10.6052 |
| 202672_s_ | -0.0198 | 202672_s_at | 0.1971 |
| 204302_s_ | 2.7175 | 204302_s_at | 43.2926 |
| 204014_at | -0.5146 | 204014_at | -6.8258 |
| 207390_s_ | -0.0353 | 207390_s_at | -1.259 |
| 207574_s_ | -0.7754 | 207574_s_at | -13.5059 |
| 209304_x_ | 0.8783 | 209304_x_at | 17.4823 |
| 206099_at | -0.8145 | 206099_at | -10.0619 |
| 201466_s_ | -0.2119 | 201466_s_at | -3.9506 |

Fig. 37-7

| | | | |
|---|---|---|---|
| 201473_at | 0.345 | 201473_at | 6.7571 |
| 205656_at | 0.5786 | 205656_at | 9.7968 |
| 201150_s_ | 0.1818 | 201150_s_at | 3.9775 |
| 201373_at | -0.1814 | 201373_at | -2.9372 |
| 205266_at | 0.5143 | 205266_at | 9.6259 |
| 202936_s_ | 0.2755 | 202936_s_at | 5.1587 |
| 207172_s_ | 0.0777 | 207172_s_at | 1.4735 |

20 genes ESC-EED signature

| Coeff.OvaCa133 | | OvaCa133Log10 Coeff.20_EED | |
|---|---|---|---|
| 200953_s_ | -0.114 | 200953_s_at | -2.4425 |
| 201901_s_ | 0.2543 | 201901_s_at | 2.3424 |
| 202936_s_ | 0.2281 | 202936_s_at | 5.0355 |
| 203131_at | 0.062 | 203131_at | 0.9131 |
| 203358_s_ | -0.3991 | 203358_s_at | -5.5646 |
| 205051_s_ | 0.2481 | 205051_s_at | 4.3484 |
| 205646_s_ | -0.1656 | 205646_s_at | -2.0451 |
| 206061_s_ | -0.8553 | 206061_s_at | -13.0288 |
| 206140_at | -0.7609 | 206140_at | -9.176 |
| 206176_at | -0.3793 | 206176_at | -5.4657 |
| 206858_s_ | -0.0624 | 206858_s_at | -0.8501 |
| 207059_at | -0.0273 | 207059_at | 0.4582 |
| 207336_at | -0.083 | 207336_at | -1.3447 |
| 207612_at | 2.5883 | 207612_at | 30.5109 |
| 207726_at | 1.2251 | 207726_at | 17.0737 |
| 208006_at | -1.5387 | 208006_at | -19.723 |
| 210656_at | -0.814 | 210656_at | -8.3881 |
| 213494_s_ | -0.0767 | 213494_s_at | -0.3333 |
| 218252_at | 0.52 | 218252_at | 7.9537 |
| 219755_at | 0.1366 | 219755_at | 2.2558 |

35pattern3 ESC signature

| Coeff.OvaCa133 | | OvaCa133log10 Coeff.35pattern3ESC | |
|---|---|---|---|
| 200635_s_ | -1.0077 | 200635_s_at | -19.3419 |
| 200644_at | -0.4692 | 200644_at | -10.8369 |
| 200859_x_ | -0.1113 | 200859_x_at | -4.0071 |
| 201207_at | 0.434 | 201207_at | 8.1866 |
| 201215_at | -0.3269 | 201215_at | -4.2468 |
| 201587_s_ | -0.549 | 201587_s_at | -11.4721 |
| 201668_x_ | -0.6589 | 201668_x_at | -11.2271 |
| 202148_s_ | 0.809 | 202148_s_at | 16.0485 |
| 202242_at | -0.4762 | 202242_at | -9.0251 |
| 202608_s_ | -0.6274 | 202608_s_at | -5.566 |
| 202806_at | 0.567 | 202806_at | 13.0162 |
| 203269_at | -1.1014 | 203269_at | -17.1543 |
| 203706_s_ | -0.2353 | 203706_s_at | -4.5631 |
| 203747_at | 0.2656 | 203747_at | 4.9252 |
| 203787_at | 0.3014 | 203787_at | 4.2405 |
| 204239_s_ | -0.4499 | 204239_s_at | -9.0921 |
| 204759_at | -0.2913 | 204759_at | -4.3627 |

Fig. 37-8

| | | | |
|---|---|---|---|
| 204948_s_ | -0.0306 | 204948_s_at | -0.5725 |
| 205439_at | -0.3408 | 205439_at | -4.1941 |
| 205709_s_ | -0.4743 | 205709_s_at | -6.3919 |
| 205723_at | 1.1451 | 205723_at | 18.0187 |
| 207131_x_ | -0.9141 | 207131_x_at | -15.0774 |
| 207345_at | 0.3347 | 207345_at | 3.3121 |
| 208284_x_ | -0.2844 | 208284_x_at | -3.7184 |
| 209368_at | 0.0494 | 209368_at | 1.593 |
| 209644_x_ | 0.0102 | 209644_x_at | 0.2005 |
| 209772_s_ | 0.2878 | 209772_s_at | 5.4745 |
| 210880_s_ | -0.4429 | 210880_s_at | -7.1328 |
| 211946_s_ | -0.0154 | 211946_s_at | -0.349 |
| 213201_s_ | 0.3957 | 213201_s_at | 6.9667 |
| 216565_x_ | 0.1884 | 216565_x_at | 5.8317 |
| 218329_at | 0.6415 | 21 329_at | 11.6328 |
| 219568_x_ | 0.0528 | 219568_x_at | 0.8007 |
| 220750_s_ | 0.9399 | 220750_s_at | 13.4881 |
| 221866_at | 0.2094 | 221866_at | 6.039 |

Fig. 37-9

Table 8. CTOP gene expression signatures for breast cancer

22_Genes EED_ESC_Signature    Agilent

| Systematic name | Gene name | Coeff.BrCa97 |
|---|---|---|
| NM_001759 | CCND2 | -0.772 |
| NM_003403 | YY1 | 2.389 |
| NM_000346 | SOX9 | 0.7058 |
| X76079 | PDGFRA | 1.2183 |
| NM_006206 | PDGFRA | 1.4302 |
| NM_004456 | EZH2 | 1.5864 |
| NM_000222 | KIT | -1.5302 |
| NM_000280 | PAX6 | -0.2031 |
| AB028449 | KIAA0928 | 1.5625 |
| AF007142 | KIAA0928 | -4.7004 |
| NM_004789 | LHX2 | 1.8523 |
| NM_001718 | BMP6 | -4.9374 |
| NM_004503 | HOXC6 | 1.2634 |
| NM_006194 | PAX9 | 1.0387 |
| NM_006940 | SOX5 | 1.316 |
| NM_003393 | WNT8B | 0.4387 |
| NM_004452 | ESRRB | 4.1186 |
| NM_012188 | FOXI1 | -1.5536 |
| AF099032 | EED | 2.3735 |
| NM_018204 | CKAP2 | 0.4967 |
| NM_020649 | CBX8 | -1.9421 |
| AF266479 | CBX8 | -1.3527 |

Dicer; HERNA; KIAA0928

38_Genes NANOG_Sox2_Oct4_Signature

| Systematic name | Gene name | Coeff.BrCa97 | |
|---|---|---|---|
| NM_001067 | TOP2A | 2.3926 | |
| NM_004725 | BUB3 | 2.1357 | |
| NM_003012 | SFRP1 | 1.7114 | |
| NM_002290 | LAMA4 | -3.9964 | |
| NM_005103 | FEZ1 | 2.8403 | |
| NM_000252 | MTM1 | -7.1829 | |
| NM_003212 | TDGF1 | 3.5886 | |
| NM_005531 | IFI16 | 5.1384 | |
| NM_003971 | SPAG9 | 0.1229 | |
| NM_003413 | ZIC3 | -1.555 | |
| NM_003150 | STAT3 | -4.6766 | |
| NM_003711 | PPAP2A | 1.0576 | |
| NM_004737 | LARGE | 1.5117 | |
| NM_018210 | FLJ10769 | -0.4446 | |
| NM_007240 | DUSP12 | 1.5175 | |
| NM_018169 | FLJ10652 | -3.0489 | |
| NM_018304 | FLJ11029 | 3.0695 | |
| Contig6323_RC | FLJ12581 | 0.5214 | Nanog |
| NM_001006 | RPS3A | -1.6437 | |
| NM_006755 | TALDO1 | -0.7873 | |
| NM_003470 | USP7 | -4.5851 | |

Fig. 38-1

| | | |
|---|---|---|
| NM_003097 | SNRPN | 2.0917 |
| NM_003407 | ZFP36 | -1.2301 |
| NM_004125 | GNG10 | 2.0969 |
| NM_001211 | BUB1B | 5.7016 |
| NM_003852 | TIF1 | 4.7871 |
| NM_015905 | TIF1 | -0.3747 |
| NM_004289 | NFE2L3 | -2.518 |
| NM_001390 | DTNA | -1.8702 |
| NM_001391 | DTNA | 5.7393 |
| NM_001392 | DTNA | -6.1426 |
| NM_005078 | TLE3 | 11.1929 |
| NM_000141 | FGFR2 | 1.8443 |
| AB029034 | KIAA1111 | 3.6734 |
| X69150 | RPS18 | -2.5616 |
| Contig24856_RC | FUS | -2.8887 |
| NM_004960 | FUS | -5.1586 |
| NM_012415 | RAD54B | -1.7619 |

27_Genes Suz12_NoPOLII_Signature

| Systematic name | Gene name | Coeff.BrCa97 |
|---|---|---|
| NM_001186 | BACH1 | -0.1707 |
| NM_001855 | COL15A1 | 1.4987 |
| NM_004403 | DFNA5 | -1.4407 |
| NM_016941 | DLL3 | 0.7486 |
| NM_018013 | FLJ10159 | 4.7153 |
| NM_002051 | GATA3 | -1.6023 |
| NM_005257 | GATA6 | -1.5748 |
| NM_004297 | GNA14 | 1.7561 |
| NM_002127 | HLA-G | 1.4559 |
| NM_004659 | MMP23A | -4.1071 |
| NM_002430 | MN1 | 0.7154 |
| Y07759 | MYO5A | -0.4316 |
| NM_000259 | MYO5A | -4.73 |
| NM_002589 | PCDH7 | 1.5597 |
| NM_002800 | PSMB9 | -1.3832 |
| NM_005739 | RASGRP1 | 0.2425 |
| NM_005825 | RASGRP2 | 0.7722 |
| NM_005045 | RELN | -0.4246 |
| NM_002968 | SALL1 | -1.196 |
| Contig43780_RC | SALL1 | 0.5388 |
| NM_003012 | SFRP1 | -0.0152 |
| NM_004209 | SYNGR3 | -0.2487 |
| NM_003221 | TFAP2B | -0.3218 |
| NM_003238 | TGFB2 | -0.7599 |
| NM_000361 | THBD | -0.1362 |
| NM_003392 | WNT5A | 3.0372 |
| Contig40434_RC | WNT5A | -4.3256 |

Fig. 38-2

27_Genes Suz12_RNAPII_Bound_Signature

| Systematic name | Gene name | Coeff.BrCa97 |
|---|---|---|
| NM_004114 | FGF13 | 0.2473 |
| NM_003467 | CXCR4 | -3.8665 |
| NM_004378 | CRABP1 | 0.0779 |
| NM_005203 | COL13A1 | -6.8011 |
| M74093 | CCNE1 | 2.6888 |
| NM_001243 | TNFRSF8 | 4.6407 |
| NM_002353 | TACSTD2 | 2.5455 |
| NM_002662 | PLD1 | -1.7209 |
| Contig52971_RC | KLF4 | 1.8847 |
| NM_001674 | ATF3 | 2.5094 |
| NM_004024 | ATF3 | -0.7972 |
| NM_005228 | EGFR | 1.0474 |
| NM_001999 | FBN2 | -1.3963 |
| NM_001750 | CAST | -3.9092 |
| NM_005384 | NFIL3 | 2.8773 |
| NM_000428 | LTBP2 | 3.8599 |
| NM_001394 | DUSP4 | -1.1518 |
| NM_006932 | SMTN | -8.2452 |
| NM_015675 | GADD45B | -8.9609 |
| NM_002820 | PTHLH | -2.938 |
| NM_002309 | LIF | -2.5717 |
| NM_000891 | KCNJ2 | 5.9689 |
| AL049946 | DKFZP564I1 | 3.8752 |
| NM_000346 | SOX9 | -2.2185 |
| NM_005253 | FOSL2 | -13.5665 |
| NM_001797 | CDH11 | -1.6398 |
| NM_001430 | EPAS1 | 7.4973 |

21_Genes Suz12_RNAPII_Bound_Signature

| Systematic name | Gene name | Coeff.BrCa97 |
|---|---|---|
| NM_003467 | CXCR4 | -3.9967 |
| NM_005203 | COL13A1 | -7.0339 |
| M74093 | CCNE1 | 2.66 |
| NM_001243 | TNFRSF8 | 5.124 |
| NM_002353 | TACSTD2 | 3.7657 |
| Contig52971_RC | KLF4 | 1.784 |
| NM_001674 | ATF3 | 1.9666 |
| NM_001999 | FBN2 | -1.4849 |
| NM_001750 | CAST | -3.8267 |
| NM_005384 | NFIL3 | 2.8603 |
| NM_000428 | LTBP2 | 4.1097 |
| NM_001394 | DUSP4 | -0.8637 |
| NM_006932 | SMTN | -6.6345 |
| NM_015675 | GADD45B | -8.6906 |
| NM_002820 | PTHLH | -2.7597 |
| NM_002309 | LIF | -2.4303 |
| NM_000891 | KCNJ2 | 5.3883 |
| AL049946 | DKFZP564I1 | 2.025 |

Fig. 38-3

| | | |
|---|---|---|
| NM_000346 | SOX9 | -1.9476 |
| NM_005253 | FOSL2 | -14.6011 |
| NM_001430 | EPAS1 | 7.1054 |

28_Genes PcG_TF_Signature

| Systematic name | Gene name | Coeff.BrCa97 |
|---|---|---|
| NM_003269 | NR2E1 | -0.6856 |
| NM_001674 | ATF3 | 6.0886 |
| NM_004024 | ATF3 | -5.9013 |
| NM_000346 | SOX9 | 1.5045 |
| NM_014795 | ZFHX1B | 2.8209 |
| NM_002228 | JUN | 0.1147 |
| NM_004364 | CEBPA | -1.9076 |
| NM_002518 | NPAS2 | -0.961 |
| NM_004392 | DACH | 0.2309 |
| NM_005982 | SIX1 | 0.9062 |
| NM_004430 | EGR3 | -0.4683 |
| NM_001452 | FOXF2 | 1.6751 |
| NM_006982 | CART1 | -0.3622 |
| NM_004503 | HOXC6 | 1.3357 |
| NM_006194 | PAX9 | 0.9532 |
| NM_004405 | DLX2 | -3.4326 |
| NM_007374 | SIX6 | -5.8852 |
| NM_006492 | ALX3 | 0.3245 |
| NM_002146 | HOXB3 | -1.6371 |
| NM_002700 | POU4F3 | 0.5268 |
| NM_006236 | POU3F3 | 1.9502 |
| M64497 | NR2F2 | -2.6901 |
| NM_005360 | MAF | -1.1721 |
| NM_006192 | PAX1 | 2.7425 |
| X51630 | WT1 | -0.785 |
| NM_014368 | LHX6 | -0.3829 |
| NM_006593 | TBR1 | -0.0959 |
| NM_001426 | EN1 | 8.1423 |

30_Genes TEZ_Signature

| Systematic name | Gene name | Coeff.BrCa97 |
|---|---|---|
| NM_018723 | A2BP1 | -7.7703 |
| NM_000657 | BCL2 | 4.5527 |
| NM_001796 | CDH8 | -0.7876 |
| NM_013445 | GAD1 | 0.5078 |
| NM_000817 | GAD1 | -1.2267 |
| NM_004125 | GNG10 | -0.1745 |
| NM_002309 | LIF | 3.0796 |
| NM_002430 | MN1 | -4.3077 |
| NM_002589 | PCDH7 | 1.5864 |
| NM_006236 | POU3F3 | 3.5924 |
| Contig55531 | SIX2 | 1.3099 |

Fig. 38-4

| | | |
|---|---|---|
| NM_016932 | SIX2 | 3.5589 |
| NM_003070 | SMARCA2 | -3.8955 |
| NM_005523 | HOXA11 | 0.4407 |
| NM_006735 | HOXA2 | 1.0749 |
| NM_006896 | HOXA7 | 0.6982 |
| NM_000522 | HOXA13 | -0.0873 |
| U81599 | HOXB13 | 1.6097 |
| NM_002146 | HOXB3 | -2.7366 |
| Contig17125_RC | HOXB8 | 5.074 |
| NM_018952 | HOXB6 | -2.3518 |
| NM_004503 | HOXC6 | -0.8139 |
| NM_014212 | HOXC11 | 1.2395 |
| NM_017410 | HOXC13 | 1.5528 |
| NM_021192 | HOXD11 | -0.4188 |
| NM_014213 | HOXD9 | -1.8174 |
| NM_006898 | HOXD3 | 3.3207 |
| NM_000523 | HOXD13 | -1.3204 |
| NM_005522 | HOXA1 | -0.812 |
| NM_002144 | HOXB1 | -2.4081 |

17_Genes TEZ_Signature

| Systematic name | Gene name | Coeff.BrCa97 |
|---|---|---|
| NM_018723 | A2BP1 | -8.9472 |
| NM_000657 | BCL2 | 4.7794 |
| NM_001796 | CDH8 | -0.8601 |
| NM_000817 | GAD1 | -1.4553 |
| NM_002309 | LIF | 2.8906 |
| NM_002430 | MN1 | -4.906 |
| NM_002589 | PCDH7 | 2.1738 |
| NM_006236 | POU3F3 | 3.8131 |
| NM_016932 | SIX2 | 3.4321 |
| NM_003070 | SMARCA2 | -3.4902 |
| U81599 | HOXB13 | 1.3075 |
| NM_002146 | HOXB3 | -2.3978 |
| Contig17125_RC | HOXB8 | 4.3277 |
| NM_018952 | HOXB6 | -2.1923 |
| NM_017410 | HOXC13 | 1.7349 |
| NM_006898 | HOXD3 | 3.1471 |
| NM_002144 | HOXB1 | -2.4528 |

29_Genes Wound_Signature

| Systematic name | Gene name | Coeff.BrCa97 |
|---|---|---|
| NM_004036 | ADCY3 | 1.8918 |
| NM_001647 | APOD | 3.0967 |
| NM_000484 | APP | 4.864 |
| NM_000784 | CYP27A1 | -3.3486 |
| NM_005758 | HNRPA3 | 7.4521 |
| NM_004499 | HNRPAB | -3.6232 |

Fig. 38-5

| | | |
|---|---|---|
| NM_013300 | HSU79274 | 4.7565 |
| NM_004508 | IDI1 | -4.9968 |
| NM_002184 | IL6ST | 1.2864 |
| NM_002318 | LOXL2 | 1.2158 |
| NM_005204 | MAP3K8 | -2.2696 |
| NM_002385 | MBP | -3.3241 |
| X59405 | MCP | -6.4975 |
| NM_014778 | KIAA0410 | -2.9841 |
| NM_014456 | PDCD4 | -5.2568 |
| NM_002611 | PDK2 | -7.3642 |
| NM_002692 | POLE2 | 2.698 |
| NM_002912 | REV3L | 2.5638 |
| AF103804 | SDFR1 | 1.6822 |
| NM_020372 | LOC57100 | -5.4147 |
| NM_003094 | SNRPE | 4.4259 |
| NM_021199 | CGI-44 | -3.1058 |
| NM_004177 | STX3A | 13.4138 |
| NM_006519 | TCTEL1 | -2.6027 |
| NM_000365 | TPI1 | 2.7362 |
| NM_000366 | TPM1 | -1.924 |
| NM_015644 | DKFZP434B | 4.2619 |
| NM_016021 | LOC51632 | 9.779 |
| NM_003762 | VAMP4 | 5.858 |

| Systematic name | Gene name | 26_Genes_BCD_TF_Signature Coeff.BrCa97 |
|---|---|---|
| NM_004405 | DLX2 | -4.3541 |
| NM_001427 | EN2 | 7.044 |
| NM_005522 | HOXA1 | -14.6684 |
| NM_000522 | HOXA13 | -5.7795 |
| Contig32082_RC | HOXA2 | -7.9717 |
| NM_019102 | HOXA5 | -6.2562 |
| NM_002145 | HOXB2 | 2.5322 |
| NM_002146 | HOXB3 | -5.797 |
| NM_018952 | HOXB6 | -5.3856 |
| Contig17125_RC | HOXB8 | 4.4533 |
| NM_017410 | HOXC13 | 4.7985 |
| X52402 | HOXC5 | 2.3814 |
| NM_006898 | HOXD3 | 6.5194 |
| Contig59870_RC | Irx2 | 1.0261 |
| NM_016358 | IRX4 | 3.5645 |
| NM_002315 | LMO1 | -2.5459 |
| M64497 | NR2F2 | -3.0111 |
| NM_006192 | PAX1 | 4.2416 |
| NM_000278 | PAX2 | 6.7347 |
| Contig33540_RC | SATB1 | 12.3451 |
| NM_000193 | SHH | 3.3884 |
| Contig55531 | SIX2 | 4.7125 |
| NM_021025 | TLX3 | -2.4552 |
| NM_014795 | ZFHX1B | 2.0437 |
| NM_006896 | HOXA7 | 4.4738 |
| NM_003317 | TITF1 | 4.0127 |

Fig. 38-6

Example of the evaluation of therapeutic efficacy of the CMAP000 drug combination in prostate cancer

| Signature | | Negative | Positive | Total | Therapeutic Ratio | Therapeutic Ratio, Log10 |
|---|---|---|---|---|---|---|
| 11BMI1pathway | | 4 | 10 | 14 | 0.4 | -0.39794 |
| 21PcG_TF | | 5 | 8 | 13 | 0.625 | -0.20412 |
| 22Suz12POLIIBound | | 9 | 2 | 11 | 4.5 | 0.653213 |
| 26Suz12NoPOLII | | 5 | 2 | 7 | 2.5 | 0.39794 |
| 28NanogSoz2Oct | | 1 | 8 | 10 | 0.125 | -0.90309 |
| 31BCD_TF | | 2 | 5 | 7 | 0.4 | -0.39794 |
| 32TEZ_ESC | | 5 | 8 | 13 | 0.625 | -0.20412 |
| 36EED_ESC | | 2 | 12 | 14 | 0.166667 | -0.77815 |
| 37pattern3_ESC | | 11 | 1 | 12 | 11 | 1.041393 |
| | | 44 | 56 | 101 | 0.785714 | |
| Prostated Cancer | CMAP000 | | | | | |
| wortmannin | PI3K inhibitor | | | | | |
| fulvestrant | ER antagonist | | | | | |
| sirolimus | mTOR inhibitor | | | | | |

Example of the evaluation of therapeutic efficacy of the CMAP11 drug combination in prostate cancer

| Signature | | Negative | Positive | Total | Therapeutic Ratio | Therapeutic Ratio, Log10 |
|---|---|---|---|---|---|---|
| 11BMI1pathway | | 5 | 11 | 16 | 0.454545 | -0.34242 |
| 21PcG_TF | | 5 | 9 | 14 | 0.555556 | -0.25527 |
| 22Suz12POLIIBound | | 11 | 3 | 14 | 3.666667 | 0.564271 |
| 26Suz12NoPOLII | | 8 | 2 | 10 | 4 | 0.60206 |
| 28NanogSoz2Oct | | 1 | 9 | 10 | 0.111111 | -0.95424 |
| 31BCD_TF | | 2 | 5 | 7 | 0.4 | -0.39794 |
| 32TEZ_ESC | | 5 | 9 | 14 | 0.555556 | -0.25527 |
| 36EED_ESC | | 3 | 12 | 15 | 0.25 | -0.60206 |
| 37pattern3_ESC | | 12 | 1 | 13 | 12 | 1.079181 |
| | | 52 | 61 | 113 | 0.852459 | |
| Prostated Cancer | CMAP11 | | | | | |
| wortmannin | PI3K inhibitor | | | | | |
| staurosporine | PKC inhibitor | | | | | |
| fulvestrant | ER antagonist | | | | | |
| sirolimus | mTOR inhibitor | | | | | |

Fig. 39-1

Example of the evaluation of therapeutic efficacy of the CMAP19 drug combination in breast cancer

| Signature | | Negative | Positive | Total | Therapeutic Ratio | Therapeutic Ratio, Log10 |
|---|---|---|---|---|---|---|
| 11BMI | | 2 | 5 | 7 | 0.4 | -0.39794 |
| 20EED | | 11 | 5 | 17 | 2.2 | 0.342423 |
| 20Suz12POLIIbound | | 5 | 2 | 7 | 2.5 | 0.39794 |
| 22NanSox2Oct4ESC | | 12 | 3 | 15 | 4 | 0.60206 |
| 25Suz12NoPOLII | | 4 | 10 | 14 | 0.4 | -0.39794 |
| 26BCD_TF | | 5 | 7 | 12 | 0.714286 | -0.14613 |
| 30PcG_TF | | 9 | 5 | 14 | 1.8 | 0.255273 |
| 35pattern3ESC | | 12 | 2 | 14 | 6 | 0.778151 |
| 33TEZ | | 7 | 4 | 11 | 1.75 | 0.243038 |
| | | 67 | 43 | 111 | 1.55814 | |
| Breast Cancer | CMAP19 | | | | | |
| wortmannin | PI3K inhibitor | | | | | |
| fulvestrant | ER antagonist | | | | | |
| trichostatin A | HDAC inhibitor | | | | | |

Fig. 39-2

| Signature | PTID | SCORE_Oct-00 | SCORE_20I | Score_20S | Score_25 | Score_26E | Score_30_ |
|---|---|---|---|---|---|---|---|
| 11BMI | Oct-00 | 0.96191 | 0.1075287 | 0.405474 | -0.24174 | -0.71361 | -0.68936 |
| 20EED | 00-1059 | 0.46086 | -0.496682 | 0.543533 | 1.409881 | -1.49159 | -1.35897 |
| 20Suz12POLIIBound | 00-1072 | -0.0374 | 1.1072651 | 0.679678 | 0.731658 | -1.56404 | -0.99634 |
| 25Suz12NoPOLII | 00-1082 | 0.83856 | -1.210657 | -0.28268 | -0.25839 | -0.74042 | -0.67215 |
| 26BCD_TF | 00-11 | 0.81302 | -0.110665 | 1.337673 | 1.558943 | 0.692529 | 0.953898 |
| 30PcG_TF | 00-145 | -0.755 | 0.2909331 | 0.541257 | -0.36341 | -1.08575 | -0.06744 |
| 35pattern3ESC | 00-151 | -0.5762 | -0.584247 | -0.04343 | 1.030752 | 0.33101 | 1.844271 |
| 36TEZ | 00-253 | 0.00258 | -1.663684 | -0.19133 | -0.68466 | -0.79415 | -0.88817 |
| 41NanSox2Oct4ESC | 00-315 | -0.7722 | 0.2432592 | -0.90575 | -0.56581 | -1.8291 | -0.7564 |
| | 00-327 | -0.7054 | 0.2248697 | 0.46337 | -0.07984 | 0.388484 | -0.11874 |
| | 00-334 | -0.5591 | -0.639241 | -1.19997 | -0.26058 | -0.78871 | -1.8403 |
| | 00-398 | 1.02628 | 0.6206748 | 1.823624 | -0.44519 | 1.370927 | 1.211768 |
| | 00-440 | 0.44906 | 1.243334 | -2.35838 | 0.534153 | 1.010697 | 1.540619 |
| | 00-452 | 0.99716 | 0.4759324 | 0.597316 | 0.599303 | -1.75641 | -0.45164 |
| | 00-479 | 1.1445 | 2.687914 | 1.8078 | 1.217175 | 1.907718 | 4.786703 |
| | 00-550 | -0.0516 | -0.694332 | 0.203626 | -0.86229 | 0.135712 | -3.07362 |
| | 00-703 | -0.6497 | -0.61933 | 0.737697 | 0.187002 | -0.21252 | 0.072647 |
| | 00-827 | 0.23448 | 0.5915353 | 1.767482 | 0.024344 | 1.334511 | 1.267703 |
| | 00-909 | -0.1745 | 1.9574443 | -0.38364 | -0.06031 | 0.403964 | -0.78893 |
| | 00-941 | 0.4205 | 1.0496038 | 0.406304 | 0.236158 | 0.428788 | 1.547738 |
| | 01-139 | 0.34162 | 0.5140253 | -0.01841 | -0.9888 | -1.32329 | -0.25226 |
| | 01-181 | -0.6332 | -1.40022 | -0.89856 | -1.38114 | -0.63443 | -2.57163 |
| | 01-189 | 0.43209 | -3.145622 | 0.588292 | -0.61949 | 0.784878 | -0.02729 |
| | 01-236 | 0.01179 | -0.112442 | 1.11406 | 0.625434 | 0.790273 | 1.751762 |
| | 01-284 | -0.2634 | 1.6483788 | 2.271214 | -0.4009 | 0.949134 | 0.324951 |
| | 01-331 | 0.21101 | 0.3644478 | 1.384641 | 0.818588 | 0.221698 | 1.581973 |
| | 01-369 | -1.426 | 1.206049 | 0.073981 | -0.68584 | 0.726052 | -1.61212 |
| | 01-424 | 0.24731 | -0.776792 | 0.722095 | 1.13537 | -0.16448 | 0.736417 |
| | 01-534 | -0.0499 | -0.166492 | 0.88598 | -0.66599 | 0.989049 | 0.87889 |
| | 01-646 | 0.446 | 1.3007703 | 0.516448 | -0.60966 | 0.123159 | 0.839971 |
| | 96-264 | -0.565 | -1.484451 | -0.56692 | -0.13543 | -1.7839 | -1.74558 |
| | 96.3 | 0.08152 | 0.8819301 | 1.107552 | 0.409658 | 1.069063 | 1.154889 |
| | 96-353 | 0.76869 | 0.1929061 | 0.164141 | 0.925091 | 0.040309 | -0.0808 |
| | 96-475 | -0.6313 | 0.3551413 | -1.3348 | 0.32213 | -1.35403 | -1.64151 |
| | 97-1026 | -0.3243 | -0.493381 | 1.13548 | 1.642454 | 2.286912 | 2.731036 |
| | 97-1027 | 0.51257 | 1.0693724 | -0.48802 | 0.215204 | -0.75789 | -1.39494 |
| | 97-403 | 0.67383 | 2.6824521 | -0.04624 | 1.186935 | 1.431401 | 2.21757 |
| | 97-587 | 0.73352 | 0.4947327 | 0.0628 | 0.163397 | 0.200763 | -2.51051 |
| | 97-608 | 0.41737 | -1.08918 | -0.51418 | 0.411949 | -0.17676 | -0.25457 |
| | 97-666 | 0.54767 | -0.037638 | 0.179911 | 0.700208 | -0.1364 | 0.729451 |
| | 97-792 | 0.03905 | -1.222316 | -0.22796 | -1.69918 | -1.3075 | -0.87499 |
| | 97-829 | -0.2888 | 1.216301 | 0.715839 | -0.88081 | 1.408314 | 1.476545 |
| | 97-930 | -0.3263 | 0.2159882 | 0.329657 | 0.330234 | -0.29189 | 1.066607 |
| | 97-949 | 0.09928 | -2.147354 | -1.16821 | -1.28582 | -1.14061 | -3.91517 |
| | 98-1014 | -0.2984 | 0.6338216 | -0.80378 | 0.129981 | 1.251817 | 1.6938 |
| | 98-1063 | 0.35955 | 1.7383797 | -1.06771 | -0.72727 | 1.389325 | 1.52939 |
| | 98-1146 | 0.25333 | -0.102543 | -0.07262 | 0.638314 | -0.39748 | 0.54992 |
| | 98-1216 | 0.64233 | 0.504704 | 1.920543 | -1.03879 | 1.879037 | 0.382261 |
| | 98-1277 | -0.4553 | 0.1508132 | -0.38395 | -1.34529 | -0.82169 | -2.79197 |
| | 98-1293 | -0.3544 | -0.838173 | -1.67604 | -0.32539 | -0.08358 | 0.007872 |
| | 98-1296 | 0.71639 | -0.950344 | 0.509507 | -0.39067 | -1.22994 | 0.483852 |

Fig. 40-1

| | | | | | | |
|---|---|---|---|---|---|---|
| 98-152 | -1.0159 | -3.627438 | -2.08901 | -2.87948 | -1.25803 | -2.79748 |
| 98-186 | 1.05218 | -0.627235 | 1.049731 | 0.813372 | 0.335694 | -0.56849 |
| 98-197 | -0.2993 | 0.1966 | 0.213832 | 0.112008 | 0.588866 | 0.291073 |
| 98-292 | -0.7392 | -5.147547 | -1.11151 | -0.49428 | -3.52968 | -0.81714 |
| 98-320 | -0.708 | -1.461871 | 0.832365 | 1.03066 | -1.39487 | 0.396886 |
| 98-343 | 0.52537 | 0.0148782 | 0.215921 | -0.00446 | 0.602083 | -0.76435 |
| 98-375 | 1.19701 | 0.5389218 | 1.530129 | -0.65023 | 0.25794 | 2.368971 |
| 98-401 | -1.2855 | -1.869603 | -1.47473 | -1.24972 | -1.53886 | -1.08258 |
| 98-417 | 0.37084 | 0.7658291 | 0.030835 | 0.503981 | 1.046994 | 1.5614 |
| 98-438 | -0.4507 | 0.4021348 | -0.12547 | 0.464192 | 0.353571 | -1.30999 |
| 98-506 | -1.0809 | -0.199737 | -1.53407 | 0.620611 | -0.39415 | -0.86609 |
| 98-543 | -0.459 | -1.401308 | -0.49395 | -0.56421 | -0.59654 | -4.14632 |
| 98-657 | -1.0142 | 0.6362533 | -0.02292 | -0.09857 | 0.139597 | 1.147706 |
| 98-679 | 0.21954 | -0.539677 | -0.47514 | 0.287657 | -1.16612 | -2.22378 |
| 98-683 | 0.03223 | 1.9544888 | 0.354163 | 0.680693 | -0.06922 | -2.31482 |
| 98-691 | 0.72043 | 1.588731 | 2.074158 | -0.25352 | 1.036908 | 1.953329 |
| 98-711 | 0.43206 | 0.7859802 | -0.40817 | -0.95511 | 0.499334 | -0.00481 |
| 98-723 | 0.01037 | 1.264726 | 1.311304 | 1.211777 | 2.252613 | 1.995518 |
| 98-771 | -0.8116 | -0.407361 | -1.34373 | -0.85147 | 0.10661 | -0.66684 |
| 98-821 | 0.33715 | 0.3601946 | 0.44464 | 0.666924 | -0.44235 | 0.158667 |
| 98-828 | 0.40962 | 1.1504875 | -0.59584 | -1.1461 | -0.51022 | 0.087598 |
| 98-853 | 0.32213 | 1.9516631 | 1.114779 | -0.56455 | -0.72907 | -4.27383 |
| 98-933 | -0.0294 | -0.956118 | 0.940644 | -0.39103 | 0.285699 | 0.74552 |
| 98-956 | 0.33514 | 0.3784403 | -0.22037 | -0.69586 | -0.45037 | -0.04807 |
| 98-967 | -0.2525 | 0.4524212 | -0.14587 | 0.138047 | 0.233243 | -1.11683 |
| 98-985 | -1.1988 | -0.621205 | -0.52993 | -0.0294 | -1.2057 | -1.98663 |
| 99-1017 | -0.8292 | -0.032457 | -2.59147 | -1.3201 | -2.15068 | 0.028277 |
| 99-1033 | -0.5167 | -1.121827 | -1.63796 | -0.57993 | -0.34796 | -1.39252 |
| 99-1067 | -0.5702 | 0.4973749 | -0.11411 | 0.396249 | -0.52711 | -0.39449 |
| 99-137 | 0.83613 | 0.6959013 | -0.56775 | 1.111006 | 0.366035 | 1.865308 |
| 99-301 | 1.78722 | 1.1582537 | -0.84053 | -1.48627 | 0.253024 | 1.883311 |
| 99-440 | -0.221 | -0.497751 | -0.13856 | 0.264509 | 0.932614 | -1.81231 |
| 99-55 | 0.50979 | 0.3811077 | 2.245043 | 1.441026 | -1.42039 | 2.135795 |
| 99-671 | 0.20779 | -0.643165 | -0.17446 | 0.425799 | -0.53365 | -0.53854 |
| 99-692 | 0.53947 | 0.0749775 | -1.22807 | -0.27722 | 0.081879 | 0.41776 |
| 99-706 | 0.37916 | 0.4397816 | -0.07814 | -0.28974 | 0.778959 | -0.43271 |
| 99-728 | 0.12934 | -0.430446 | -0.45553 | 0.13078 | 0.050868 | -0.23024 |
| 99-77 | -0.2849 | -1.652958 | 0.557512 | -0.08246 | -2.2132 | -1.34769 |
| 99-830 | -0.4953 | -0.730479 | 0.138848 | 0.187354 | 1.166418 | 1.20836 |
| 99-927 | 0.1524 | 0.3293103 | -1.67031 | -1.2031 | -0.48234 | -1.05054 |

Fig. 40-2

| Score_35p | Score_36_ | SCORE_41_ | Surv(mo) | STATUS | PTID |
|---|---|---|---|---|---|
| 1.50674 | 1.901027 | -1.7289775 | 14.47 | 1 | Oct-00 |
| 1.408365 | 2.015897 | 0.1009832 | 23.63 | 1 | 00-105 |
| -0.42164 | -2.2953 | 0.3895306 | 41.67 | 0 | 00-107 |
| 0.604532 | 0.620649 | -3.420073 | 41.63 | 0 | 00+108 |
| 2.645107 | -0.15056 | 5.5573732 | 5.3 | 1 | 00-11 |
| 0.104745 | 0.892127 | -1.5340255 | 51.23 | 0 | 00-145 |
| 1.492696 | 2.645077 | 3.6721685 | 6.33 | 1 | 00-151 |
| 3.084581 | -0.70607 | 0.6538002 | 12.33 | 0 | 00-253 |
| -0.00645 | -0.72831 | 0.975813 | 45.2 | 0 | 00-315 |
| 0.96579 | -0.95303 | -0.8044742 | 9.73 | 1 | 00-327 |
| -1.09094 | 0.406305 | -0.4407094 | 37.5 | 0 | 00-334 |
| 0.979371 | 1.864093 | 1.792879 | 29.13 | 1 | 00-398 |
| 1.145635 | 0.851517 | 1.7225366 | 28.87 | 1 | 00-440 |
| 1.174036 | 1.764831 | 1.4877148 | 33.8 | 1 | 00-452 |
| 2.879385 | 3.037023 | 4.9763867 | 1.9 | 1 | 00-479 |
| -0.26087 | -1.46235 | 0.1641843 | 33.43 | 0 | 00-550 |
| 0.962562 | -0.33251 | -2.0560367 | 42.63 | 0 | 00-703 |
| 1.52079 | 2.009745 | 1.1003669 | 13.27 | 1 | 00-827 |
| 1.982361 | 3.107376 | 4.1867388 | 11.17 | 1 | 00-909 |
| 1.271365 | 2.125286 | 0.2667754 | 24.33 | 1 | 00-941 |
| -1.36373 | 0.418389 | 0.8739134 | 39.83 | 0 | 01-139 |
| 0.90852 | -1.85149 | -4.411408 | 31.13 | 0 | 01-181 |
| 0.415273 | 1.951843 | 1.2178925 | 36.17 | 0 | 01-189 |
| 2.358456 | 0.3845 | -0.7090986 | 2.63 | 0 | 01-236 |
| -0.69362 | 2.990579 | 2.811509 | 2.73 | 0 | 01-284 |
| 2.317892 | 1.570652 | 1.4670156 | 24.13 | 1 | 01-331 |
| 0.923371 | 0.675365 | 0.3315458 | 25.53 | 0 | 01-369 |
| -1.33975 | 0.287336 | 0.9735953 | 25.43 | 0 | 01-424 |
| -1.55881 | 0.044209 | 1.7801453 | 31.13 | 1 | 01-534 |
| -0.04229 | 1.834159 | 0.8839886 | 19.83 | 1 | 01-646 |
| -0.84836 | -0.48038 | 0.1088874 | 82.93 | 0 | 96-264 |
| -0.6082 | 2.298498 | 0.4094108 | 33.8 | 1 | 96-3 |
| 0.34839 | -0.62385 | 1.765411 | 28.37 | 1 | 96-353 |
| -0.36427 | -4.27412 | -0.1595398 | 87.27 | 0 | 96-475 |
| -0.04982 | -1.81402 | 2.4393504 | 13.1 | 1 | 97-102 |
| 0.077879 | 1.969236 | 3.1573328 | 1.07 | 1 | 97-102 |
| 3.985666 | 3.015871 | 1.1561226 | 8.67 | 1 | 97-403 |
| 0.280089 | 1.161811 | 1.0531038 | 39.27 | 1 | 97-587 |
| -0.89769 | -1.12236 | 0.2554275 | 81.17 | 0 | 97-608 |
| -0.32509 | 1.296486 | -2.8410408 | 51.27 | 1 | 97-666 |
| -0.59828 | -3.7906 | 0.705837 | 74.63 | 0 | 97-792 |
| 2.874784 | 2.837507 | -1.0039332 | 12.33 | 1 | 97-829 |
| 0.667111 | 0.558518 | 0.881112 | 39.6 | 1 | 97-930 |
| -1.86615 | -3.05633 | -0.9414502 | 57.83 | 0 | 97-949 |
| 0.328601 | 2.261053 | -0.595559 | 20.3 | 1 | 98-101 |
| 2.416837 | 2.383755 | 2.0188571 | 19.17 | 1 | 98-106 |
| 0.567315 | 1.531766 | 0.529438 | 42.8 | 1 | 98-114 |
| 2.282567 | 3.587759 | 2.9617816 | 16.93 | 1 | 98-121 |
| -2.9359 | 0.541665 | -2.3288308 | 55.93 | 0 | 98-127 |
| -1.3228 | -0.2575 | -2.1223018 | 59.4 | 0 | 98-129 |
| -0.98196 | 0.429112 | 0.5534408 | 63.53 | 0 | 98-129 |

Fig. 40-3

| | | | | |
|---:|---:|---:|---:|:---|
| -1.5989 | -2.15563 | -2.4997124 | 73.33 | 0 98-152 |
| 0.127172 | 0.46805 | 0.5394592 | 49.43 | 1 98-186 |
| -0.31814 | -1.61966 | -1.0984413 | 70.87 | 0 98-197 |
| -0.94174 | -2.14283 | -5.3777684 | 66.03 | 0 98-292 |
| 0.49462 | 1.763055 | 1.5252986 | 17 | 1 98-320 |
| 0.50087 | -2.30058 | -0.8959898 | 49.5 | 0 98-343 |
| 1.372483 | 1.896368 | -0.5307698 | 14.13 | 1 98-375 |
| -4.74152 | 1.100917 | -0.0827876 | 68.37 | 0 98-401 |
| -3.29572 | 0.750665 | 1.9380192 | 27.2 | 1 98-417 |
| -1.49873 | 0.662564 | -0.6880226 | 55.37 | 1 98-438 |
| -0.66998 | -9.34864 | -2.8650306 | 71.1 | 0 98-506 |
| -1.85691 | -0.85352 | 0.1766786 | 24.1 | 0 98-543 |
| -0.90565 | 0.76554 | -0.8396632 | 39.6 | 1 98-657 |
| -3.4396 | -4.9374 | -2.8100846 | 59.83 | 0 98-679 |
| 0.689713 | 0.703917 | 1.467549 | 33.57 | 1 98-683 |
| 0.087847 | 3.004676 | 1.4373773 | 4.9 | 1 98-691 |
| -1.99357 | -0.14981 | -1.6244643 | 60.77 | 0 98-711 |
| 0.178465 | -3.14312 | 2.8645582 | 12.47 | 1 98-723 |
| 0.119217 | 0.333374 | -0.9664293 | 68.33 | 0 98-771 |
| -2.5713 | 0.674186 | -0.415141 | 35.67 | 0 98-821 |
| -0.8464 | -1.57848 | -3.9917919 | 43.8 | 0 98-828 |
| 2.689107 | 2.512448 | -2.4063208 | 5.17 | 0 98-853 |
| 0.806289 | 0.47813 | 0.2158241 | 28.1 | 1 98-933 |
| -0.49788 | -3.16578 | -3.5072021 | 59.47 | 0 98-956 |
| 0.510325 | 1.541892 | 2.0769964 | 21.33 | 1 98-967 |
| 0.568963 | -3.5725 | -1.8796516 | 34.8 | 0 98-985 |
| -0.83427 | 0.735823 | -5.8737338 | 54.3 | 0 99-101 |
| -0.32107 | -3.63358 | -4.083871 | 43.37 | 0 99-103 |
| -0.50187 | 1.165643 | 0.2865317 | 45.27 | 1 99-106 |
| 2.088746 | 1.476497 | 1.1494056 | 22.57 | 1 99-137 |
| 2.616504 | 3.351124 | 3.4460215 | 9.53 | 1 99-301 |
| 1.140379 | -0.25356 | -0.5395946 | 35.2 | 0 99-440 |
| 0.174861 | 0.901503 | 2.9473747 | 11.6 | 1 99-55 |
| -1.49619 | -1.06621 | -0.2696436 | 58.53 | 0 99-671 |
| 0.071999 | 1.216063 | 1.3582898 | 31.9 | 1 99-692 |
| -2.49625 | -0.03714 | -0.5049537 | 59.23 | 0 99-706 |
| 0.561434 | 1.028084 | -0.8443484 | 48.63 | 0 99-728 |
| 1.56363 | -2.75543 | -1.5963217 | 13.97 | 0 99-77 |
| 1.822919 | 2.396158 | 1.8783864 | 22.5 | 1 99-830 |
| -2.95724 | 0.595036 | -2.8123275 | 35.1 | 0 99-927 |

Fig. 40-4

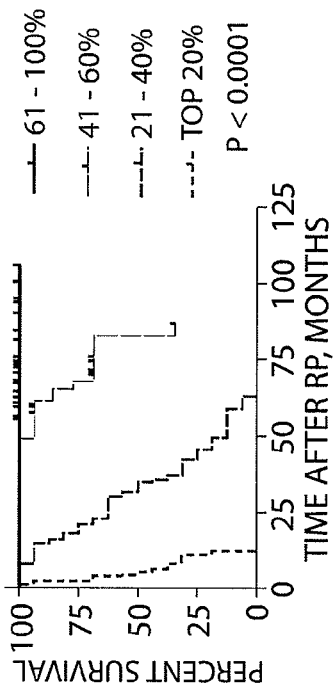
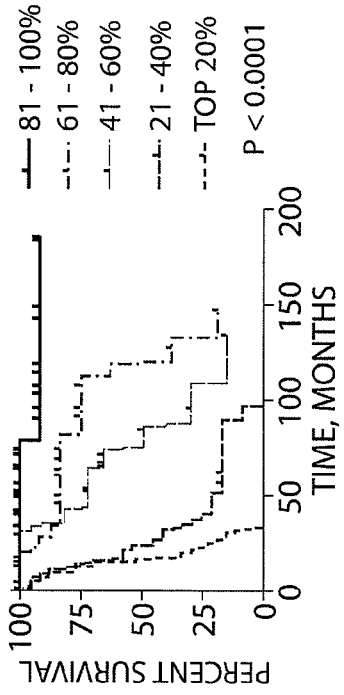
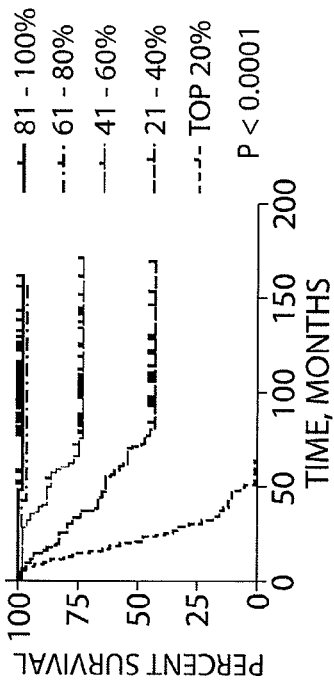
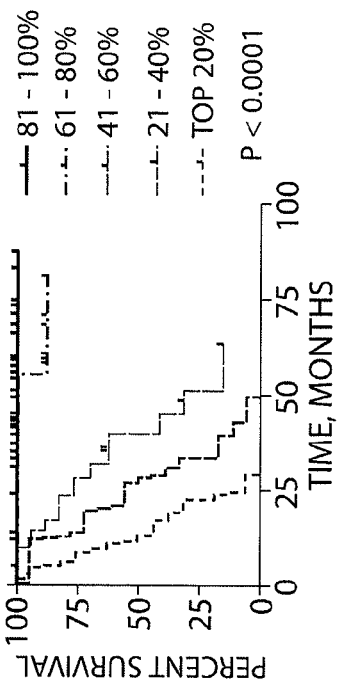
Fig. 46

PROGNOSTIC AND DIAGNOSTIC METHOD FOR CANCER THERAPY

RELATED APPLICATIONS

This application claims priority to U.S. Provisional Application 60/875,061, filed on Dec. 15, 2006 and to U.S. Provisional Application 60/823,577, filed on Aug. 25, 2006 and to U.S. Provisional Application 60/822,705, filed on Aug. 17, 2006 and to U.S. Provisional Application 60/787,818, filed on Mar. 31, 2006, all of which are incorporated by reference in their entireties.

STATEMENT AS TO FEDERALLY SPONSORED RESEARCH

This invention was made using federal funds awarded by the National Institutes of Health, National Cancer Institute under contract number 1RO1CA89827-01. The government has certain rights to this invention.

FIELD OF THE INVENTION

The invention relates to diagnostic and prognostic methods and kits for cancer therapy.

BACKGROUND

A wide variety of cancer treatment protocols have been developed in recent years. Often, very aggressive cancer therapy is reserved for late stage cancers due to unwanted side effects produced by such therapy. However, even such aggressive therapy commonly fails at such a late stage. The ability to identify cancers responsive only to the most aggressive therapies at an earlier stage could greatly improve the prognosis for patients having such cancers.

Only very recently, however, have markers predictive of such outcomes been identified. Glinsky, G. V. et al., J. Clin. Invest. 113: 913-923 (2004) teaches that gene expression profiling predicts clinical outcomes of prostate cancer. van 't Veer et al., Nature 415: 530-536 (2002) teaches that gene expression profiling predicts clinical outcomes of breast cancer. Glinsky et al., J. Clin. Invest. 115: 1503-1521 (2005) teaches that altered expression of the BMI1 oncogene is functionally linked with self-renewal state of normal and leukemic stem cells as well as a poor prognosis profile of an 11-gene death-from-cancer signature predicting therapy failure in patients with multiple types of cancer. These studies utilized the microarray gene expression analysis approach.

There is, therefore, a need for methods for early diagnosis of cancer and for prognostic assays for cancer therapy that are readily adaptable to the clinical setting. Such methods should utilize technologies that can be readily carried out in clinical laboratories, and should accurately predict the resistance of various cancers to be applied to standard therapeutic regimens.

SUMMARY OF THE INVENTION

The present invention is directed to novel methods and kits for diagnosing the presence of cancer within a patient, and for determining whether a subject who has cancer is susceptible to different types of treatment regimens. The cancers to be tested include, but are not limited to, prostate, breast, lung, gastric, ovarian, bladder, lymphoma, mesothelioma, medulloblastoma, glioma, and AML.

One embodiment of the present invention is directed to a method for diagnosing cancer or predicting cancer-therapy outcome by detecting the expression levels of multiple markers in the same cell at the same time, and scoring their expression as being above a certain threshold, wherein the markers are from a particular pathway related to cancer, with the score being indicative or a cancer diagnosis or a prognosis for cancer-therapy failure. This method can be used to diagnose cancer or predict cancer-therapy outcomes for a variety of cancers. The simultaneous co-expression of at least two markers in the same cell from a subject is a diagnostic for cancer and a predictor for the subject to be resistant to standard cancer therapy. The markers can come from any pathway involved in the regulation of cancer, including specifically the PcG pathway and the "stemness" pathway. The markers can be mRNA, DNA, or protein.

These and other embodiments of the present invention rely at least in part upon the novel finding that the expression of multiple markers above a threshold level in the same cell at the same time, wherein the markers are found within pathways related to cancer, can be used as an assay to diagnose cancer disorders and to predict whether a patient already diagnosed with cancer will be therapy-responsive or therapy-resistant. An element of the assay is that two or more markers are detected simultaneously within the same cell. Marker detection can be made through a variety of detection means, including bar-coding through immunofluorescence. The markers detected can be a variety of products, including mRNA, DNA, and protein. For mRNA based markers, PCR can be used as a detection means. Additionally, protein products or gene copy number can be identified through detection means known in the art. The markers detected can be from a variety of pathways related to cancer. Suitable pathways for markers within the scope of the present invention include any pathways related to oncogenesis and metastasis, and more specifically include the Polycomb group (PcG) chromatin silencing pathway and the "stemness" pathway.

In another embodiment, the invention is directed to a method for diagnosing cancer or predicting cancer-therapy outcome in a subject, said method comprising the steps of:

a) obtaining a sample from the subject, b) selecting a marker from a pathway related to cancer, c) screening for a simultaneous aberrant expression level of two or more markers in the same cell from the sample, and d) scoring their expression level as being aberrant when the expression level detected is above or below a certain detection threshold coefficient, wherein the detection threshold coefficient is determined by comparing the expression levels of the samples obtained from the subjects to values in a reference database of sample phenotypes obtained from subjects with either a known diagnosis or known clinical outcome after therapy, wherein the presence of an aberrant expression level of two or more markers in individual cells and presence of cells aberrantly expressing two or more such markers is indicative of a cancer diagnosis or a prognosis for cancer-therapy failure in the subject. The subset of markers to be used within the methods of the present invention include any markers associated with cancer pathways.

In preferred embodiments, the markers can be selected from the genes identified in FIGS. 27-38. The markers can comprise anywhere ranging from two markers listed within each table up to the whole set of genes listed within each of these tables. The markers can comprise any percentage of genes selected from each of these tables, including 90%, 80%, 70%, 60%, or 50% of the genes identified in FIGS. 27-38.

In this method, an aberrant co-expression level of the markers can be indicative of the presence of cancer in the subject, or predictive of cancer-therapy failure in the subject. The markers can be selected from any suitable cancer pathway, including in preferred embodiments markers from the Polycomb or "stemness" pathway. These markers can be genes selected from the group consisting of ADA, AMACR+p63, ANK3, BCL2L1, BIRC5, BMI-1, BUB1, CCNB1, CCND1, CES1, CHAF1A, CRIP1, CRYAB, ESM1, EZH2, FGFR2, FOS, Gbx2, HCFC1, IER3, ITPR1, JUNB, KLF6, KI67, KNTC2, MGC5466, Phc1, RNF2, Suz12, TCF2, TRAP100, USP22, Wnt5A and ZFP36. In preferred embodiments, the markers are selected from the group consisting of BMI1, Ezh2, H2A, H3, transcription factors, and methylation patterns. In one preferred embodiment, the aberrant co-expression level detected is of BMI1 and Ezh2, and in another preferred embodiment the aberrant co-expression level detected is of H2A and H3. The markers being detected are in the form of either mRNA, DNA, or protein.

In a preferred embodiment, the sample phenotypes are selected from the group consisting of cancer, non-cancer, recurrence, non-recurrence, relapse, non-relapse, invasiveness, non-invasiveness, metastatic, non-metastatic, localized, tumor size, tumor grade, Gleason score, survival prognosis, lymph node status, tumor stage, degree of differentiation, age, hormone receptor status, PSA level, histologic type, and disease free survival.

The aberrant expression level of two or more markers can be detected by any detection means known in the art, including, but not limited to, subjecting the cells to an analysis selected from the group consisting of multicolor quantitative immunofluorescence co-localization analysis, fluorescence in situ hybridization, and quantitative RT-PCR analysis.

In another embodiment, the present invention is directed to a method of determining a detection threshold coefficient for classifying a sample phenotype from a subject, the method comprising the steps of:
a) obtaining a sample from the subject,
b) selecting two or more markers from a pathway related to cancer,
c) screening for a simultaneous aberrant expression level of the two or more markers in the same cell from the sample;
d) scoring the marker expression in the cells by comparing the expression levels of the samples obtained from the subjects to values in a reference database of samples obtained from subjects with either a known diagnosis or known clinical outcome after therapy, and
e) determining the detection threshold coefficient for the sample classification accuracy at different detection thresholds using reference database of samples from subjects with known phenotypes.

Detection threshold coefficients which are indicative of a cancer diagnosis or a prognosis for cancer-therapy failure have an absolute value within the range of .gtoreq.0.5. to .gtoreq.0.999. Preferred levels of detection threshold coefficients which are indicative of a cancer diagnosis or a prognosis for cancer-therapy failure have an absolute value of .gtoreq.0.5, .gtoreq.0.6, .gtoreq.0.7, .gtoreq.0.8, .gtoreq.0.9, .gtoreq.0.95, .gtoreq.0.99, .gtoreq.0.995., and .gtoreq.0.999.

In another embodiment, the method further comprises determining the best performing magnitude of said detection threshold and using said magnitude to assess the reliability of said established detection threshold in classifying a sample phenotype. In another embodiment, the method further comprises using the best performing magnitude of said detection threshold to score an unclassified sample and assign a sample phenotype to said sample.

In another embodiment, the present invention is directed to a method for simultaneously detecting an aberrant co-expression level of two or more markers a single cell, said method comprising the steps of:
a) obtaining a sample of tissue,
b) selecting a marker defined by a pathway,
c) screening for a simultaneous aberrant expression level of the two or more markers, and
d) scoring their expression level as being aberrant when the expression level detected is above or below a certain detection threshold coefficient, wherein the detection threshold coefficient is determined by comparing the expression levels of the samples obtained from the subjects to values in a reference database of sample phenotypes obtained from subjects with either a known diagnosis or known clinical outcome after therapy.

The present invention is also directed to kits useful in detecting the simultaneous aberrant co-expression levels of two or more markers in a single cell.

A. Chromosomal locations of genes encoding transcripts comprising a 50-gene cancer therapy outcome signature.

B-D. Annotated haplotypes associated with the MCM6 (B), STK6 (C), and NUP62 (D) genes in CEU, YRI, CHB, and JPT HapMap populations. Stars indicate SNPs with population-specific profiles of genotype and allele frequencies.

Figure 3A:
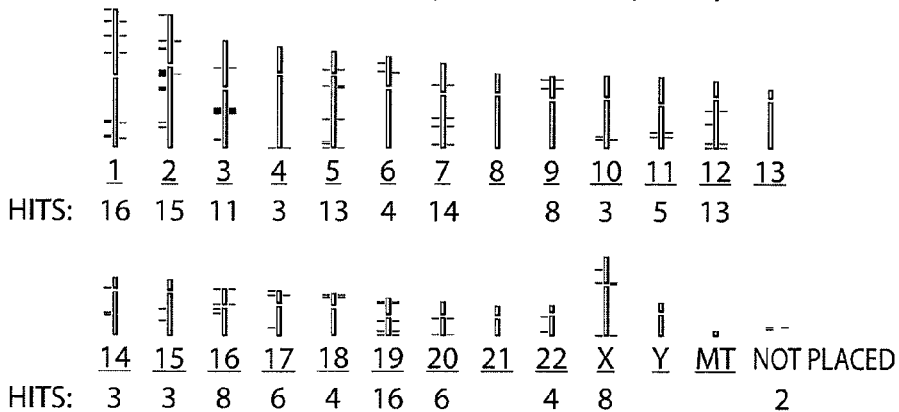
Figures 1, 3B:
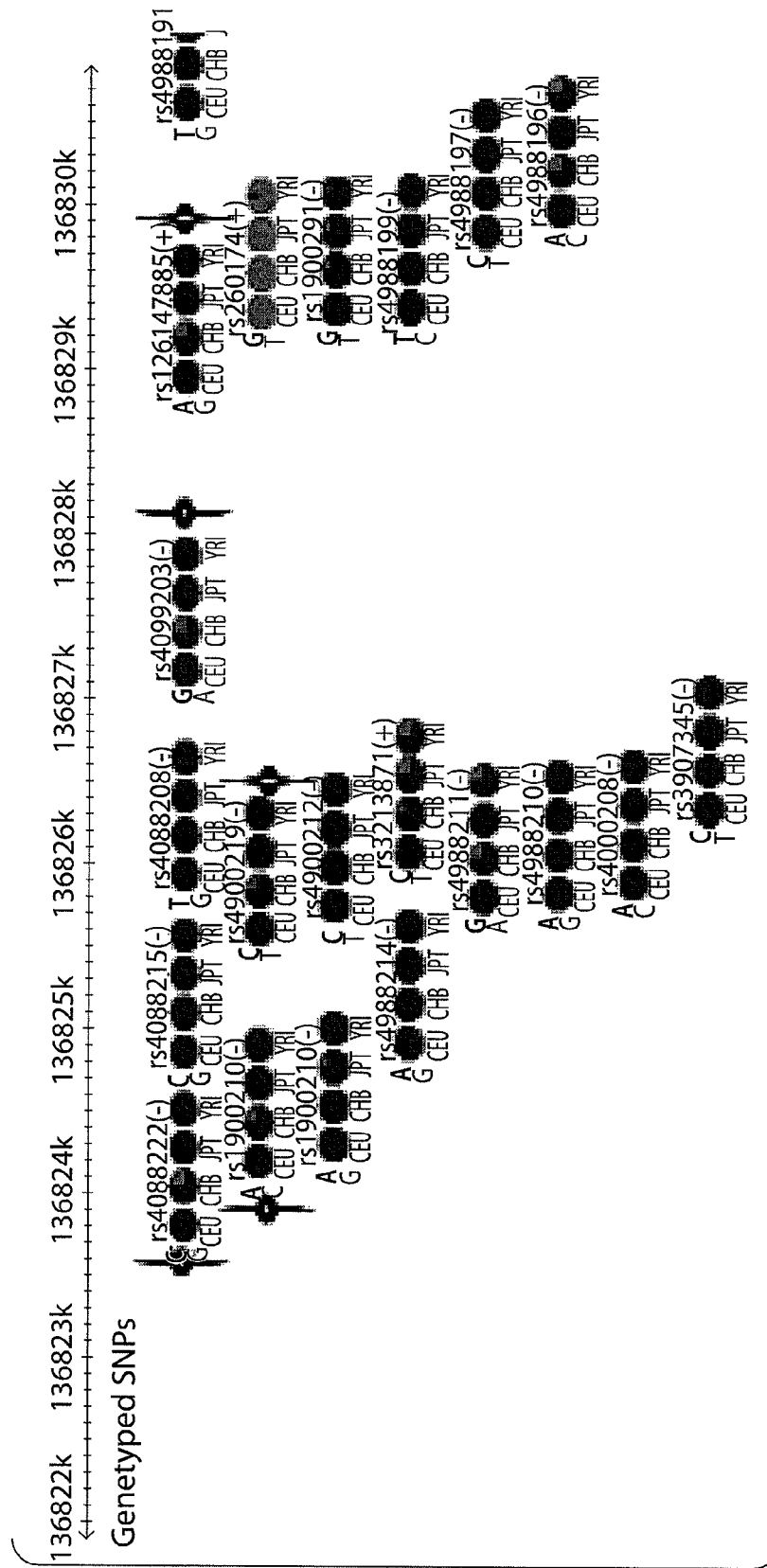
Figures 2, 3B:
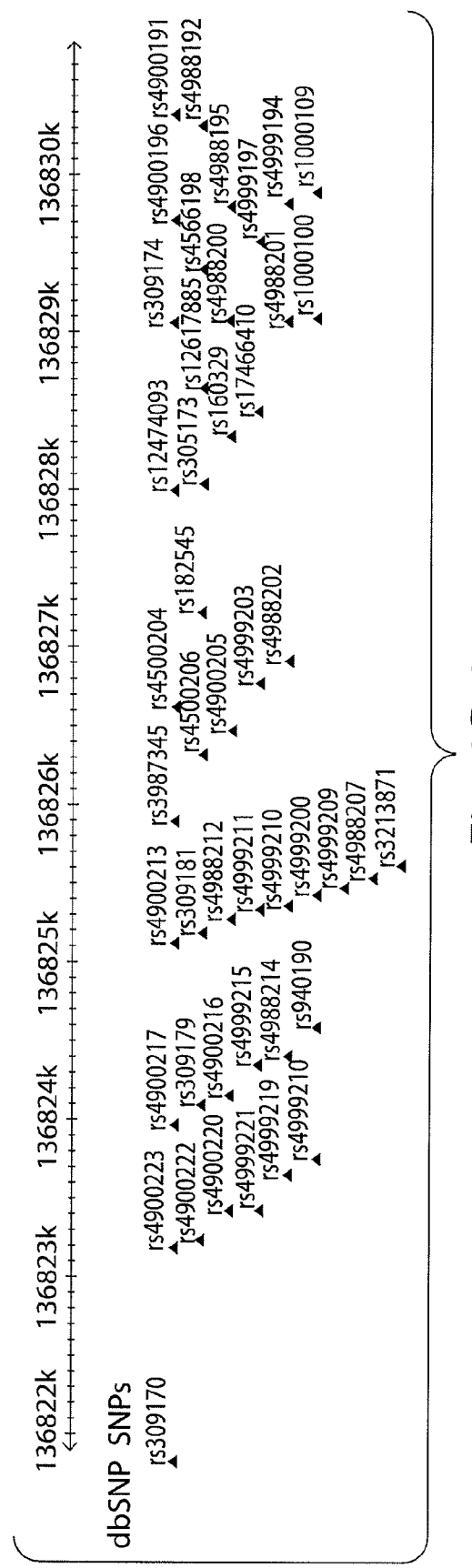
Figures 3, 3B:
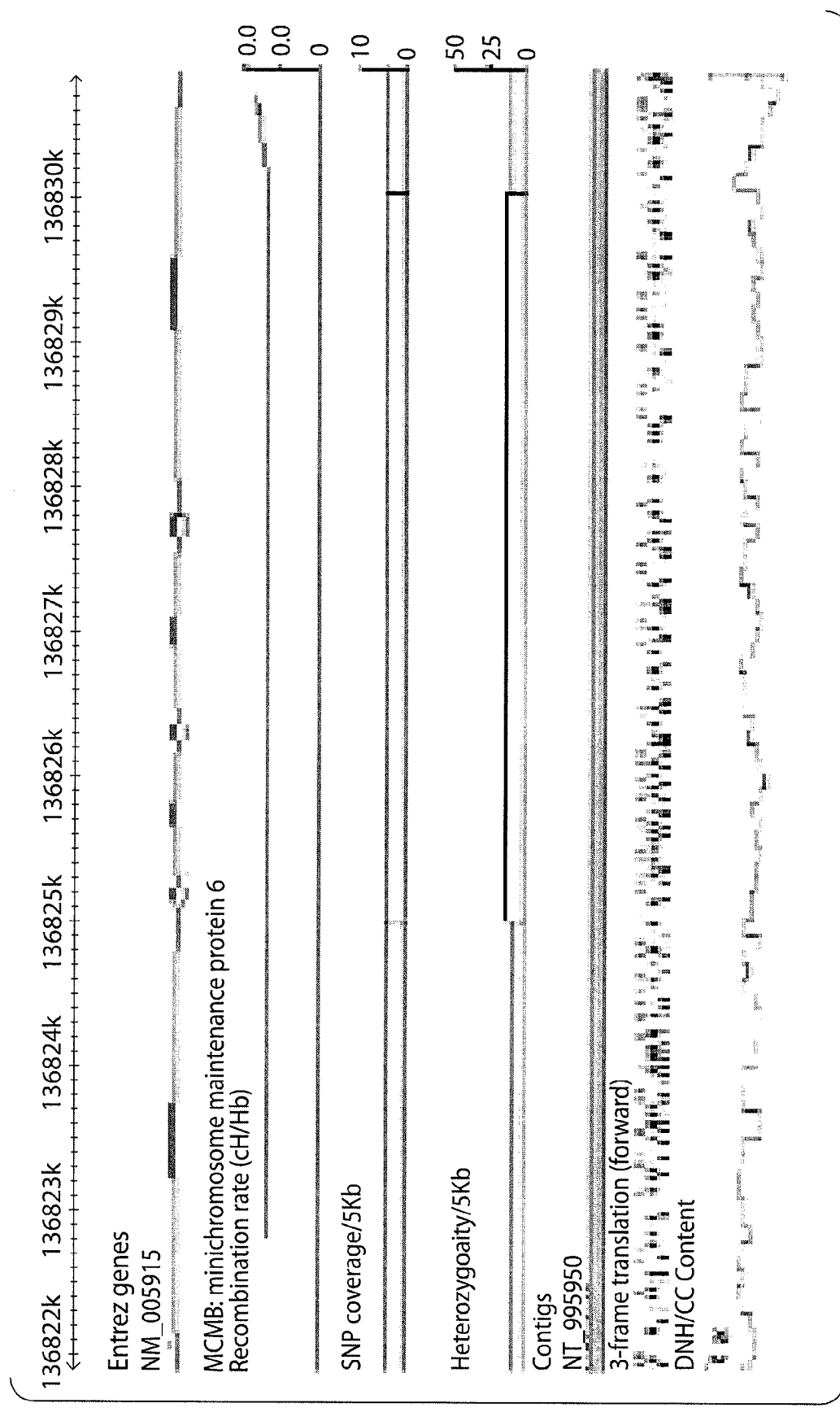
Figures 3, 3B, 4:
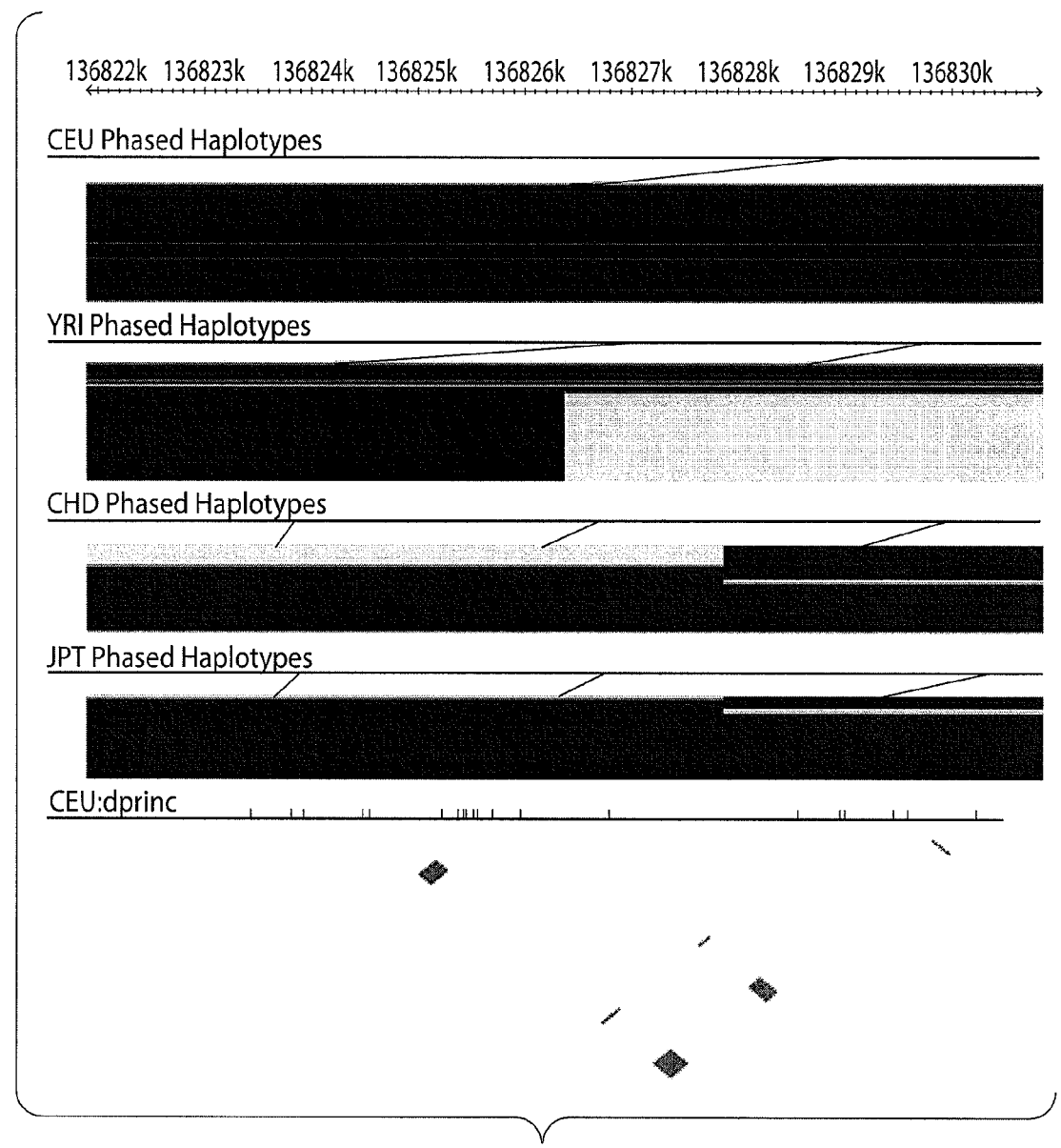
Figures 1, 3C:
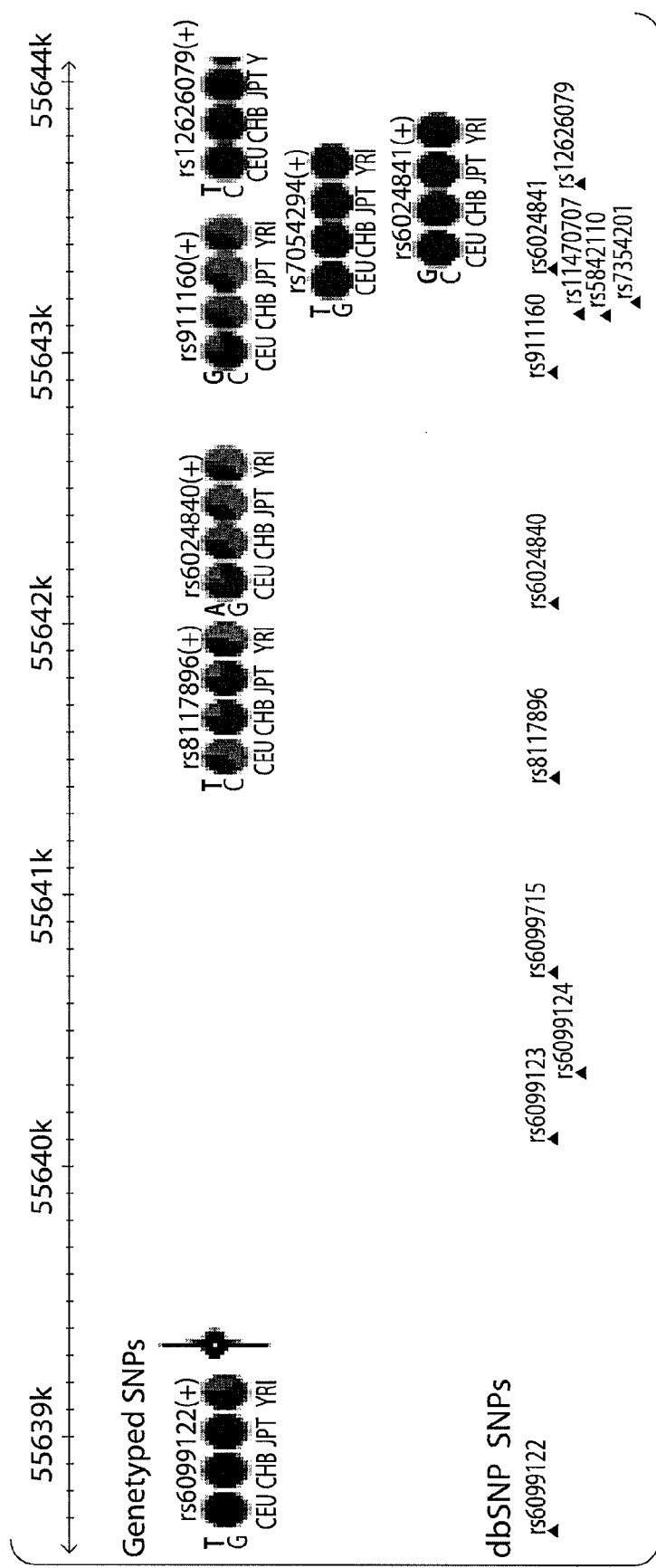
Figures 2, 3C:
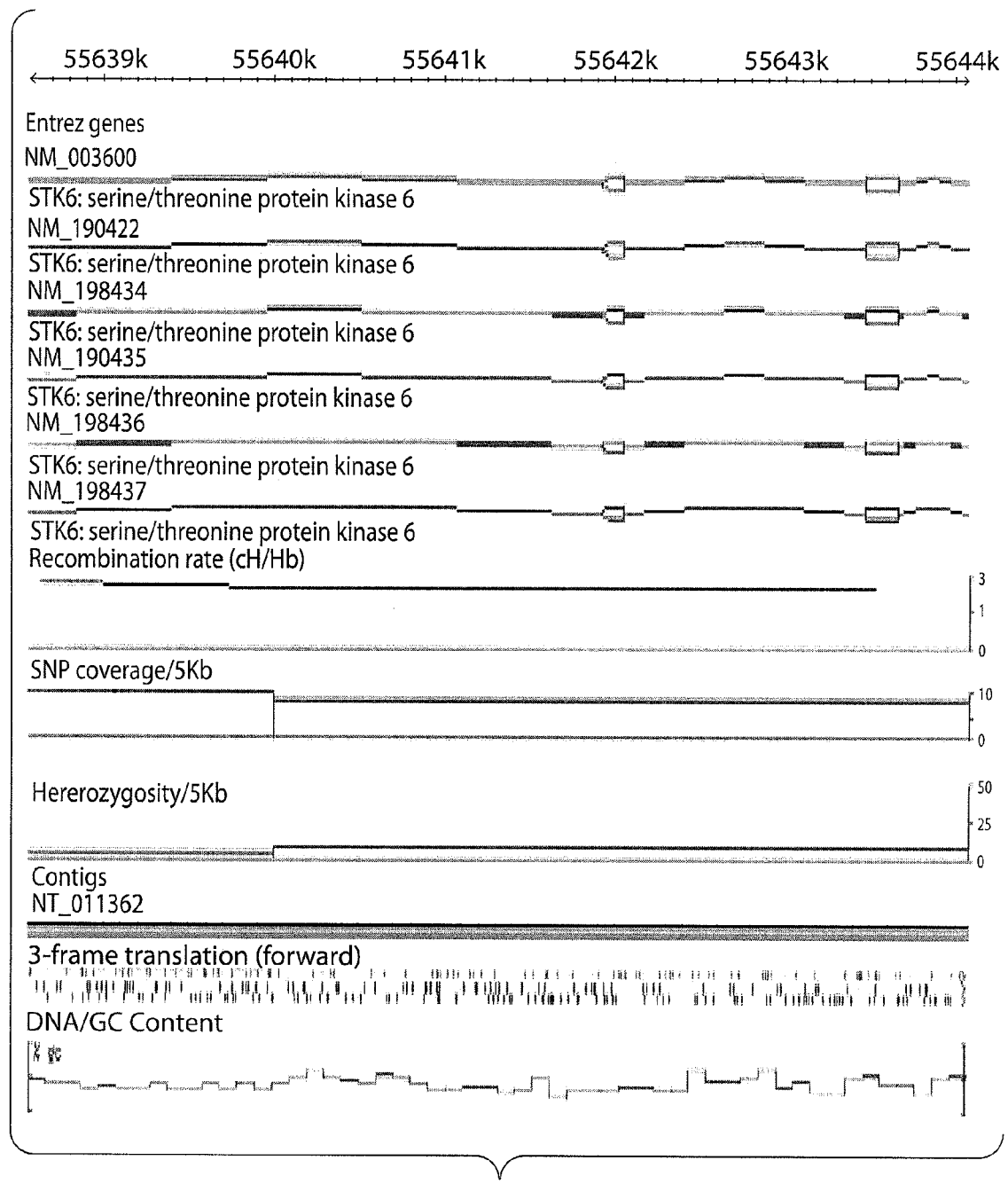
Figures 3, 3C:
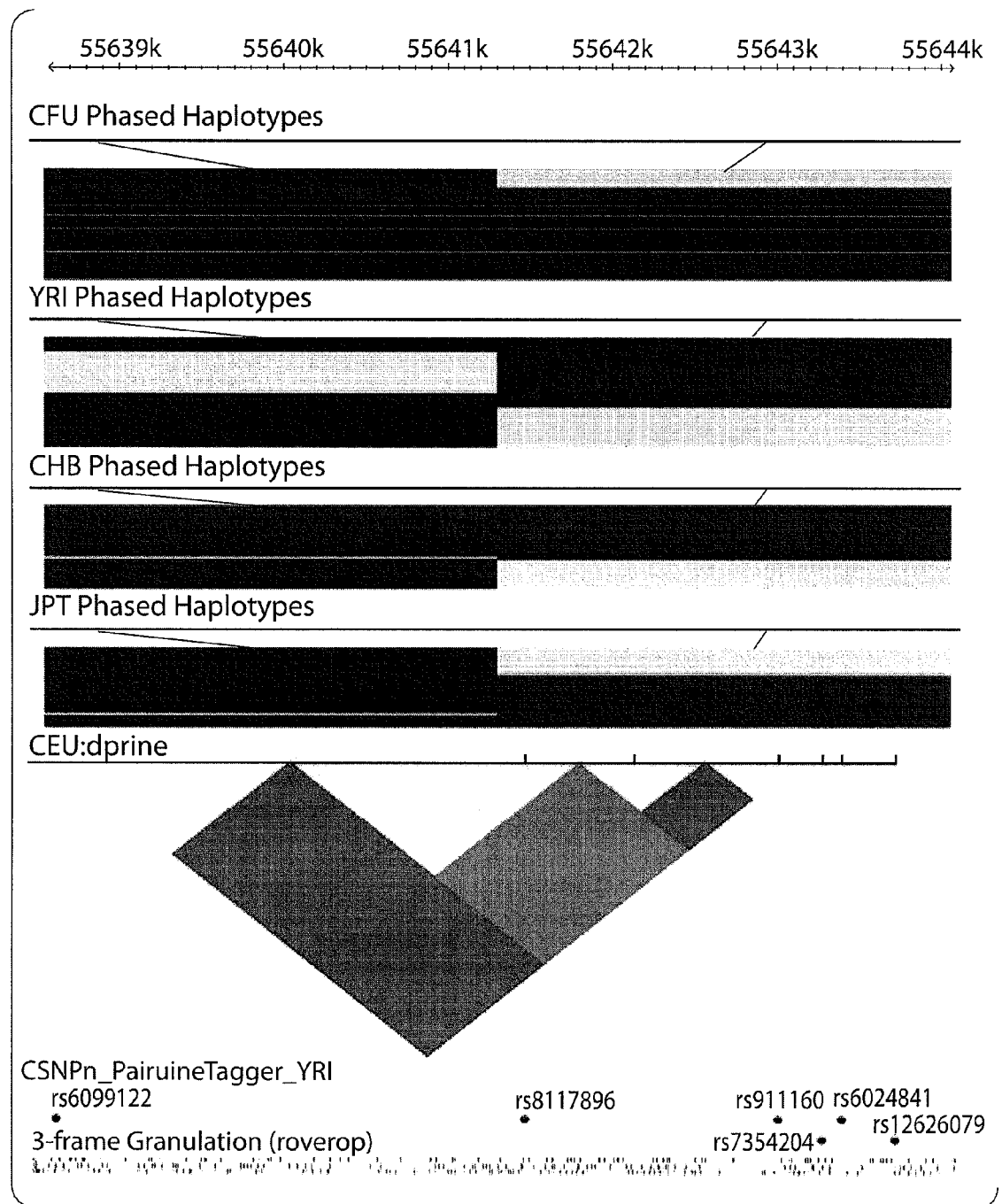
Figures 1, 3D:
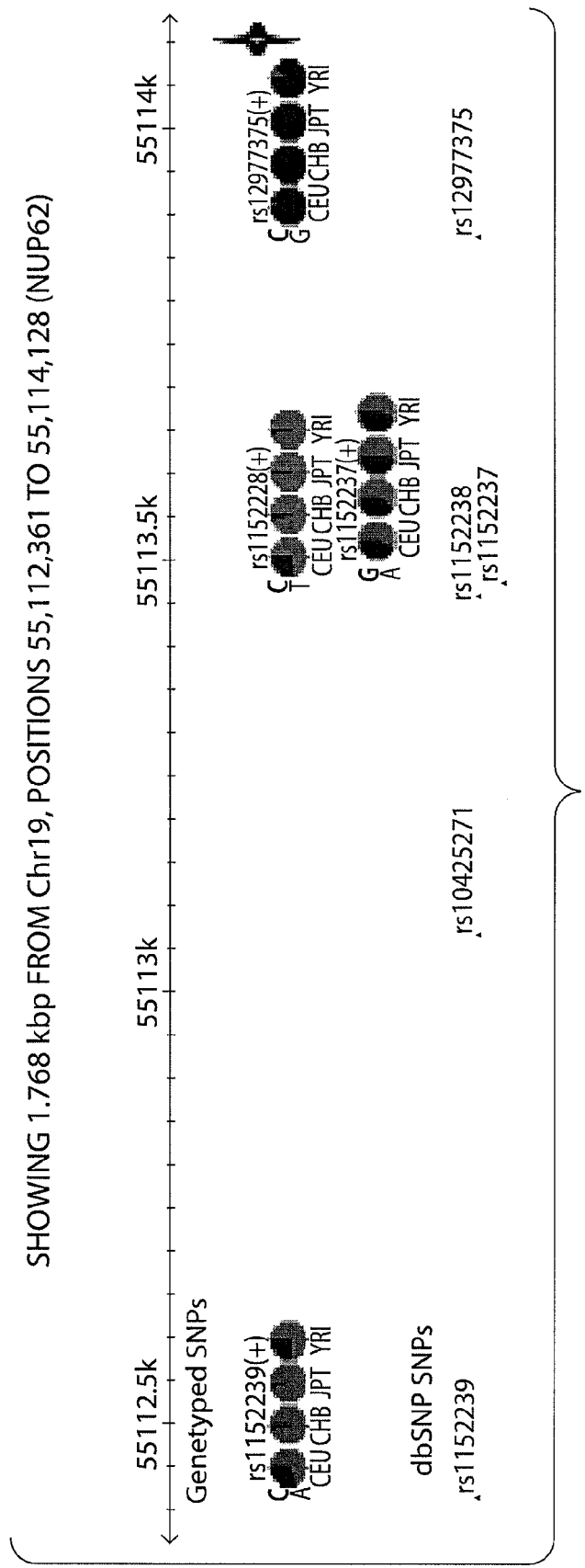
Figures 2, 3D:
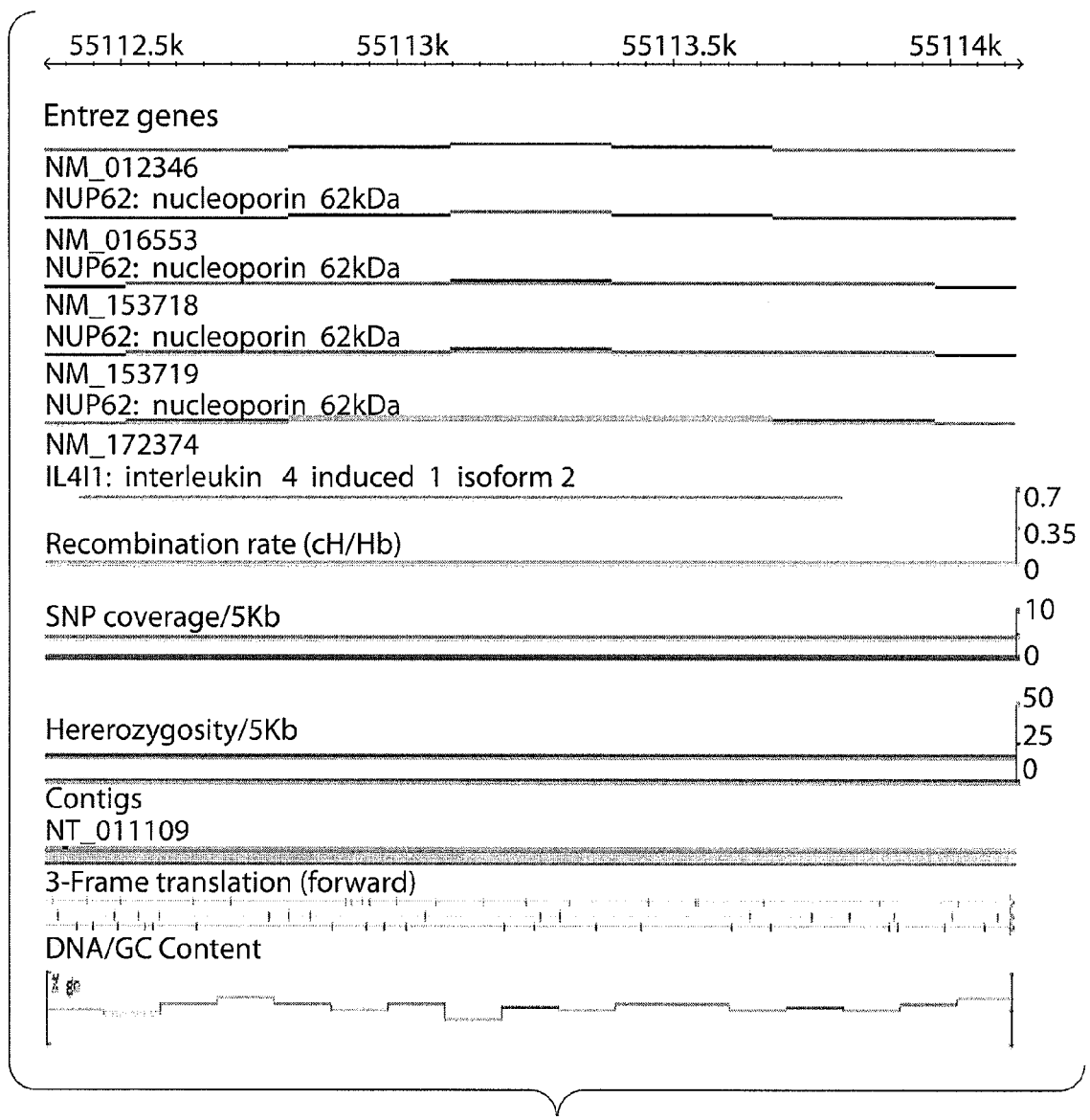
Figures 3, 3D:
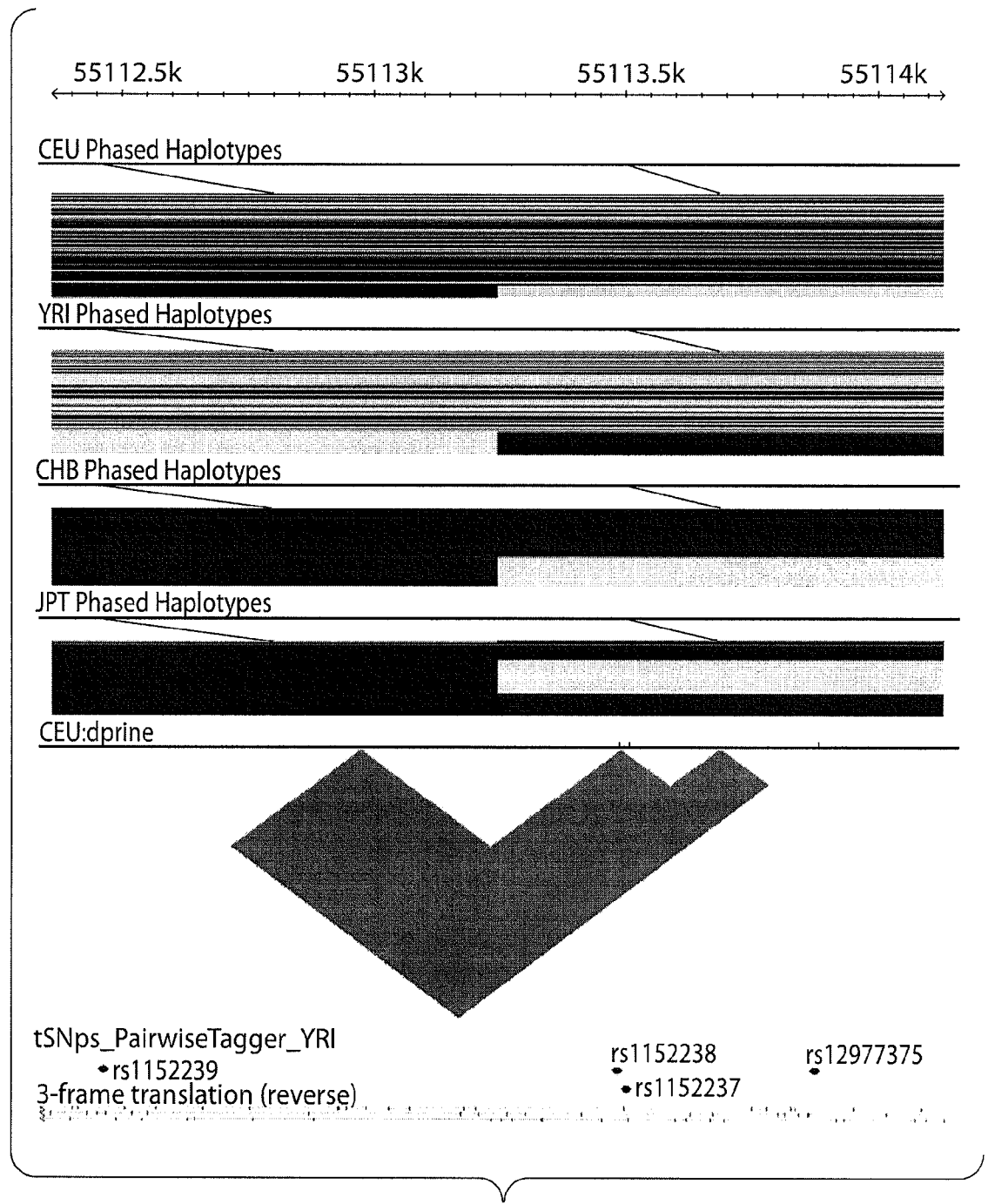
Figures 1, 4A:
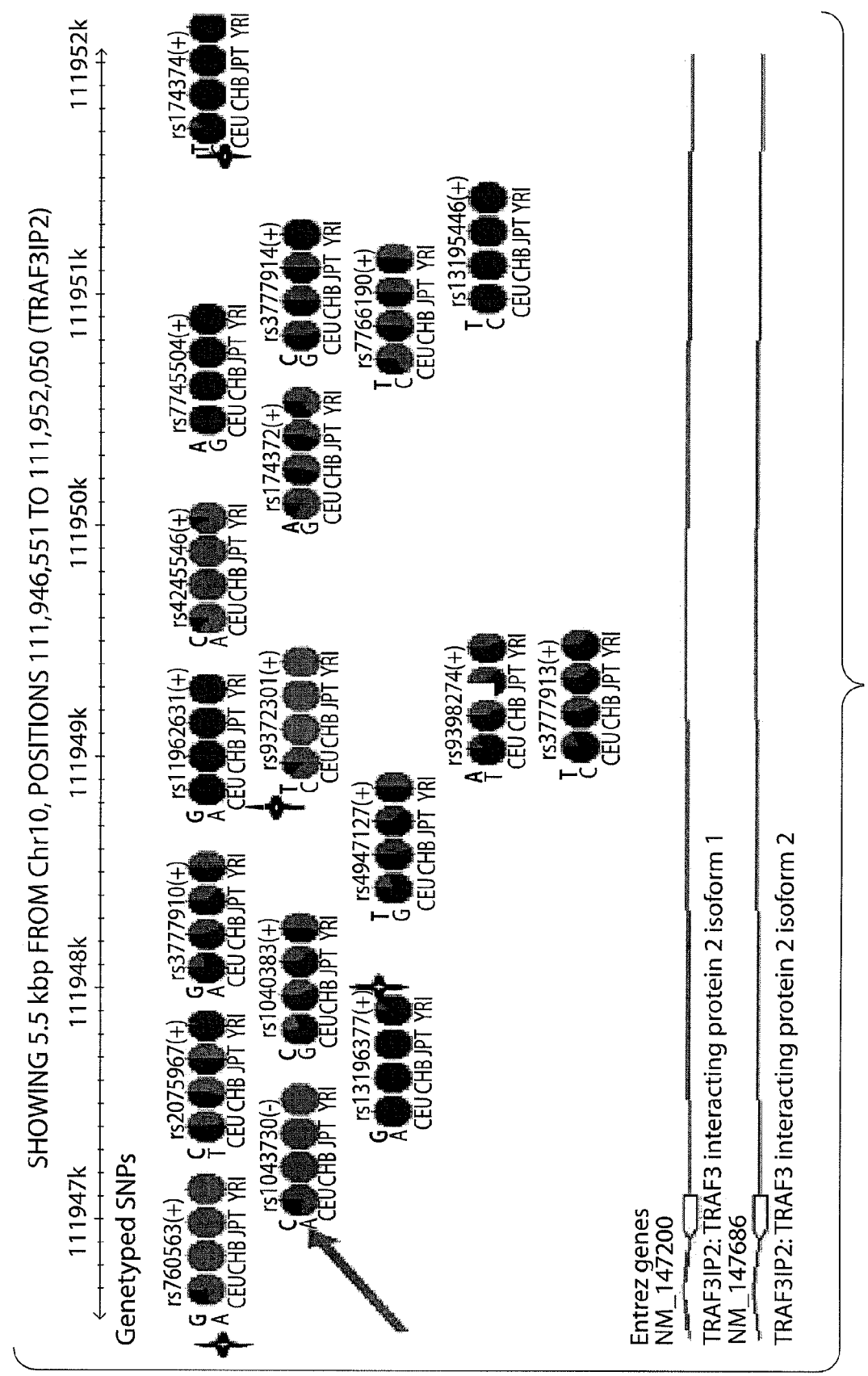
Figures 2, 4A:
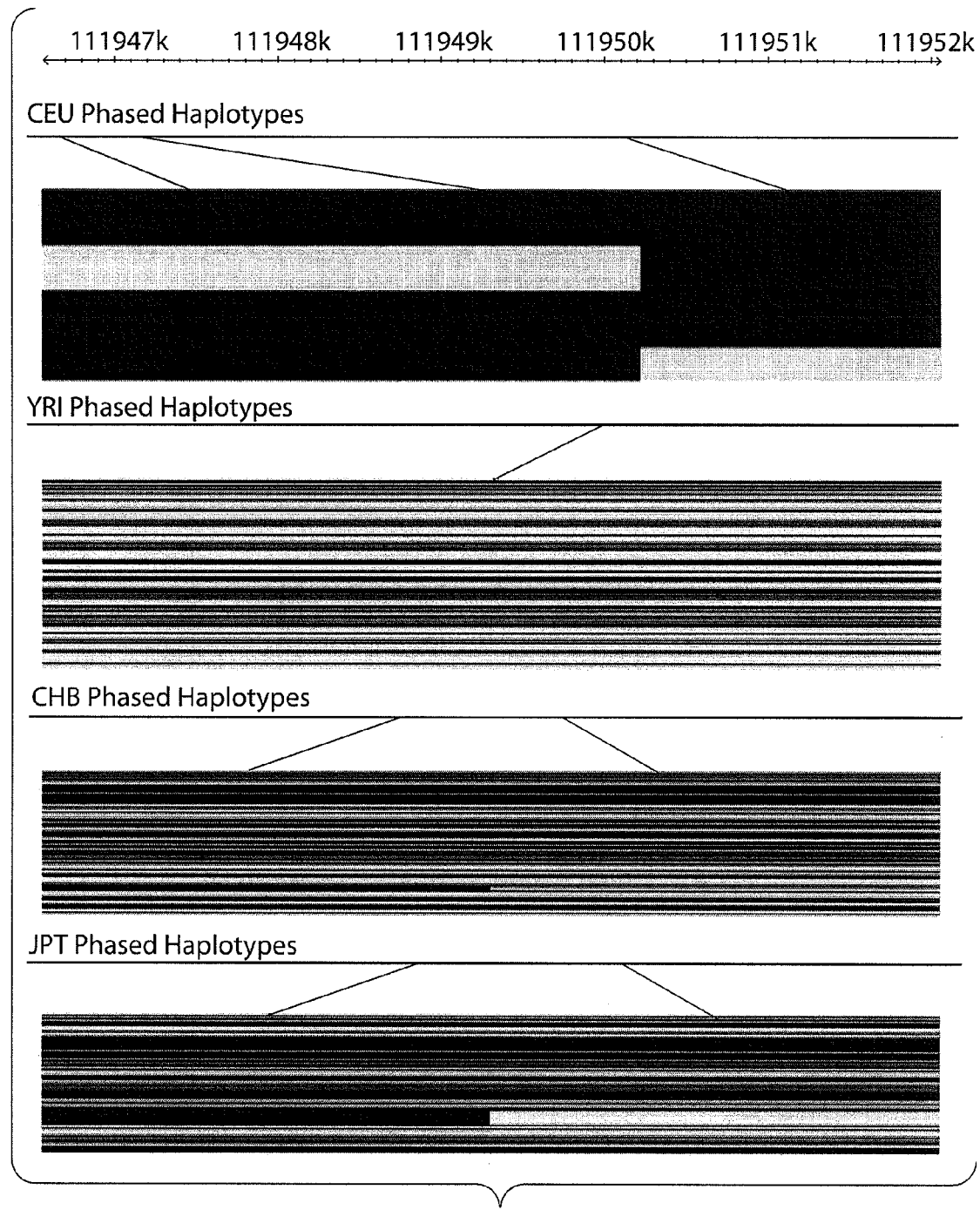
Figures 1, 4B:
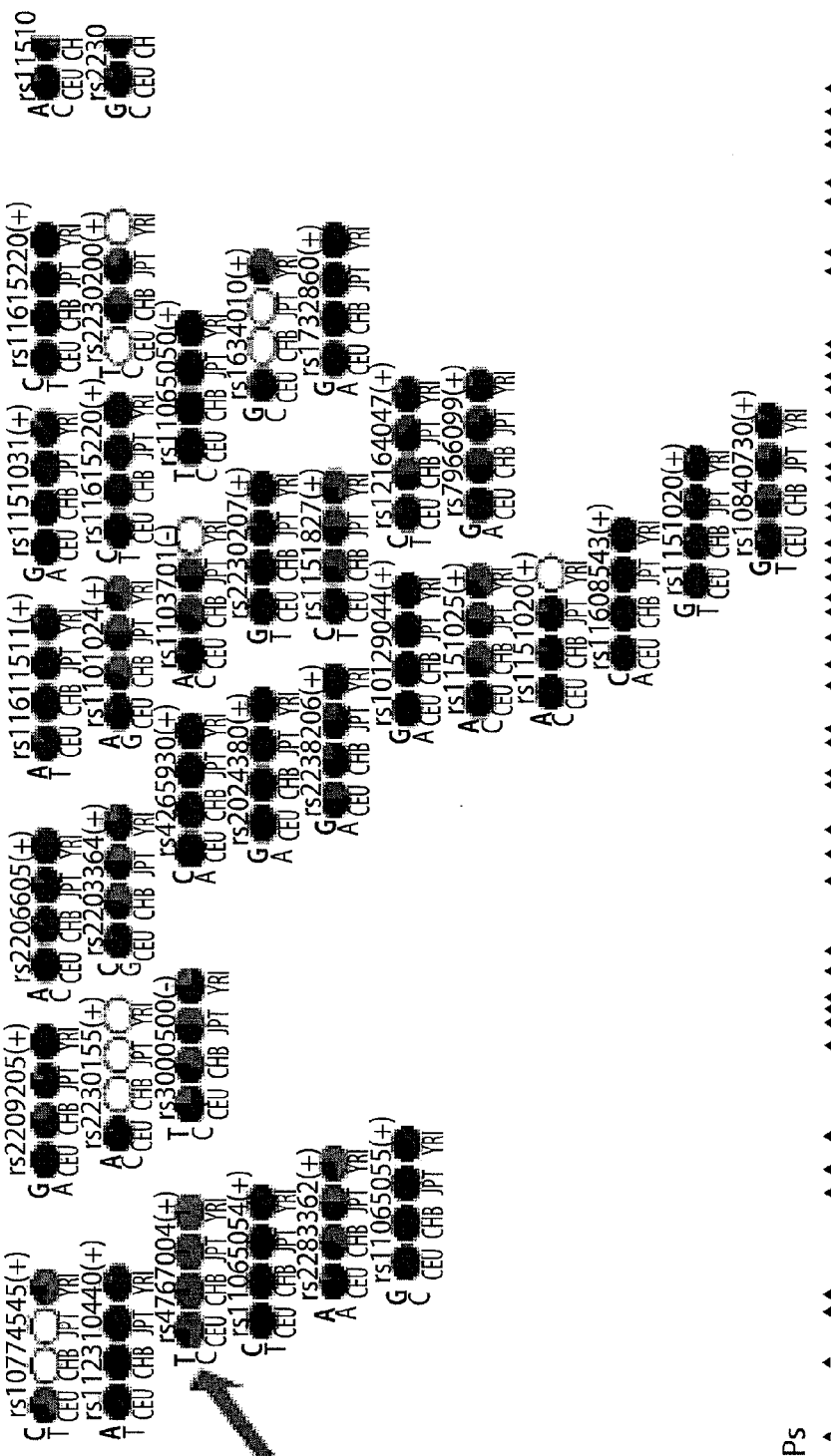
Figures 2, 4B:
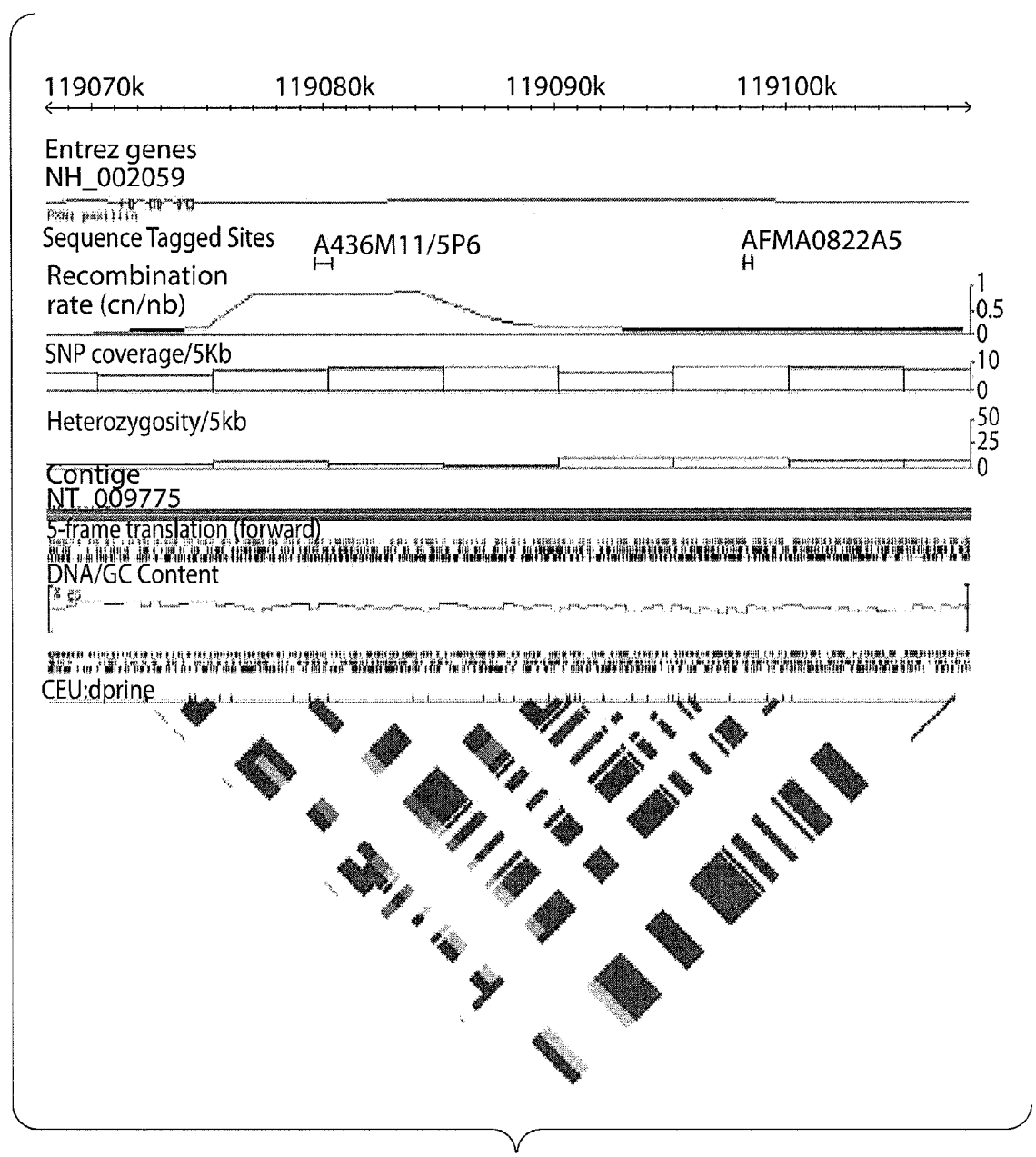
Figures 3, 4B:
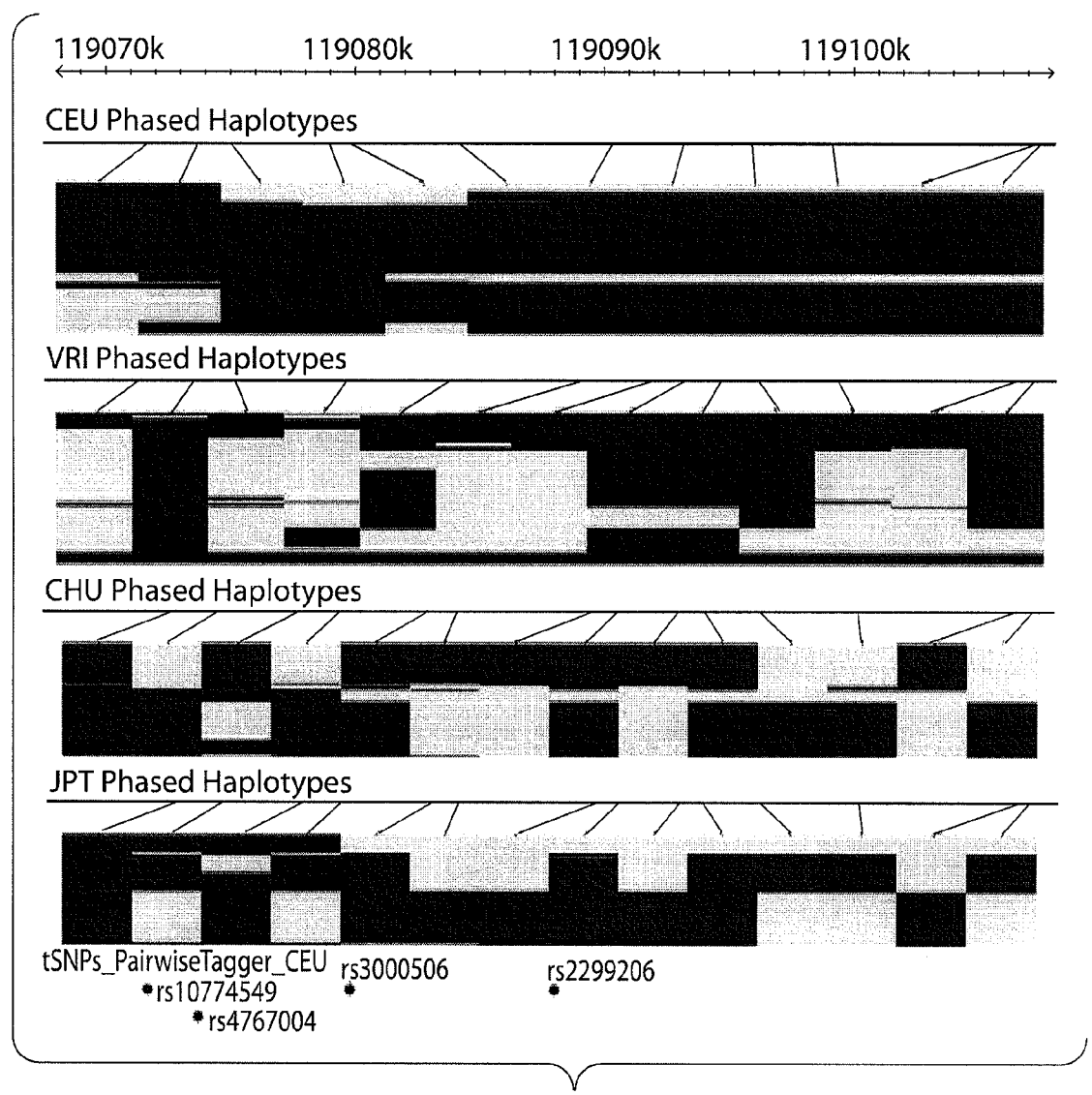
Figures 1, 4C:
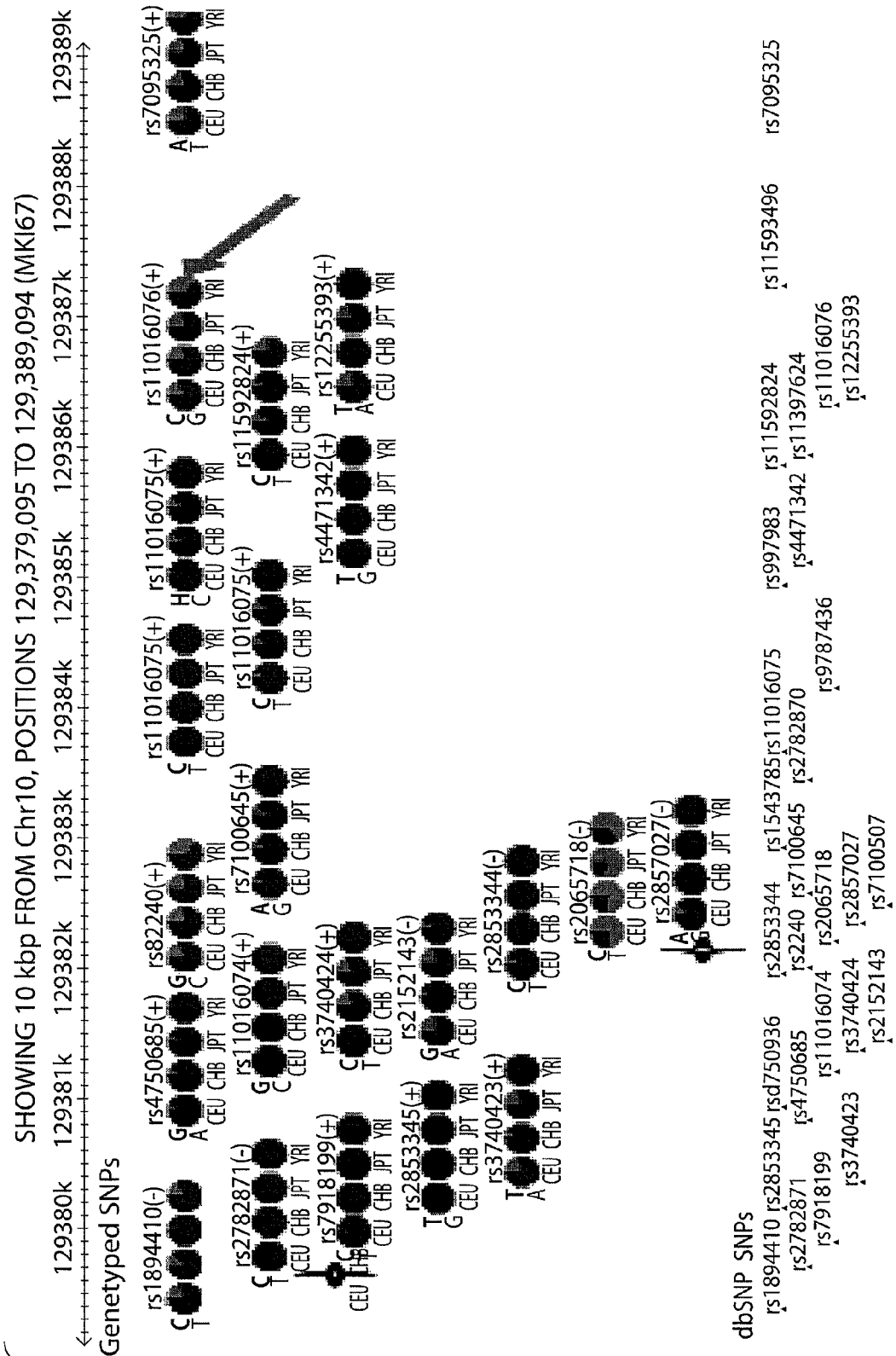
Figures 2, 4C:
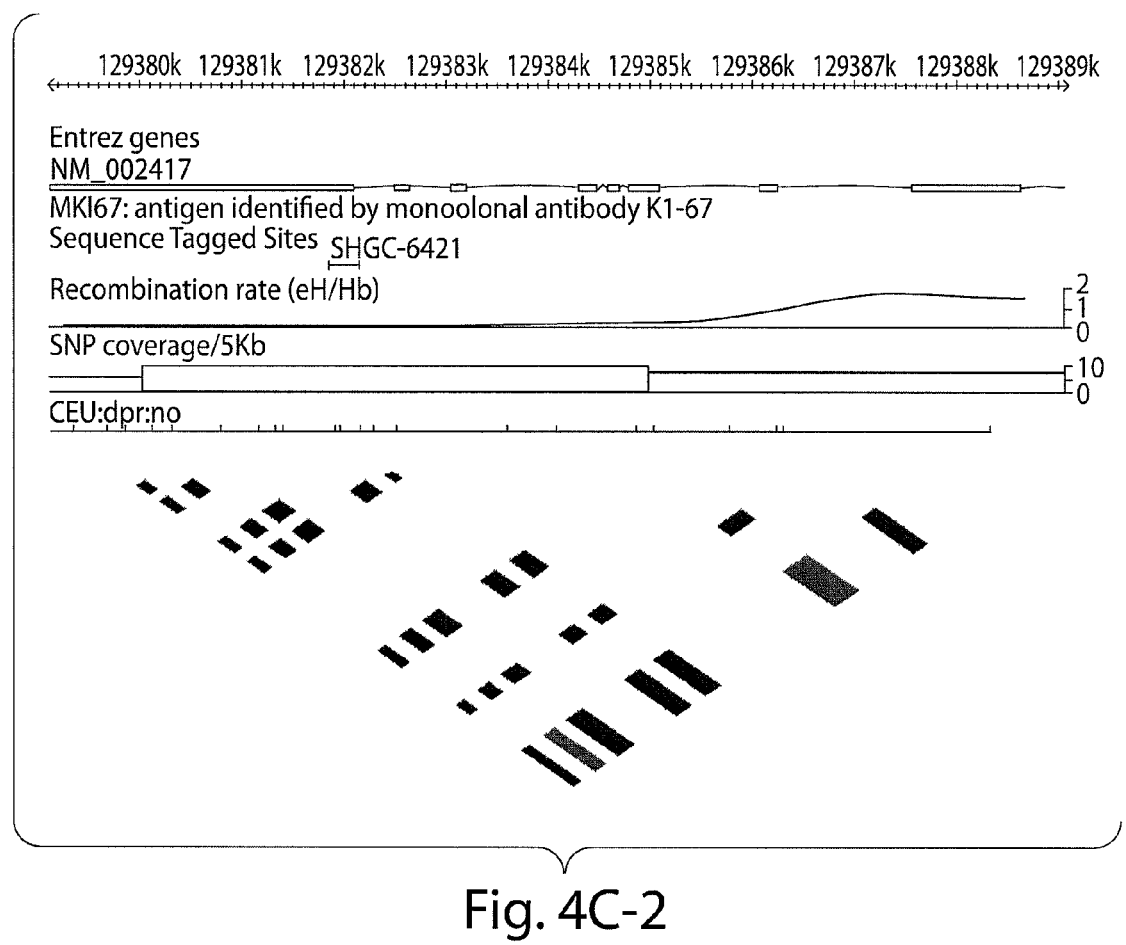
Figures 3, 4C:
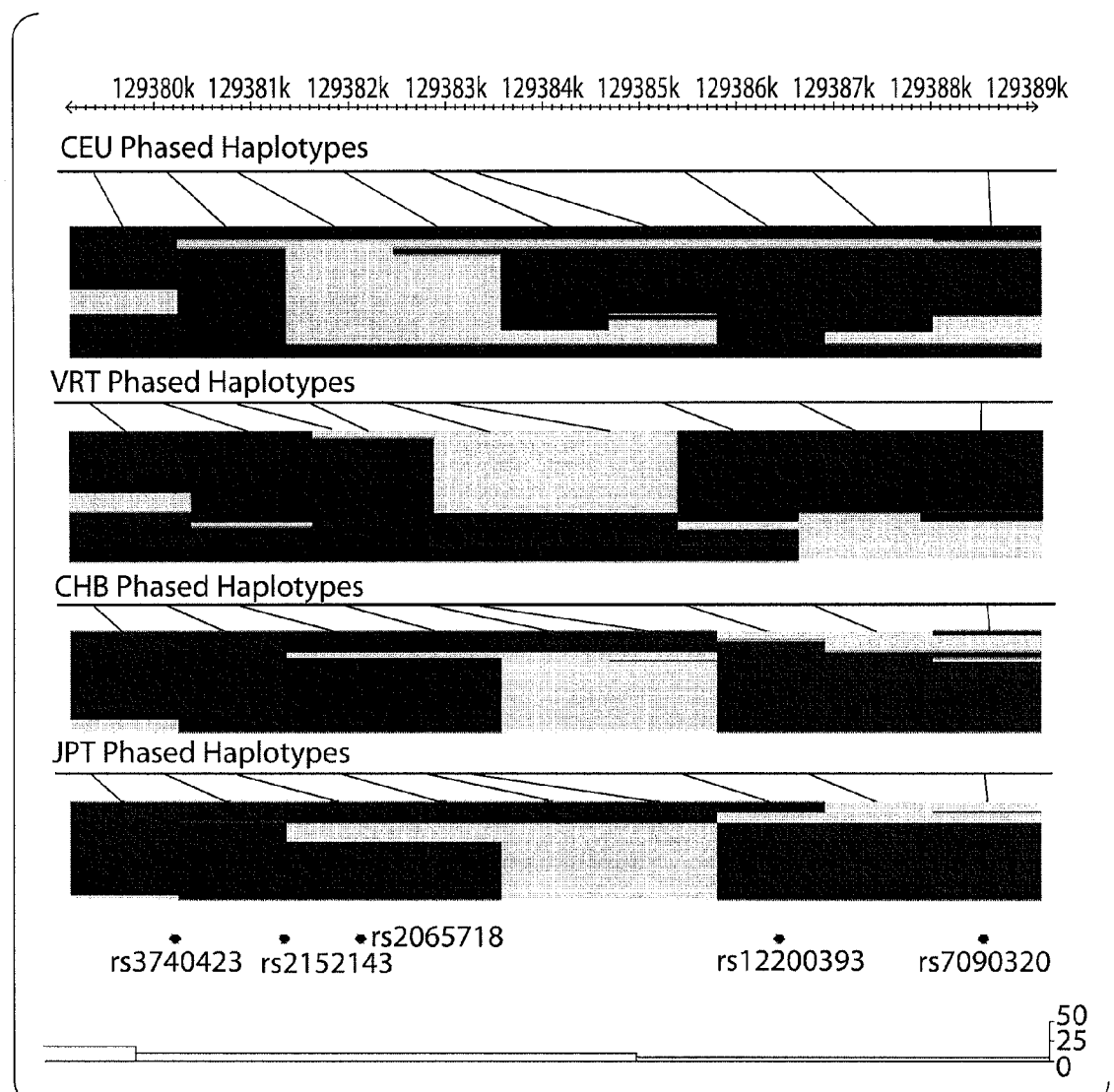
Figure 4D:
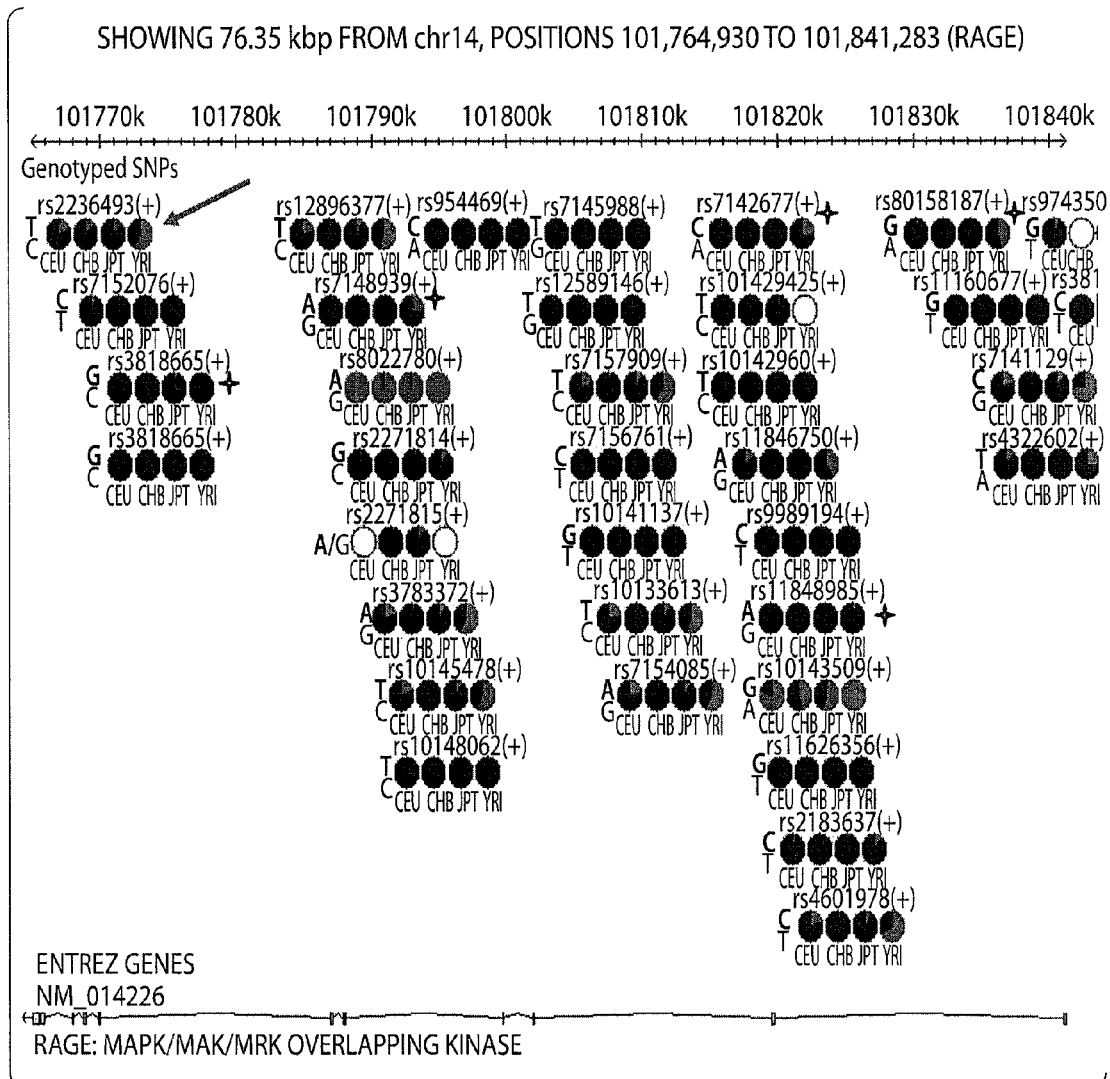
Figures 1, 5A:
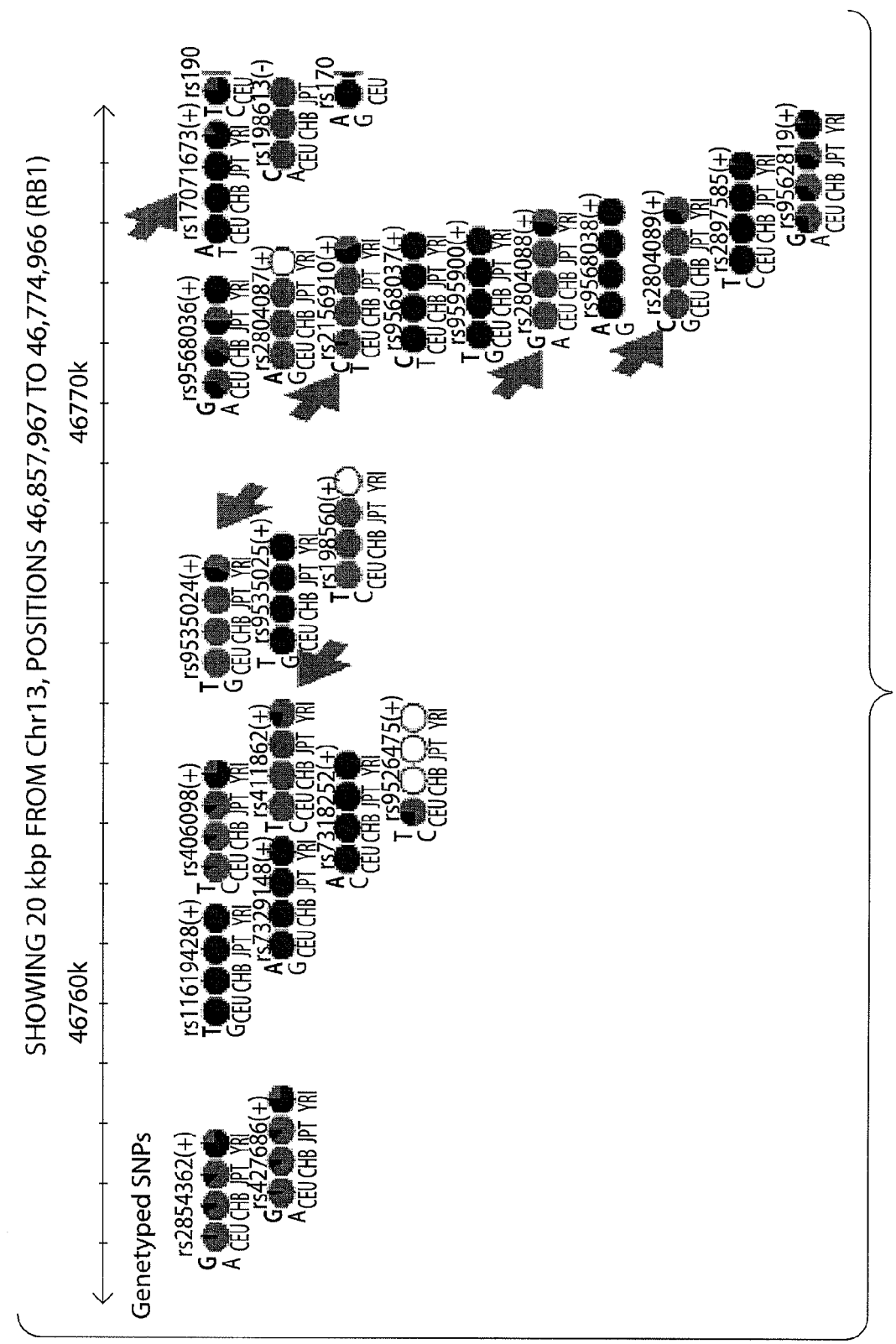
Figures 2, 5A:
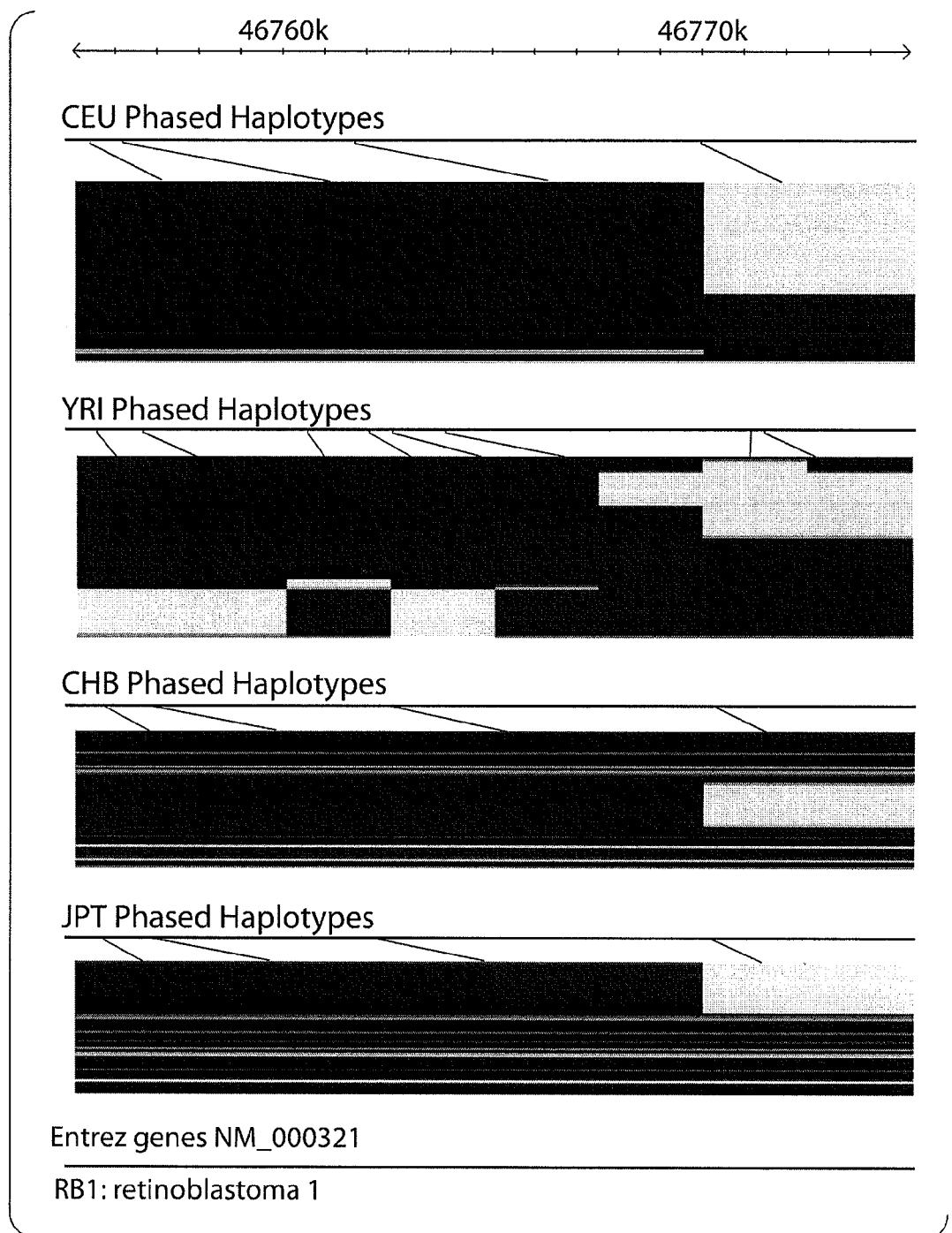
Figure 5B:
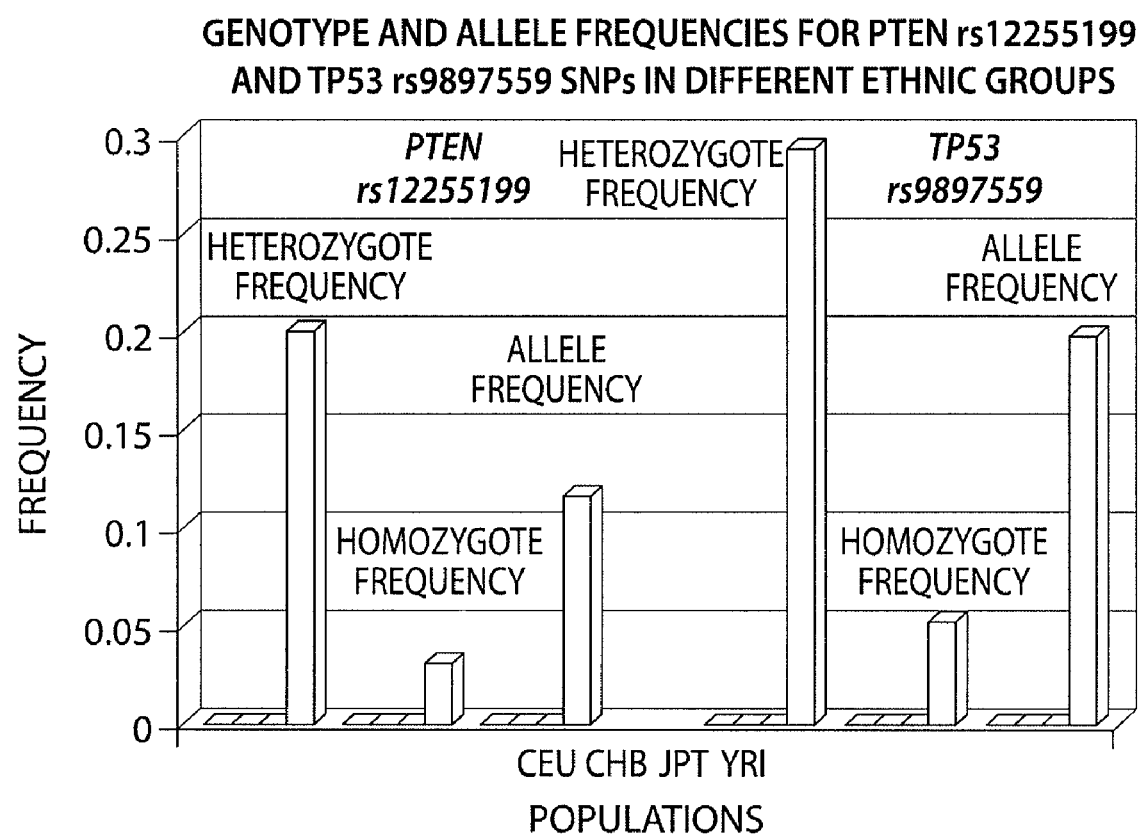
Figure 5C:
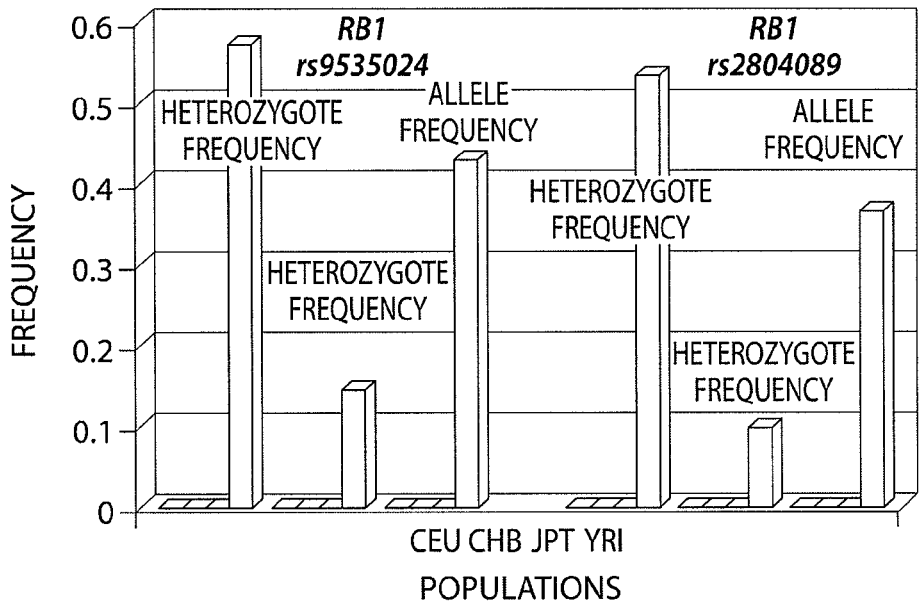
Figure 5D:
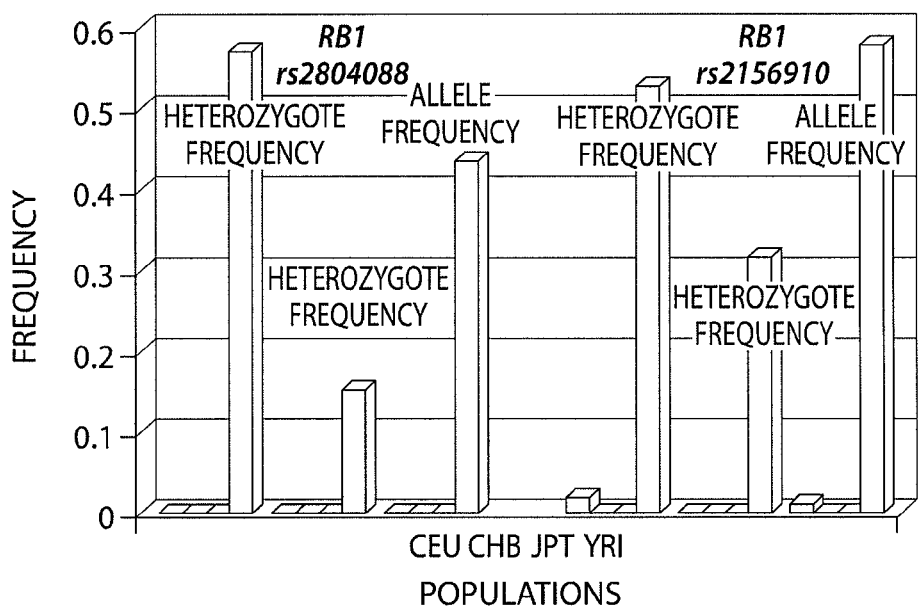
Figure 5E:
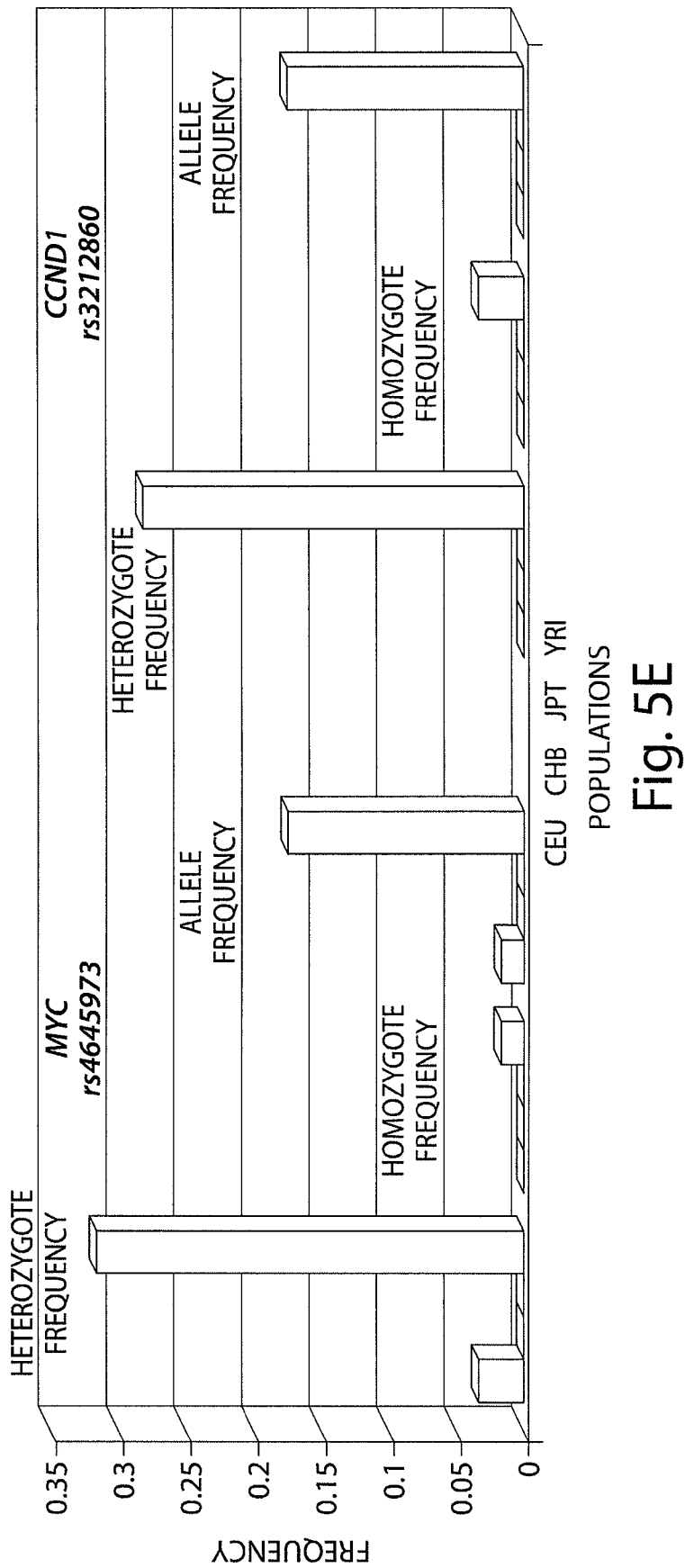
Figure 5F:
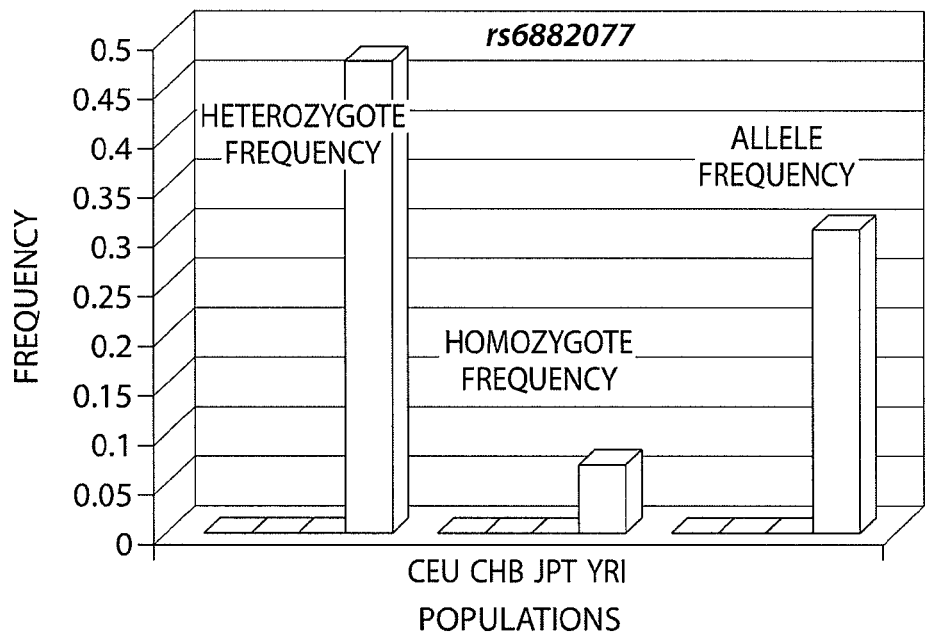
Figure 5G:
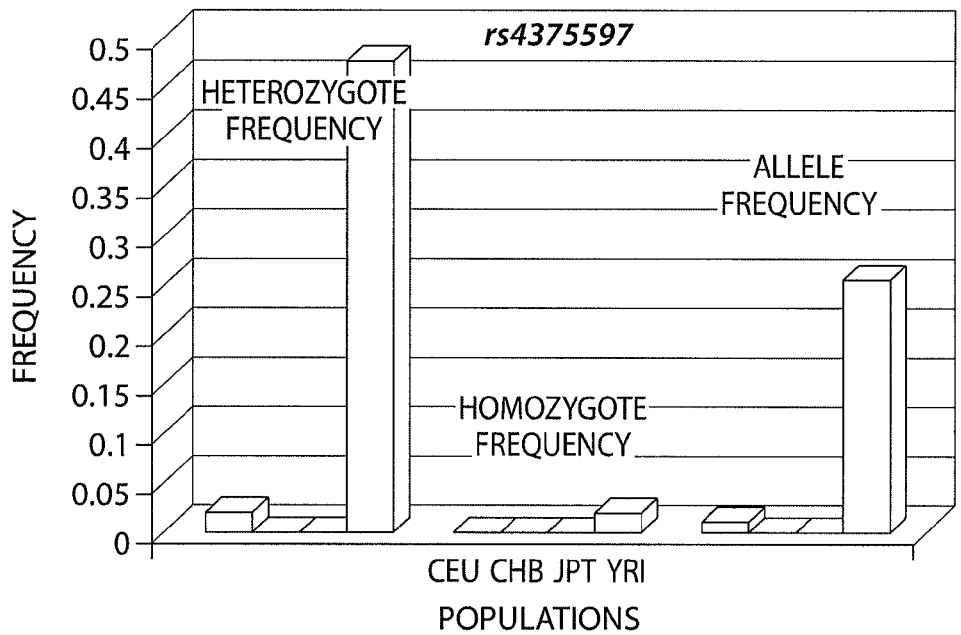

FIG. 4 shows HapMap analysis identifying non-synonymous coding SNPs associated with CTOP genes and manifesting population-specific profiles of genotype and allele frequencies.

A-D. Annotated haplotypes associated with the TRAF3IP2 (A), PXN (B), MKI67 (C), and RAGE (D) genes in CEU, YRI, CHB, and JPT HapMap populations. Arrows indicate non-synonymous coding SNPs with population-specific profiles of genotype and allele frequencies.

Figures 1, 20:
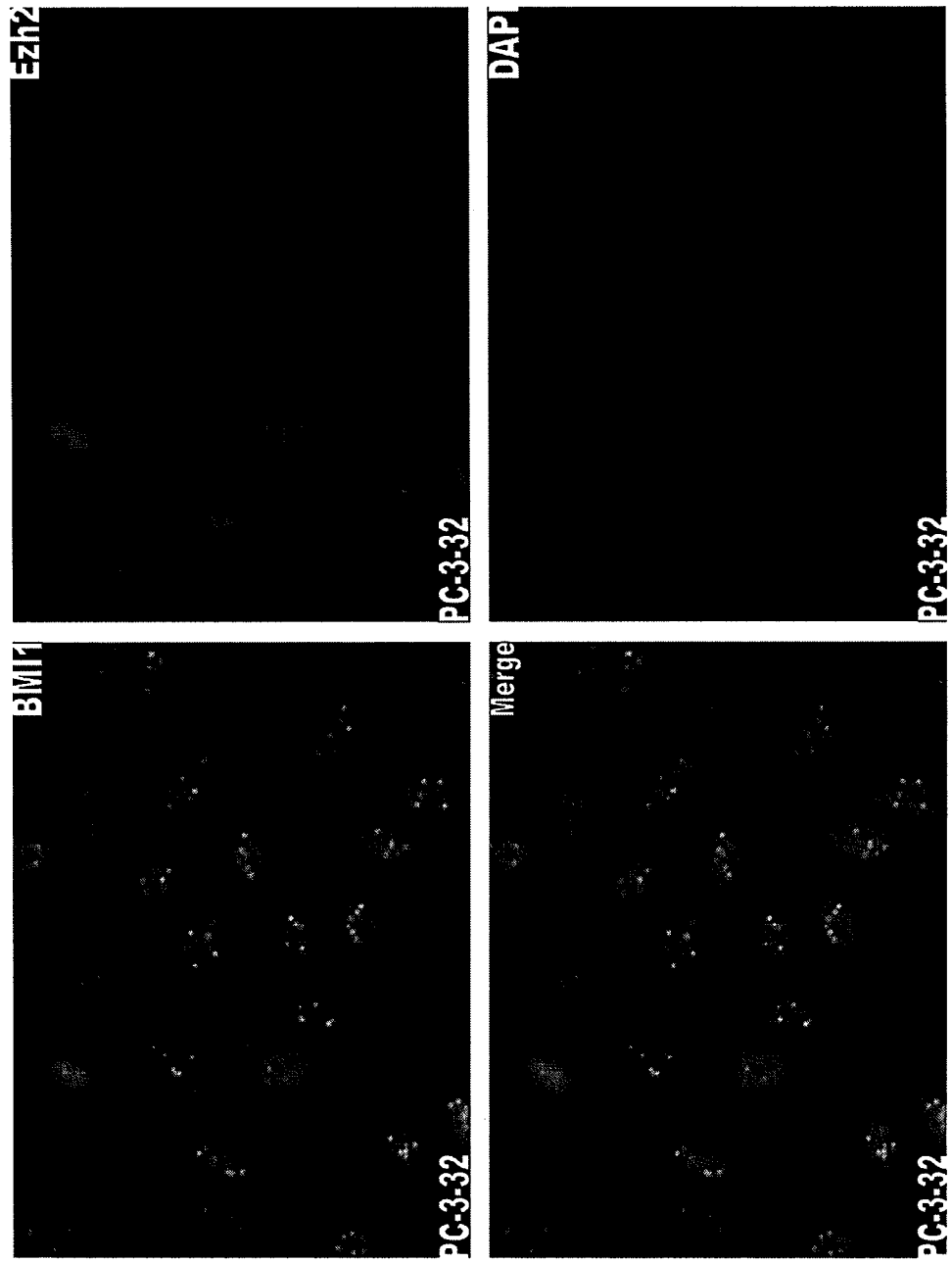
Figures 2, 20:
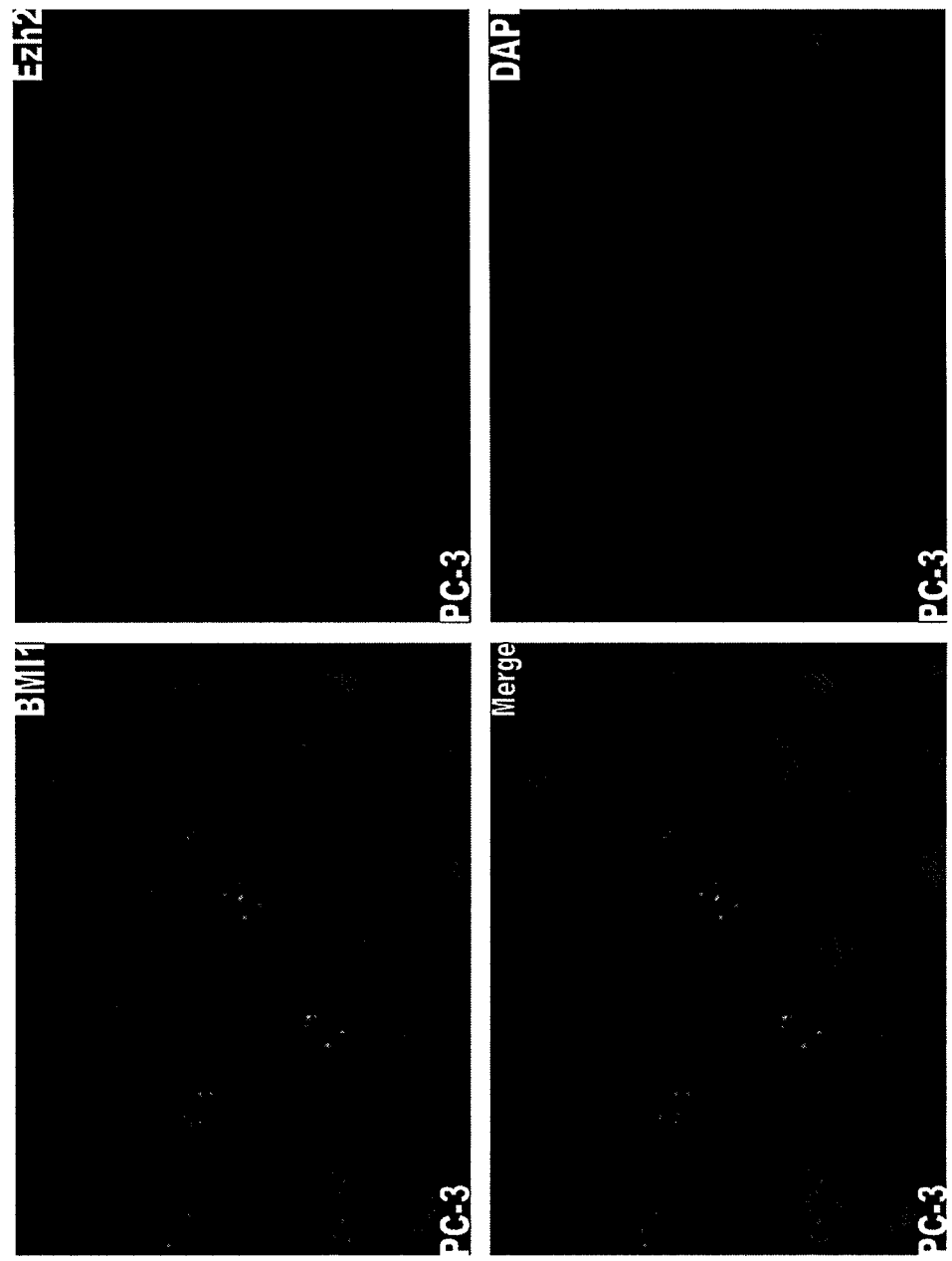
Figures 3, 20:
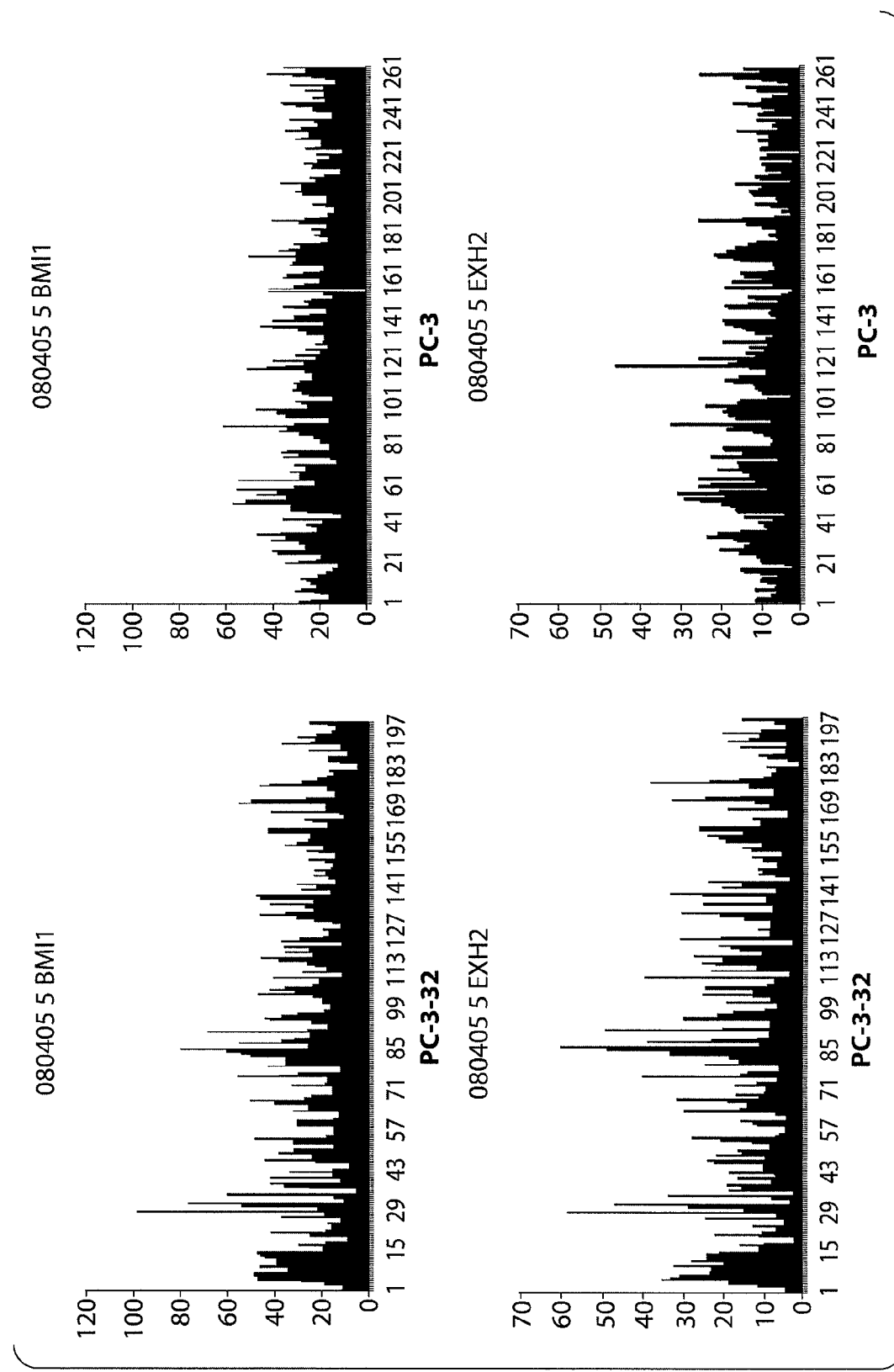
Figures 4, 20:
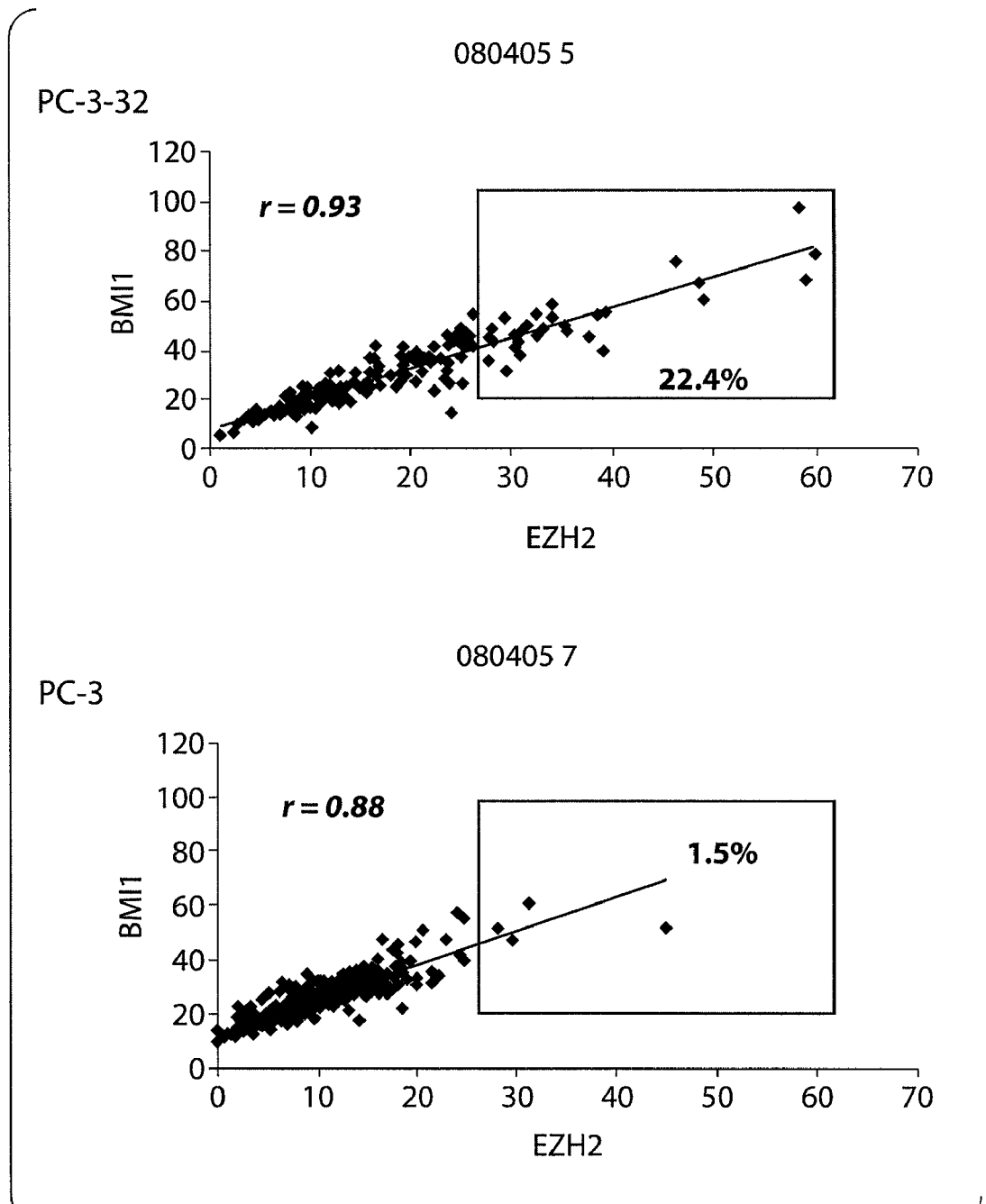
Figures 5, 20:
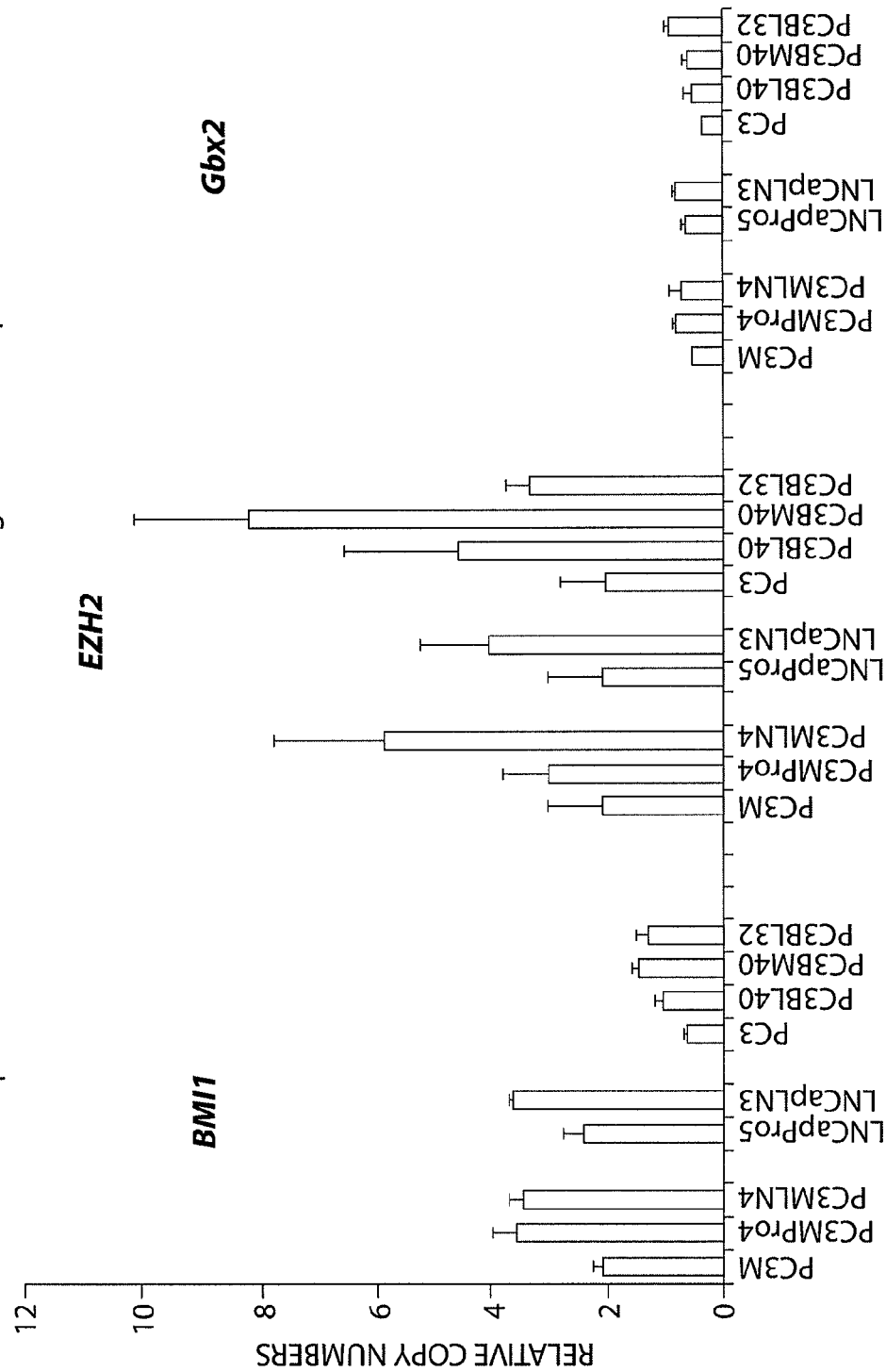

FIG. 5 shows population-specific profiles of genotype and allele frequencies of SNPs associated with oncogenes and tumor suppressor genes.

A. Annotated haplotypes associated with the RB1 gene in CEU, YRI, CHB, and JPT HapMap populations. Arrows indicate SNPs with population-specific profiles of genotype and allele frequencies.

B-H. Bar graph plots demonstrating population-specific profiles of genotype and allele frequencies in different HapMap populations for individual SNPs associated with oncogenes and tumor suppressor genes. For each SNP the frequencies shown within each set of bar graphs in the following order (from left to right): CEU, CHB, JPT, YRI. A, C, D, RB1 gene; B. PTEN and TP53 genes, E, MYC and CCND1; F, hTERT gene; G, AKT1 gene.

Figures 6, 20:
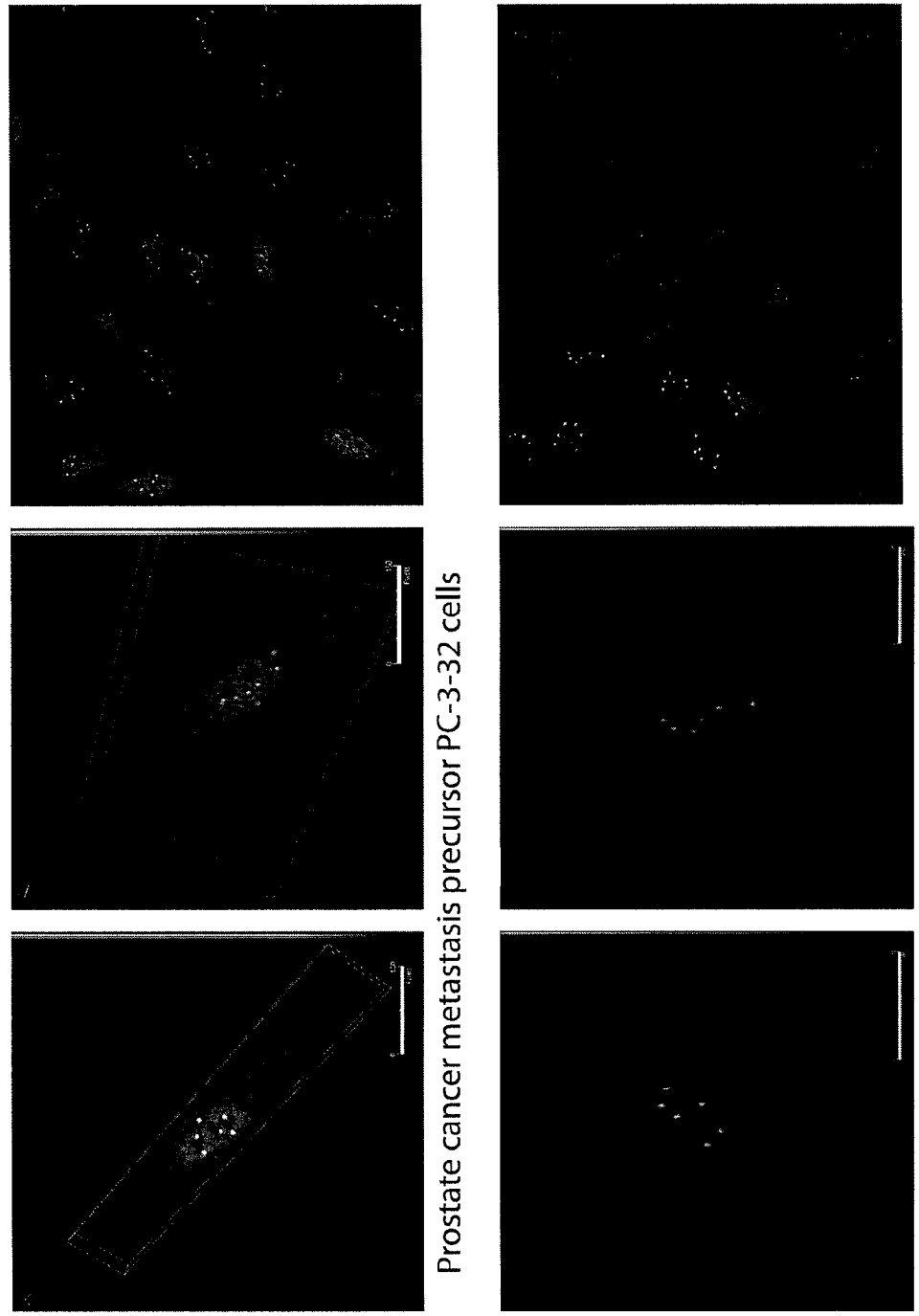

FIG. 6 shows that SNP-based gene expression signatures predict therapy outcome in prostate and breast cancer patients.

A-D. Genes expression of which is regulated by SNP variations in normal individuals provide gene expression models predicting therapy outcome in breast (A, C) and prostate (B, D) cancer patients.

A, B. Kaplan-Meier analysis of therapy outcome classification performance in breast cancer (A) and prostate cancer (B) patients of gene expression-based CTOP models generated from genetic loci expression of which is regulated by the 14q32 master regulatory locus.

C, D. Kaplan-Meier analysis of therapy outcome classification performance in breast cancer (C) and prostate cancer (D) patients of gene expression-based CTOP models generated from transcriptionally most variable genetic loci.

E-H. Genes containing high-population differentiation non-synonymous SNPs (E, F) and genes representing loci in which natural selection most likely occurred (G, H) provide gene expression-based therapy outcome prediction models for breast (E, G) and prostate (F, H) cancer patients.

E, F. Kaplan-Meier analysis of therapy outcome classification performance in breast cancer (E) and prostate cancer (F) patients of gene expression-based CTOP models generated from genetic loci containing high-population differentiation non-synonymous SNPs.

G, H. Kaplan-Meier analysis of therapy outcome classification performance in breast cancer (G) and prostate cancer (H) patients of gene expression-based CTOP models generated from genetic loci in which natural selection most likely occurred.

I, J. Kaplan-Meier analysis of therapy outcome classification performance in breast cancer (I) and prostate cancer (J) patients of gene expression-based CTOP models generated from genetic loci regulated by SNP variations in normal individuals.

K, L. Kaplan-Meier analysis of therapy outcome classification performance in breast cancer (E) and prostate cancer (F) patients of gene expression-based CTOP models generated from genetic loci selected based on similarity of SNP profiles with population specific SNP profiles of known CTOP genes.

M, N. Kaplan-Meier analysis of therapy outcome classification performance in breast cancer (E) and prostate cancer (F) patients of gene expression-based CTOP models generated from a proteomics-based 50-gene signature.

Figures 7, 27:
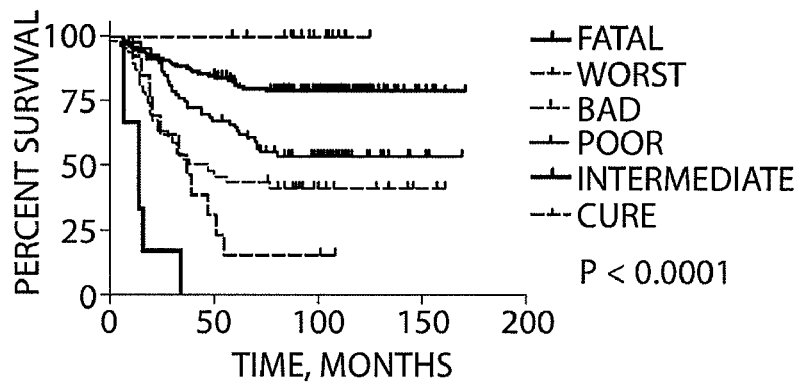

FIG. 7 shows microarray analysis identifying clinically relevant cooperating oncogenic pathways in human prostate and breast cancers. Kaplan-Meier survival analysis for prostate cancer (A-D) and breast cancer (E-H) with deregulated individual pathways associated with BMI1 (A, E), Myc (B, F), or Her2/neu (C, G) activation. Plots D and H show Kaplan-Meier analysis based on patients' stratification taking into account evidence for activation of multiple pathways in individual tumors. Gene expression signature-based patients' stratification for Kaplan-Meier survival analysis were performed as described in Glinsky et al., J. Clin. Invest. 115: 1503-1521 (2005) and Glinsky et al., J. Clin. Invest. 113: 913-923 (2004).

Figures 8, 27:
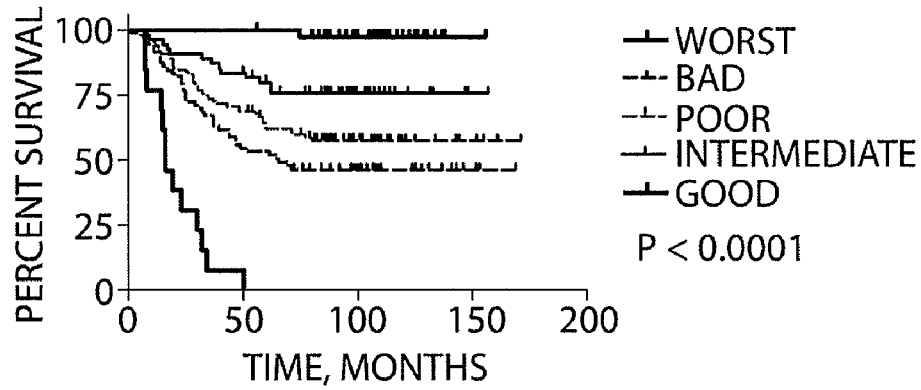
Figures 12, 27:
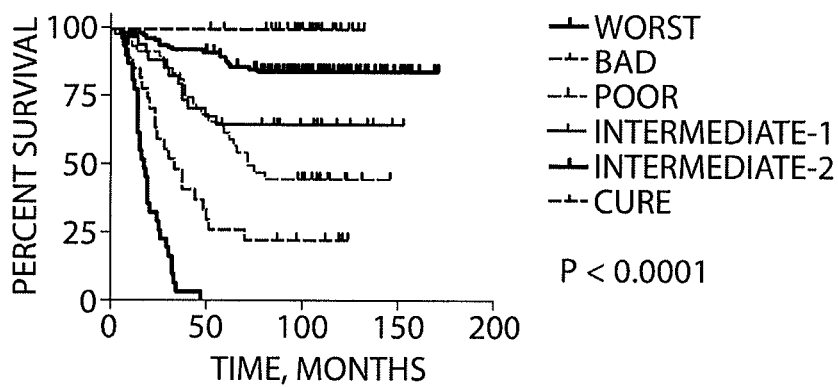

FIG. 8 shows how comparative cross-species translational genomics integrates knowledge written in two languages (DNA sequence variations and mRNA expression levels) and three writing systems reflecting defined phenotype/gene expression pattern associations (SNP variations; transgenic mouse models of cancers; genomics of stem cell biology).

Figure 9:
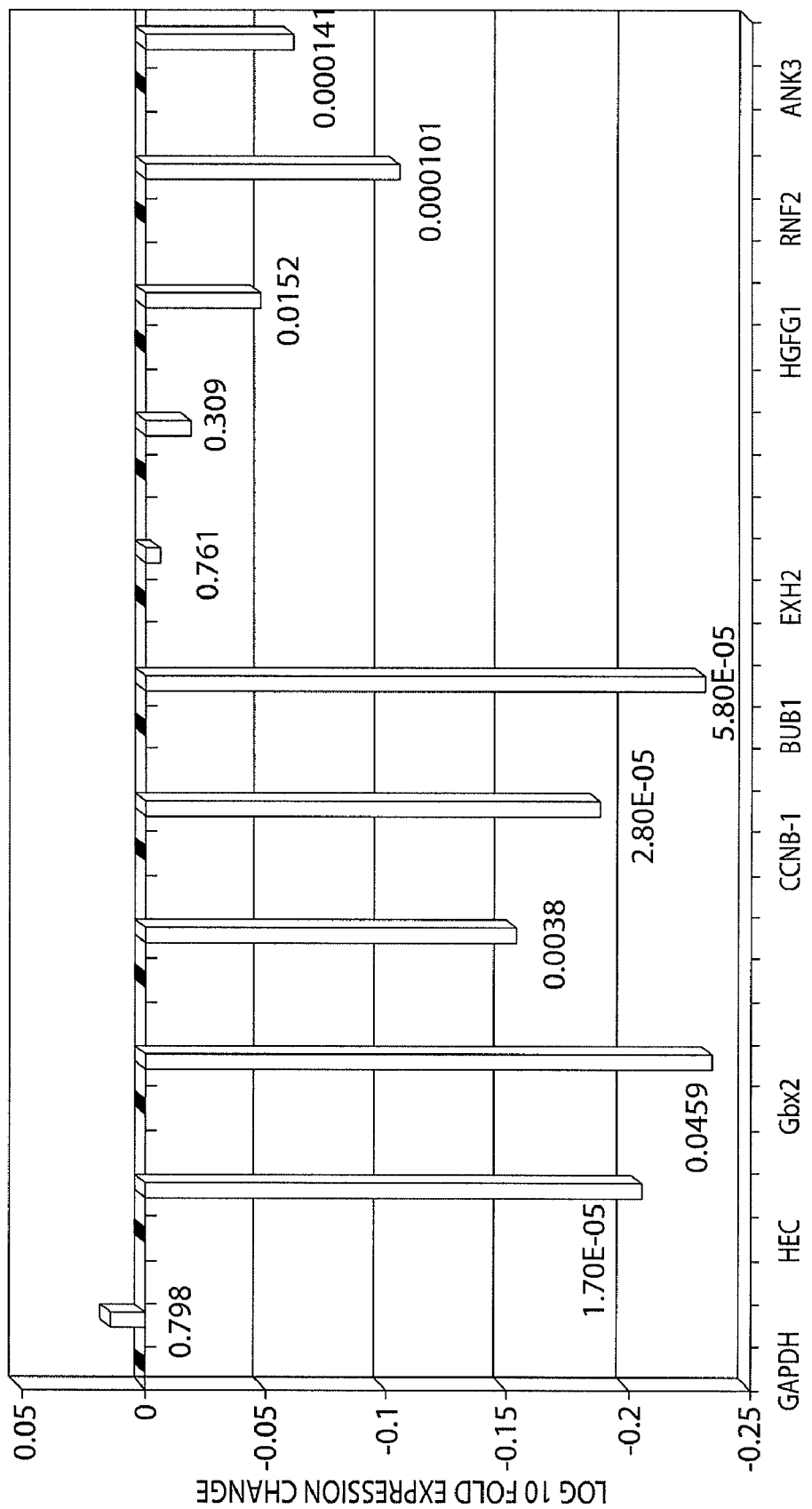

FIG. 9 shows Q-RT-PCR analysis of mRNA abundance levels of a representative set of genes comprising the BM-1-pathway signature in BM-1 siRNAitreayed PC-3-32 human prostate carcinoma cells.

Figure 10:
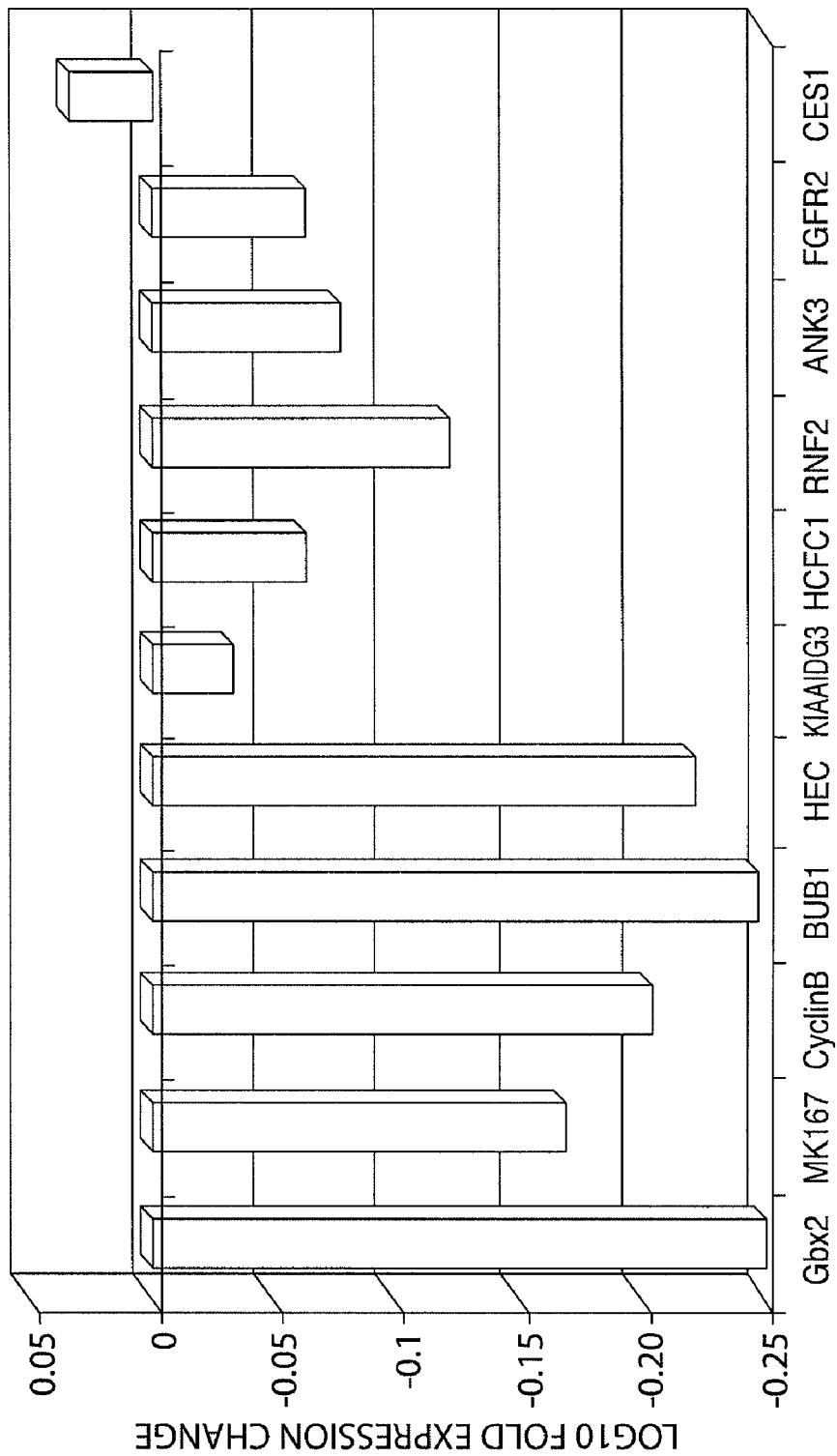

FIG. 10 shows siRNA-mediated changes of the transcript abundance levels of 11 genes comprising BM-1-pathway signature.

Figure 11:
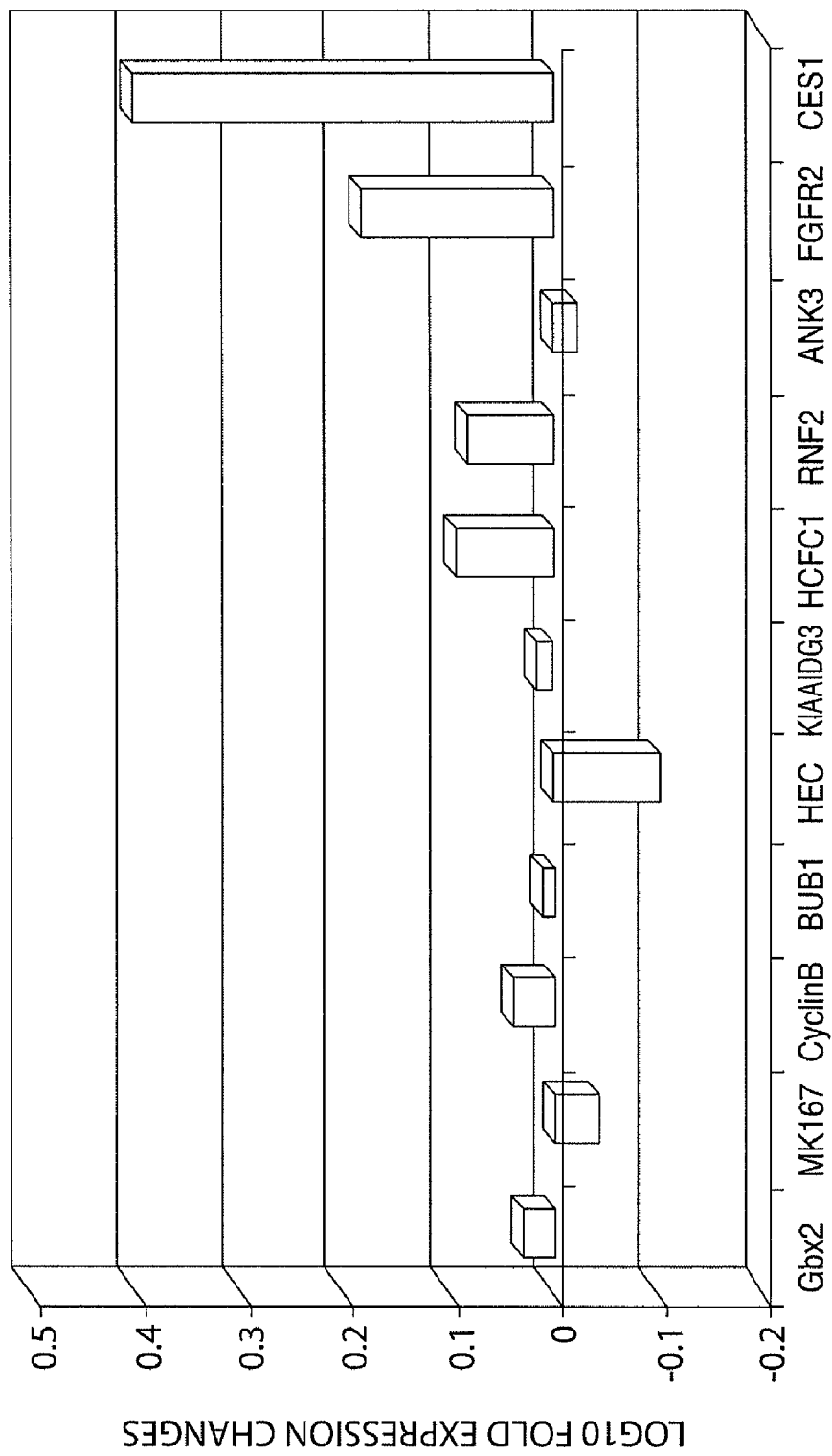

FIG. 11 shows EZH2 siRNA-mediated changes of the transcript abundance levels of 11 genes comprising the BM-1-pathway signature.

Figures 1, 12:
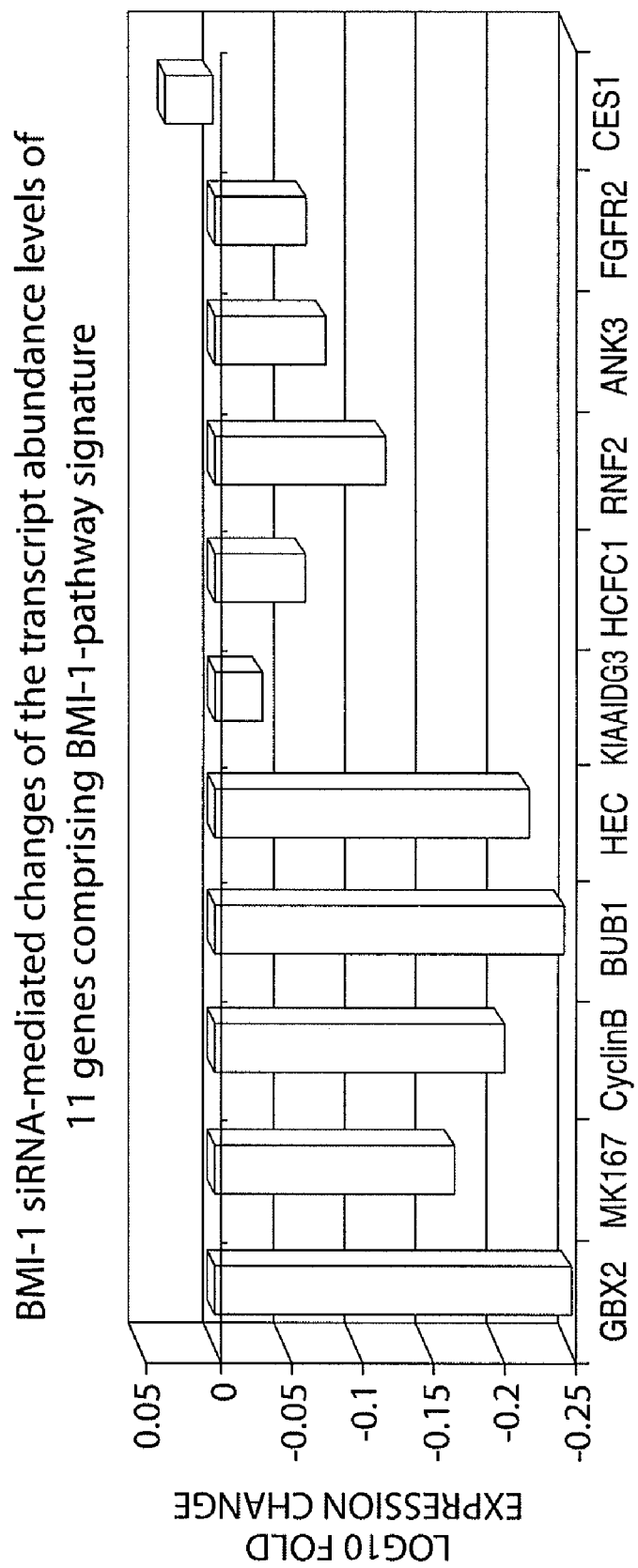
Figures 2, 12:
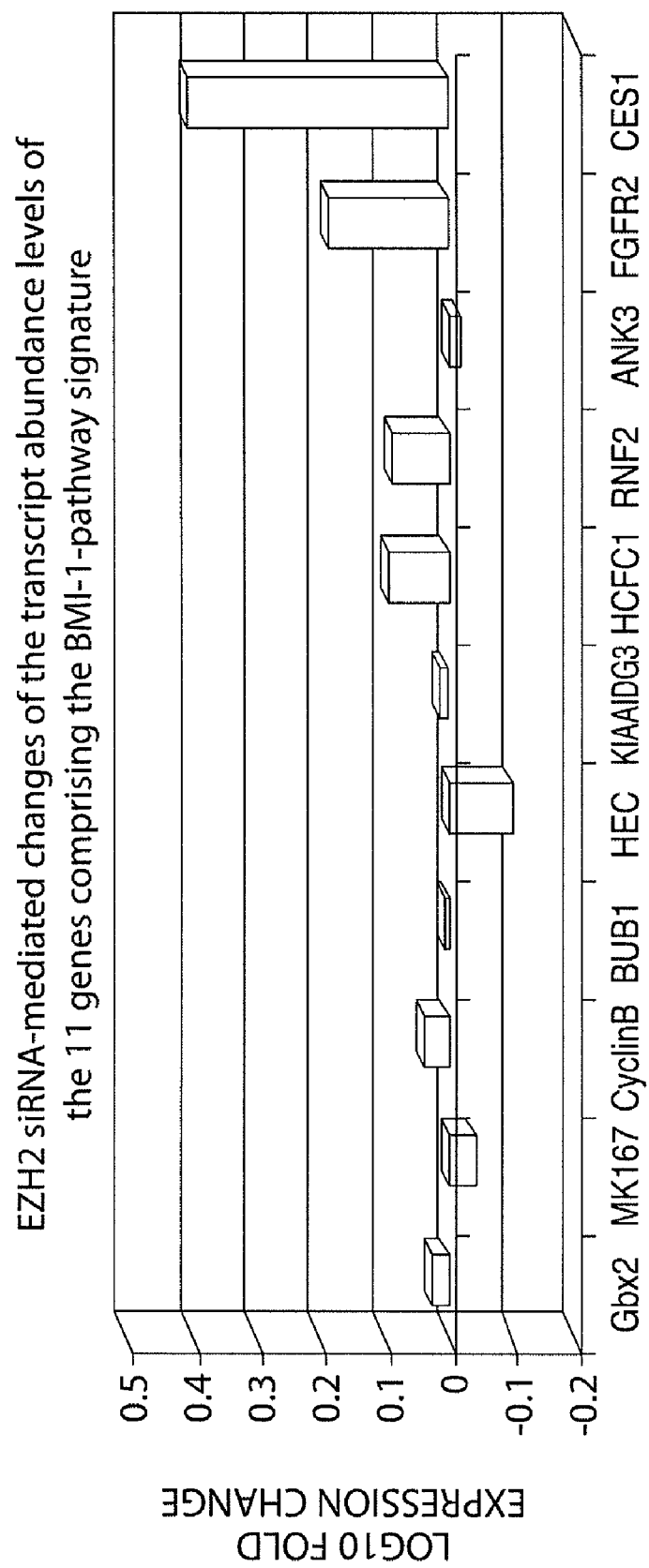

FIG. 12 shows siRNA-mediated changes of the transcript abundance levels of 11 genes comprising BM-1-pathway signature. A. BM-1 siRNA. B. EZH2 siRNA.

Figure 13:
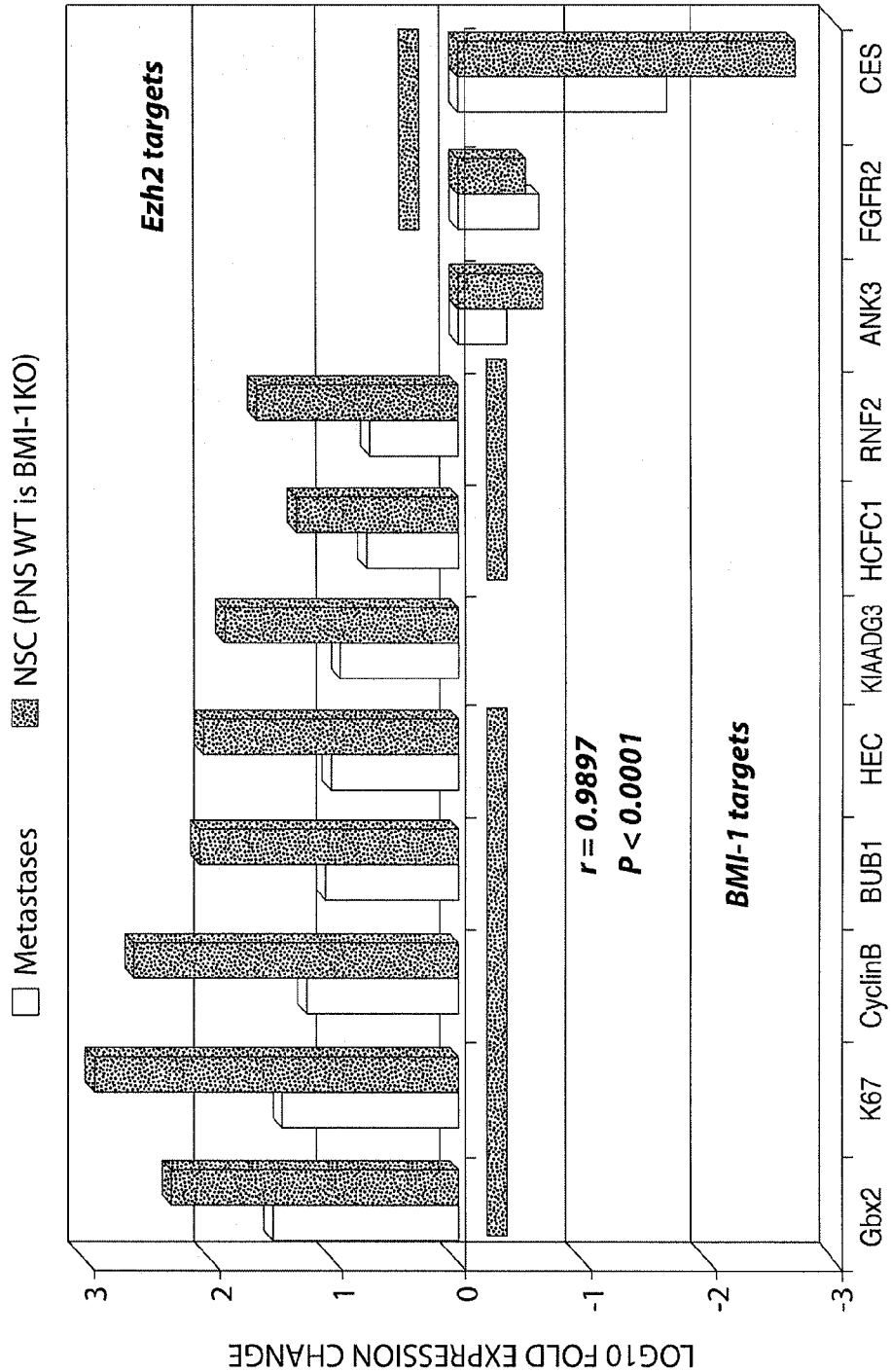

FIG. 13 shows expression profiles of 11 gene MM-1-signature in distant metastatic lesions of the TRAMP transgenic mouse model of prostate cancer and PNS neurospheres.

Figure 14:
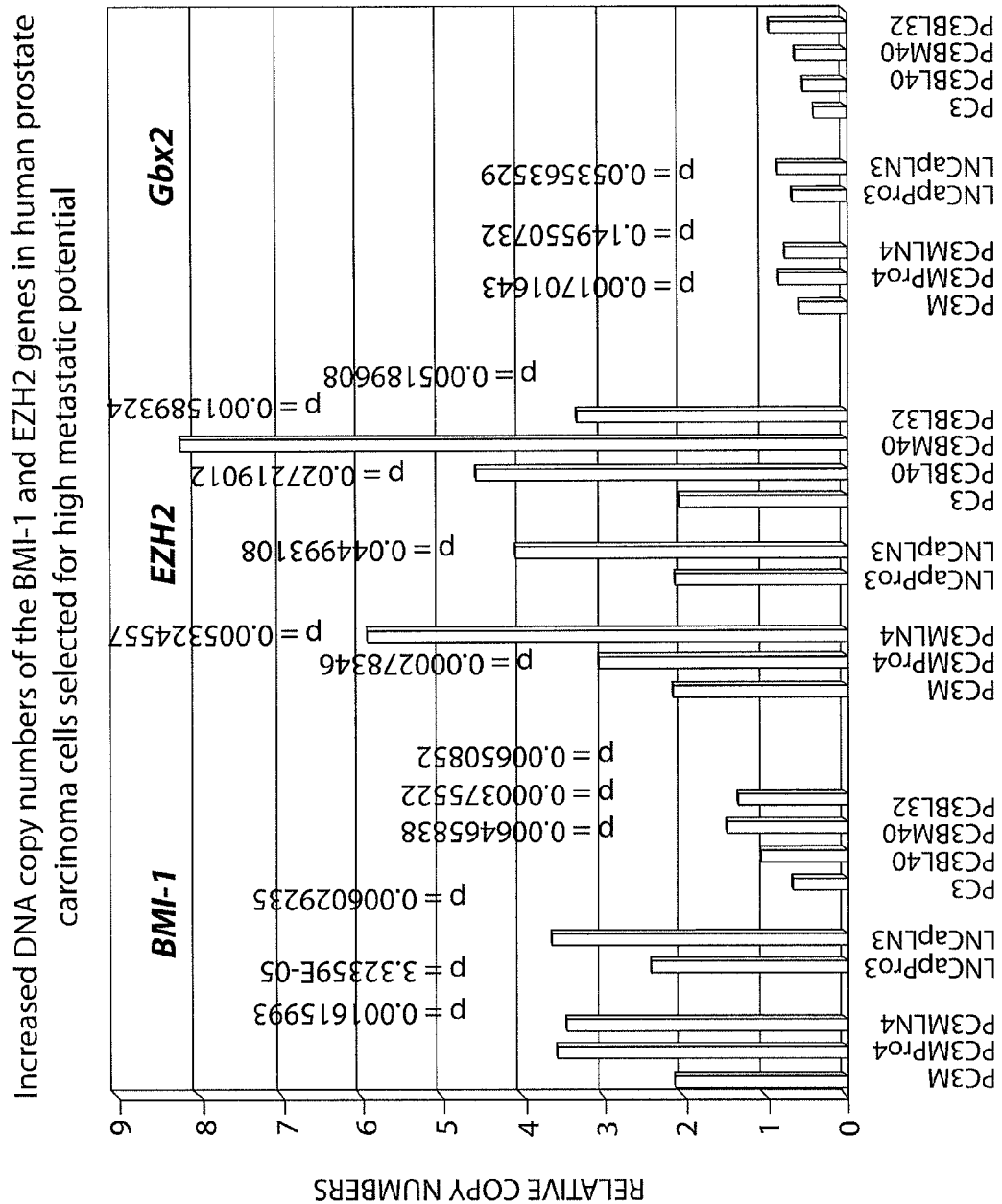

FIG. 14 shows increased DNA copy numbers of the BM-1 and Ezh2 genes in human prostate carcinoma cells selected for high metastatic potential.

Figure 15:
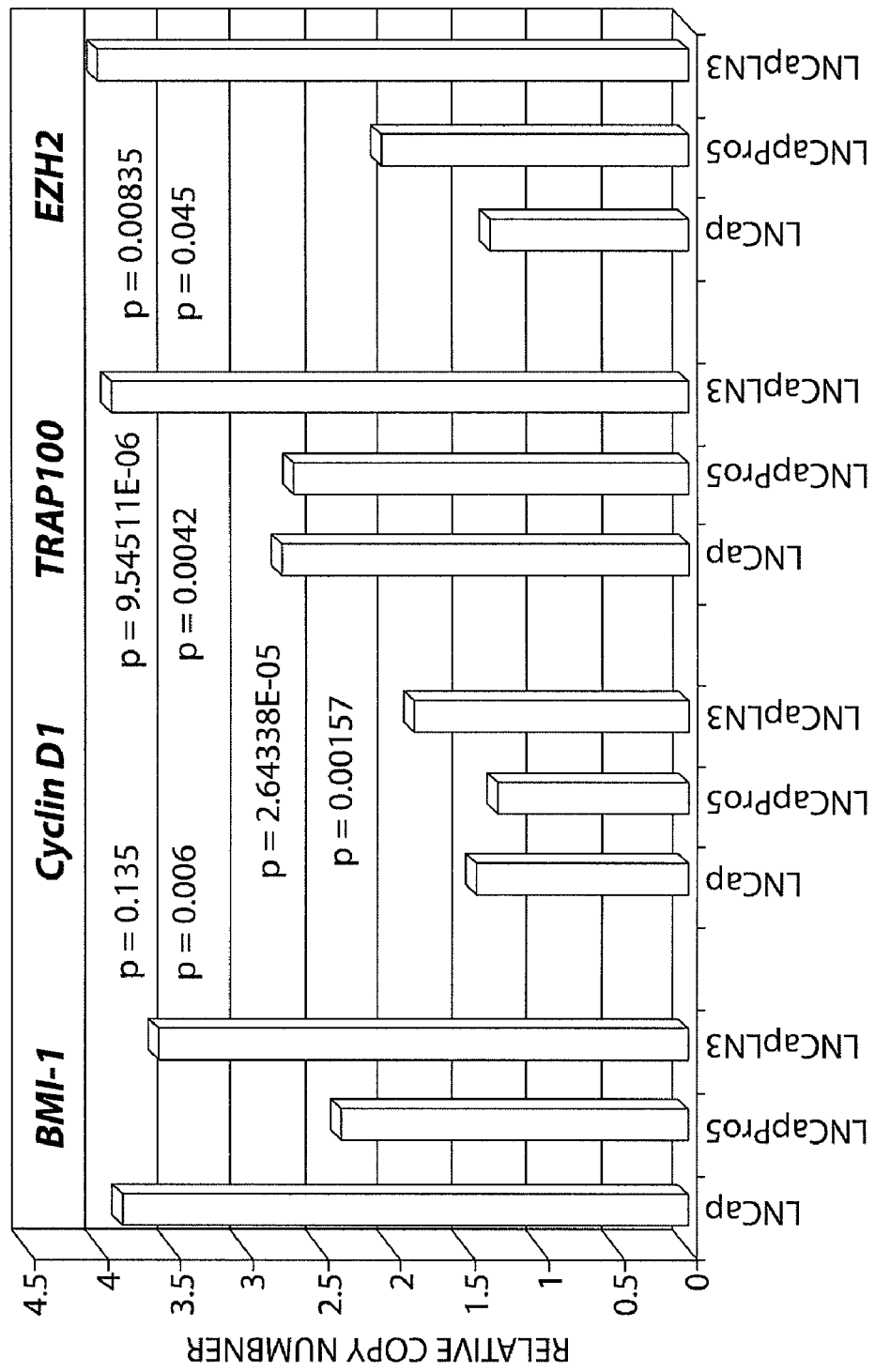

FIG. 15 shows the quadruplicon of prostate cancer progression in the LNCap progression model.

Figure 16:
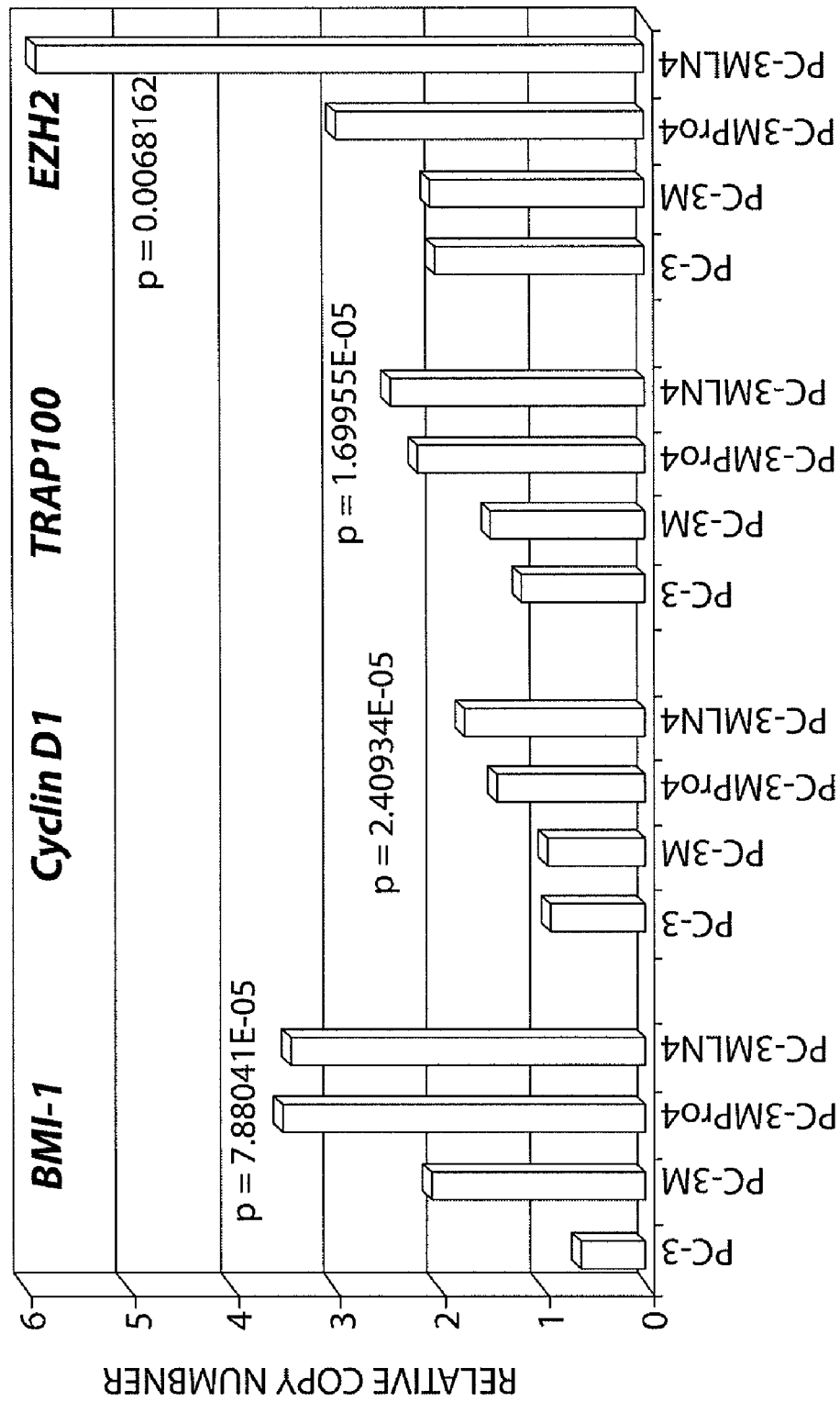

FIG. 16 shows the quadruplicon of prostate cancer progression in the PC-3 progression model.

Figure 17:
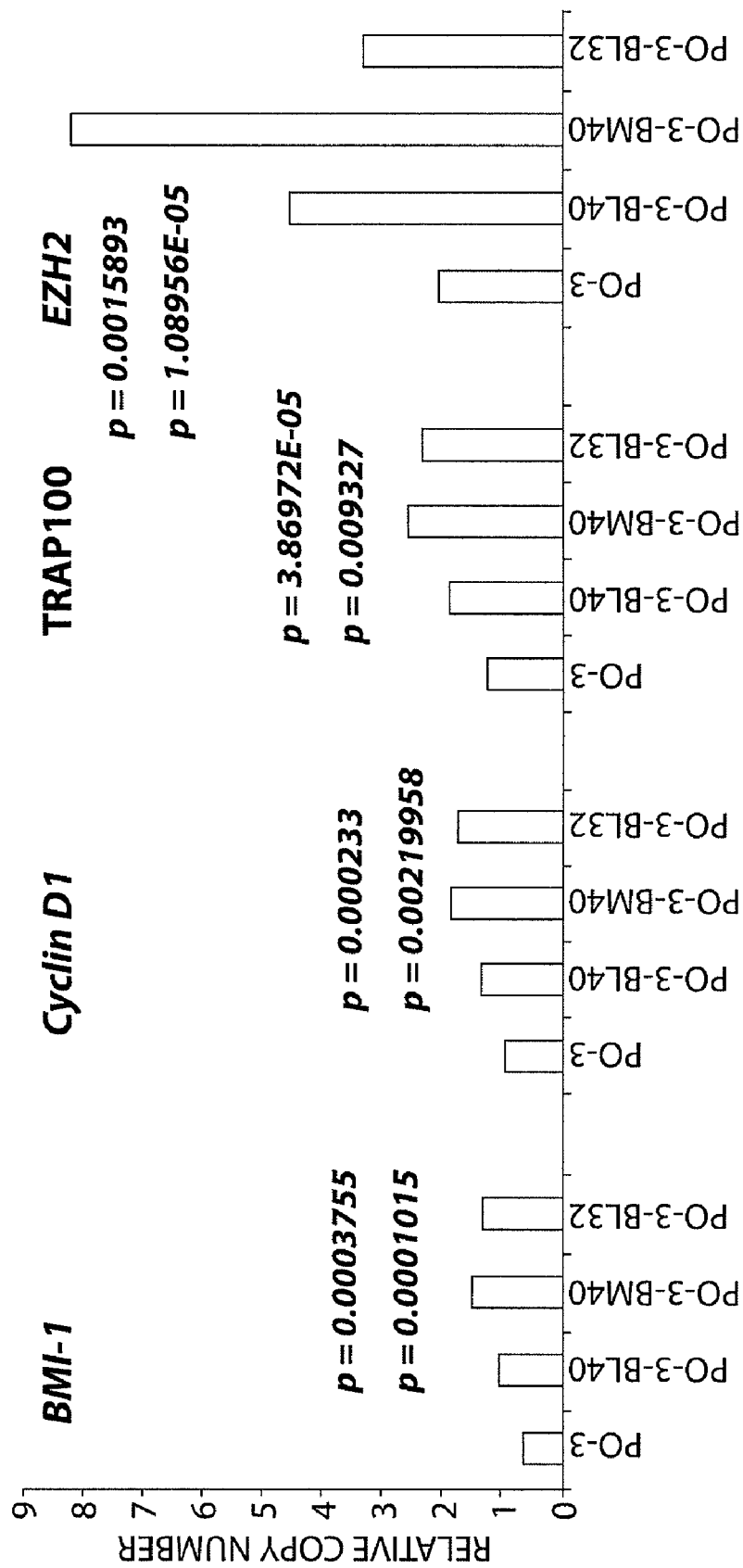

FIG. 17 shows the quadruplicon of prostate cancer progression in the PC-3 bone metastasis progression model.

Figure 18:
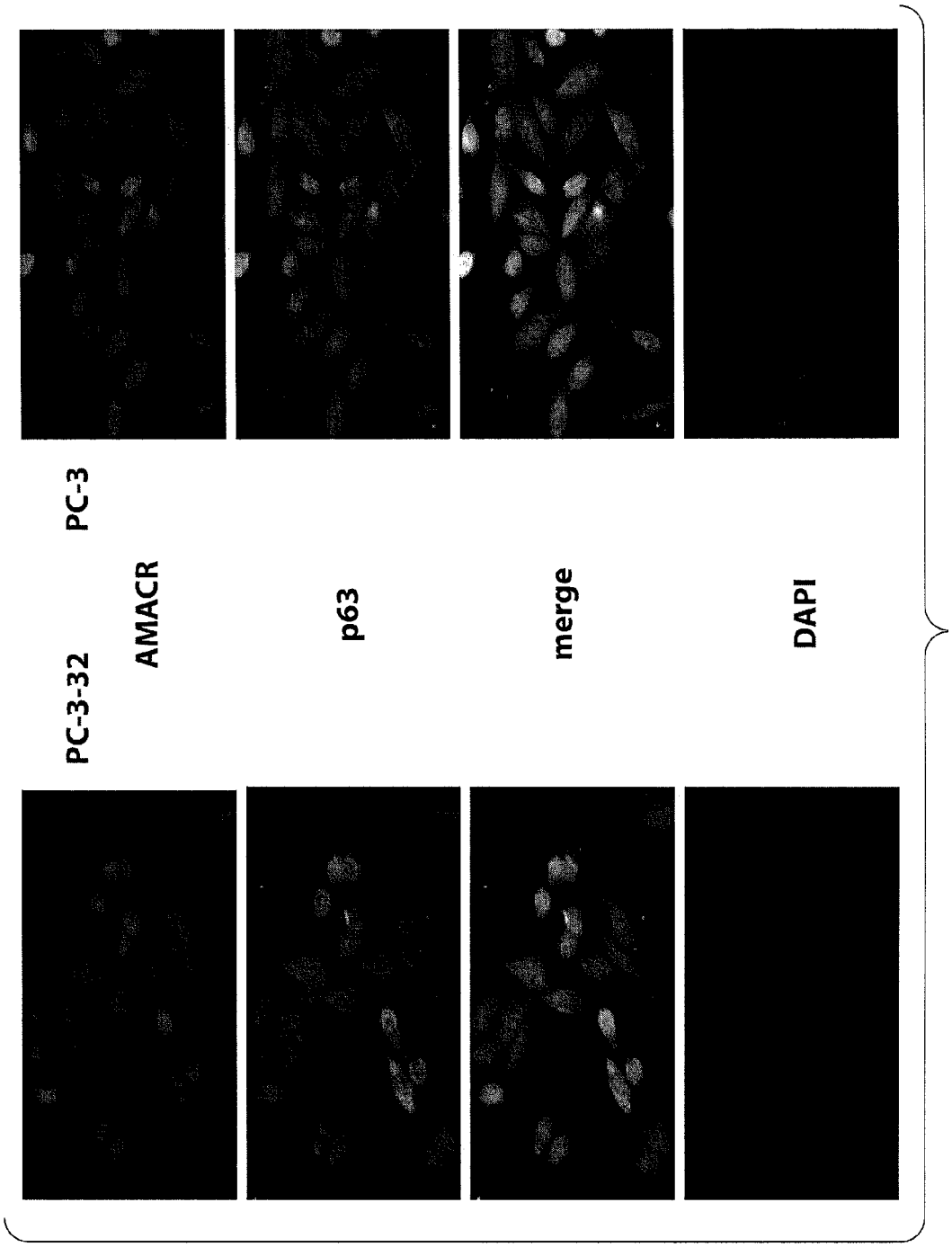

FIG. 18 shows expression levels in PC-3-32 and PC-3 cells.

Figure 19:
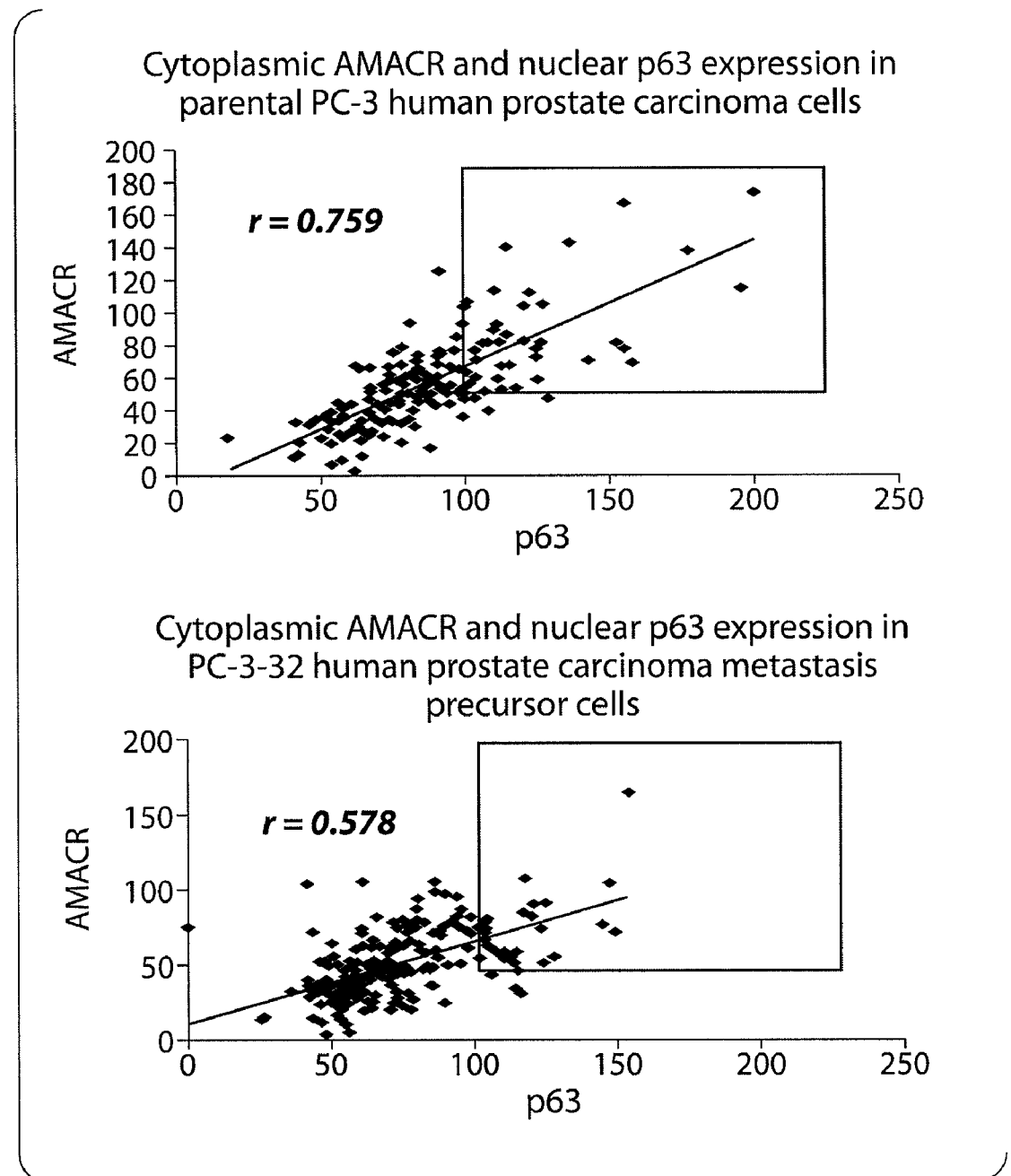

FIG. 19 shows cytoplasmic AMACR and nuclear p63 expression in parental PC-3 human prostate carcinoma cells and PC-3-32 human prostate carcinoma metastasis precursor cells.

FIG. 20 shows that high expression levels of the BMI1 and Ezh2 oncoproteins in human prostate carcinoma metastasis precursor cells are associated with marked accumulation of a dual-positive high BMI1/Ezh2-expressing cell population and increased DNA copy number of the BMI1 and Ezh2 genes.

A-D. A quantitative immunofluorescence co-localization analysis of the BMI1 (mouse monoclonal antibody) and Ezh2 (rabbit polyclonal antibody) oncoproteins in PC-3-32 human prostate carcinoma metastasis precursor cells and parental PC-3 cells. The protein expression differences and the accumulation of dual-positive high BMI1/Ezh2-expressing cells were confirmed using a second distinct combination of antibodies: rabbit polyclonal antibodies for BMI1 detection and mouse monoclonal antibodies for Ezh2 detection. A, immunofluorescent analysis of PC-3-32 cells; B, immunofluorescent analysis of PC-3 cells; C, the histograms representing typical distributions of the BMI1 (top panels) and Ezh2 (bottom panels) expression levels in PC-3 and PC-3-32 cells; D, the plots illustrating the levels of dual positive high BMI1/Ezh2-expressing cells in metastatic PC-3-32 cells (22.4%; top panel) and parental PC-3 cells (1.5%; bottom panel). The results of one of two independent experiments are shown.

E. A quantitative reverse-transcription PCR (Q-RT-PCR) analysis of DNA copy numbers of the BMI1 and Ezh2 genes in multiple experimental models of human prostate cancer. Note marked increase of the BMI1 and Ezh2 gene copy numbers in highly metastatic variants compared to the low metastatic counterparts in the multiple independently selected lineages. The results of one of two independent experiments are shown.

F. 3D-view of dual-positive high BMI1/Ezh2-expressing human prostate carcinoma cells in cultures of blood-borne metastasis precursor cells and parental cells. Adherent cultures of parental PC-3 (bottom three panels) and blood-borne PC-3-32 (top three panels) human prostate carcinoma cells were stained for visualization of the BMI1 and Ezh2 oncoproteins and analyzed using a multi-color fluorescent confocal microscopy. Note a higher proportion of cells with large discrete nuclear PcG bodies in the population of PC-3-32 human prostate carcinoma cells (typically, these cells contain six PcG bodies per nucleus). Blue, DNA; Green, BMI1; Red, Ezh2.

Figures 1, 21:
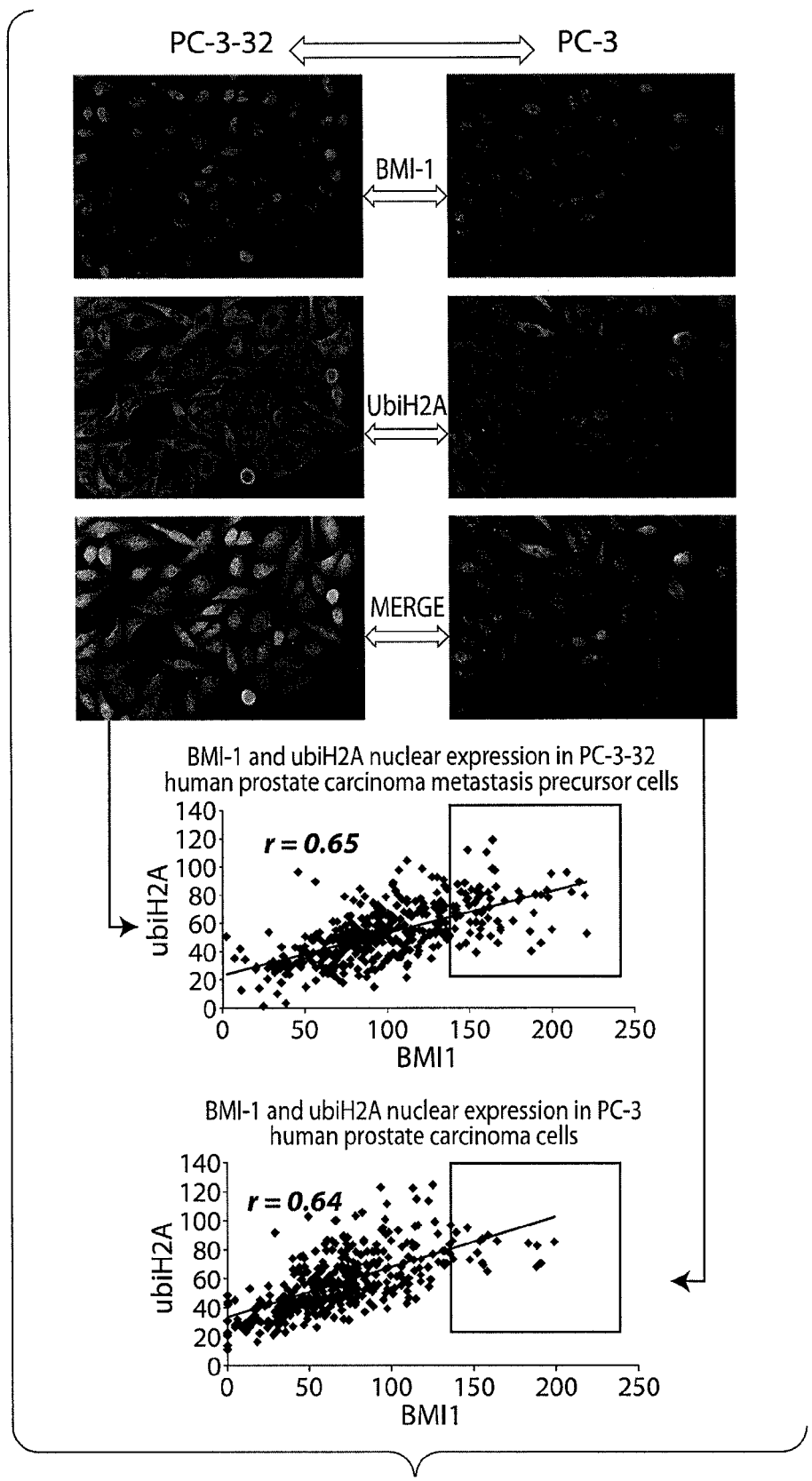
Figures 2, 21:
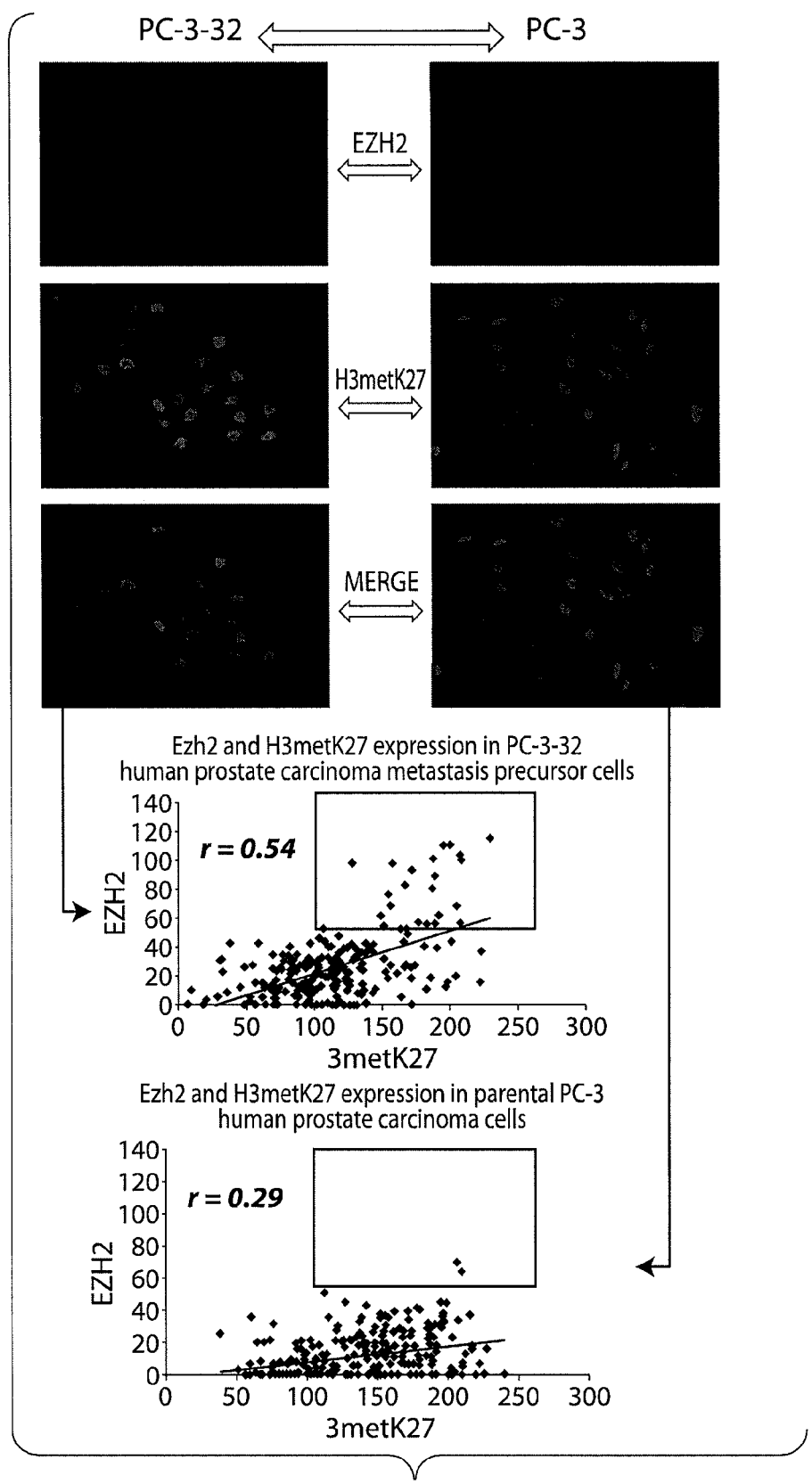
Figures 3, 21:
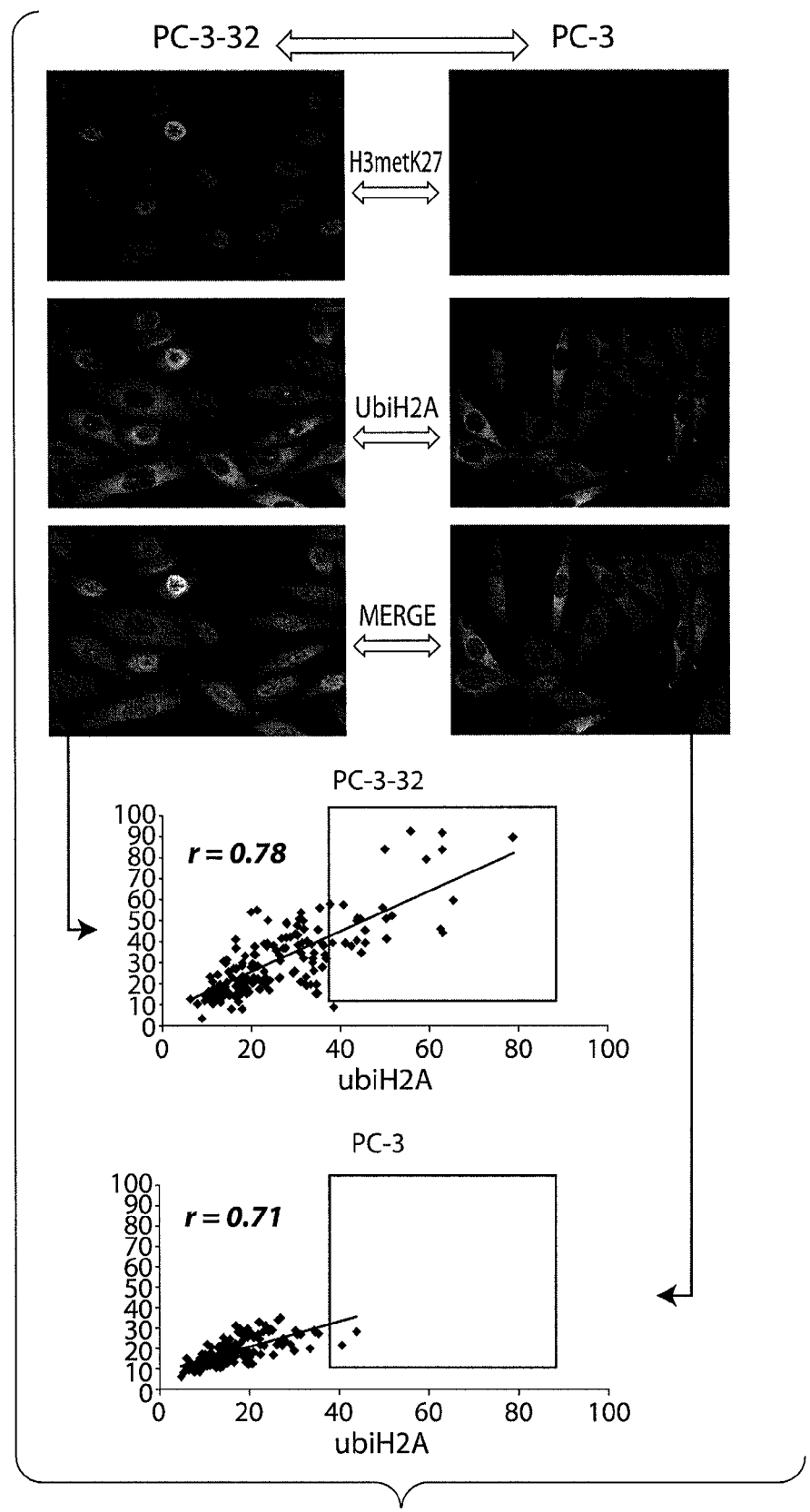
Figures 1, 22A:
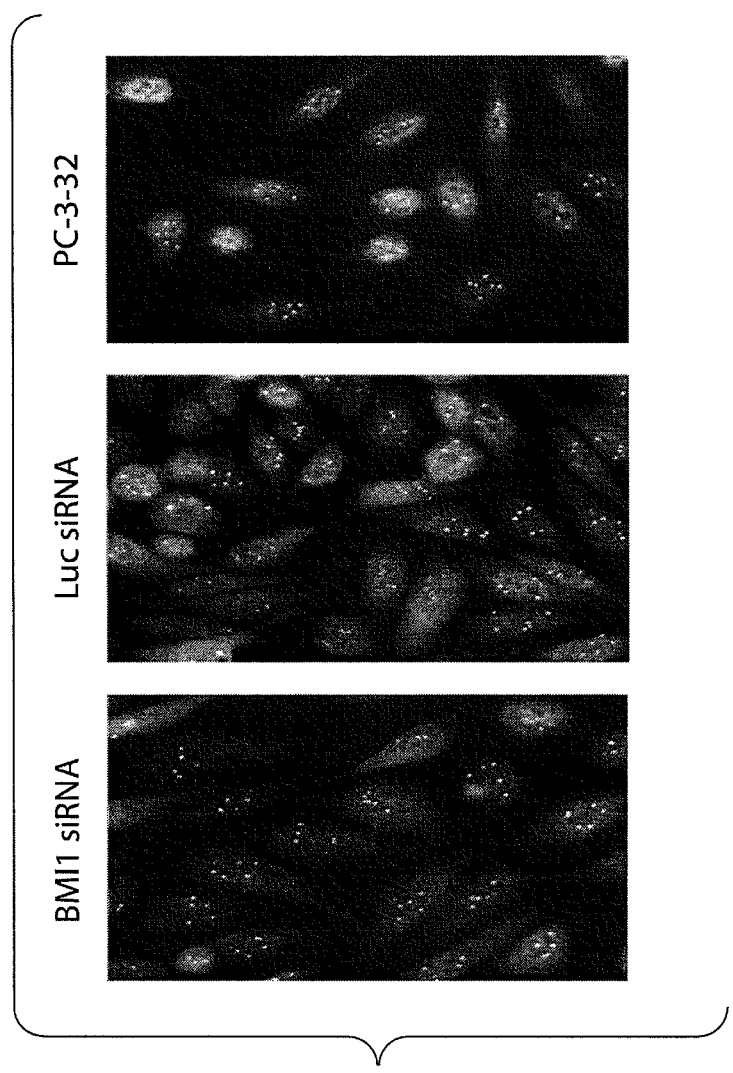
Figures 2, 22A:
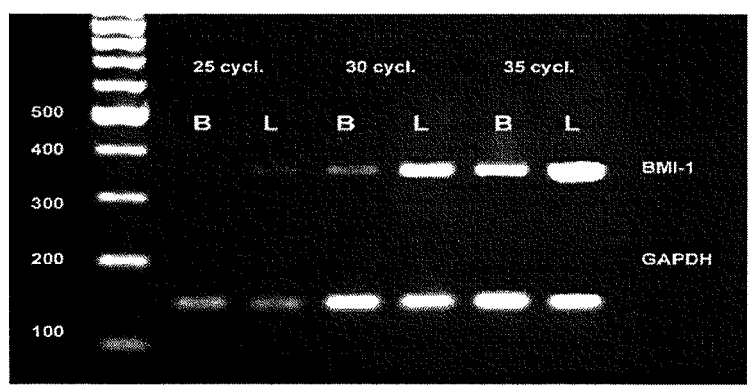
Figures 3, 22A:
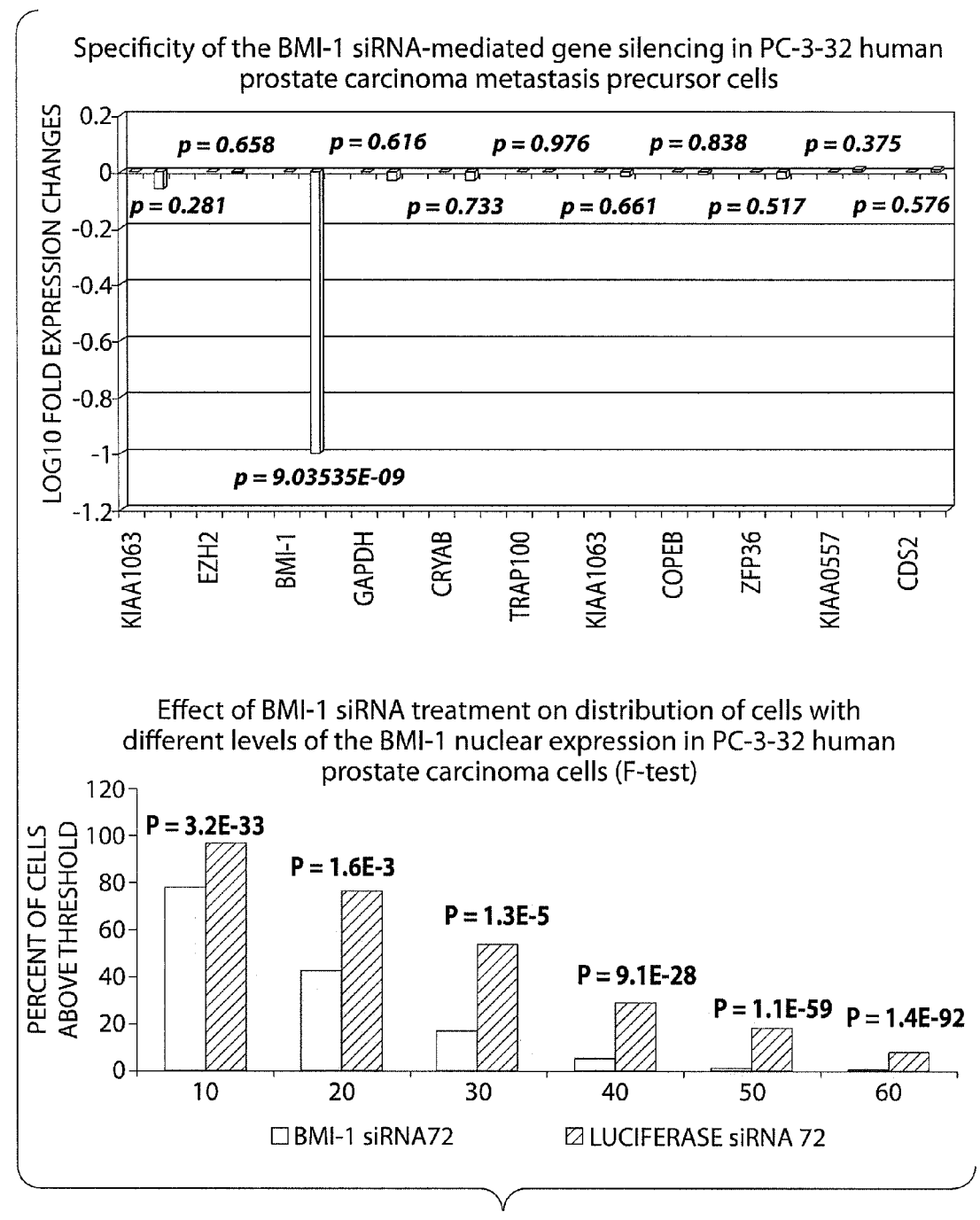
Figure 22A:
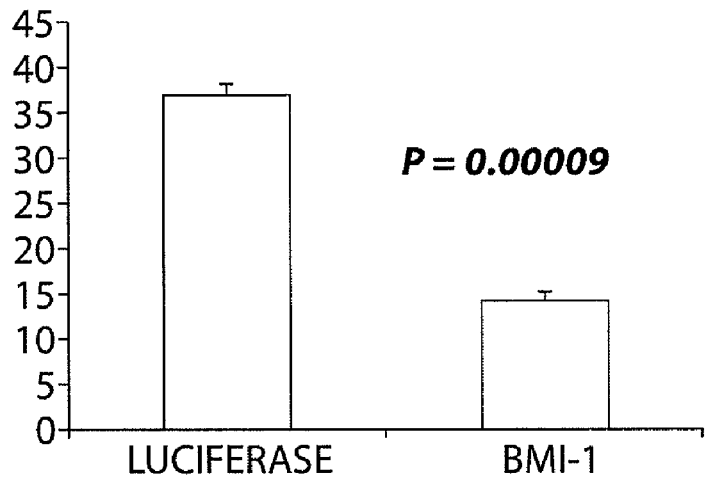
Figure 4:
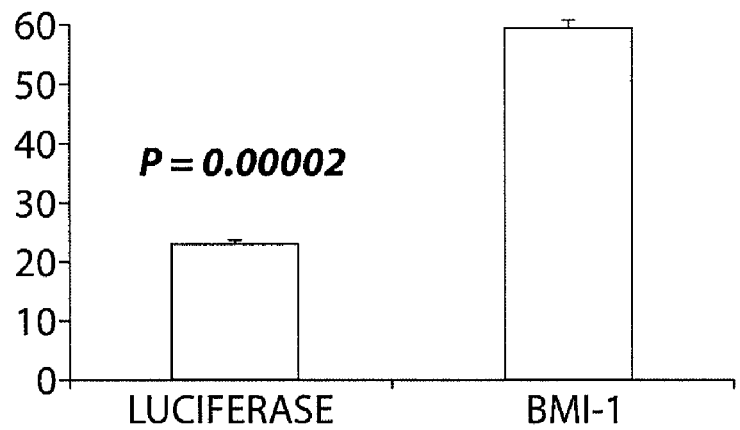
Figures 1, 22B:
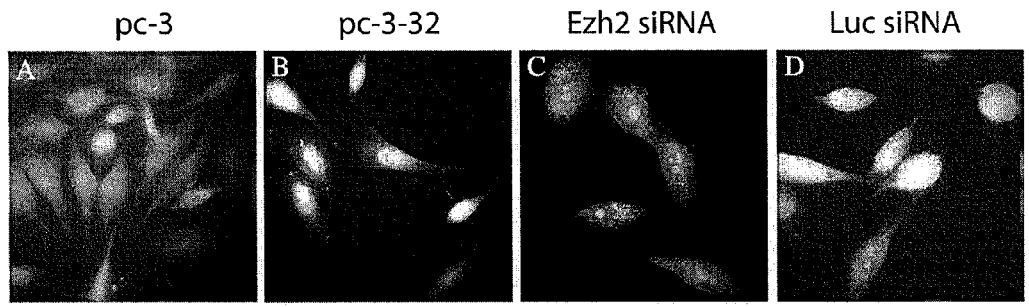
Figures 2, 22B:
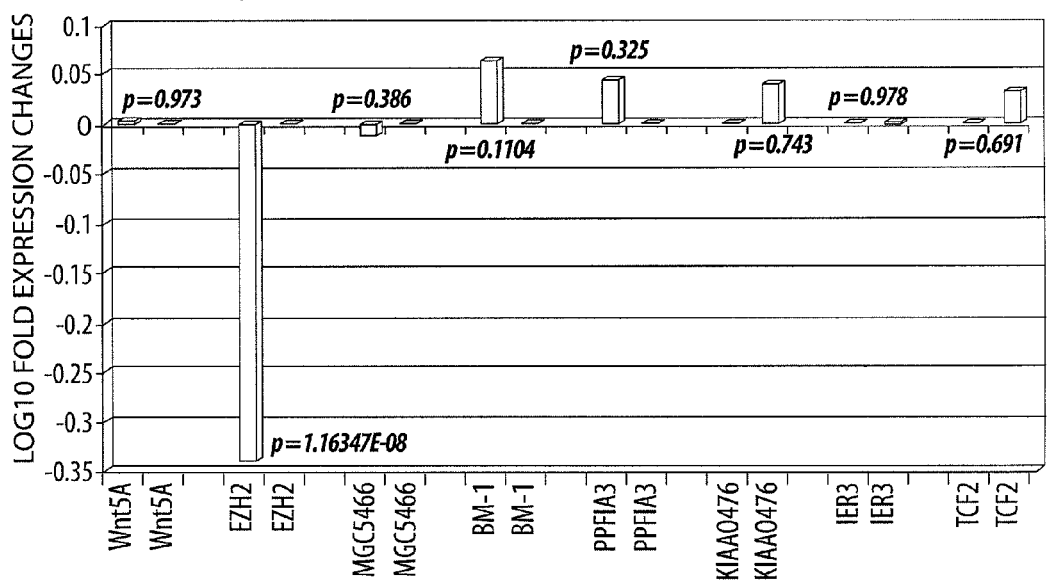
Figures 3, 22B:
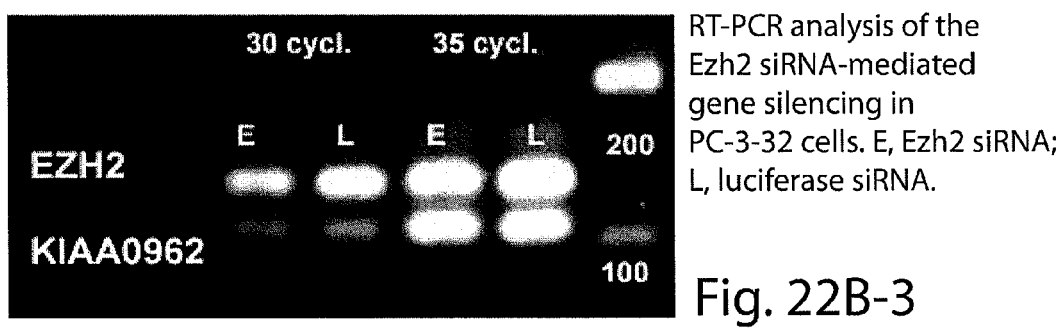
Figure 22B:
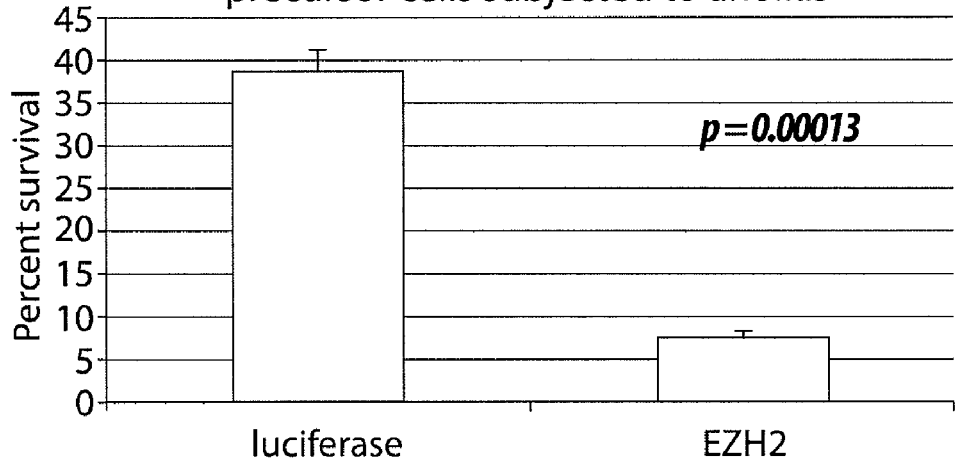
Figure 4:
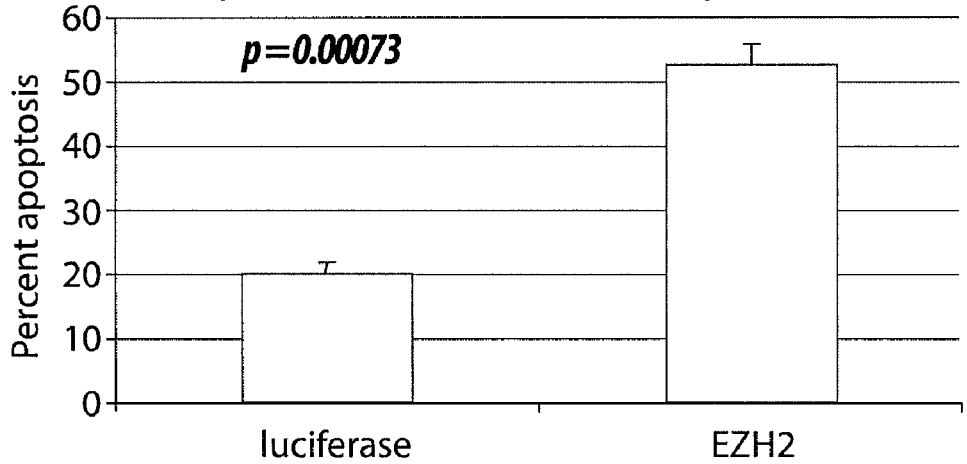

FIG. 21 shows results of activation of the PcG chromatin silencing pathway in metastatic human prostate carcinoma cells. A quantitative immunofluorescence co-localization analysis was utilized to measure the expression of the BMI1, Ezh2, H3metK27, and UbiH2A markers in human prostate carcinoma cells and calculate the numbers of dual-positive cells expressing various two-marker combinations. Note that high expression of the BMI1 and Ezh2 oncoproteins in PC-3-32 human prostate carcinoma metastasis precursor cells compared to parental PC-3 cells is associated with increased levels of hi stone H3 lysine 27 methylation (H3metK27), hi stone H2A lysine 119 ubiquitination (UbiH2A), and marked enrichment for dual-positive cell populations expressing high levels of BMI1/UbiH2A, Ezh2/H3metK27, and H3metK27/UbiH2A two-marker combinations.

FIG. 22 shows that targeted reduction of the BMI1 (3A) or Ezh2 (3B) expression increases sensitivity of human prostate carcinoma metastasis precursor cells to anoikis. Anoikis-resistant PC-3-32 prostate carcinoma cells were treated with BMI1- or Ezh2-targeting siRNAs and continuously monitored for expression levels of the various mRNAs, BMI and Ezh2 oncoproteins, as well as cell growth and viability under various culture conditions. PC-3-32 cells with reduced, expression of either BMI1 or Ezh2 oncoproteins acquired sensitivity to anoikis as demonstrated by the loss of viability and increased apoptosis compared to the control LUC siRNA-treated cultures growing in detached conditions.

Figure 23A:
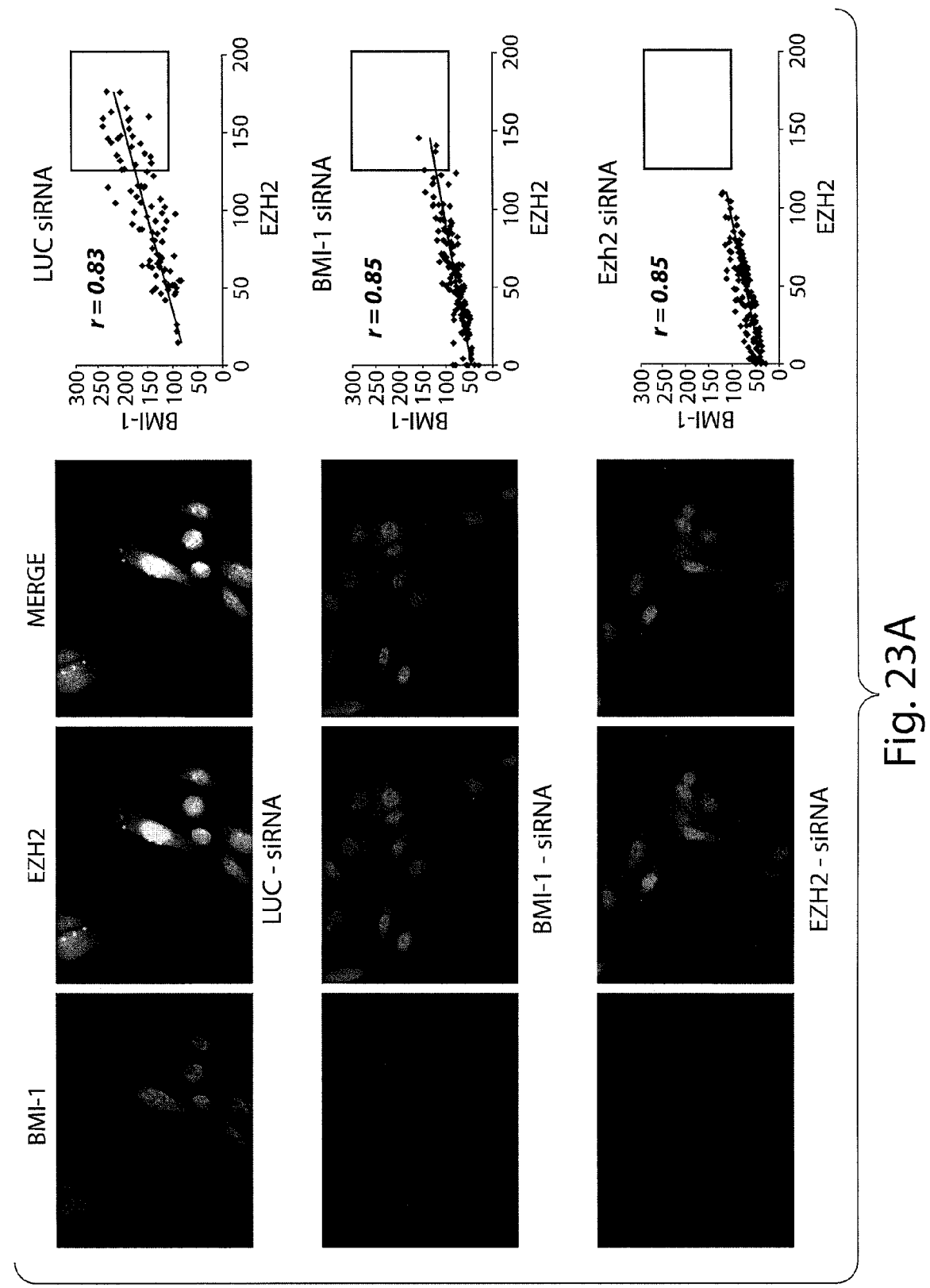
Figure 23B:
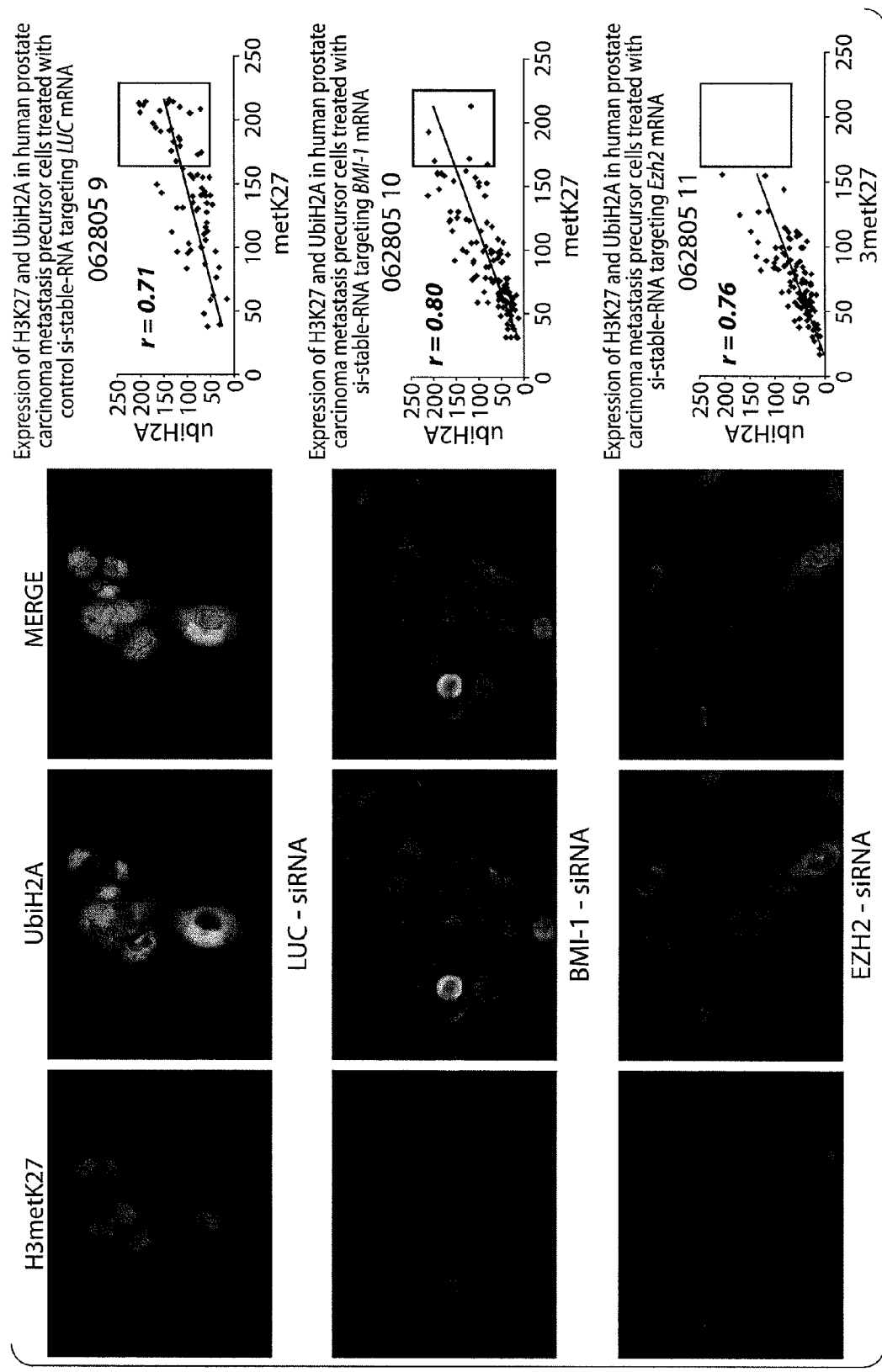

FIG. 23 shows that treatment of human prostate carcinoma metastasis precursor cells with stable siRNAs targeting either BMI1 or Ezh2 gene products depletes a sub-population of dual positive high BMI1/Ezh2-expressing cells. Blood-borne PC-3-32 prostate carcinoma cells were treated with chemically modified resistant to degradation LUC-, BMI1-, or Ezh2-targeting stable siRNAs and continuously monitored for expression levels of the BMI1 and Ezh2 oncoproteins. Two consecutive applications of the stable siRNAs caused a sustained reduction of the BMI1 and Ezh2 expression and depletion of the sub-population of dual positive high BMI1/Ezh2-expressing carcinoma cells. The results at the 11-day post-treatment time point are shown.

Figure 24A:
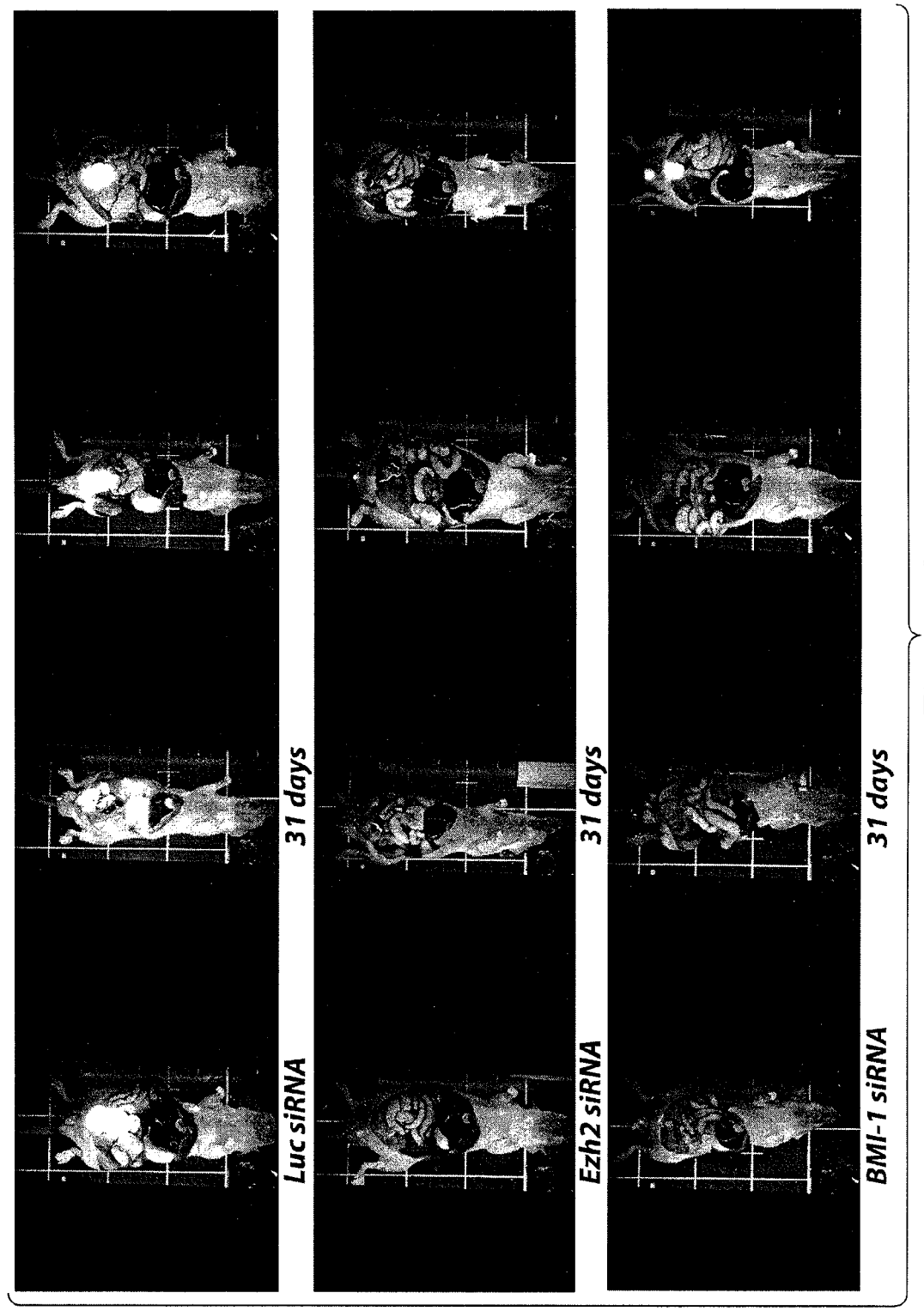
Figures 1, 24B:
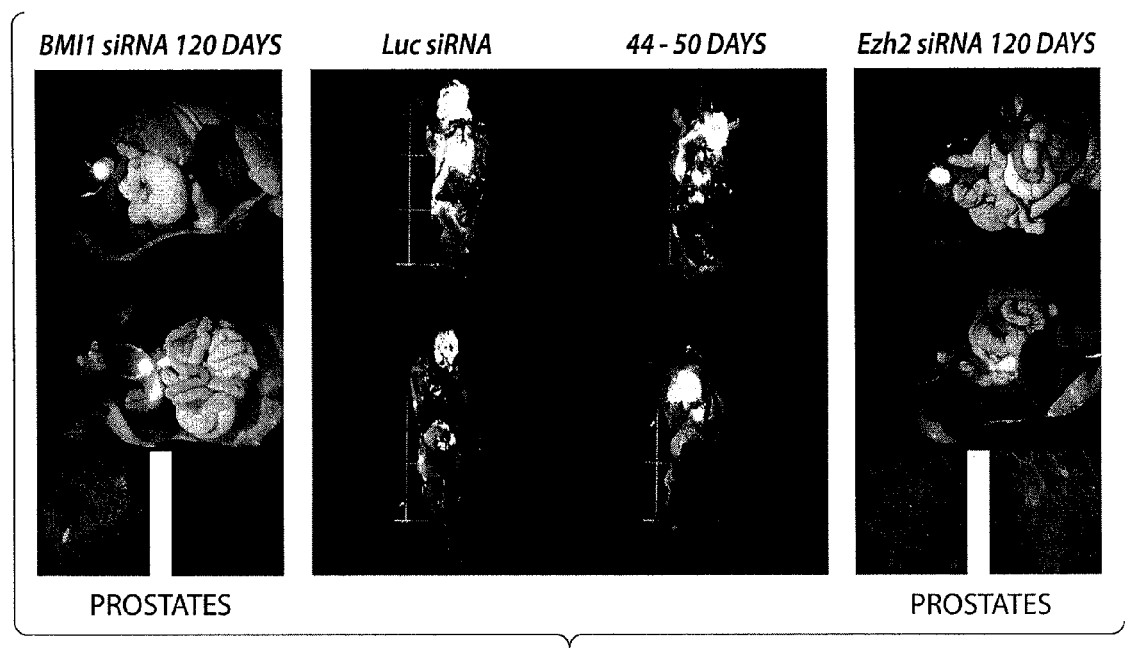
Figure 24B:
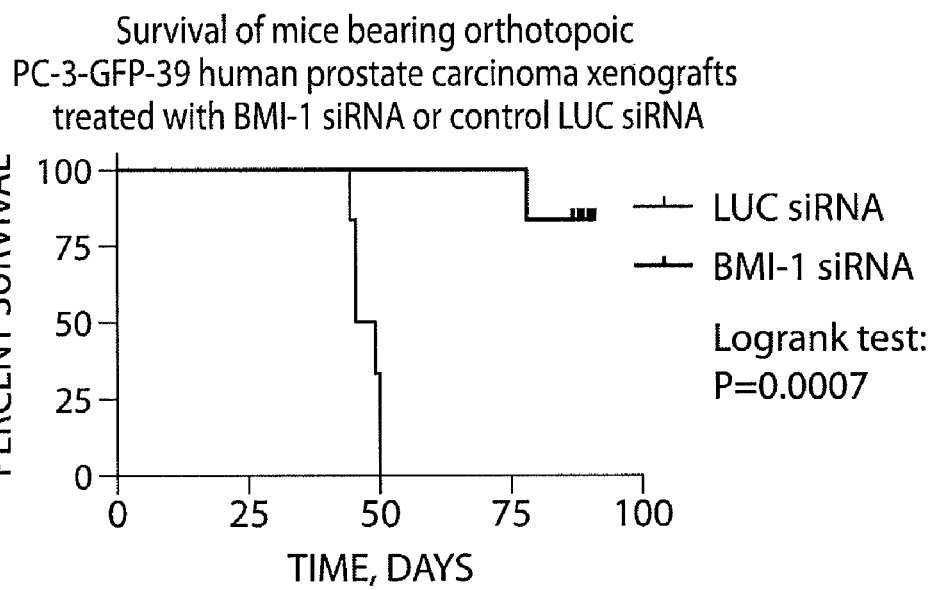
Figure 2:
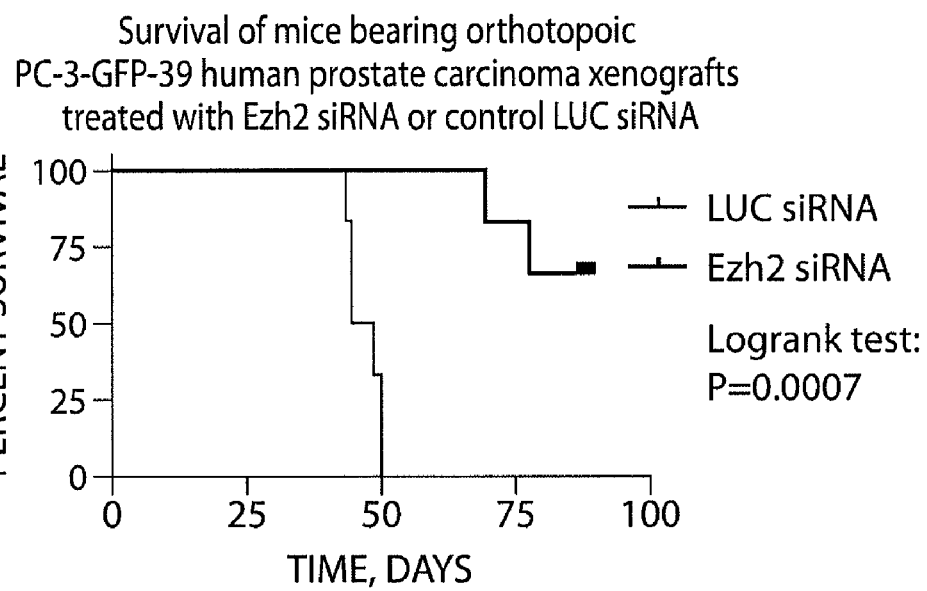

FIG. 24 shows that human prostate carcinoma metastasis precursor cells depleted for a sub-population of dual positive high BMI1/Ezh2-expressing cells manifest a dramatic loss of malignant potential in vivo. Adherent cultures of blood-borne PC-3-GFP-39 prostate carcinoma cells were treated with chemically modified degradation-resistant stable siRNAs targeting BMI1 or Ezh2 mRNAs or control LUC siRNA. 24 hrs after second treatment, $1.5 \times 10^6$ cells were injected into prostates of nude mice. Note that all control animals developed highly aggressive rapidly growing metastatic prostate cancer and died within 50 days of experiment. Only 20% of mice in the BMI1- and Ezh2-targeting therapy groups developed less malignant more slowly growing tumors. 150 days after tumor cell inoculation, 83% and 67% of animals remain alive and disease-free in the therapy groups targeting the BMI1 and Ezh2 oncoproteins, respectively (p=0.0007; log-rank test). Six animals per group were monitored for survival.

Figures 1, 25:
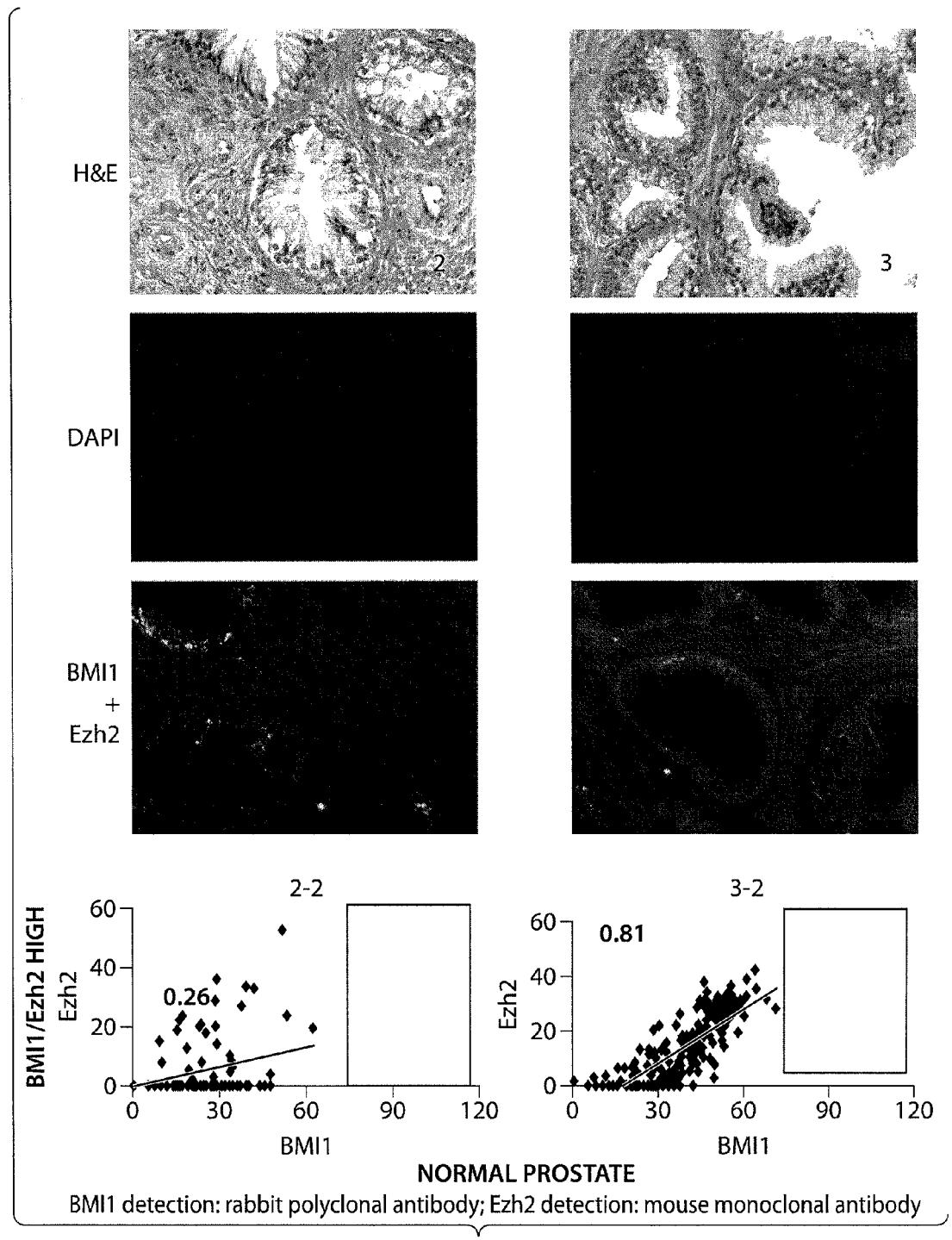
Figures 2, 25:
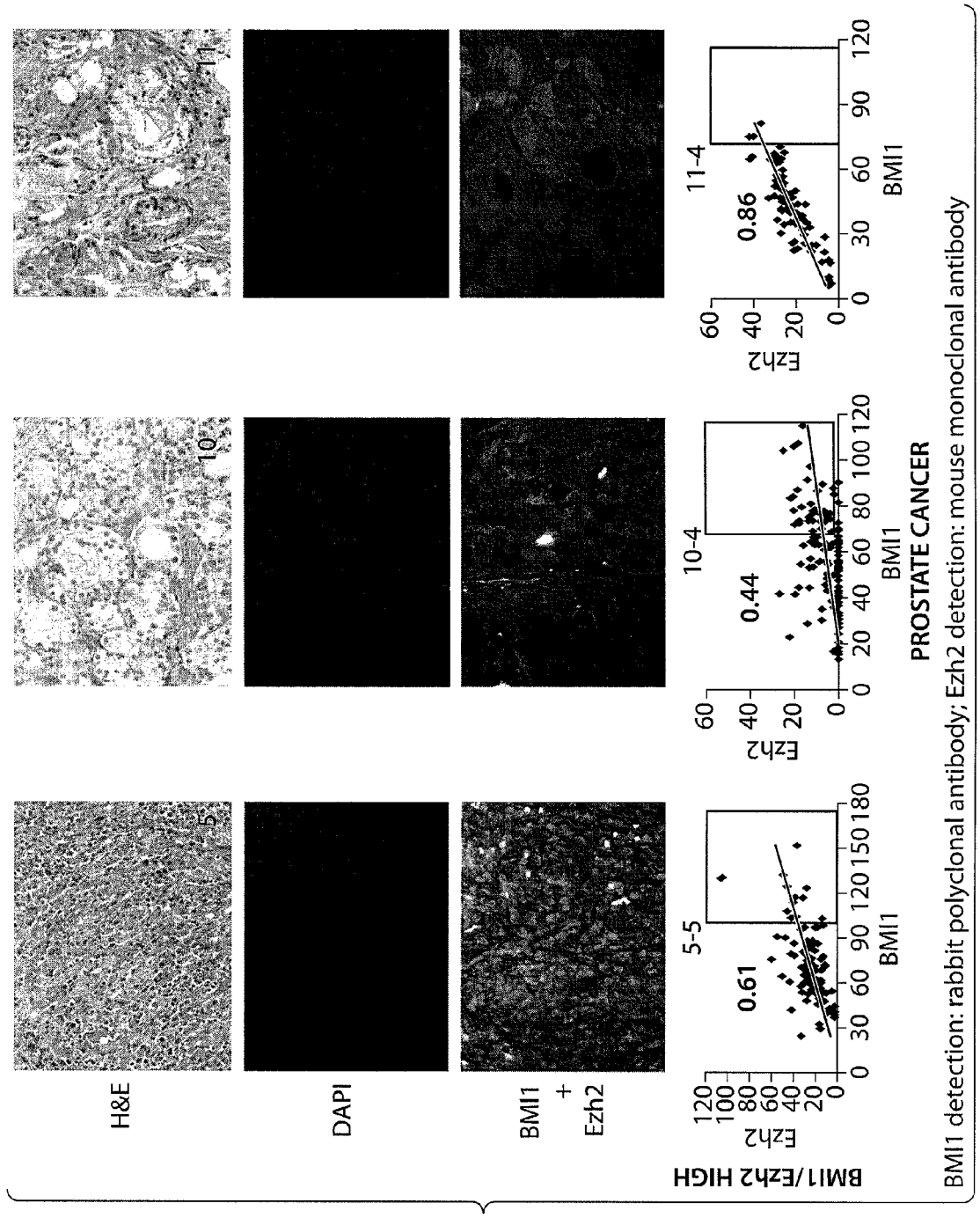

FIG. 25 shows that tissue microarray analysis (TMA) of primary prostate tumors from patients diagnosed with prostate adenocarcinomas reveals increased levels of dual-positive BMI1/Ezh2 high-expressing cells. BMI1 and Ezh2 oncoprotein expression were measured in prostate TMA samples from cancer patients and healthy donors using a quantitative co-localization immunofluorescence method and the number of dual positive high BMI1/Ezh2-expressing nuclei was calculated for each sample. Note that primary prostate tumors from patients diagnosed with prostate adenocarcinomas manifest a diverse spectrum of accumulation of dual positive BMI1/Ezh2 high-expressing cells and patients with higher levels of BMI1 or Ezh2 expression in prostate tumors manifest therapy-resistant malignant phenotype (FIG. 26). A majority (79%-92% in different cohorts of patients) of human prostate tumors contains dual positive high BMI1/Ezh2-expressing cells exceeding the threshold expression levels in prostate samples from normal individuals.

FIG. 26 shows that Increased BMI1 and Ezh2 expression is associated with high likelihood of therapy failure and disease relapse in prostate cancer patients after radical prostatectomy. Kaplan-Meier survival: analysis demonstrates that cancer patients with more significant elevation of the BMI1 and Ezh2 expression [having higher tumor (T) to adjacent normal tissue (N) ratio, T/N: FIG. 26A; or having tumors with higher levels of BMI1 (28B) or Ezh2 (28C) expression) are more likely to fail therapy and develop a disease recurrence after radical prostatectomy. FIG. 26E shows the Kaplan-Meier survival analysis of 79 prostate cancer patients stratified into five sub-groups using eight-covariate cancer therapy outcome (CTO) algorithm. CTO algorithm integrates individual prognostic powers of BMI1 and Ezh2 expression values and six clinico-pathological covariates (preoperative PSA, Gleason score, surgical margins, extra-capsular invasion, seminal vesicle invasion, and age).

FIG. 27 shows breast cancer CTOP signatures in Affymetrix format, with predictive outcomes.

Figures 10, 28:
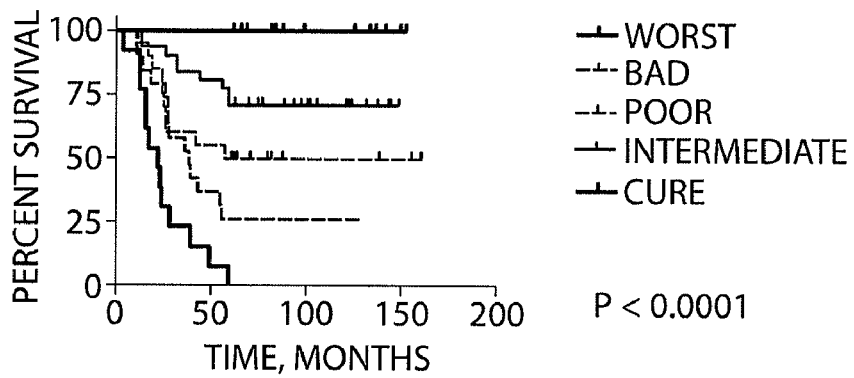

FIG. 28 shows breast cancer CTOP signatures in Agilent Rosetta Chip format, with predictive outcomes.

Figures 5, 29:
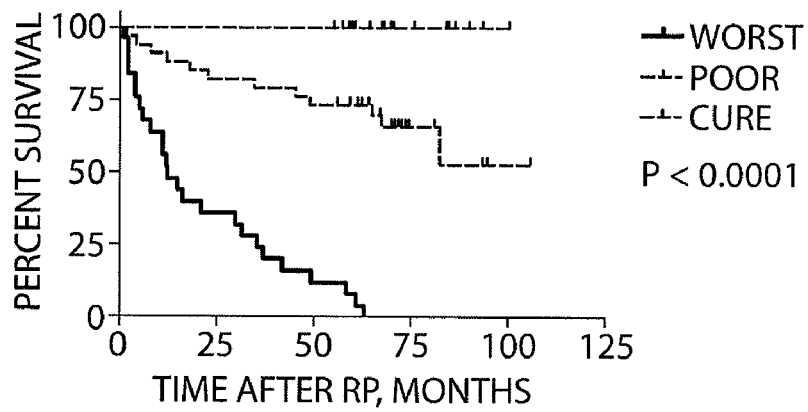
Figures 6, 29:
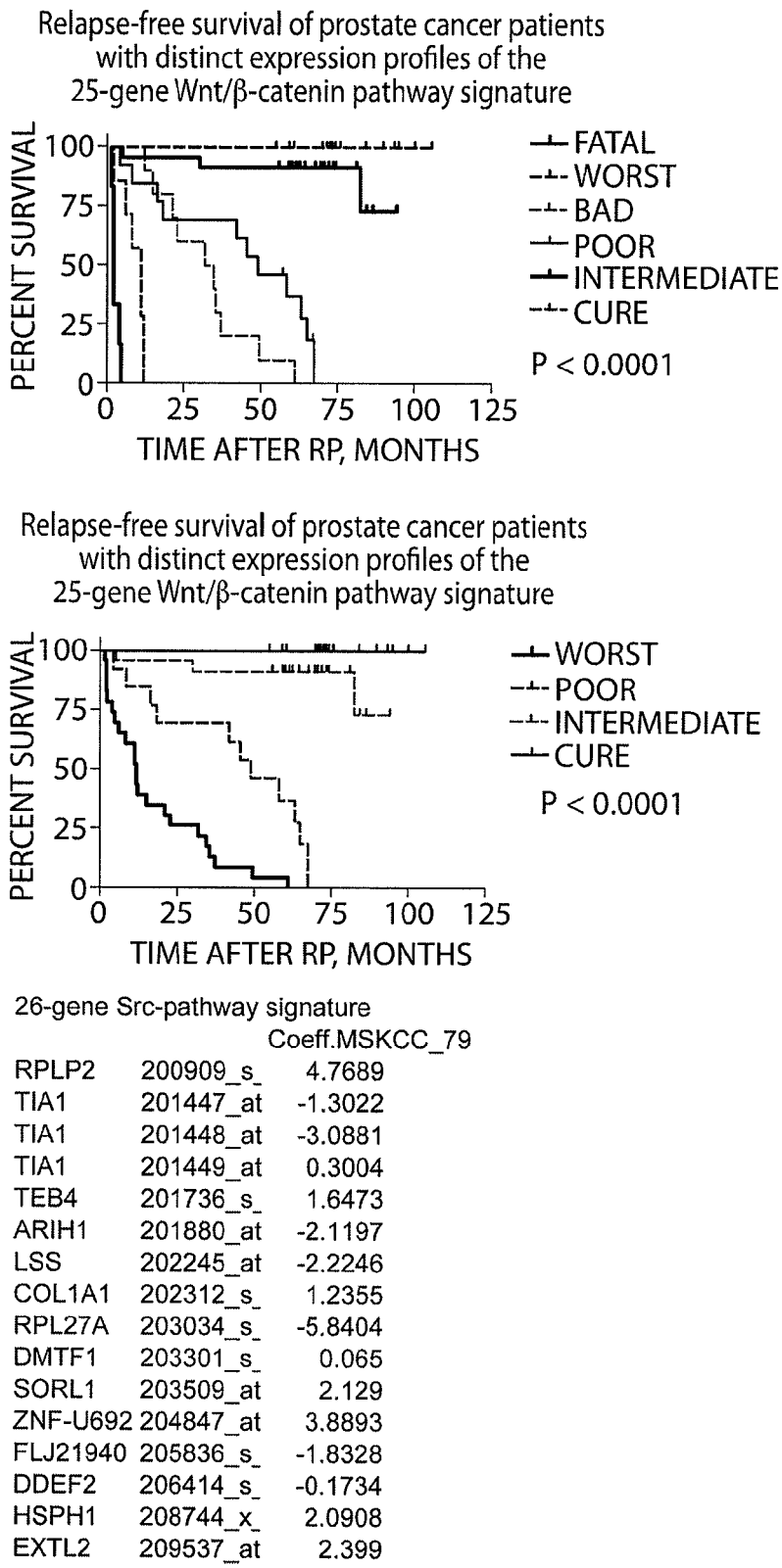
Figures 11, 29:
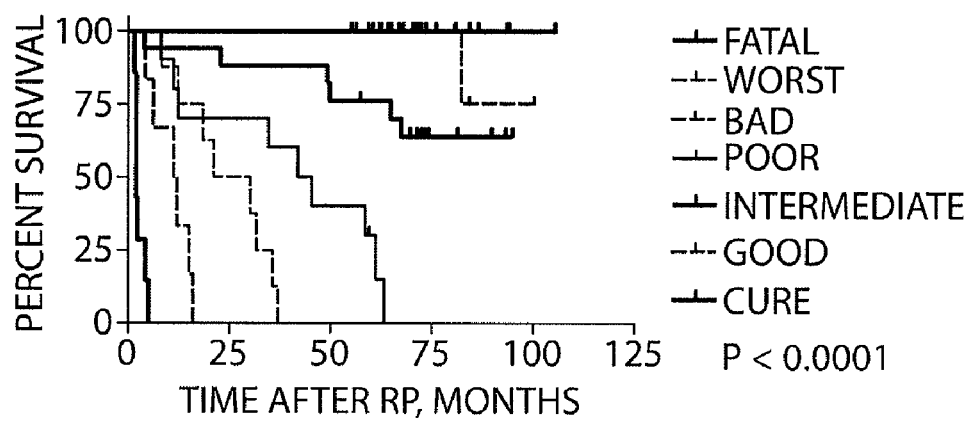

FIG. 29 shows prostate cancer CTOP signatures in Affymetrix format, with predictive outcomes.

FIG. 30 shows PI3K pathway CTOP signatures.

FIG. 31 shows SNP based CTOP signatures NG2007.

FIG. 32 shows the parent methylation Signatures.

FIG. 33 shows the histones H3 and H2A CTOP signatures.

FIG. 34 shows the CTOP gene expression signatures for prostate cancer.

FIG. 35 shows the CTOP gene expression signatures for breast cancer.

Figures 1, 36:
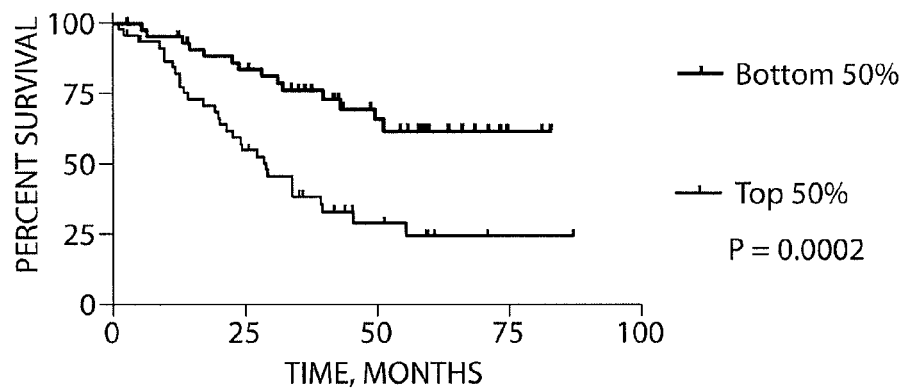
Figures 3, 36:
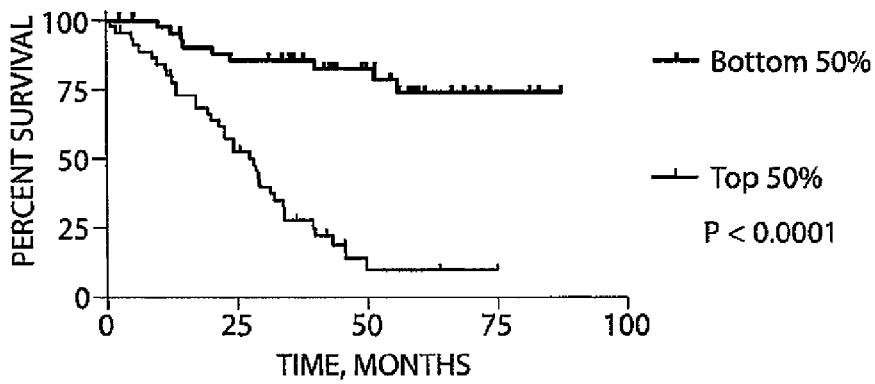
Figures 4, 36:
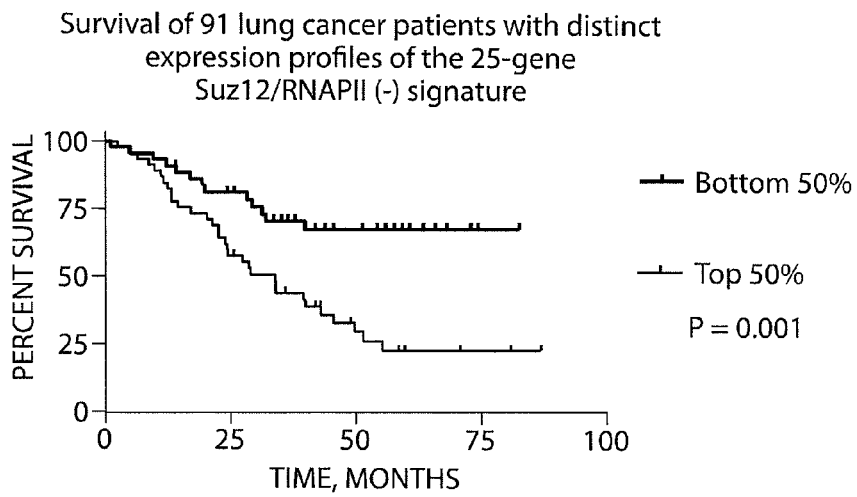
Figures 5, 36:
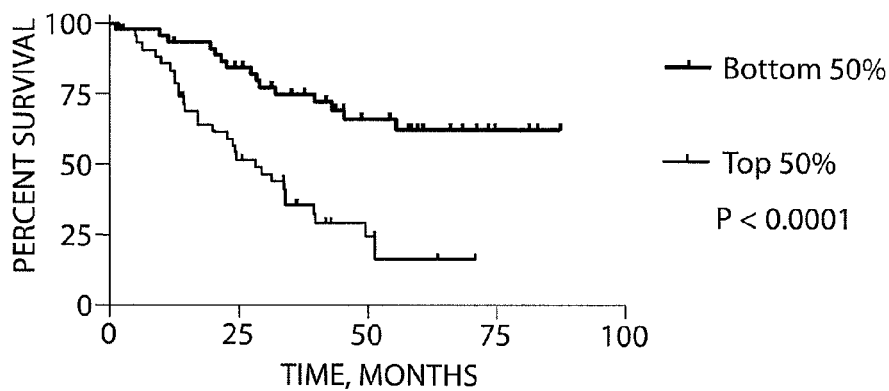
Figures 6, 36:
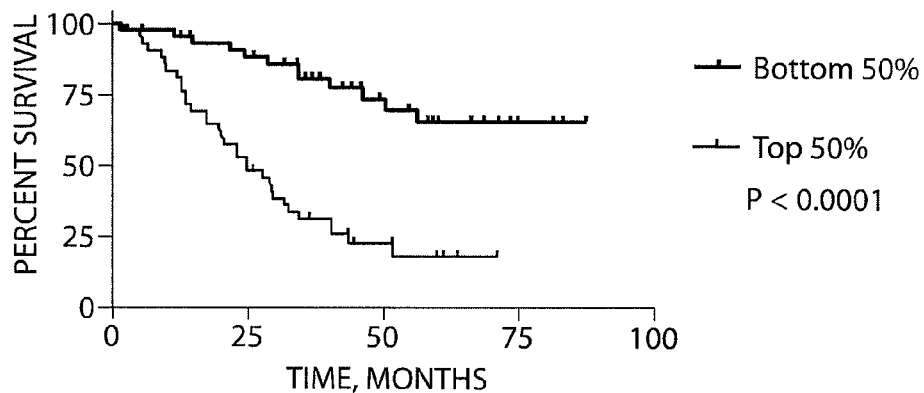
Figures 7, 36:
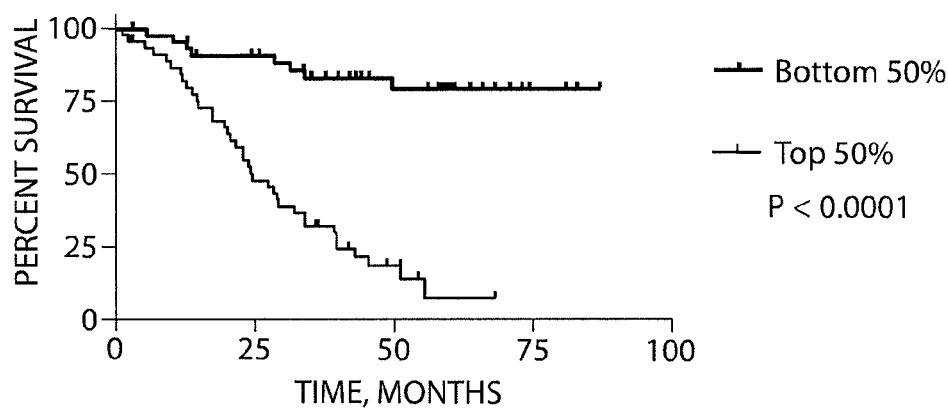
Figures 8, 36:
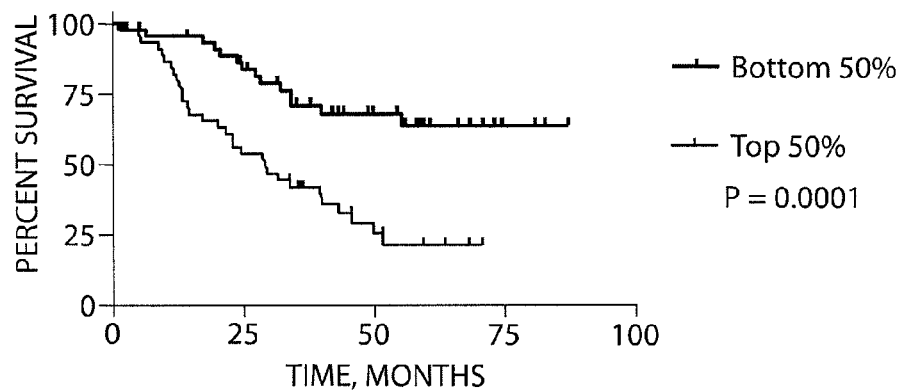
Figures 9, 36:
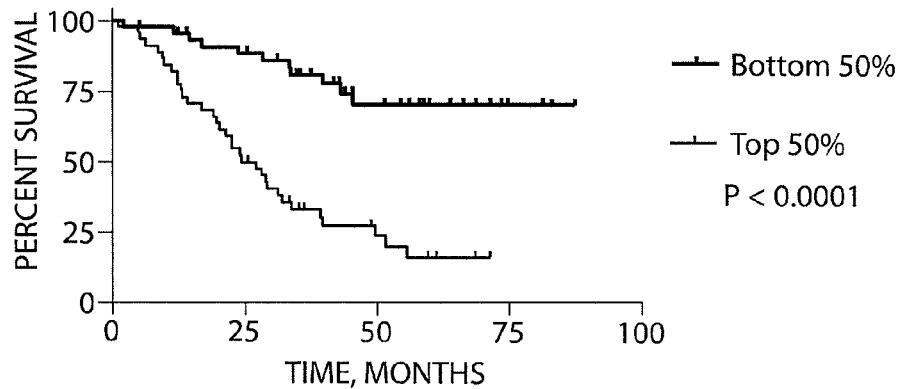
Figures 10, 36:
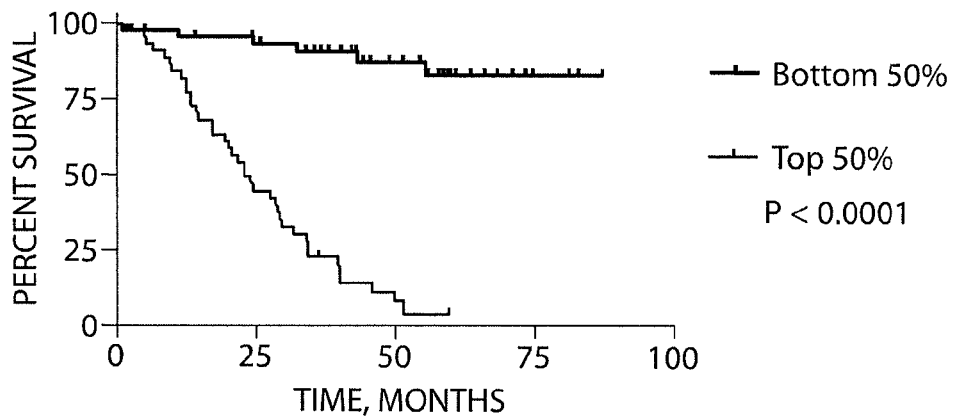
Figures 11, 36:
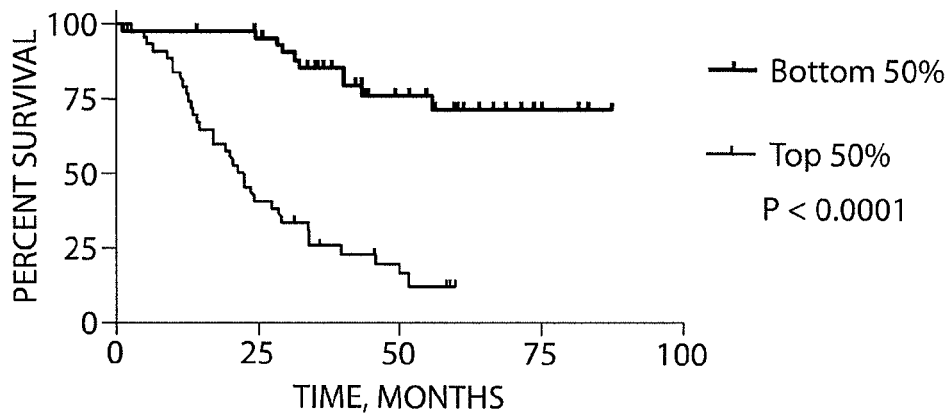
Figures 12, 36:
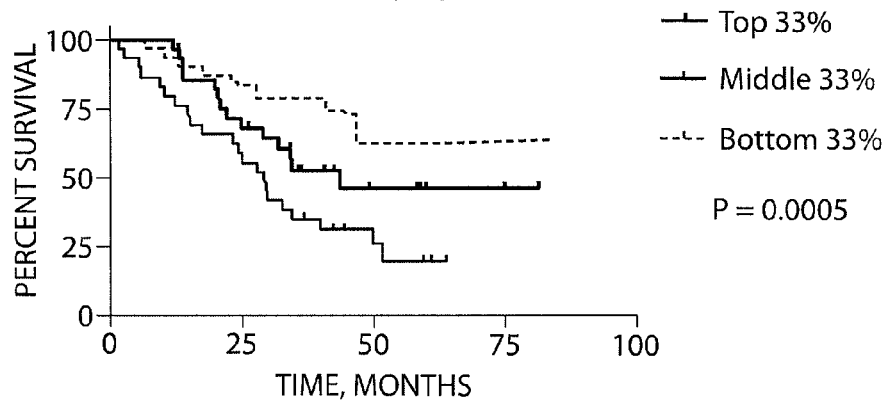
Figures 13, 36:
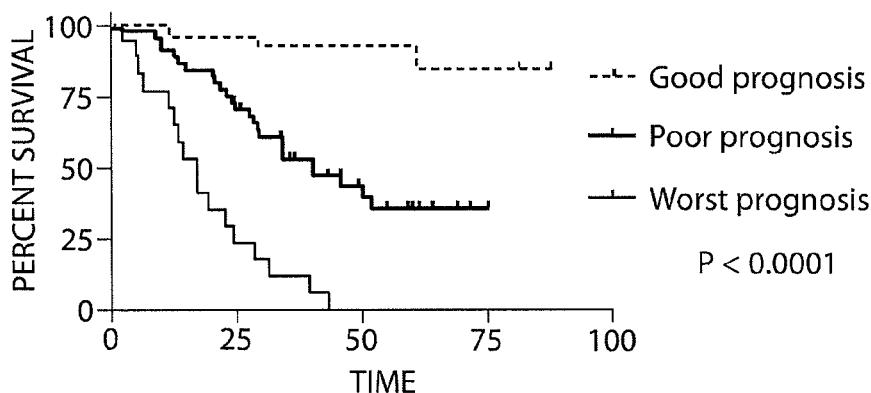

FIG. 36 shows the CTOP gene expression signature and survival data for lung cancer.

FIG. 37 shows the CTOP gene expression signature for ovarian cancer.

FIG. 38 shows the CTOP gene expression signatures for breast cancer.

FIG. 39 shows examples of the evaluation of the CMAP00 and CMAP11 drug combinations in prostate cancer and the CMAP19 drug combination in breast cancer.

FIG. 40 shows CTOP scores for lung cancer.

Figure 41:
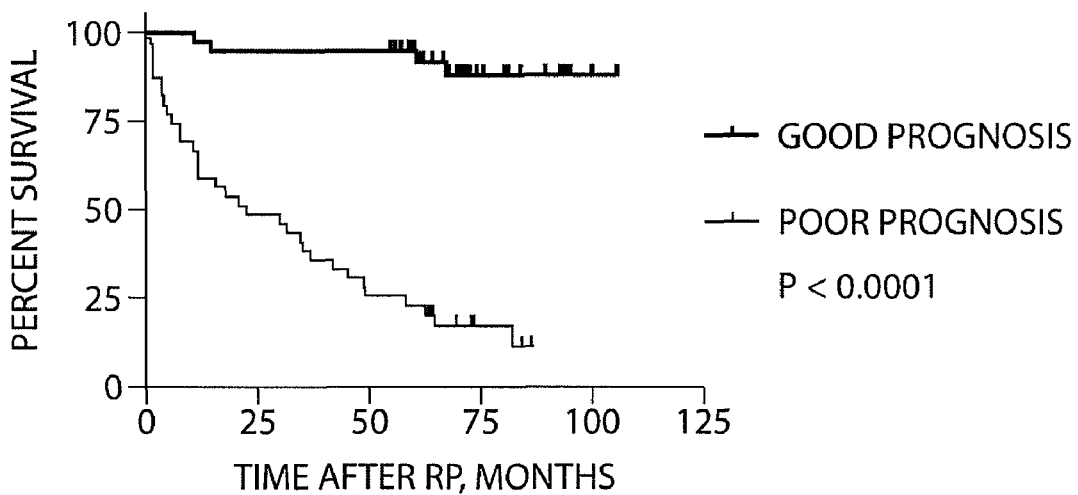
Figure 1:
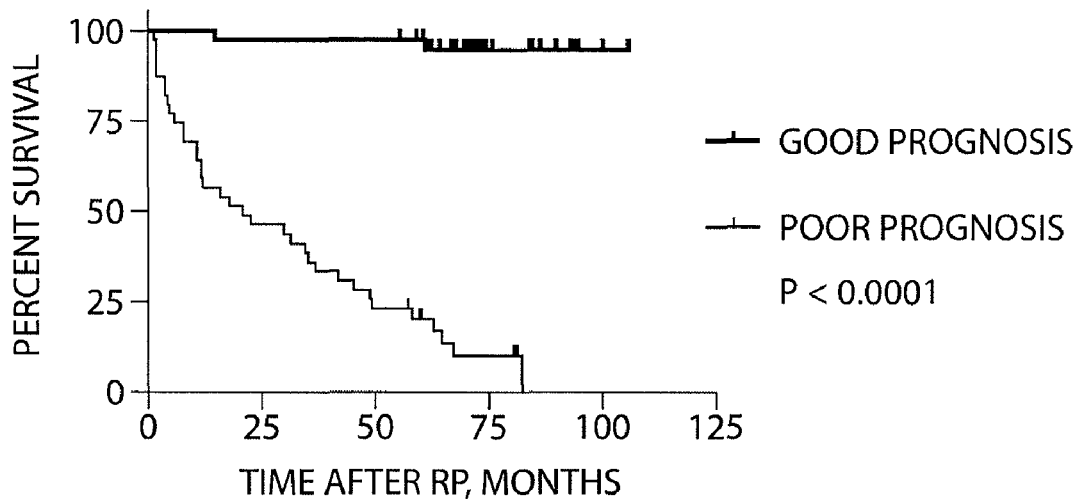
Figures 2, 41:
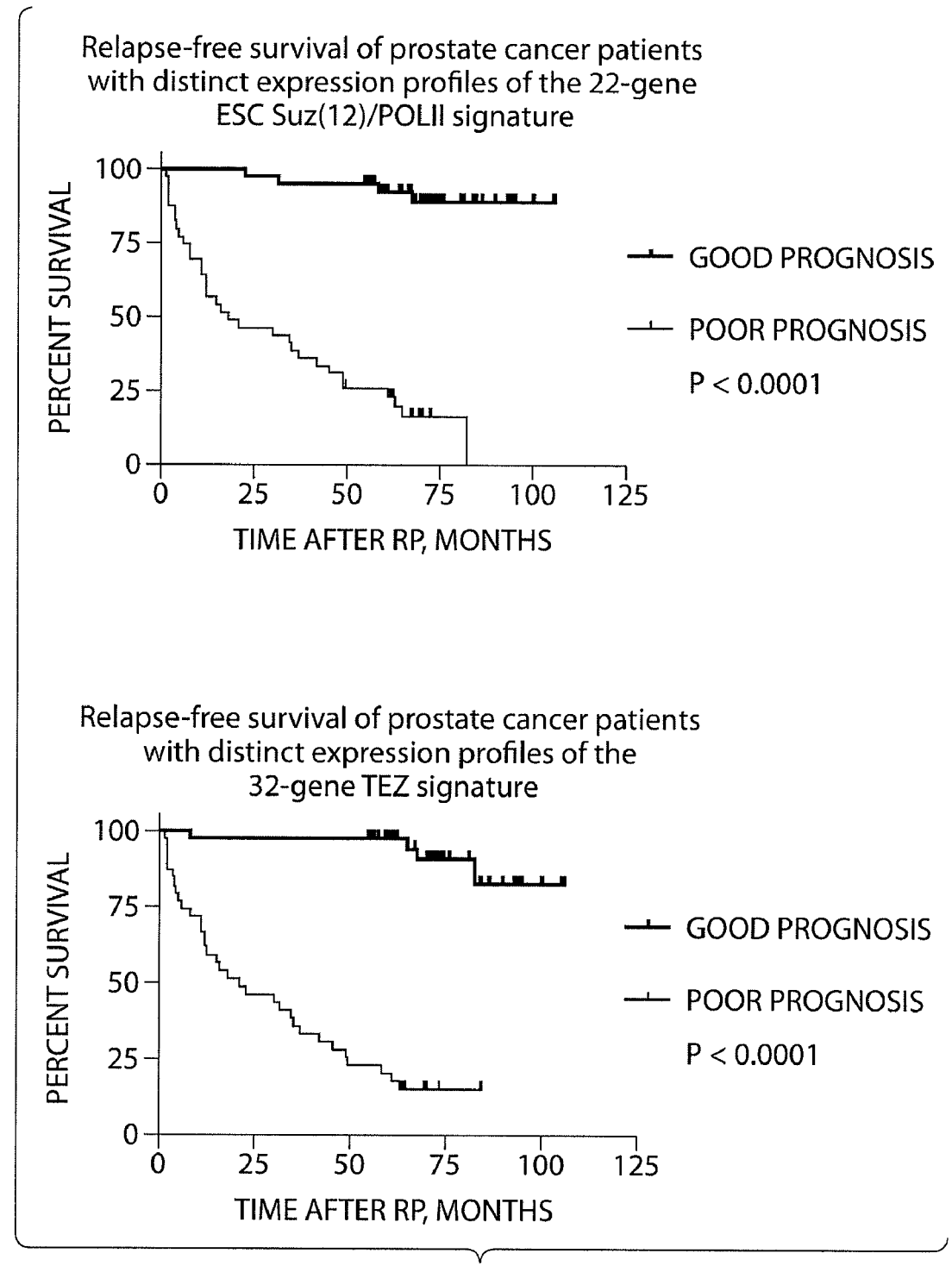
Figures 3, 41:
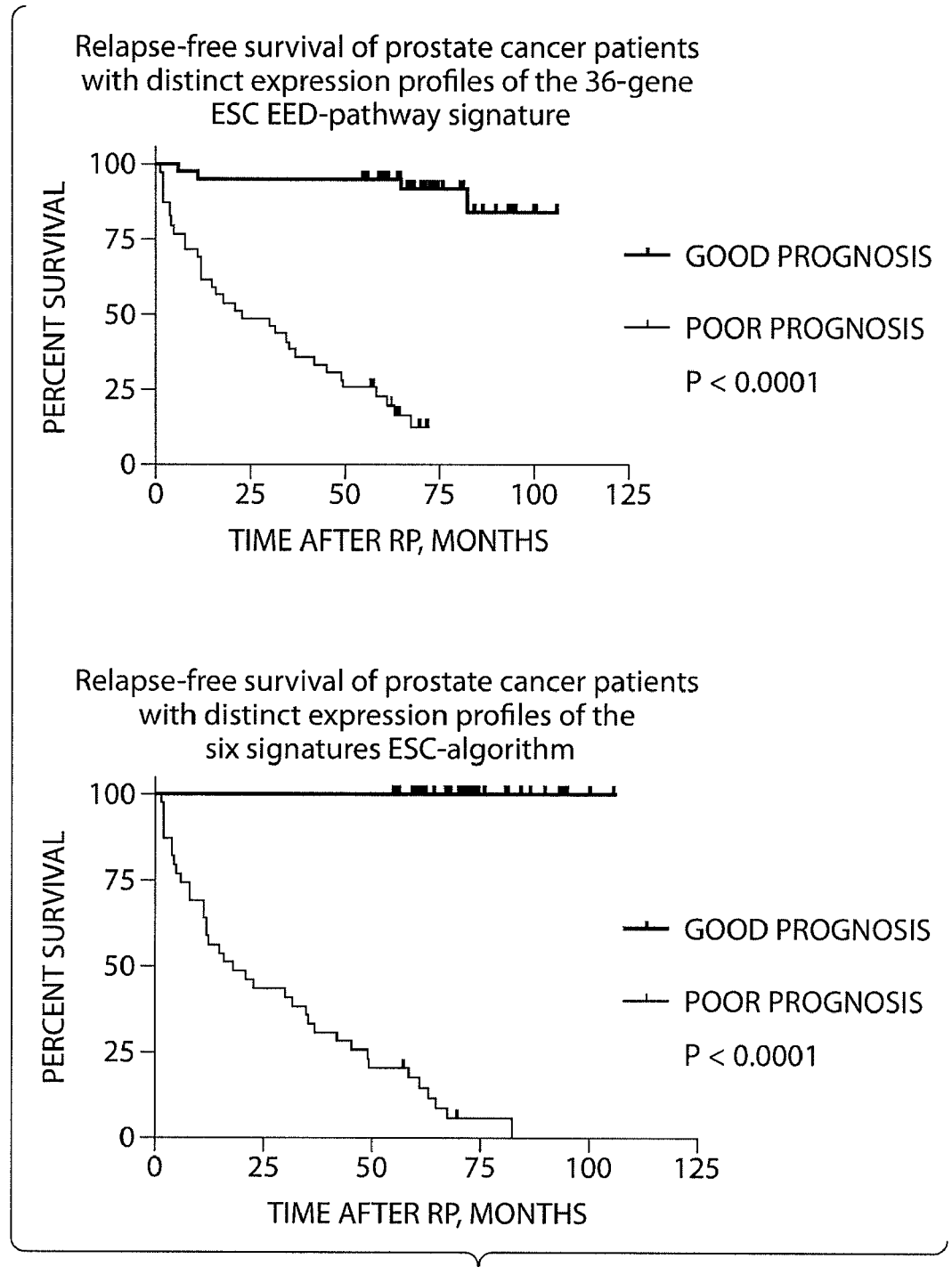
Figures 4, 41:
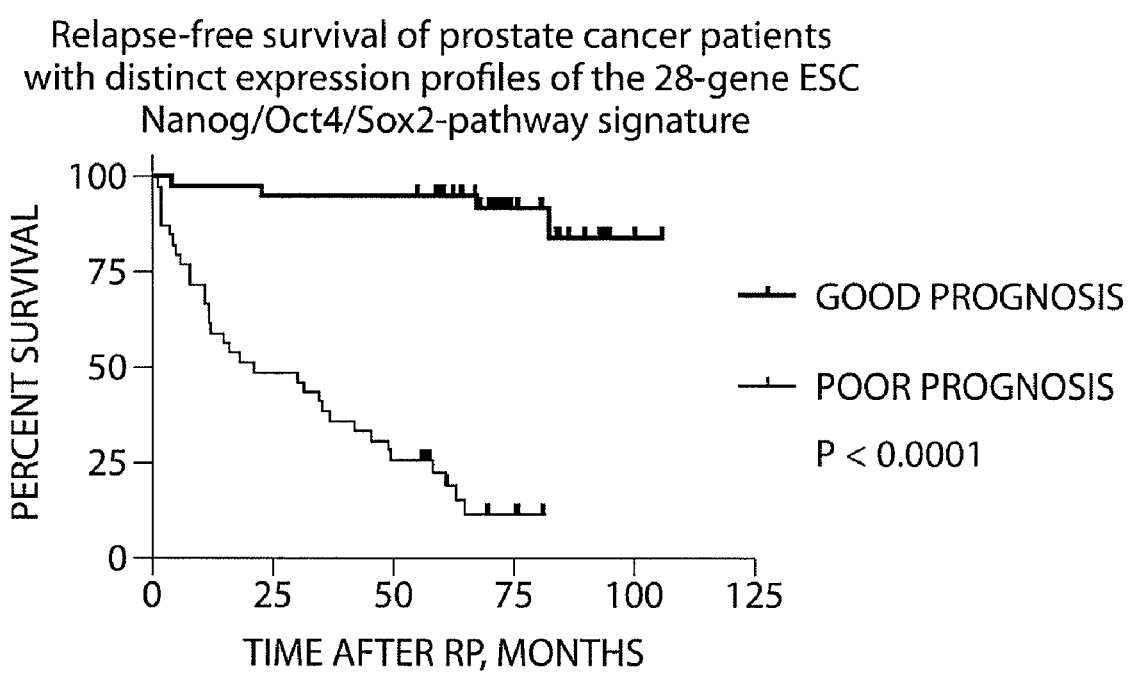

FIG. 41 shows Kaplan-Meier survival analysis of seventy-nine prostate cancer patients stratified into sub-groups with distinct expression profiles of the individual Polycomb pathway ESC signatures (top six panels) or six ESC signatures algorithm (bottom panel) in primary prostate tumors. In each individual signature panel, patients were sorted in descending order based on the values of the corresponding signature CTOP scores and divided into poor prognosis (top 50% scores) and good prognosis (bottom 50% scores) sub-groups. In the last panel, patients were sorted in descending order based on the values of the cumulative CTOP scores and divided into poor prognosis (top 50% scores) and good prognosis (bottom 50% scores) sub-groups. The cumulative CTOP scores represent the sum of the six individual CTOP scores calculated for each patient.

Figure 42:
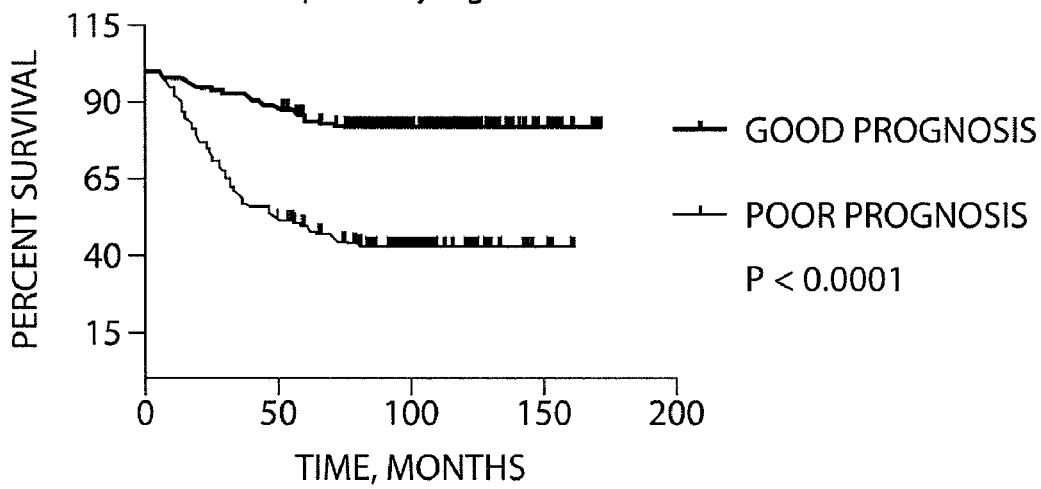
Figure 1:
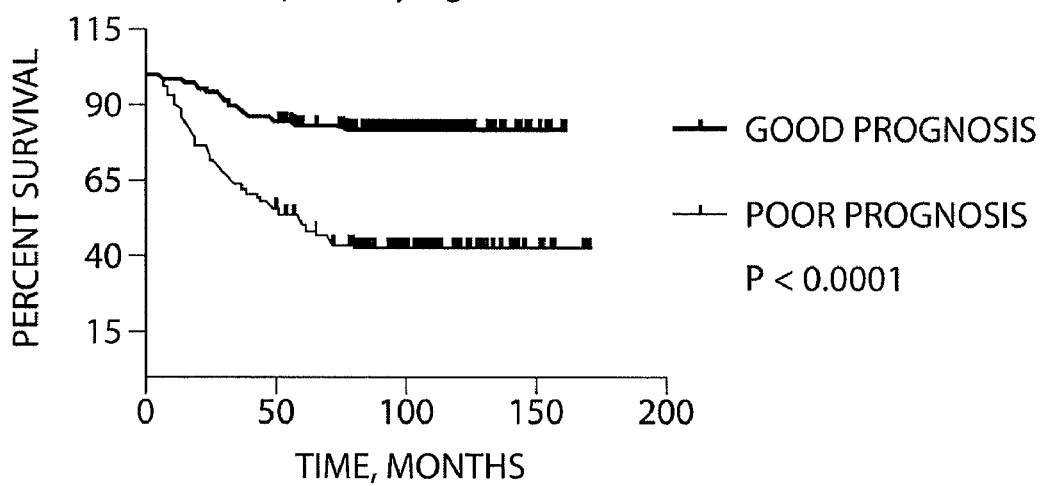
Figure 42:
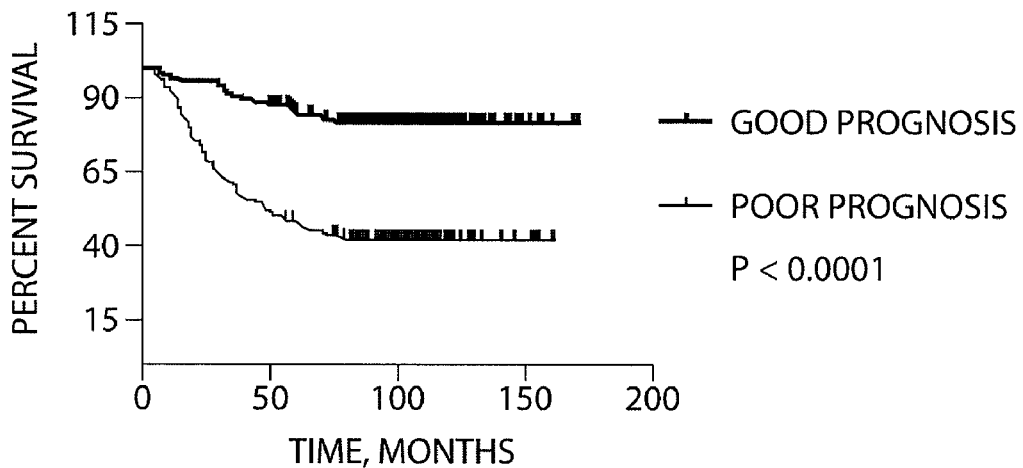
Figure 2:
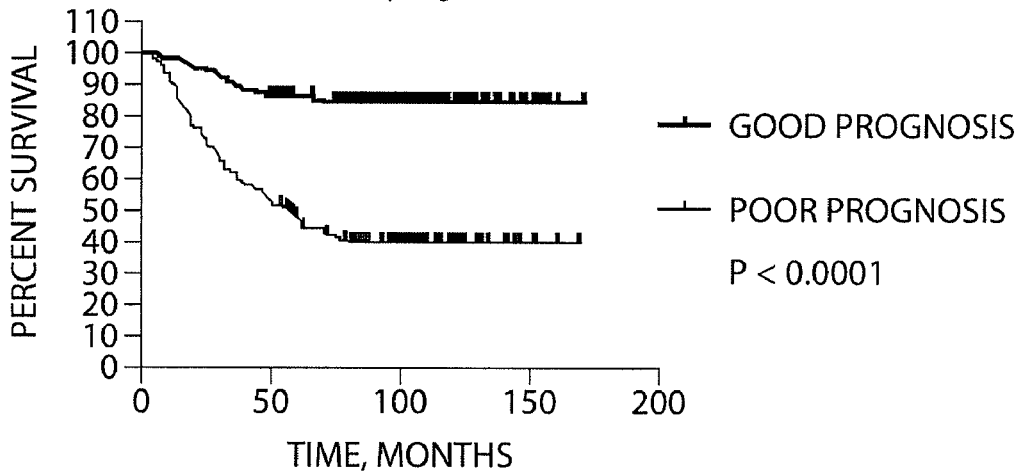
Figures 3, 42:
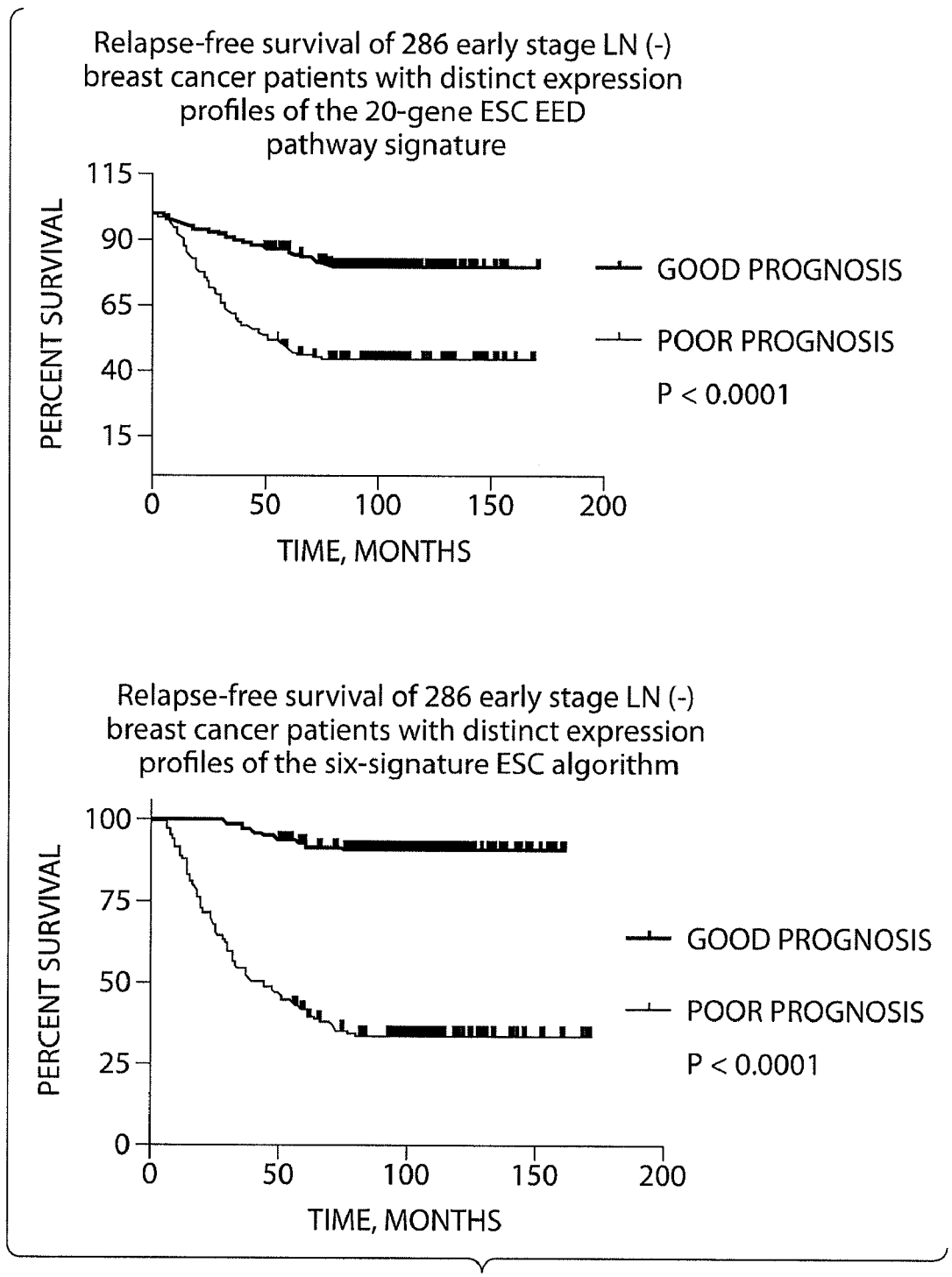
Figures 4, 42:
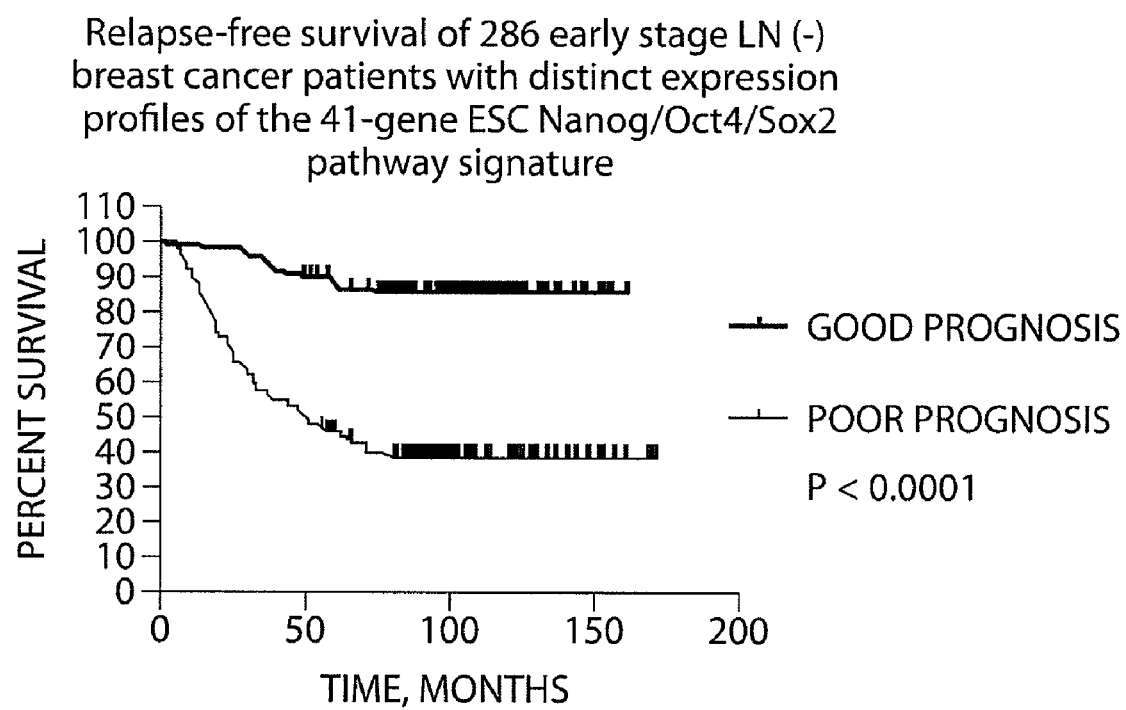
Figures 5, 42:
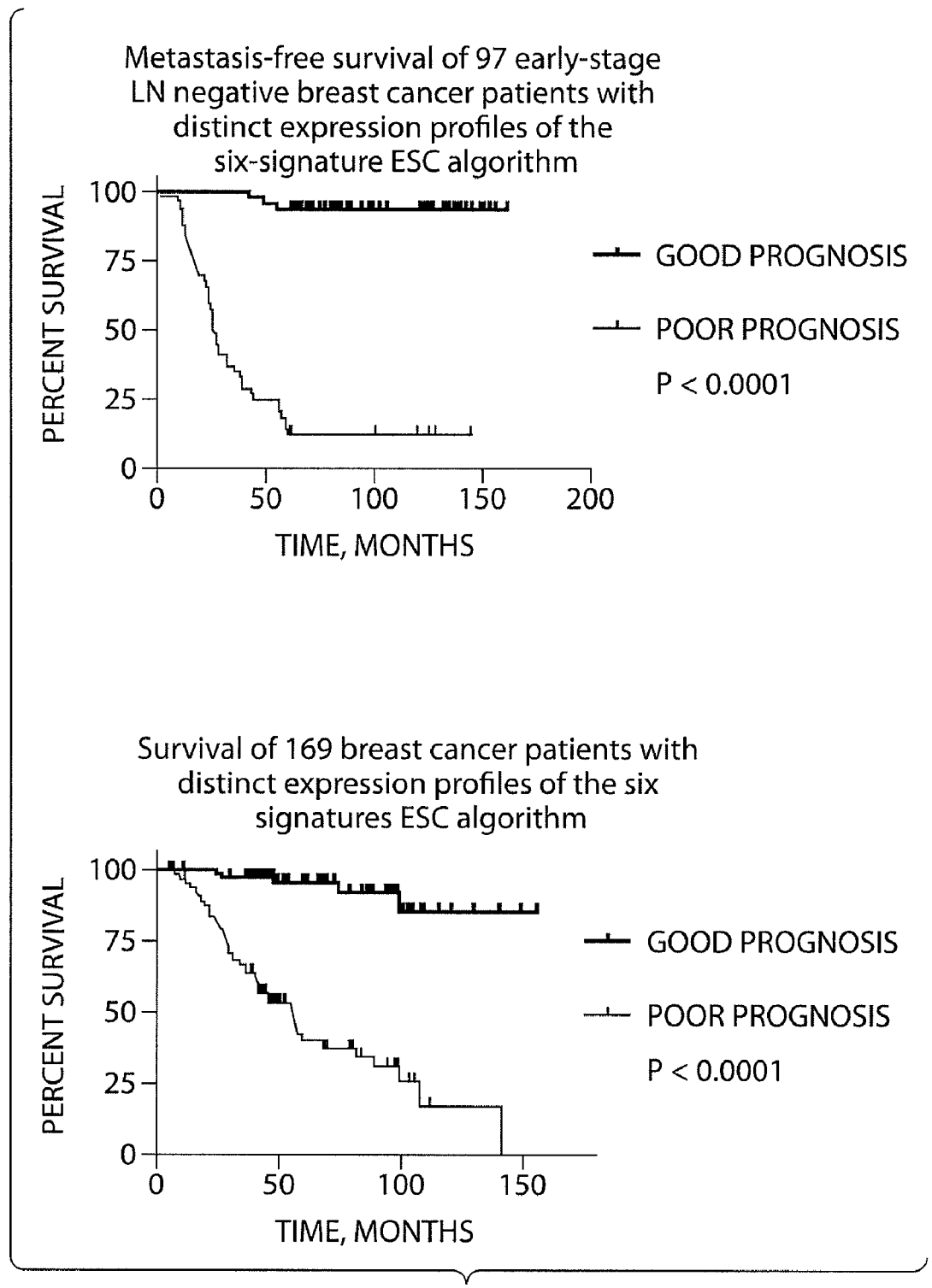
Figures 6, 42:
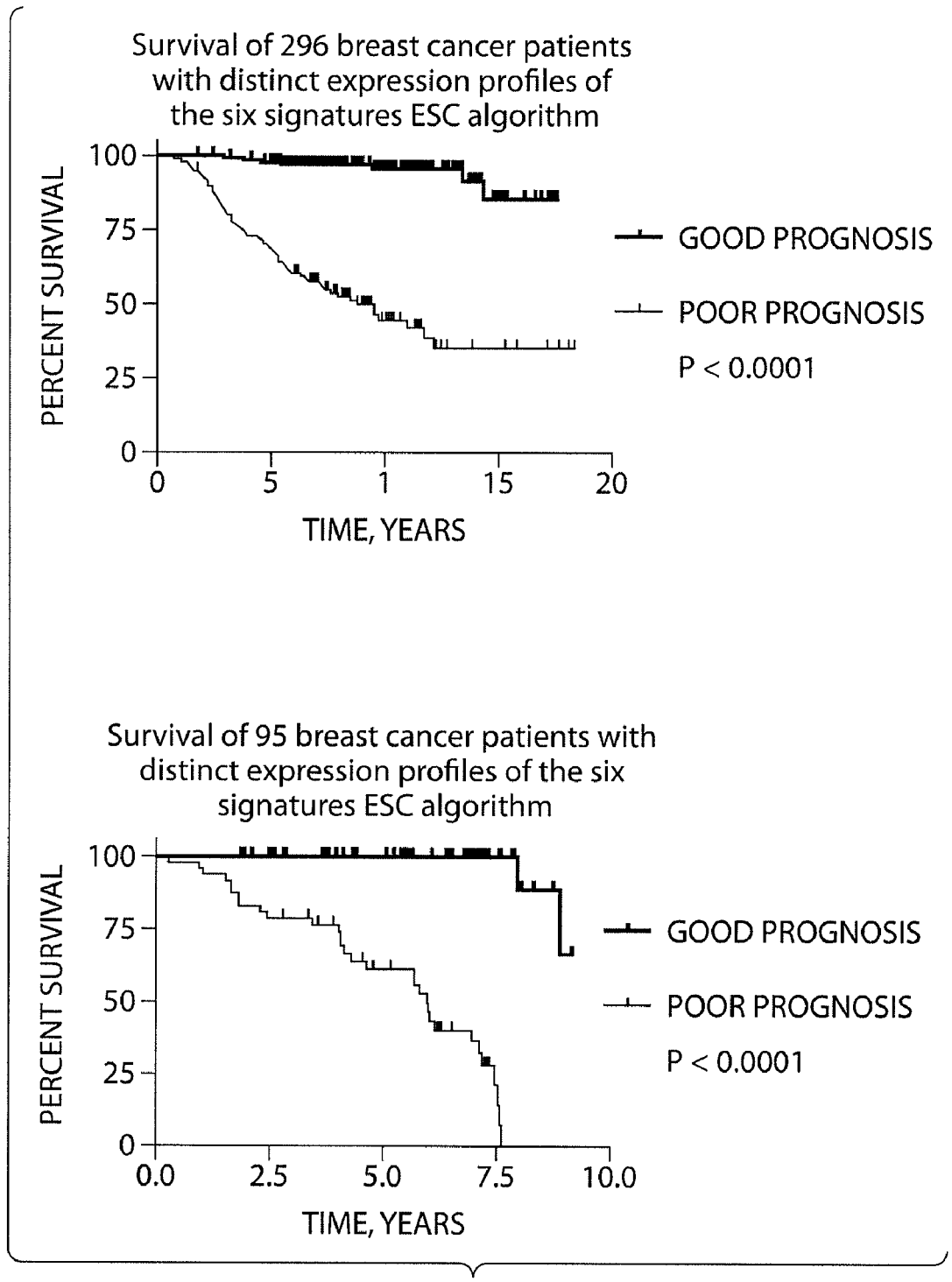

FIG. 42 shows Kaplan-Meier survival analysis of two-hundred eighty-six early-stage LN negative breast cancer patients stratified into sub-groups with distinct expression profiles of the individual Polycomb pathway ESC signatures (top six panels) or six ESC signatures algorithm (single middle panel) in primary breast tumors. Bottom four panels show patients' classification performance of the six ESC signatures algorithm in four different breast cancer therapy outcome data sets. Patients' stratification was performed using either individual CTOP scores (top six panels) or cumulative CTOP scores (bottom five panels) as described in the legend to the FIG. 41.

Figures 1, 43:
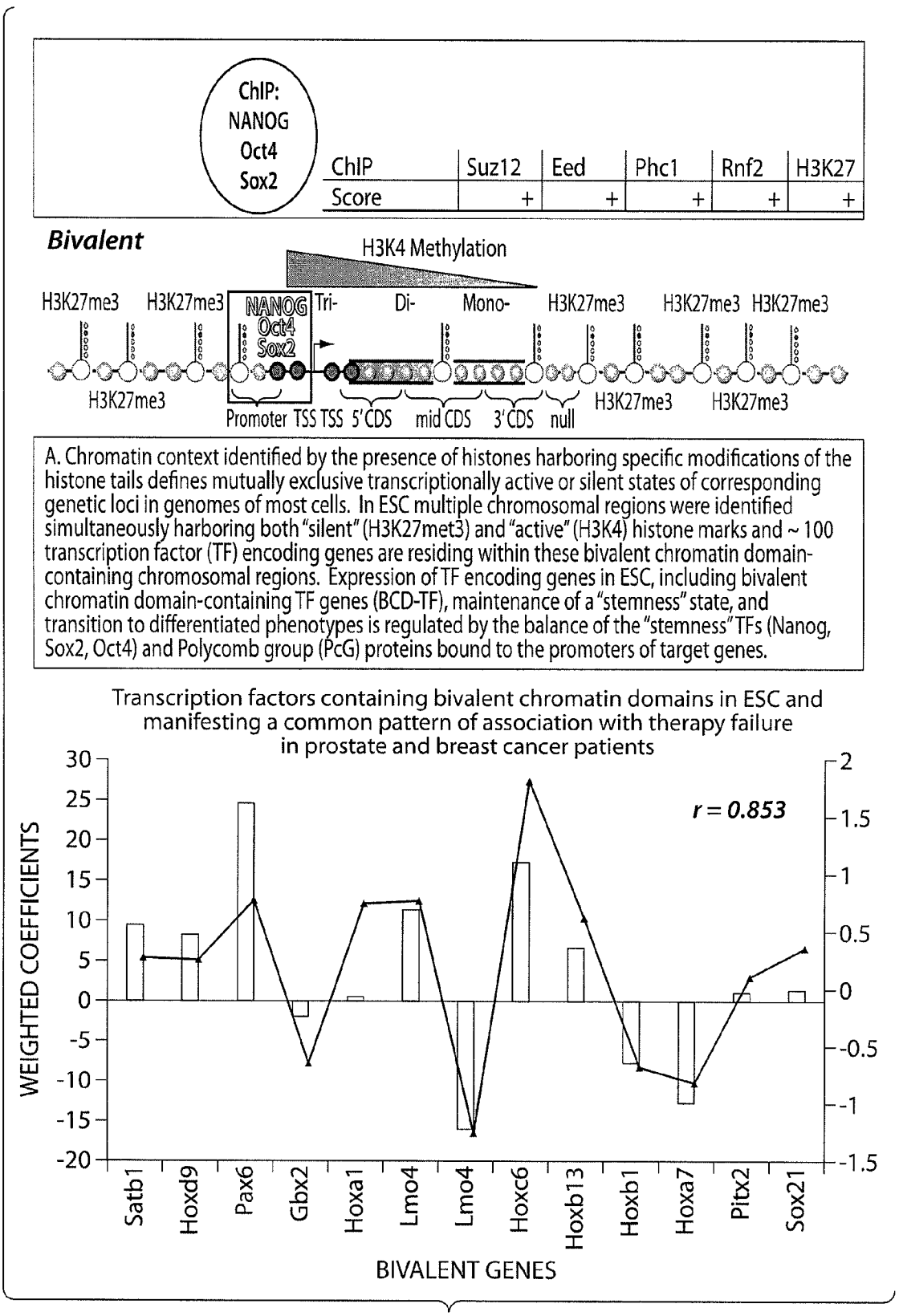
Figures 2, 43:
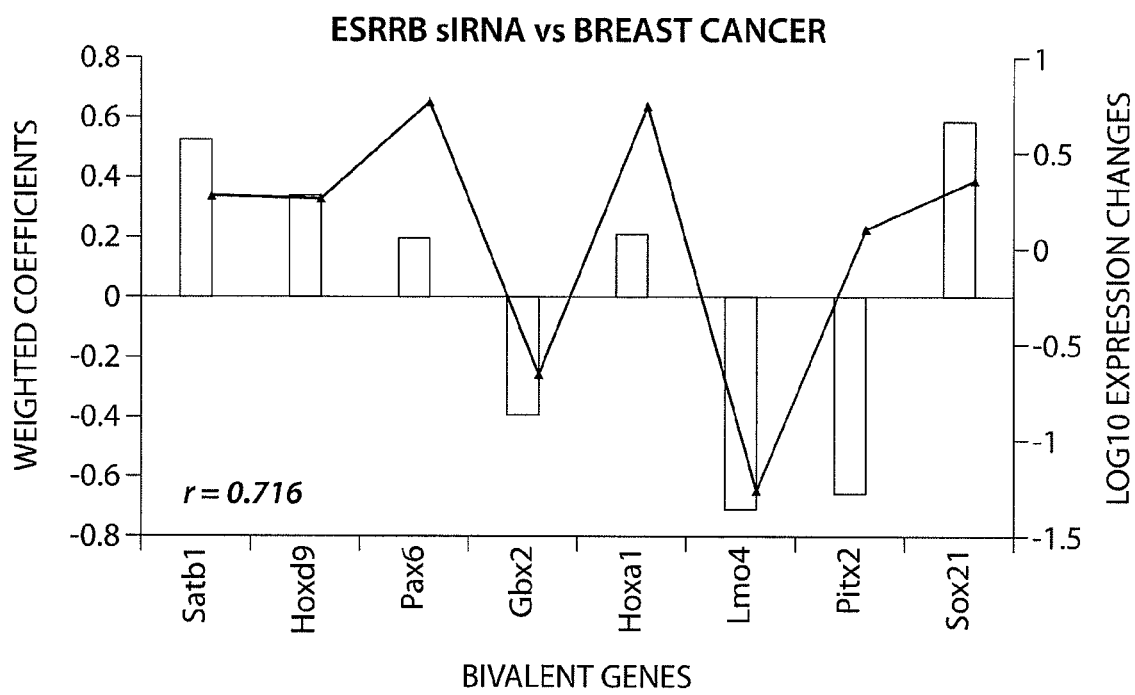
Figures 3, 43:
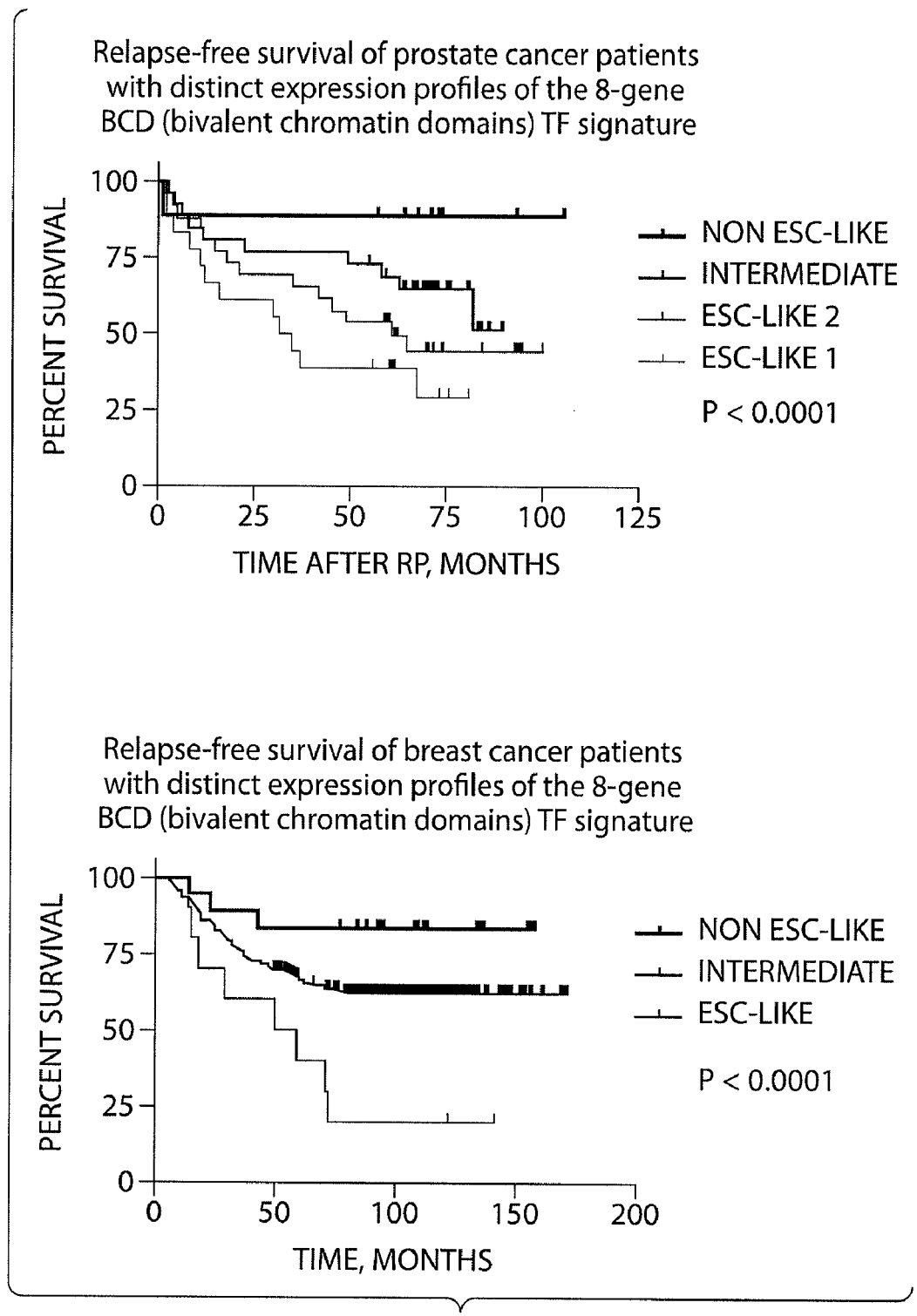

FIG. 43 shows bivalent chromatin domain-containing transcription factors (BCD-TF) manifest "stemness" expression profiles in therapy-resistant prostate and breast tumors.

A. Chromatin context identified by the presence of histones harboring specific modifications of the histone tails defines mutually exclusive transcriptionally active or silent states of corresponding genetic loci in genomes of most cells. In ESC multiple chromosomal regions were identified simultaneously harboring both "silent" (H3K27met3) and "active" (H3K4) histone marks and ~100 transcription factor (TF) encoding genes are residing within these bivalent chromatin domain-containing chromosomal regions. Expression of selected TF encoding genes in ESC, including bivalent chromatin domain-containing TF genes (BCD-TF), maintenance of a "stemness" state, and transition to differentiated phenotypes is regulated by the balance of the "stemness" TFs (Nanog, Sox2, Oct4) and Polycomb group (PcG) proteins bound to the promoters of target genes.

B. Thirteen-gene BCD-TF signature manifesting highly concordant (r=0.853; P<0.001) gene expression profiles in breast and prostate tumors from patients with therapy-resistant disease phenotypes.

C. Eight-gene BCD-TF signature (derived from thirteen-gene BCD-TF signatures) manifesting highly concordant expression profiles (r=0.716; p<0.001) in ESC and therapy-resistant breast and prostate tumors. Kaplan-Meier analysis demonstrates that prostate and breast cancer patients with tumors harboring ESC-like expression profiles of the eight-gene BCD-TF signature are more likely to fail therapy (bottom two panels). Gene expression profiles of clinical samples were independently generated for therapy-resistant breast and prostate tumors using multivariate Cox regression analysis of microarrays of tumor samples from 286 breast cancer and 79 prostate cancer patients with known log-term clinical outcome after therapy. Gene expression profiles of mouse ESC were derived by comparing microarray analyses of pluripotent self-renewing ESC (control ESC cultures treated with HP siRNA) versus ESC treated with Esrrb siRNA (day 6). At this time point, Esrrb siRNA-treated ESC do not manifest "stemness" phenotype and form colonies of differentiated cells.

Figures 1, 44:
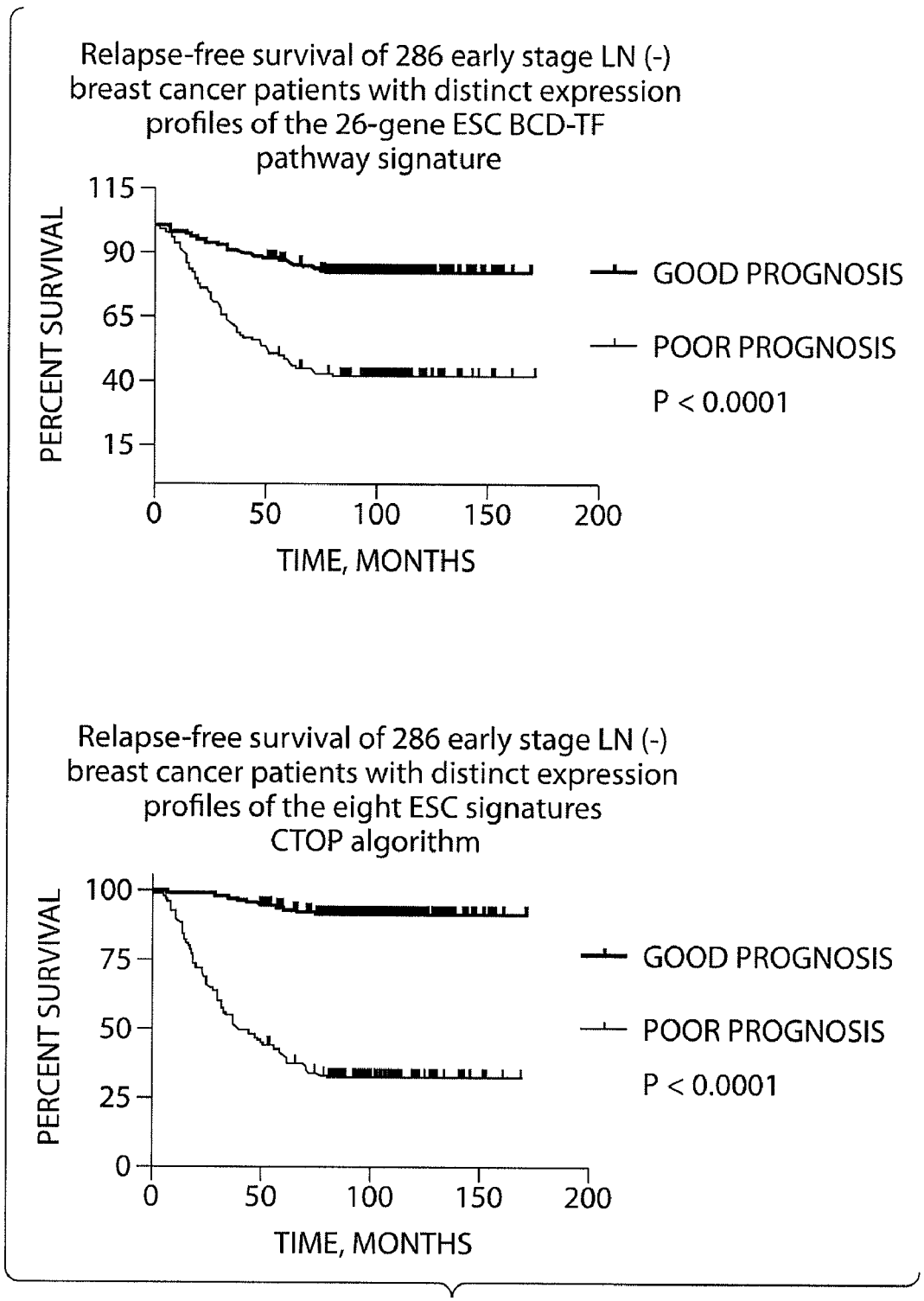
Figure 44:
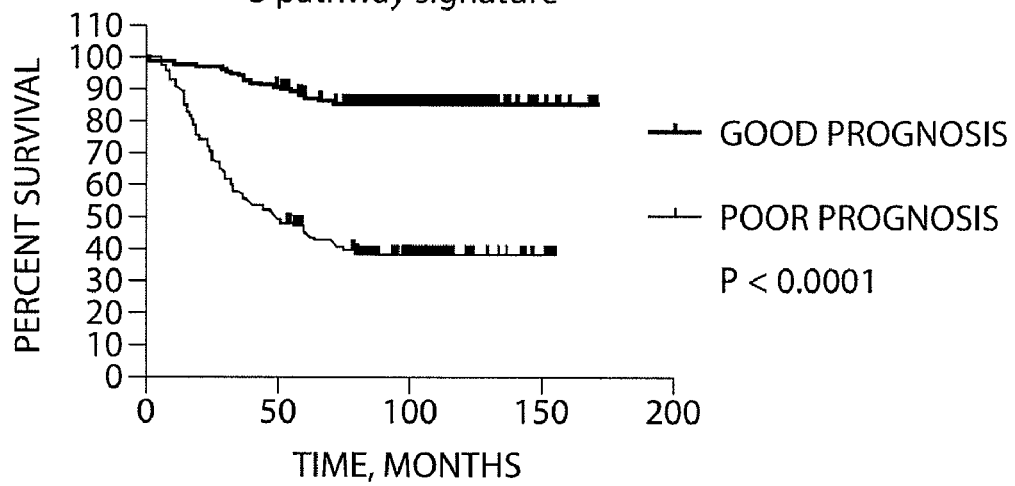
Figure 2:
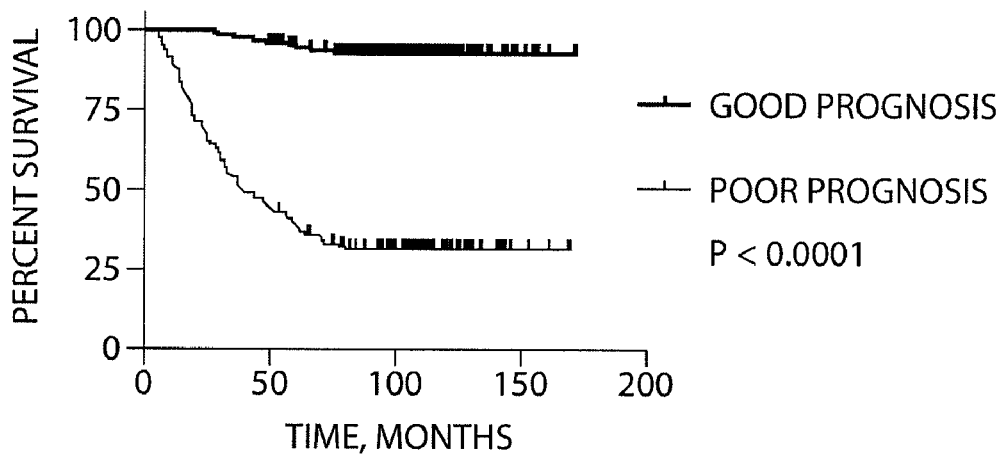
Figures 3, 44:
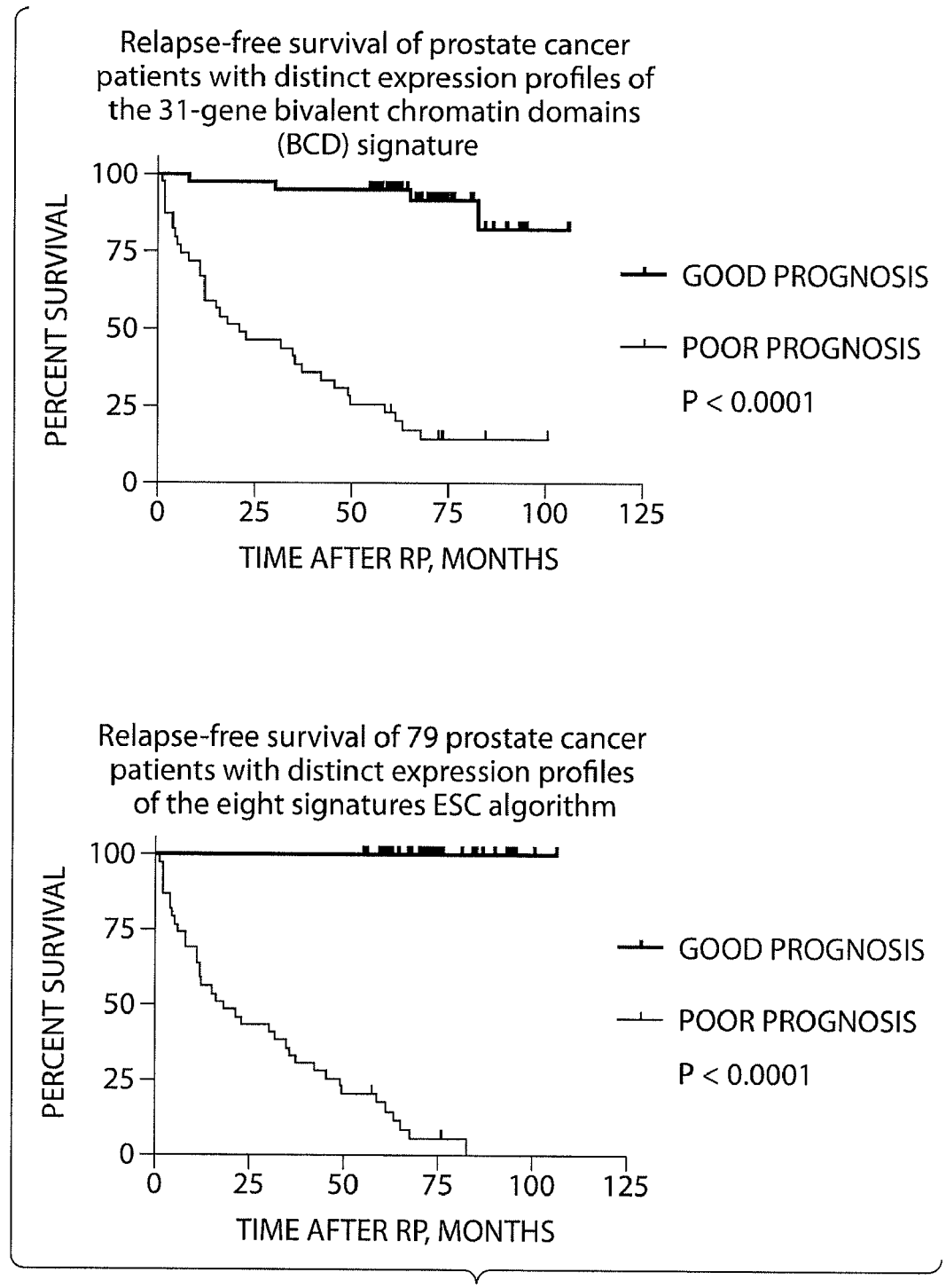
Figures 4, 44:
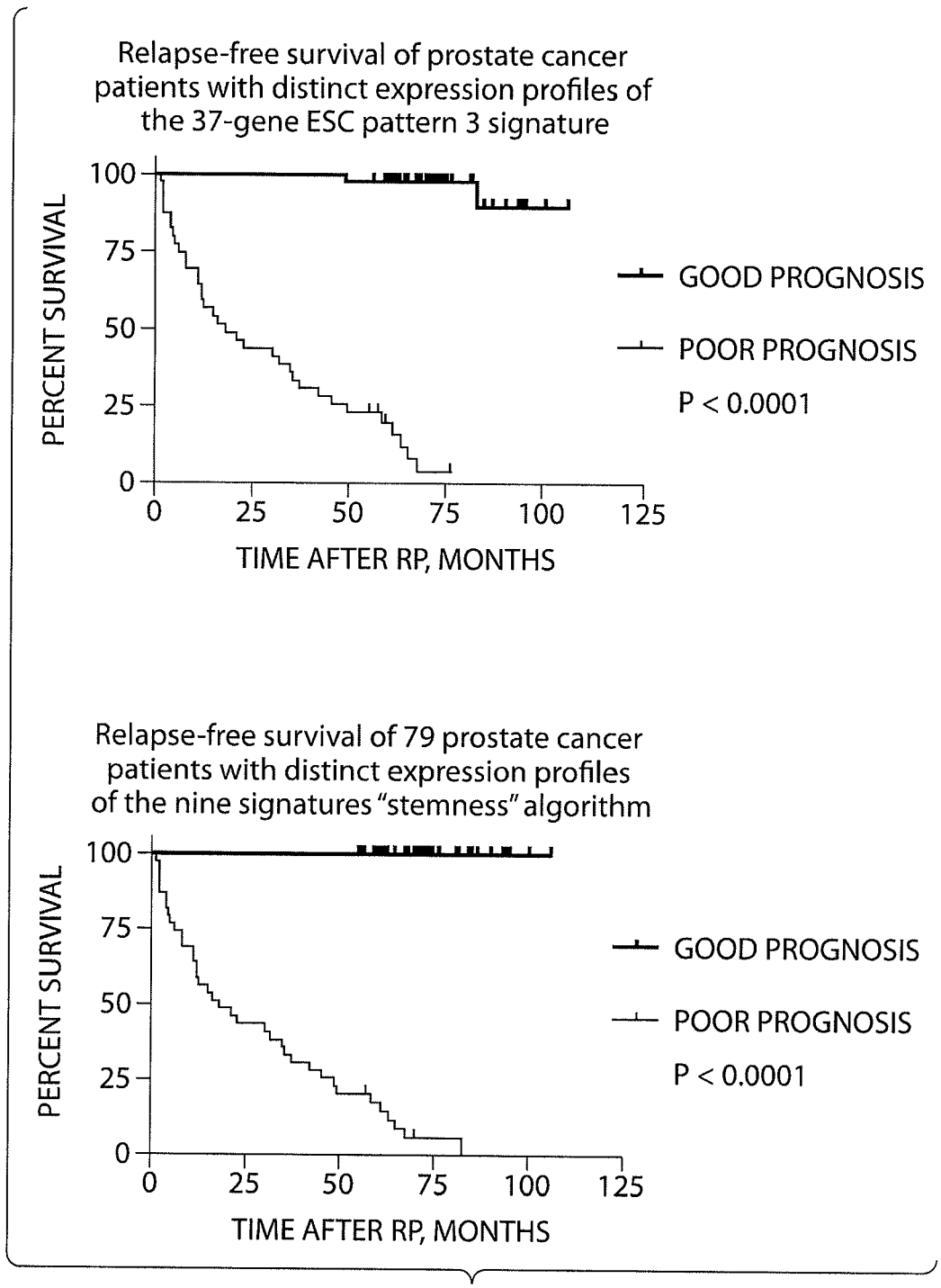

FIG. 44 shows Kaplan-Meier survival analysis of two-hundred eighty-six early-stage LN negative breast cancer patients (top four panels) and seventy-nine prostate cancer patients (bottom four panels) stratified into sub-groups with distinct expression profiles of the individual CTOP signatures [bivalent chromatin domain transcription factors (BCD-TF) and ESC pattern 3 signatures], eight ESC signatures algorithm, and nine "stemness" signatures algorithm in primary breast or prostate tumors. Patients' stratification was performed using either individual CTOP scores (for individual signatures) or cumulative CTOP scores (for CTOP algorithms) as described in the legend to the FIG. 41.

Figure 45:
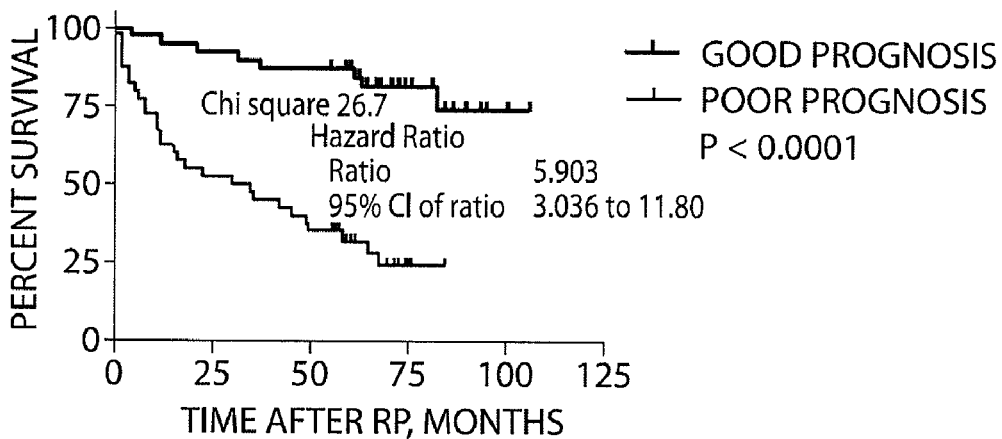
Figure 1:
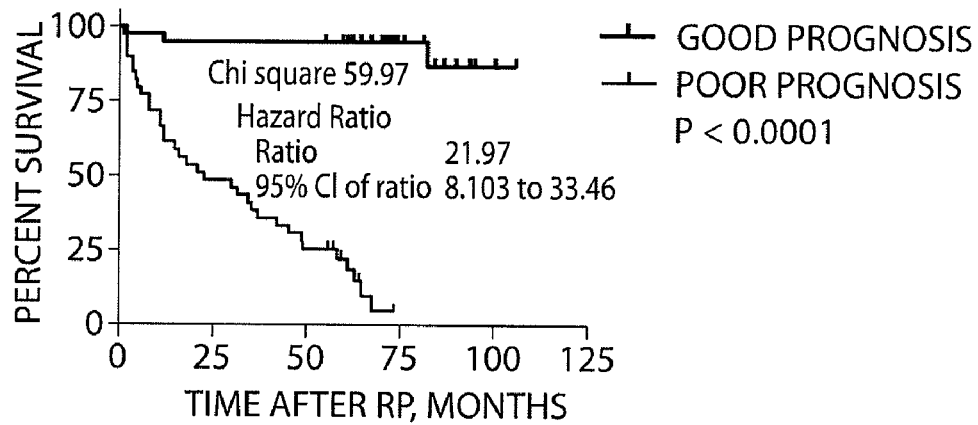
Figure 45:
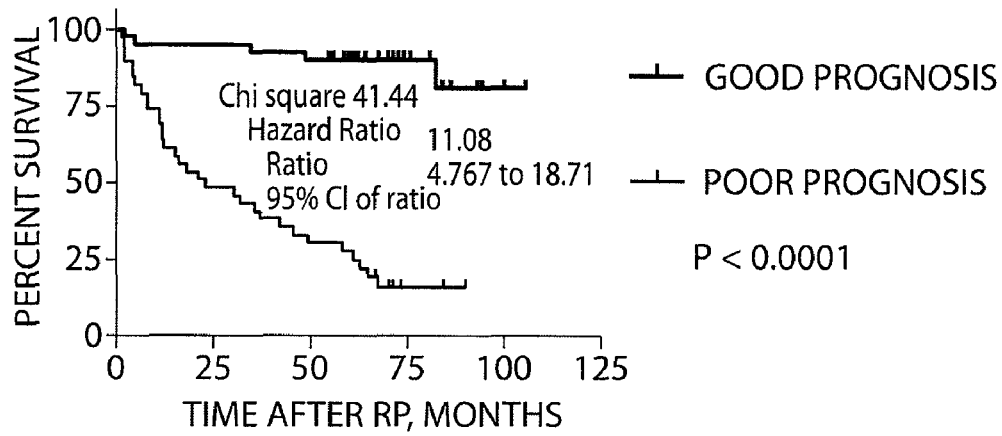
Figure 2:
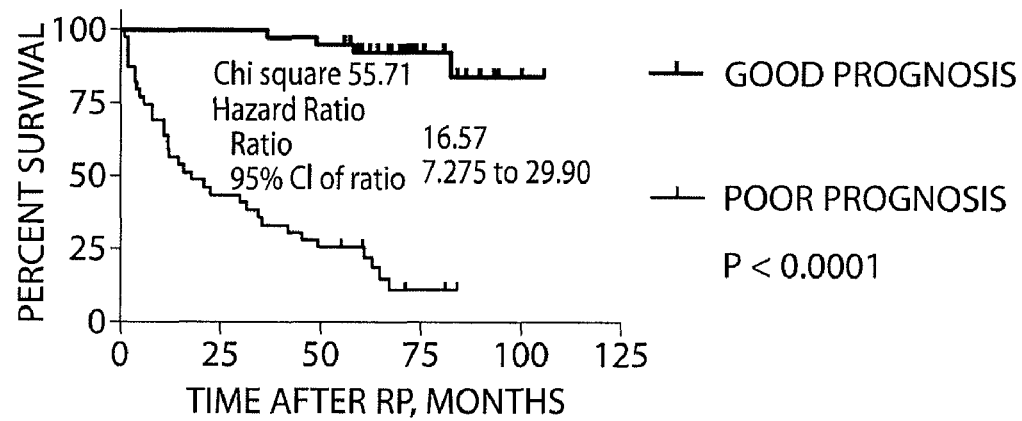
Figure 45:
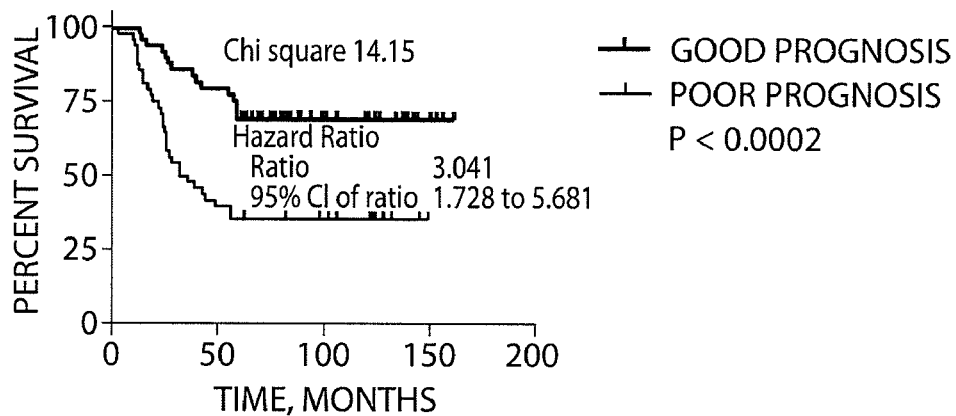
Figure 3:
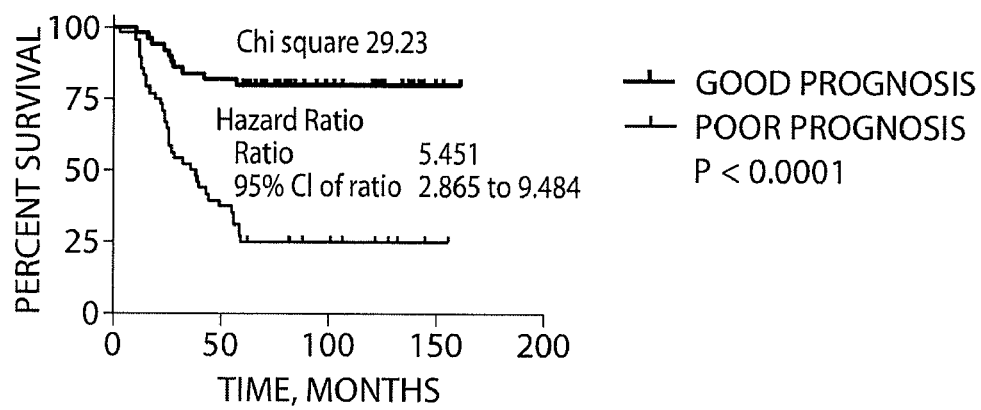
Figure 45:
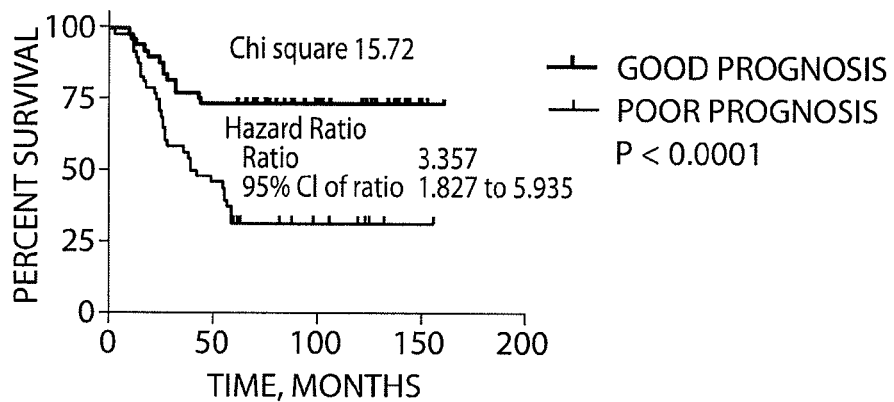
Figure 4:
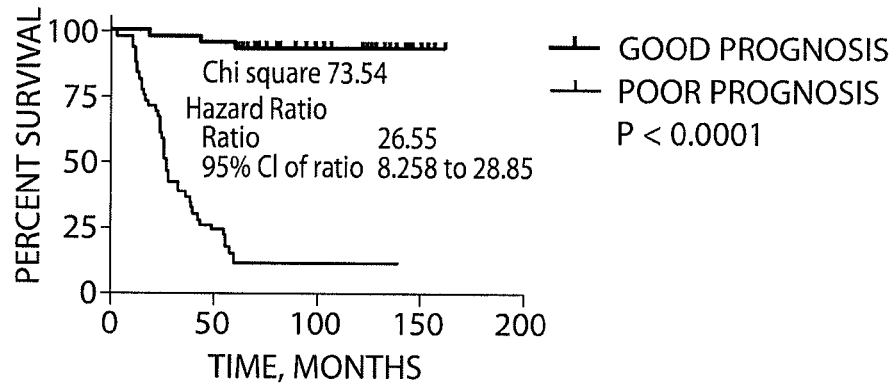
Figure 45:
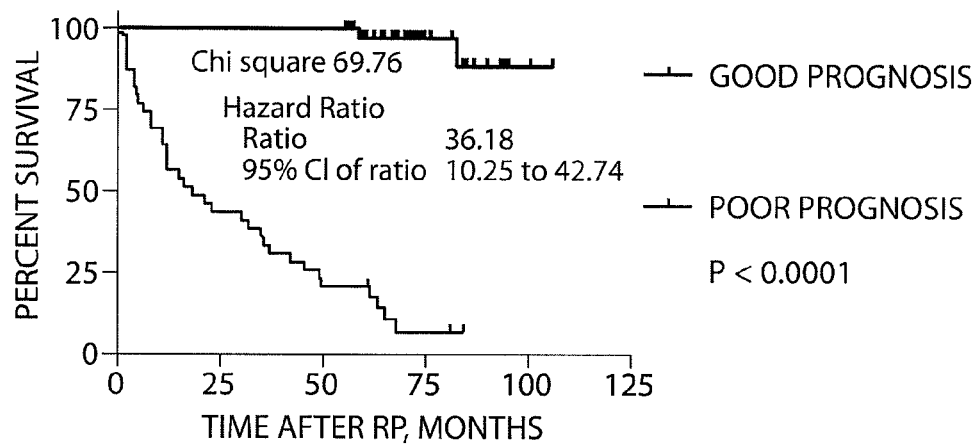
Figure 5:
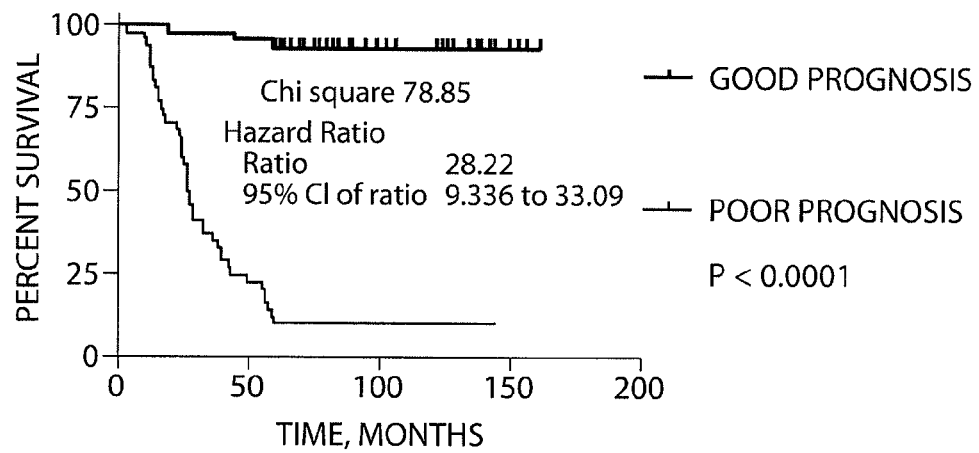

FIG. 45 shows Kaplan-Meier survival analysis of seventy-nine prostate cancer patients (top four panels) and ninety-seven early-stage LN negative breast cancer patients (middle four panels) stratified into sub-groups with distinct expression profiles of the individual CTOP signatures [histones H3 and H2A signatures; Polycomb (PcG) pathway methylation signature] and two signatures PcG methylation/histones H3/H2A algorithm (bottom two panels) in primary prostate and breast tumors. Patients' stratification was performed using either individual CTOP scores (for individual signatures) or cumulative CTOP scores (for CTOP algorithm) as described in the legend to the FIG. 41.

FIG. 46 shows Kaplan-Meier survival analysis of two-hundred eighty-six early-stage LN negative breast cancer patients (top left panel), seventy-nine prostate cancer patients (top right panel), ninety-one early-stage lung cancer patients (bottom left panel), and one-hundred thirty-three ovarian cancer patients (bottom right panel) stratified into sub-groups with distinct expression profiles of the nine "stemness" signatures algorithm in primary breast, prostate, lung, and ovarian tumors. Patients' stratification was performed using cumulative CTOP scores of the nine "stemness" signatures as described in the legend to the FIG. 41. Patients were sorted in descending order based on the values of the cumulative CTOP scores and divided into five sub-groups at 20% increment of the cumulative CTOP score values.

Figures 1, 47:
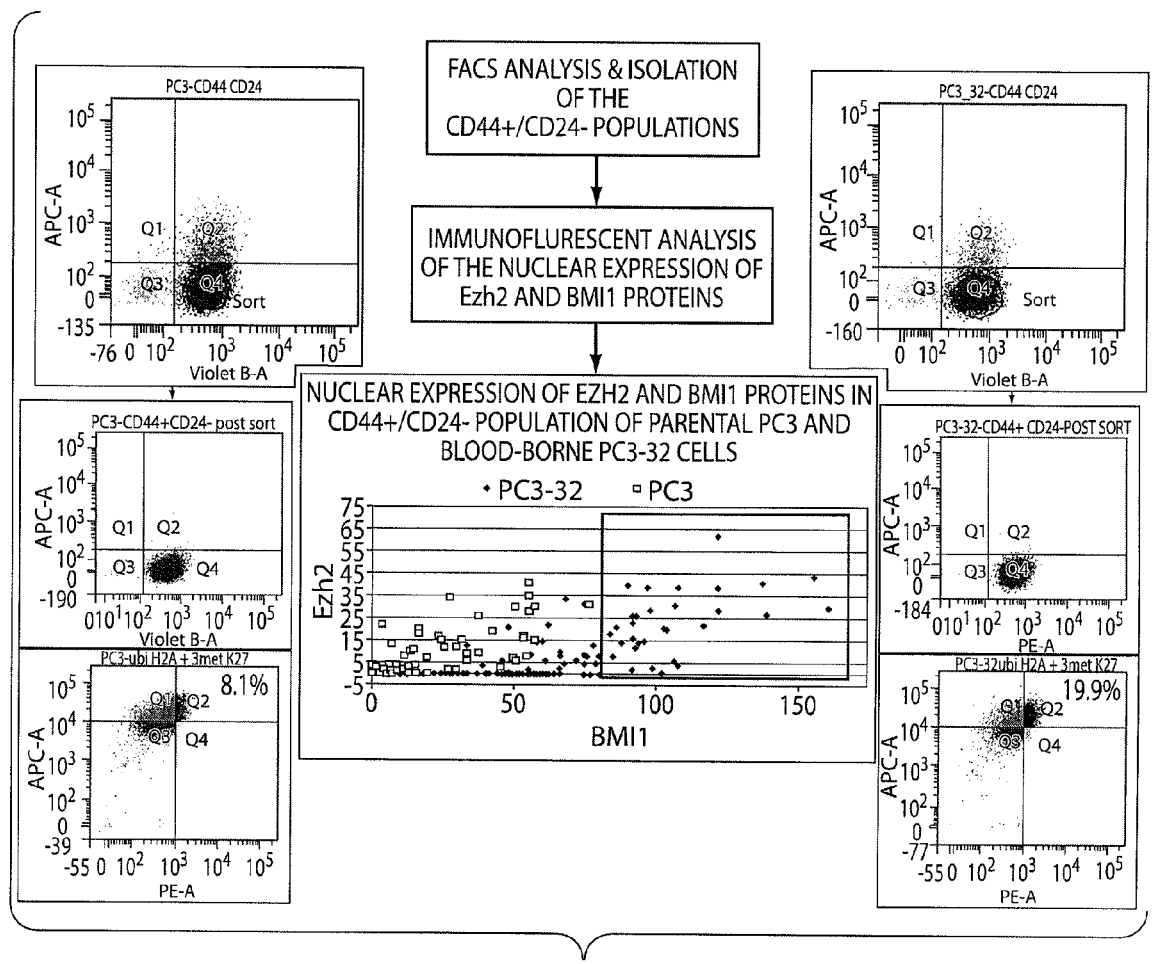
Figures 2, 47:
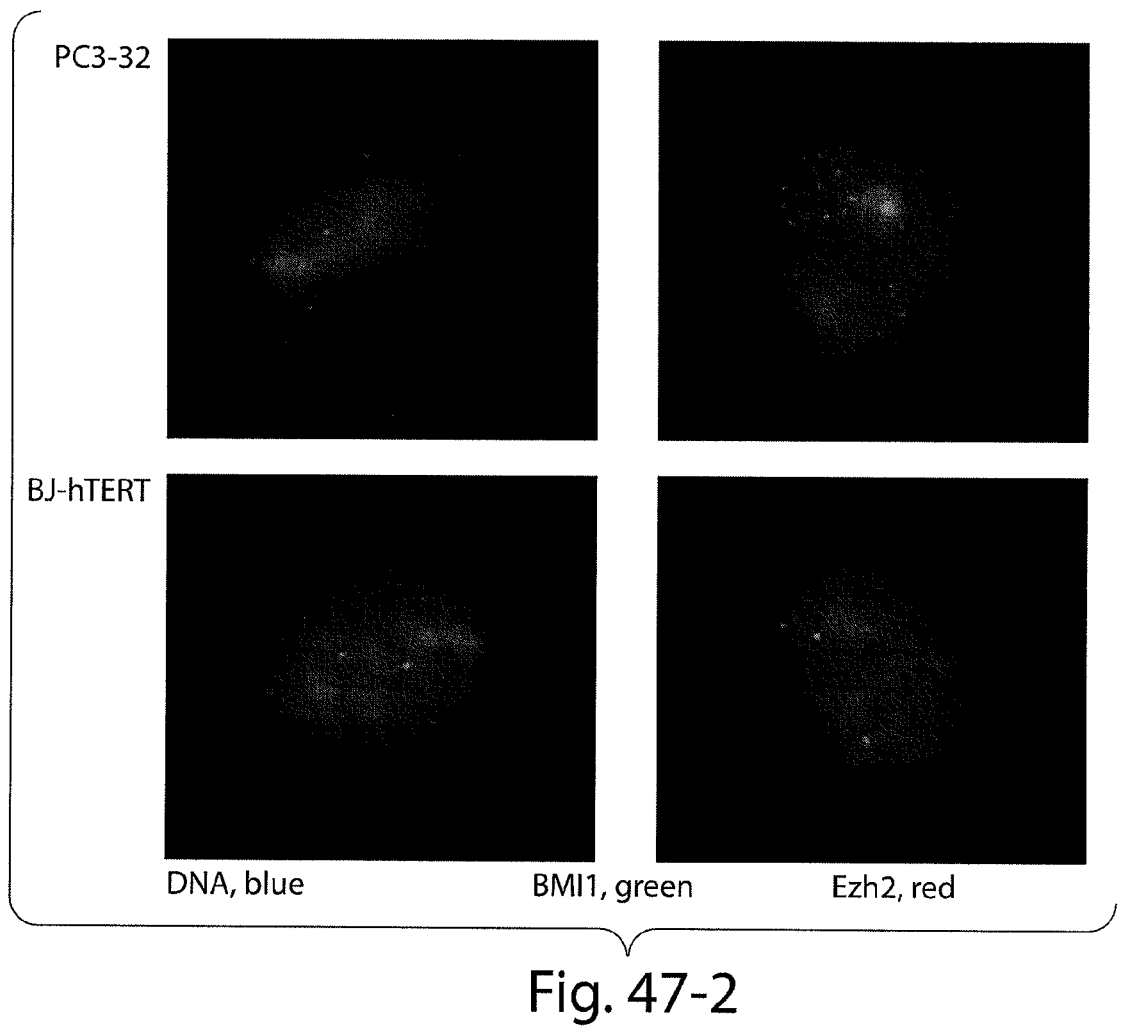
Figures 3, 47:
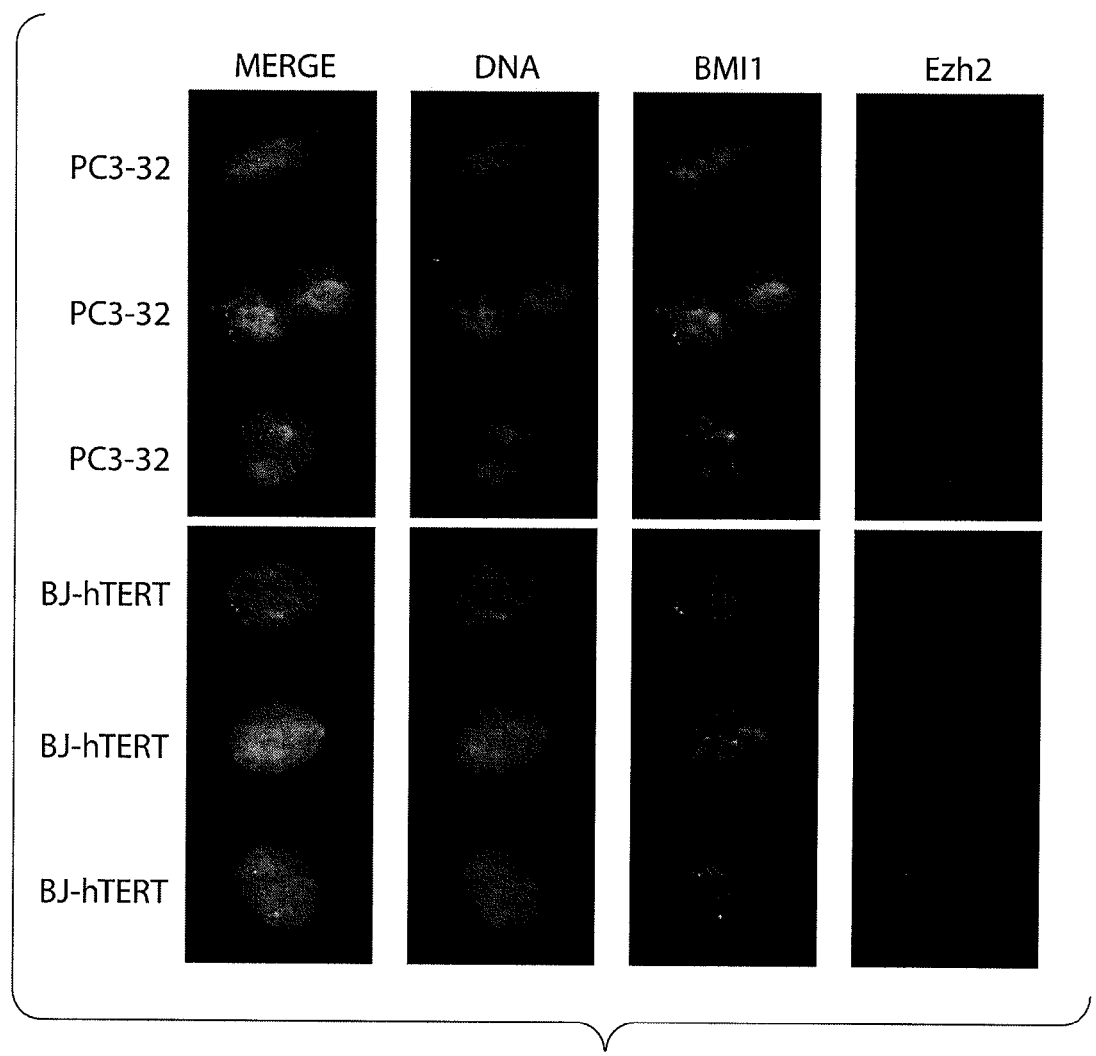
Figure 47:
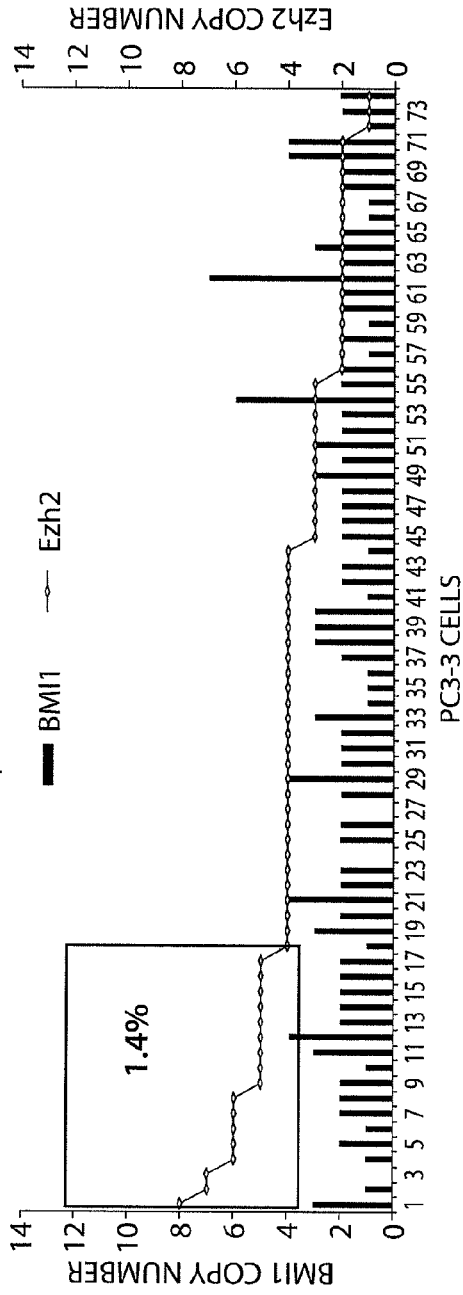
Figure 4:
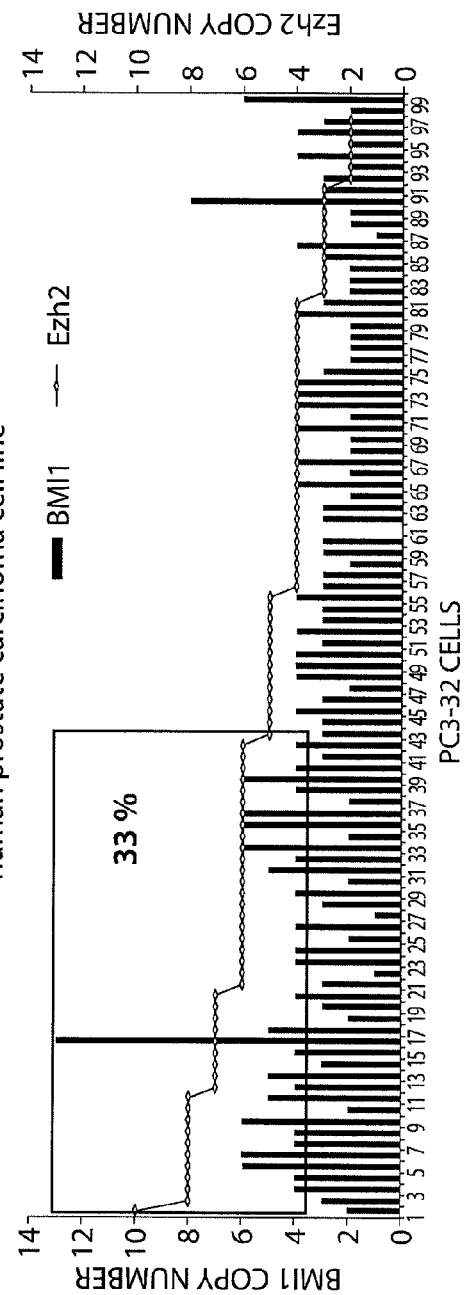
Figures 5, 47:
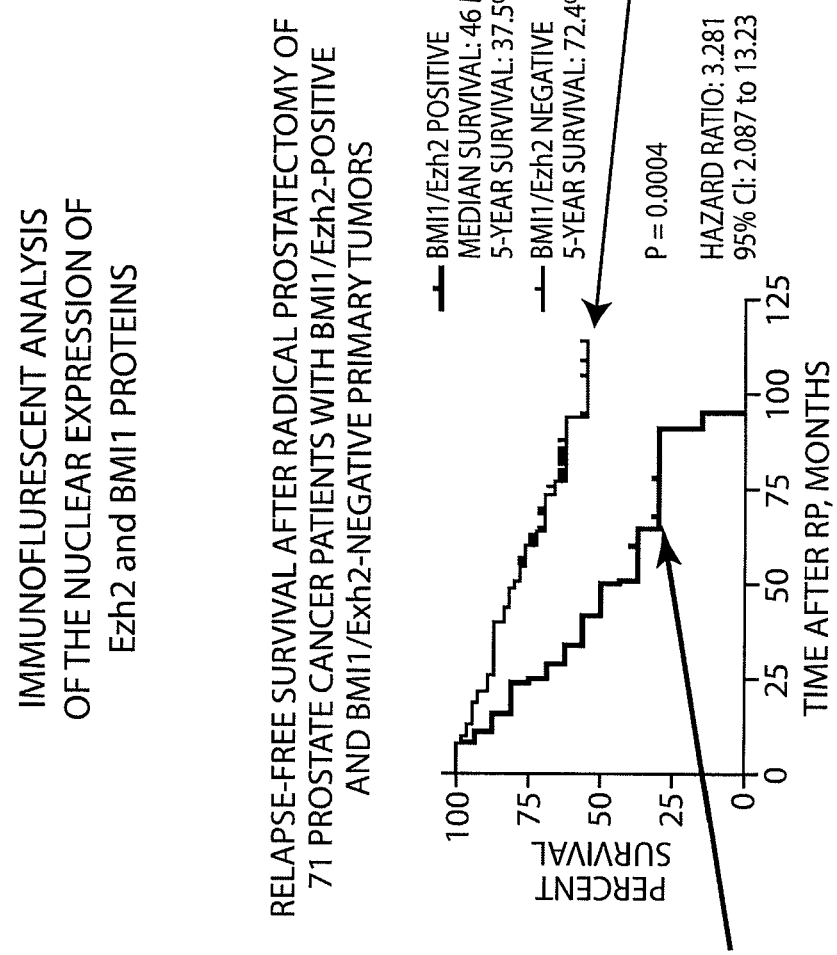

FIG. 47 shows validation of the Polycomb pathway activation in metastatic and therapy-resistant human prostate cancer.

A. Blood-borne PC-3-32 human prostate carcinoma cells contain increased levels of CD44+/CD24− cancer stem cell-like population of dual-positive BMI1/Ezh2 high-expressing cells (middle panel) with increased levels of H3met3K27 and H2AubiK119 histones (bottom two FACS figures). CD44+CD24− cancer stem cell-like populations were isolated using sterile FACS sorting from parental PC-3 and blood-borne PC-3-32 metastasis precursor cells and subjected to multicolor quantitative immunofluorescence co-localization analysis (18) for BMI1 and Ezh2 Polycomb proteins (middle panel) or Polycomb pathway substrates H3met3K27 and H2AubiK119 histones (bottom two FACS figures).

B. Multi-color FISH analysis reveals marked enrichment of blood-borne human prostate carcinoma metastasis precursor cells for cell population with co-amplification of both BMI1 and Ezh2 genes. Color microphotographs of nuclei of blood-borne PC-3-32 human prostate carcinoma cells with high-level co-amplification of both BMI1 and Ezh2 genes. For comparison, nuclei of diploid hTERT-immortalized human fibroblasts containing two copies of the BMI1 and Ezh2 genes are shown. Bottom two panels present quantitative FISH analysis of the DNA copy numbers of BMI1 and Ezh2 genes in parental PC-3 and blood-borne PC-3-32 human prostate carcinoma cells.

C. Kaplan-Meier survival analysis of seventy-one prostate cancer patients with distinct levels of dual-positive BMI1/Ezh2 high expressing cells in primary prostate tumors. Prostate cancer TMA were subjected to multi-color quantitative immunofluorescence co-localization analysis of expression of the BMI1 and Ezh2 proteins. Prostate cancer patients having >1% of dual-positive BMI1/Ezh2 high expressing cells manifested statistically significant increased likelihood of therapy failure after radical prostatectomy.

DETAILED DESCRIPTION

The present invention is directed to novel methods and kits for diagnosing the presence of cancer within a patient, and for determining whether a subject who has cancer is susceptible to different types of treatment regimens. The cancers to be tested include, but are not limited to, prostate, breast, lung, gastric, ovarian, bladder, lymphoma, mesothelioma, medulloblastoma, glioma, mantle cell lymphoma, and AML.

In some embodiments, the kits and methods of the present invention can be used to predict various different types of clinical outcomes. For example, the invention can be used to predict recurrence of disease state after therapy, non-recurrence of a disease state after therapy, therapy failure, short interval to disease recurrence (e.g., less than two years, or less than one year, or less than six months), short interval to metastasis in cancer (e.g., less than two years, or less than one year, or less than six months), invasiveness, non-invasiveness, likelihood of metastasis in cancer, likelihood of distant metastasis in cancer, poor survival after therapy, death after therapy, disease free survival and so forth.

One embodiment of the present invention is directed to a method for diagnosing cancer or predicting cancer-therapy outcome by detecting the expression levels of multiple markers in the same cell at the same time, and scoring their expression as being above a certain threshold, wherein the markers are from a particular pathway related to cancer, with the score being indicative of a cancer diagnosis or a prognosis for cancer-therapy failure. This method can be used to diagnose cancer or predict cancer-therapy outcomes for a variety of cancers. The simultaneous co-expression of at least two markers in the same cell from a subject is a diagnostic for cancer and a predictor for the subject to be resistant to standard cancer therapy. The markers can come from any pathway involved in the regulation of cancer, including specifically the PcG pathway and the "stemness" pathway. The markers can be mRNA (messenger RNA), DNA, microRNA, or protein.

The subset of markers to be used within the methods of the present invention include any markers associated with cancer pathways. In preferred embodiments, the markers can be selected from the genes identified in FIGS. 27-38. The markers can comprise anywhere ranging from two markers listed within each table up to the whole set of genes listed within each of these tables. The markers can comprise any percentage of genes selected from each of these tables, including 90%, 80%, 70%, 60%, or 50% of the genes identified in each of FIGS. 27-38.

These and other embodiments of the present invention rely at least in part upon the novel finding that the expression of multiple markers above a threshold level in the same cell at the same time, wherein the markers are found within pathways related to cancer, can be used as an assay to diagnose cancer disorders and to predict whether a patient already diagnosed with cancer will be therapy-responsive or therapy-resistant. An element of the assay is that two or more markers are detected simultaneously within the same cell.

Marker detection can be made through a variety of detection means, including bar-coding through immunofluorescence. The markers detected can be a variety of products, including mRNA, DNA, microRNA, and protein. For mRNA or microRNA based markers, PCR can be used as detection means. Additionally, protein products, gene expression, or gene copy number can be identified through detection means known in the art.

Detection means, in case of a nucleic acid probe, include measuring the level of mRNA or cDNA to which a probe has been engineered to bind, where the probe binds the intended species and provides a distinguishable signal. In some embodiments, the probes are affixed to a solid support, such as a microarray. In other embodiments, the probes are primers for nucleic acid amplification of a set of genes. Q-RT-PCR amplification can be used. Detecting expression for measurement or determining protein expression levels can also be accomplished by using a specific binding reagent, such as an antibody. In general, expression levels of the markers can be analyzed by any method now known or later developed to assess gene expression, including but not limited to measurements relating to the biological processes of nucleic acid amplification, transcription, RNA splicing, and translation. Direct and indirect measures of gene copy number (e.g., as by fluorescence in situ hybridization or other type of quantitative hybridization measurement, or by quantitative PCR), transcript concentration (e.g., as by Northern blotting, expression array measurements, quantitative RT-PCR, or comparative genomic hybridization) and protein concentration (e.g., as by quantitative 2D gel electrophoresis, mass spectrometry, Western blotting, ELISA, or other method for determining protein concentration), can also be used.

One of skill in the art would recognize that different affinity reagents could be used with the present invention, such as one or more antibodies (monoclonal or polyclonal) and the invention can include using techniques, such as ELISA, for the analysis. Thus, specific antibodies (specific to the markers to be detected) can be used in a kit and in methods of the present invention. In a kit of the present invention, the kit would include reagents and instructions for use, where the reagents could be protein-specific differentially-labeled fluorescent antibodies; protein-specific antibodies from different species (mouse, rabbit, goat, chicken, etc.) and differentially labeled species-specific antibodies; DNA and RNA-based probes with different fluorescent dyes; bar-coded nucleic acid- and protein-specific probes (each probes having a unique combination of colors).

The markers detected can be from a variety of pathways related to cancer. Suitable pathways for markers within the scope of the present invention include any pathways related to oncogenesis and metastasis, and more specifically include the Polycomb group (PcG) chromatin silencing pathway and the "stemness" pathway.

Representative cancer pathways within the context of the present invention include but are not limited to, the Polycomb pathway, the Polycomb pathway target genes, "stemness" pathways, DNA methylation pathways, BMI1, Ezh2, Suz12, Suz12/PolII, EED, PcG-TF, BCD-TF, TEZ, Nanog/Sox2/Oct4, Myc, He2/neu, CCND1, E2F3, PI3K, beta-catenin, ras, src, PTEN, p53, Rb, p16/ARF, p21, Wnt, and Hh pathways.

The Polycomb group (PcG) gene BMI1 is required for the proliferation and self-renewal of normal and leukemic stem cells. Over-expression of Bmi1 oncogene causes neoplastic transformation of lymphocytes and plays an essential role in the pathogenesis of myeloid leukemia. Another PcG protein, Ezh2, has been implicated in metastatic prostate and breast cancers, suggesting that PcG pathway activation is relevant for epithelial malignancies. Here it is demonstrated that activation of the BMI1 oncogene-associated PcG pathway plays an essential role in metastatic prostate cancer, thus mechanistically linking the pathogenesis of leukemia, self-renewal of stem cells, and prostate cancer metastasis.

In another aspect, the methods of the present invention provide for the diagnosis, prognosis, and treatment strategy for a patient with a disorder of the above mentioned types. Treatment includes determining whether a patient has an expression pattern of markers associated with cancer and administering to the patient a therapeutic adapted to the treatment of the disorder. In one embodiment, the method can include the identification of increased BMI1 and Ezh2 expression and the formulation of a treatment plan specific to this phenotype.

In another embodiment of the present invention, the detection of appropriate or inappropriate activation of "stemness" genetic pathways can be used to diagnose cancer and to predict the likelihood of cancer therapy success or failure. Inappropriate activation of "stemness" genes in cancer cells may be associated with aggressive clinical behavior and increased likelihood of therapy failure. A sub-set of human prostate tumors represents a genetically distinct highly malignant sub-type of prostate carcinoma with high propensity toward metastatic dissemination even at the early stage of disease. Such a high propensity toward metastatic dissemination of this type of prostate tumors is associated with the early engagement of normal stem cells into malignant process. Elucidation of such inappropriate activation of "stemness" gene expression can help tailor cancer therapy to a patient's individual needs.

The invention is directed to prognostic assays for cancer therapy that can be used to diagnose cancer and to predict the resistance of various cancers to standard therapeutic regimens. The invention is directed to methods and compositions for predicting the outcome of cancer therapy for individual patients. In one embodiment, the method is used to predict whether a particular cancer patient will be therapy-responsive or therapy-resistant. The invention can be used with a variety of cancers, including but not limited to, breast, prostate, ovarian, lung, glioma, and lymphoma.

The invention is directed to personalized medicine for cancer patients, and encompasses the selection of treatment options with the highest likelihood of successful outcome for individual cancer patients. The present invention is directed to the use of a an assay to predict the outcome after therapy in patients with early stage cancer and provide additional information at the time of diagnosis with respect to likelihood of therapy failure.

In another embodiment of the present invention, the detection of the state of transcription factors can be used to diagnose the presence of cancer and to predict the likelihood of cancer therapy success or failure. The determination of a common pattern of the transcription factor expression can be used as a profile to help determine clinical outcome. The invention is also directed to a particular sub-set of BCD-TF genes defined here as the eight gene BCD-TF signature that manifests "stemness" expression profiles in therapy-resistant prostate and breast tumors (FIG. 43).

In another embodiment of the present invention, the detection of the methylation state of target genes can be used to diagnose cancer and to predict the likelihood of cancer therapy success or failure. More particularly, PcG target genes with promoters frequently hypermethylated in cancer manifest distinct expression profiles associated with therapy-resistant and therapy-sensitive prostate and breast cancers (FIG. 44), implying that differences in gene expression between tumors with distinct outcome after therapy may be driven, in part, by the distinct promoter hypermethylation patterns of the PcG target genes. These differences can be exploited to generate highly informative gene expression signatures of the PcG target genes hypermethylated in cancer for stratification of prostate and breast cancer patients into sub-groups with statistically distinct likelihood of therapy failure (FIG. 44).

The invention involves both a method to classify patients into sub-groups predicted to be either therapy-responsive or therapy-resistant, and a method for determining alternate therapies for patients who are classified as resistant to standard cancer therapies. The method of the present invention is based on an accurate classification of patients into subgroups with poor and good prognosis reflecting a different probability of disease recurrence and survival after standard therapy.

In one embodiment, the invention relates to a method for diagnosing cancer or predicting cancer-therapy outcome in a subject, said method comprising the steps of:
 a) obtaining a sample from the subject,
 b) selecting a marker from a pathway related to cancer,
 c) screening for a simultaneous aberrant expression level of two or more markers in the same cell from the sample, and
 d) scoring their expression level as being aberrant when the expression level detected is above or below a certain detection threshold coefficient, wherein the detection threshold coefficient is determined by comparing the expression levels of the samples obtained from the subjects to values in a reference database of samples obtained from subjects with either a known diagnosis or known clinical outcome after therapy, wherein the presence of an aberrant expression level of two or more markers in individual cells and presence of cells aberrantly expressing two or more such markers is indicative of a cancer diagnosis or a prognosis for cancer-therapy failure in the subject.

An aberrant expression level is a level of expression that can either be higher or lower than the expression level as compared to reference samples. The reference samples can have a variety of phenotypes, including both diseased phenotypes and non-diseased phenotypes. The sample phenotypes within the scope of the present invention include, but are not limited to, cancer, non-cancer, recurrence, non-recurrence, relapse, non-relapse, invasiveness, non-invasiveness, metastatic, non-metastatic, localized, tumor size, tumor grade, Gleason score, survival prognosis, lymph node status, tumor stage, degree of differentiation, age, hormone receptor status, PSA level, histologic type, and disease free survival.

A detection threshold coefficient within the context of the present invention is a value above which or below which a patient or sample can be classified as either being indicative of a cancer diagnosis or a prognosis for cancer-therapy failure. The detection threshold coefficients are defined by a plurality of measurements of samples in the reference database; sorting the samples in descending order of the values of measurements; assignment of the probability of samples having a phenotype in sub-groups of samples defined at different increments of the values of measurements (e.g., samples comprising top 10%; 20%; 30%; 40%; 50%; 60%; 70%; 80%; 90% of the values); selecting the statistically best-performing detection threshold coefficient defined as the value of measurements segregating samples with the values below and above the threshold into subgroups with statistically distinct probability of having a phenotype (cancer vs non-cancer; therapy failure vs cure; etc.), ideally, segregating patients into subgroups with 100% probability of therapy failure and with 100% probability of a cure or as close to this probability values as practically possible.

This value of markers measurements is defined as the best performing magnitude of the detection threshold. The samples of unknown phenotype are then placed into corresponding subgroups based on the values of markers measurements and assigned the corresponding probability of having a phenotype. To determine these measurements, one skilled in the art can utilize different statistical programs and approaches such as the univariate and multivariate Cox regression analysis and Kaplan-Meier survival analysis.

Detection threshold coefficients which are indicative of a cancer diagnosis or a prognosis for cancer-therapy failure have an absolute value within the range of .gtoreq.0.5. to .gtoreq.0.999. Preferred levels of detection threshold coefficients which are indicative of a cancer diagnosis or a prognosis for cancer-therapy failure have an absolute value of .gtoreq.0.5, .gtoreq.0.6, .gtoreq.0.7, .gtoreq.0.8, .gtoreq.0.9, .gtoreq.0.95, .gtoreq.0.99, .gtoreq.0.995., and .gtoreq.0.999.

The present invention is also directed to a method of determining detection threshold coefficients for classifying a sample phenotype from a subject. This method comprises the steps of selecting two or more markers from a pathway related to cancer, screening for a simultaneous aberrant expression level of the two or more markers in the same cell from the sample and scoring the marker expression in the cells by comparing the expression levels of the samples obtained from the subjects to values in a reference database of samples obtained from subjects with either a known diagnosis or known clinical outcome after therapy, and determining the sample classification accuracy at different detection thresholds using reference database of samples from subjects with known phenotypes.

In another embodiment, the method of determining detection threshold coefficients for classifying a sample phenotype from a subject further comprises the additional step of determining the best performing magnitude of said detection threshold and using said magnitude to assess the reliability of said established detection threshold in classifying a sample phenotype.

Selection of the statistically best-performing detection threshold coefficient is defined as the value of measurements of the segregating samples with the values below and above the threshold, which are then split into subgroups with a statistically distinct probability of having a phenotype (cancer vs non-cancer; therapy failure vs cure, etc.). More preferably, patients or samples can be segregated into subgroups with 100% probability of therapy failure and with 100% probability of a cure, or as close to this probability values as practically possible. This value of markers measurements is defined as the best performing magnitude of the detection threshold. Additionally, the best performing magnitude of the detection threshold coefficient can be used to score an unclassified sample and assign a sample phenotype to said sample.

The present invention is also directed to a kit to detect the presence of two or more markers from a pathway related to cancer. The kit can contain as detection means protein-specific differentially-labeled fluorescent antibodies; protein-specific antibodies from different species (mouse, rabbit, goat, chicken, etc.) and differentially labeled species-specific antibodies; DNA and RNA-based probes with different fluorescent dyes; bar-coded nucleic acid- and protein-specific probes (each probes having a unique combination of colors), and any other detection means known in the art. The kit can include a marker sample collection means and a means for determining whether the sample expresses in the same cell at the same time two or more markers from a pathway related to cancer. Optionally, the kit contains a standard and/or an algorithmic device for assessing the results and additional reagents and components including for example DNA amplification reagents, DNA polymerase, nucleic acid amplification reagents, restrictive enzymes, buffers, a nucleic acid sampling device, DNA purification device, deoxynucleotides, oligonucleotides (e.g. probes and primers) etc.

The following non-standard abbreviations are used herein: DFI, disease-free interval; FBS, fetal bovine serum; MSKCC, Memorial Sloan-Kettering Cancer Center; NPEC, normal prostate epithelial cells; PC, prostate cancer; PSA, prostate specific antigen; Q-RT-PCR, quantitative reverse-transcription polymerase chain reaction; RP, radical prostatectomy; SKCC, Sidney Kimmel Cancer Center; AMACR, alpha-methylacyl-coenzyme A racemase; Ezh2, enhancer of zeste homolog 2; FACS, fluorescence activated cell sorting.

Human Genome Haplotype Map Leads to Identification of Relevant Markers

The recent completion of the initial phase of a haplotype map of the human genome provides an opportunity for integrative analysis on a genome-wide scale of microarray-based gene expression profiling and SNP variation patterns for discovery of cancer-causing genes and genetic markers of therapy outcome. Here the approach is used for analysis of SNPs of cancer-associated genes, expression profiles of which predict the likelihood of treatment failure and death after therapy in patients diagnosed with multiple types of cancer. Unexpectedly, the analysis reveals a common SNP pattern for a majority (60 of 74; 81%) of analyzed cancer treatment outcome predictor (CTOP) genes.

The analysis suggests that heritable germ-line genetic variations driven by a geographically localized form of natural selection determining population differentiations may have a significant impact on cancer treatment outcome by influencing the individual's gene expression profile. A CTOP algorithm can be built which combines the prognostic power of multiple gene expression-based CTOP models. Application of a CTOP algorithm to large databases of early-stage breast and prostate tumors identifies cancer patients with 100% probability of a cure with existing cancer therapies as well as patients with nearly 100% likelihood of treatment failure, thus providing a clinically feasible framework essential for the introduction of rational evidence-based individualized therapy selection and prescription protocols.

Relevant Genes for Cancer Diagnosis and Treatment Prediction

Figure 1A:
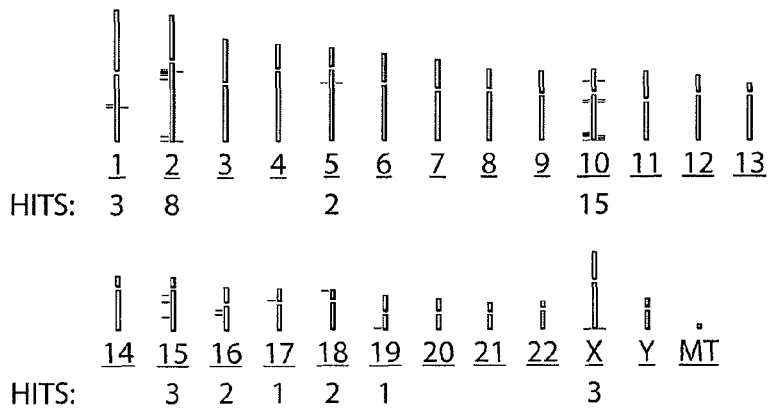
FIG. 1 shows HapMap analysis revealing population-specific profiles of genotype and allele frequencies of SNPs associated with cancer therapy outcome predictor (CTOP) genes comprising an 11-gene death-from-cancer signature.
A. Chromosomal locations of genes encoding transcripts comprising an 11-gene death-from-cancer signature
B, E. Annotated haplotypes associated with the BMI1 (B) and BUB1 (E) genes in CEU, YRI, CHB, and JPT HapMap populations. Arrows indicate SNPs with population-specific profiles of genotype and allele frequencies.
C, D, F-H. Bar graph plots demonstrating population-specific profiles of genotype and allele frequencies in different HapMap populations for individual SNPs associated with genes comprising an 11-gene death-from-cancer signature. For each SNP the frequencies shown within each set of bar graphs in the following order (from left to right): CEU, CHB, JPT, YRI.
B-D, BMI1 gene; F-H, CCNB1, KNTC2, HCFC1, FGFR2, and BUB1 genes.
Figures 1, 1B:
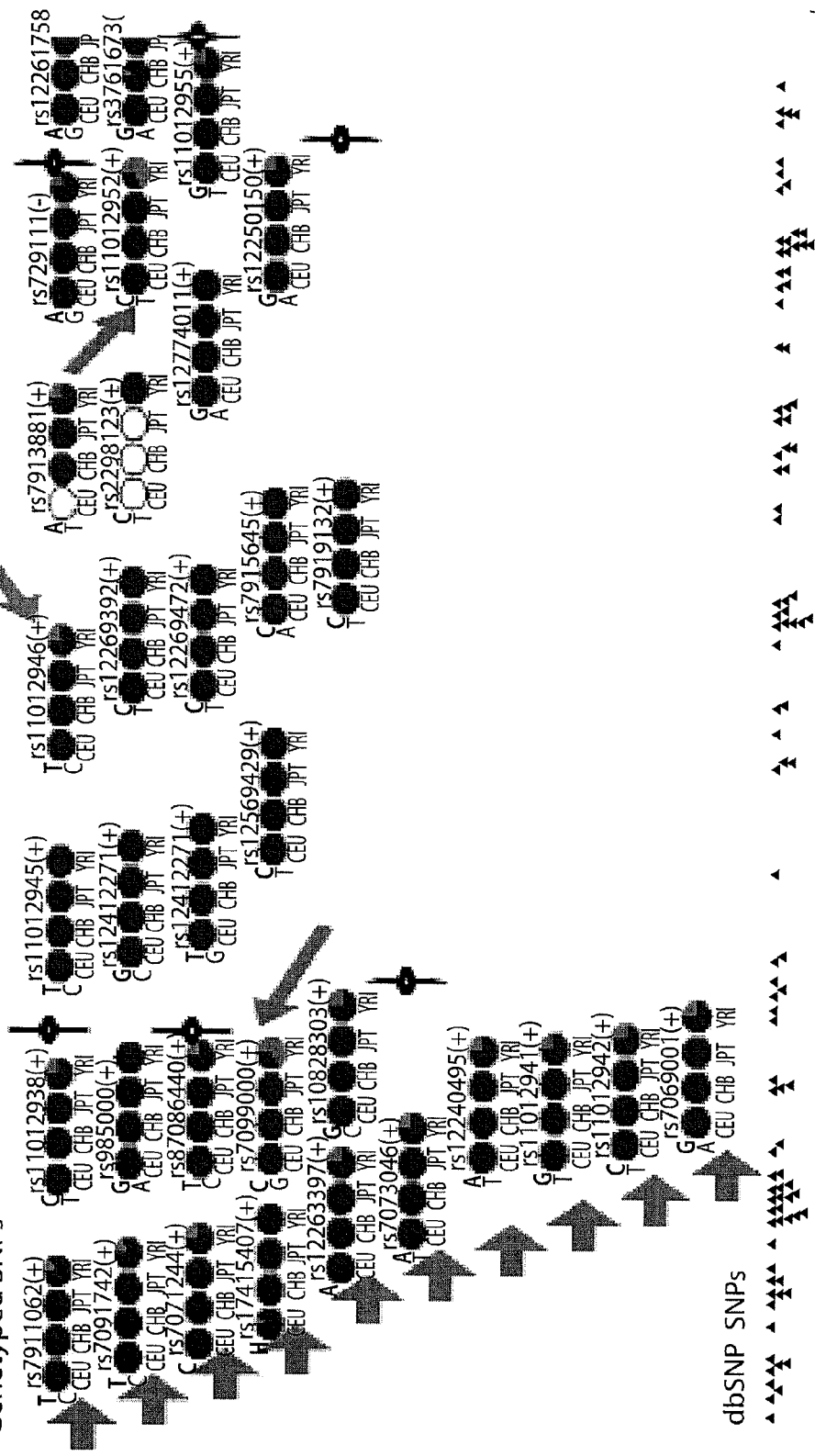
Figures 1, 1B, 2:
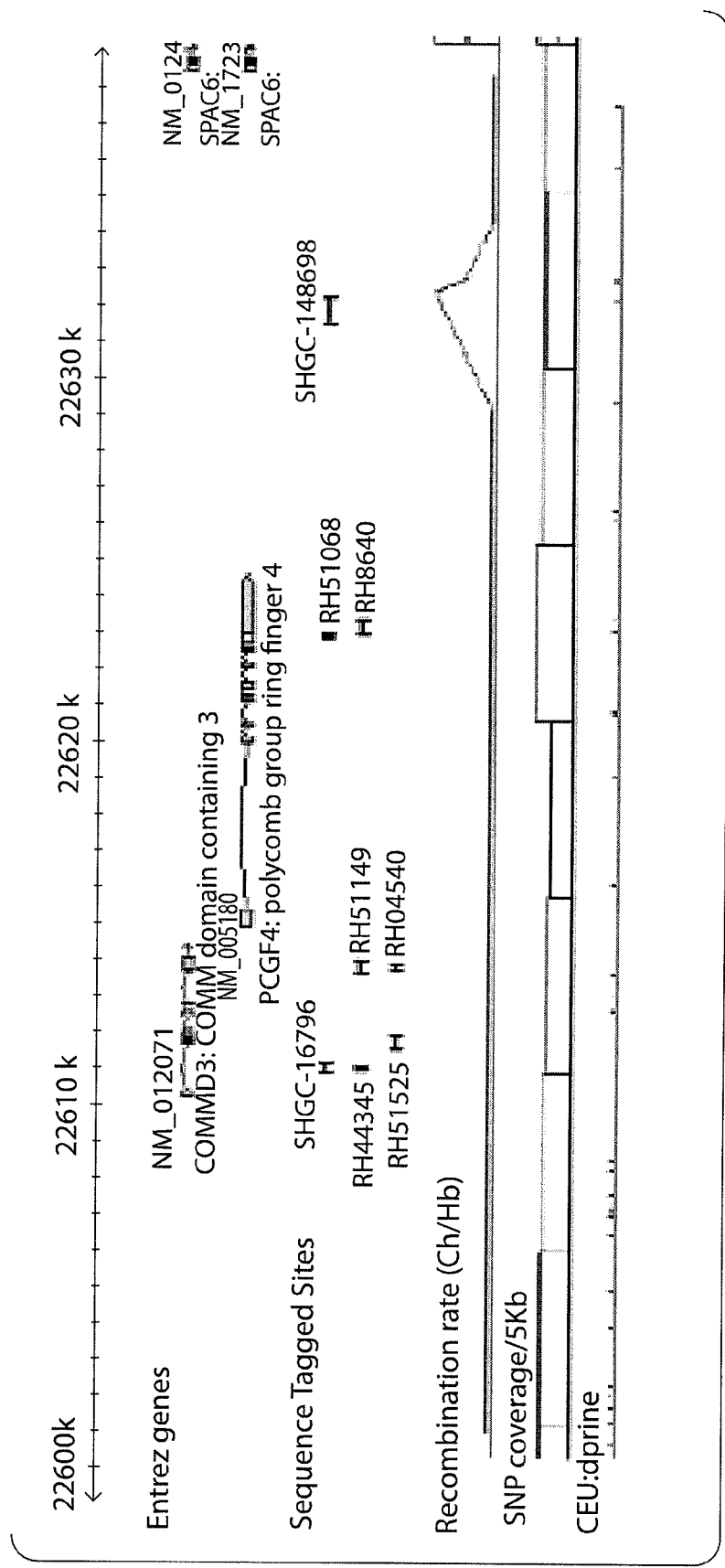
FIG. 2 shows HapMap analysis revealing population-specific profiles of genotype and allele frequencies of SNPs associated with CTOP genes predicting the likelihood of disease relapse in prostate cancer patients after radical prostatectomy.
A. Chromosomal locations of genes encoding transcripts comprising prostate cancer recurrence predictor signatures.
B-D. Bar graph plots demonstrating population-specific profiles of genotype and allele frequencies in different HapMap populations for individual SNPs associated with genes comprising prostate cancer recurrence predictor signatures. For each SNP the frequencies shown within each set of bar graphs in the following order (from left to right): CEU, CHB, JPT, YRI.
B, KLF6 (COPEB) gene; C, Wnt5, TCF2, CHAF1A, and KIAA0476 genes; D, PPFIA3, CDS2, FOS, and CHAF1A genes.
Figures 1, 1B, 2, 3:
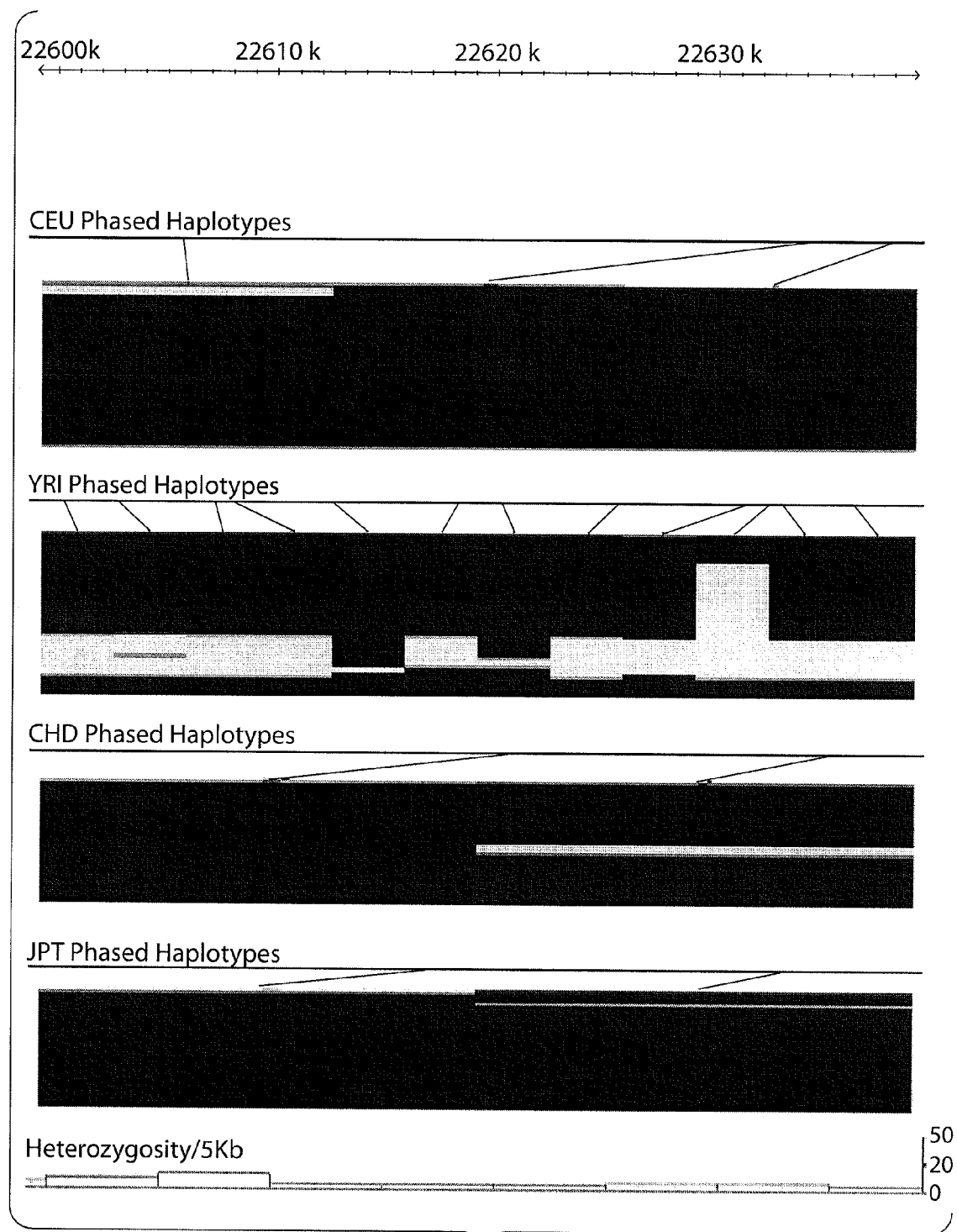
FIG. 3 shows HapMap analysis revealing population-specific profiles of genotype and allele frequencies of SNPs associated with cancer therapy outcome predictor (CTOP) genes comprising a 50-gene proteomics-based cancer therapy outcome signature.
Figure 1C:
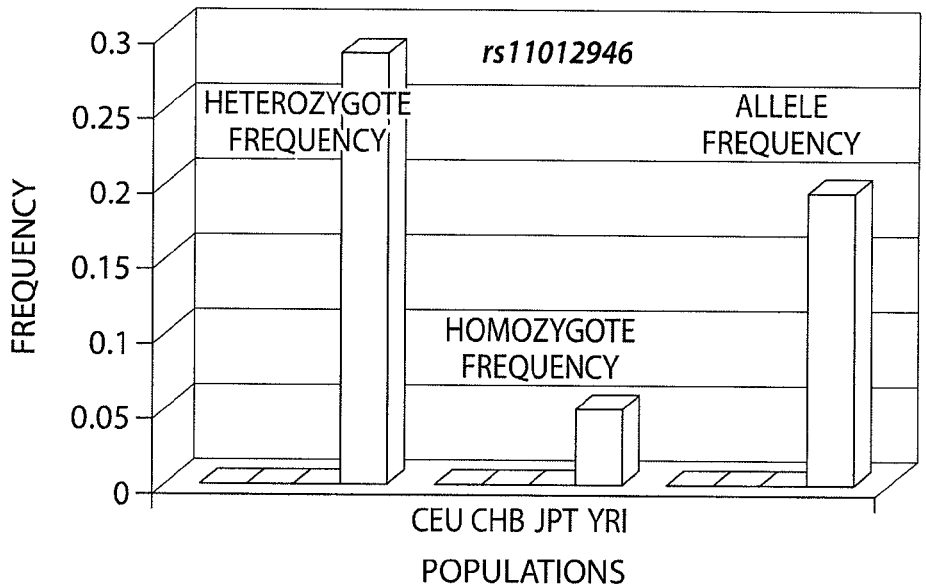
Figure 1D:
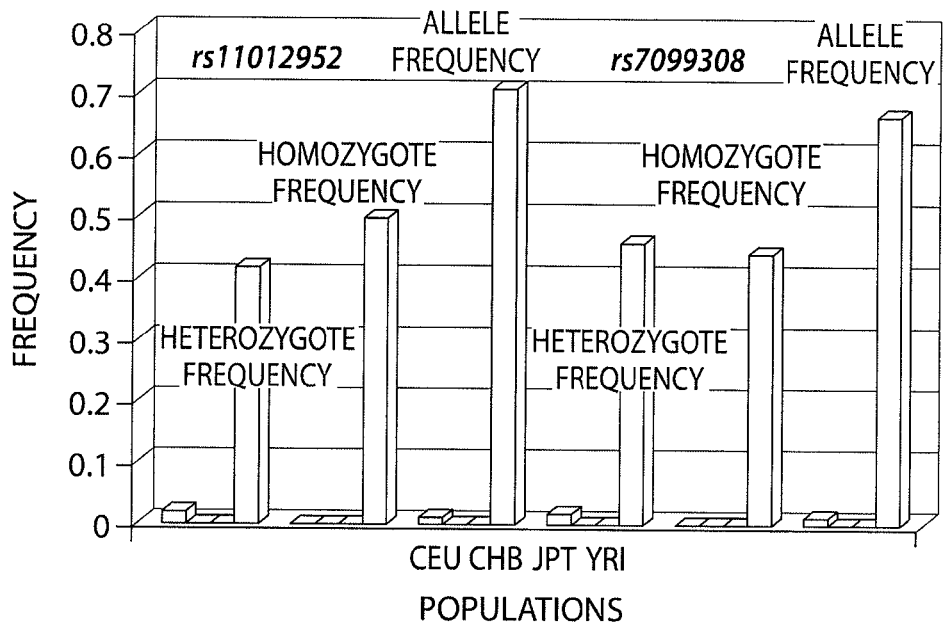
Figures 1, 1E:
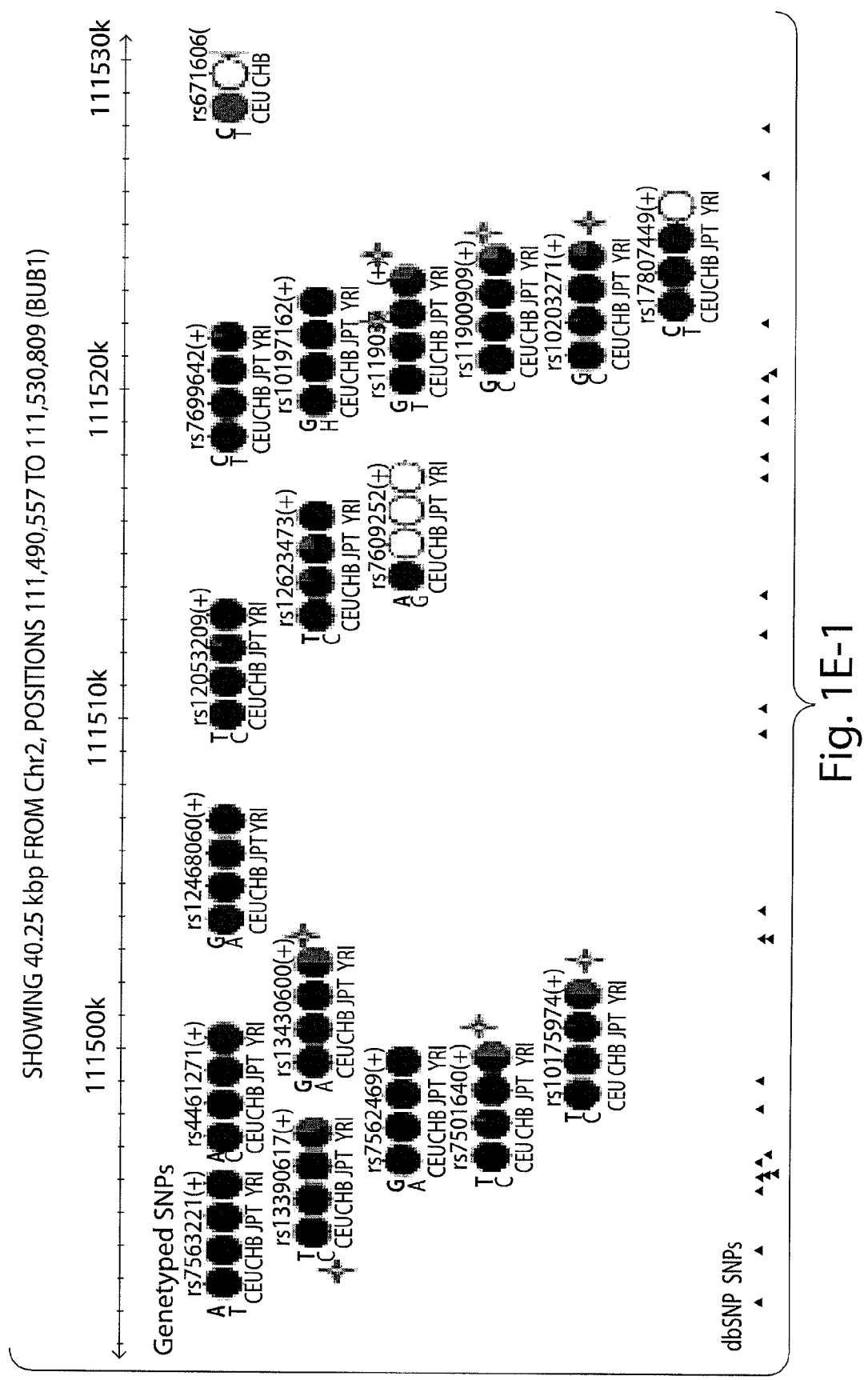
Figures 1, 1E, 2:
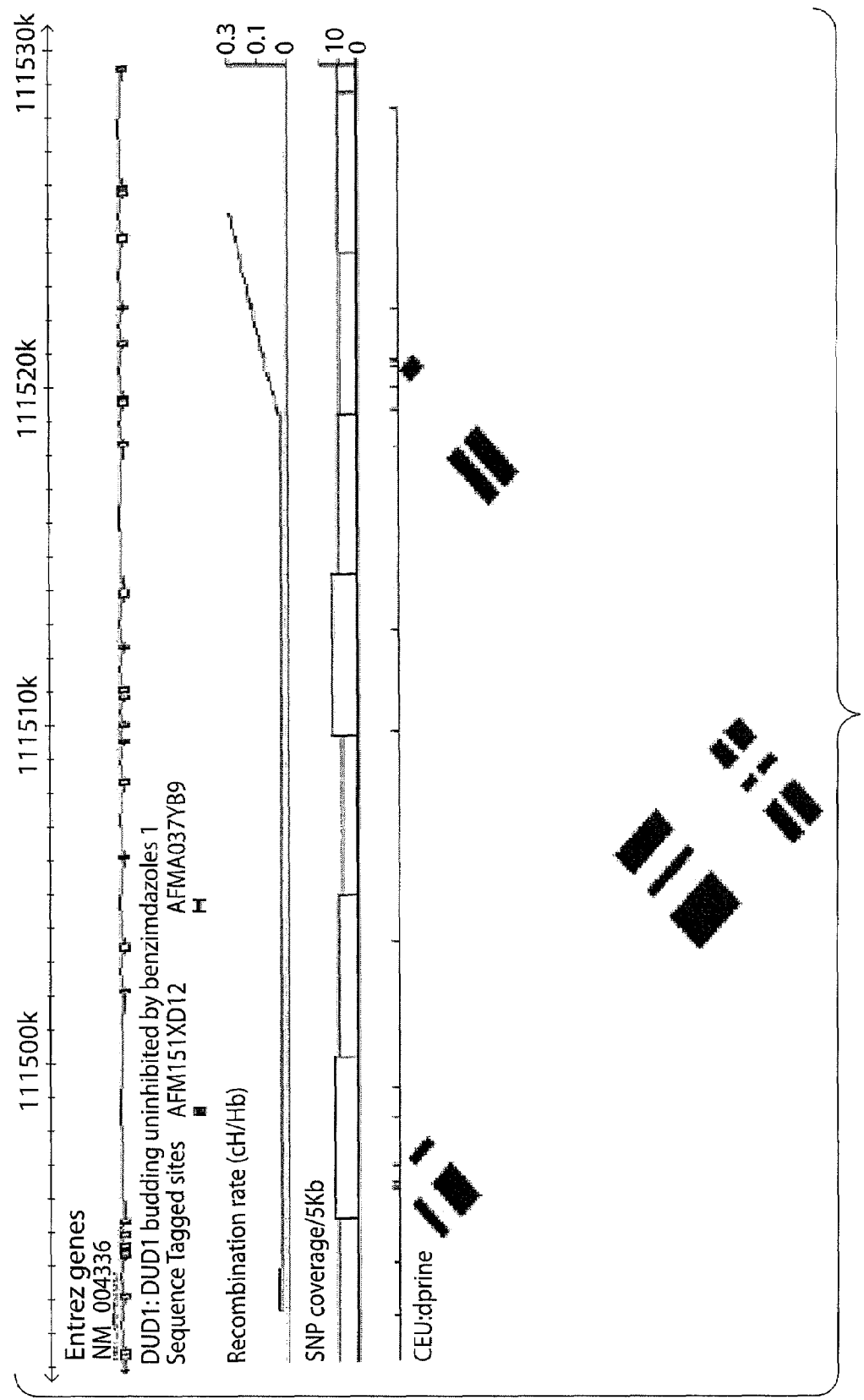
Figures 1, 1E, 2, 3:
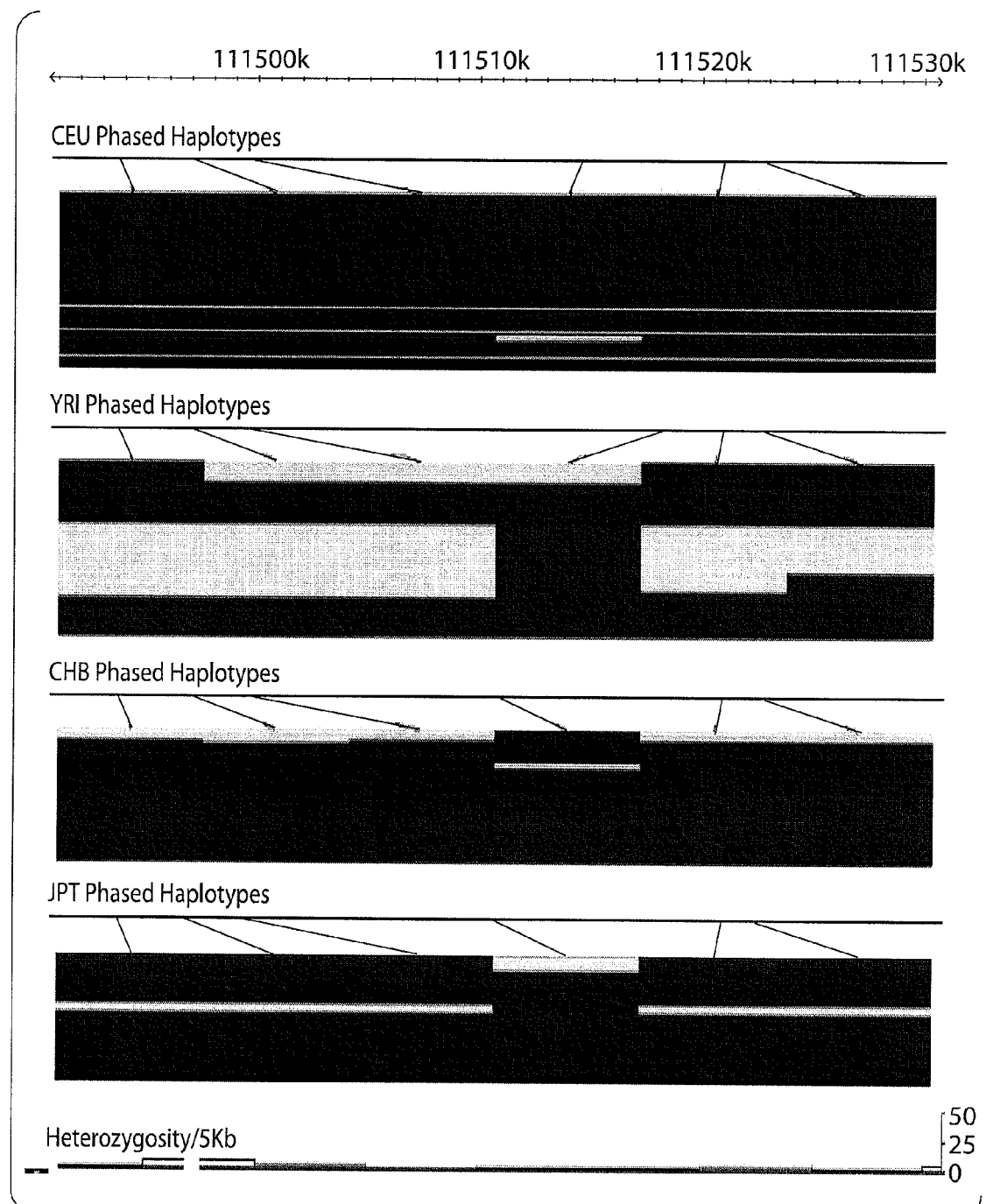
Figure 1F:
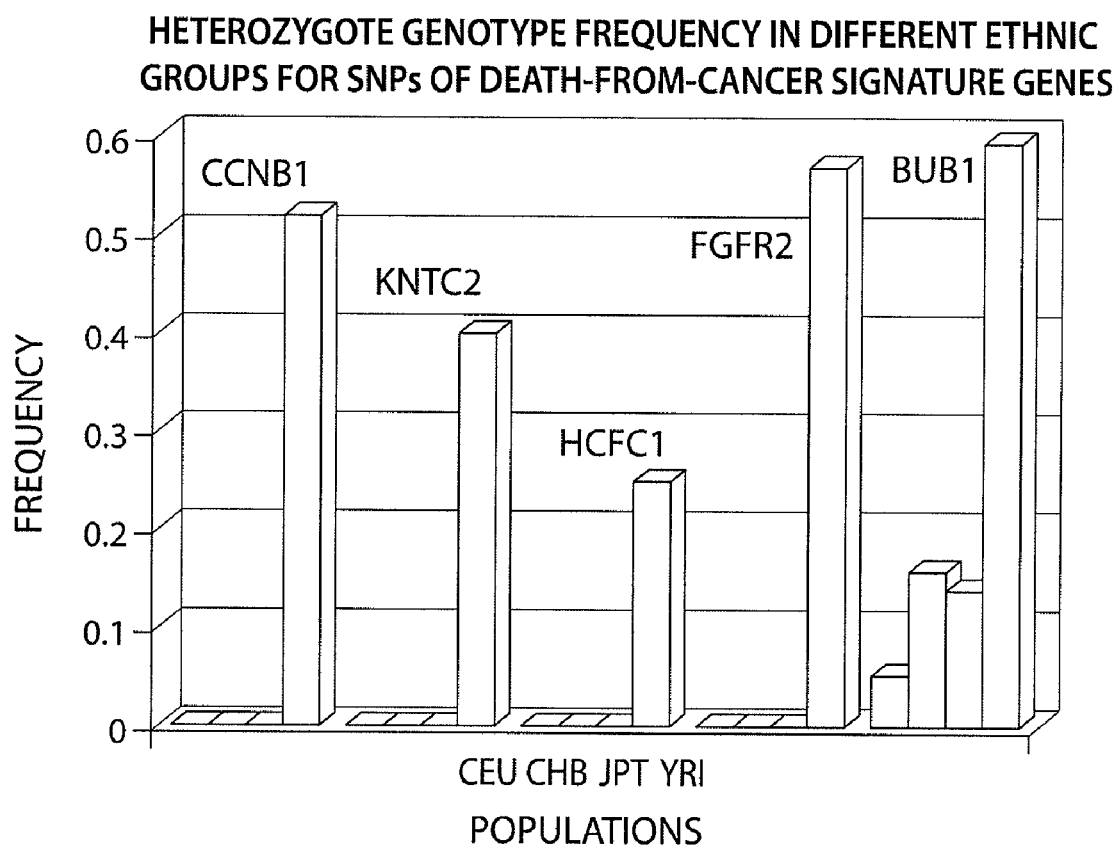
Figure 1G:
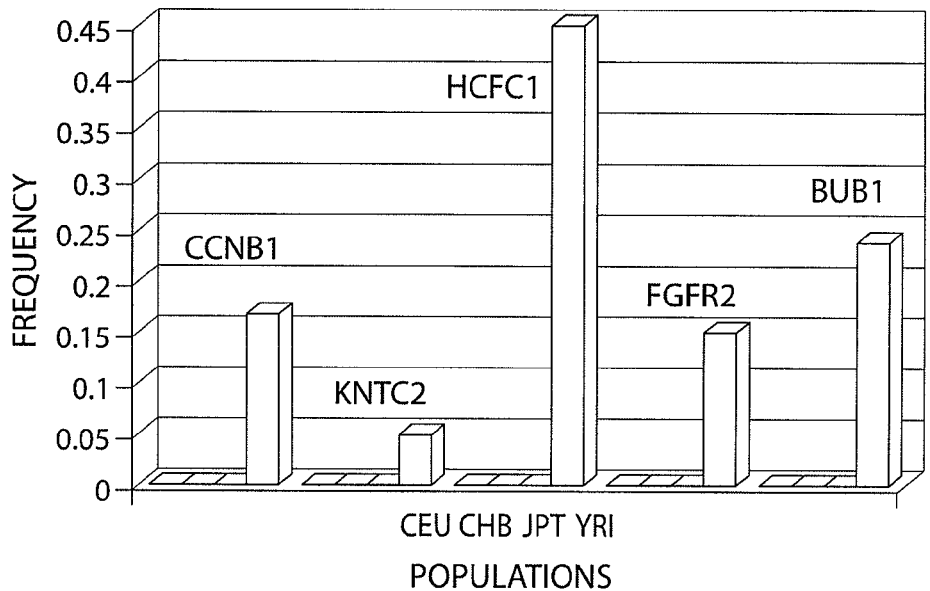
Figure 1H:
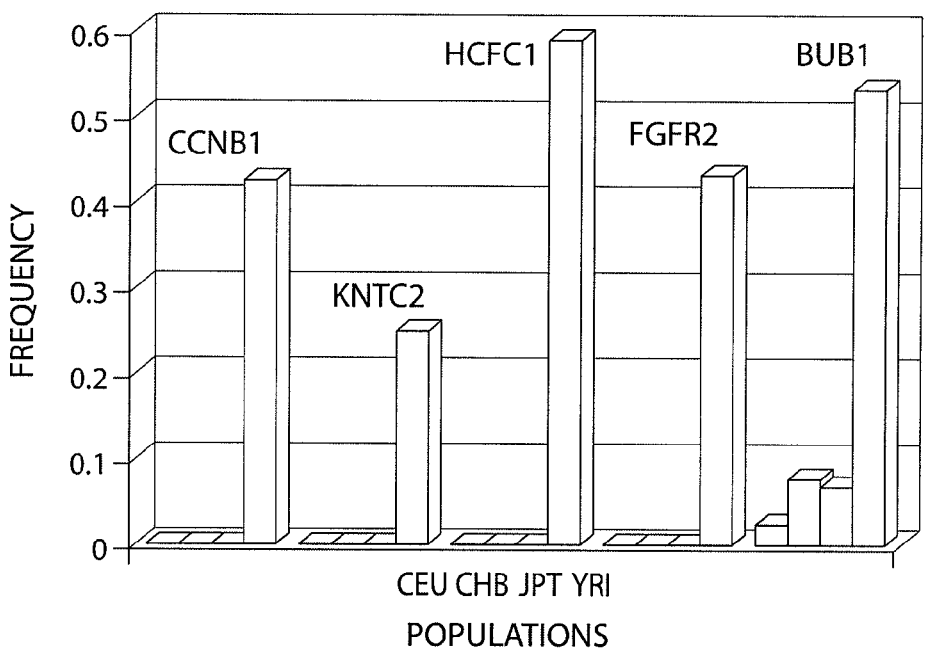
Figure 2A:
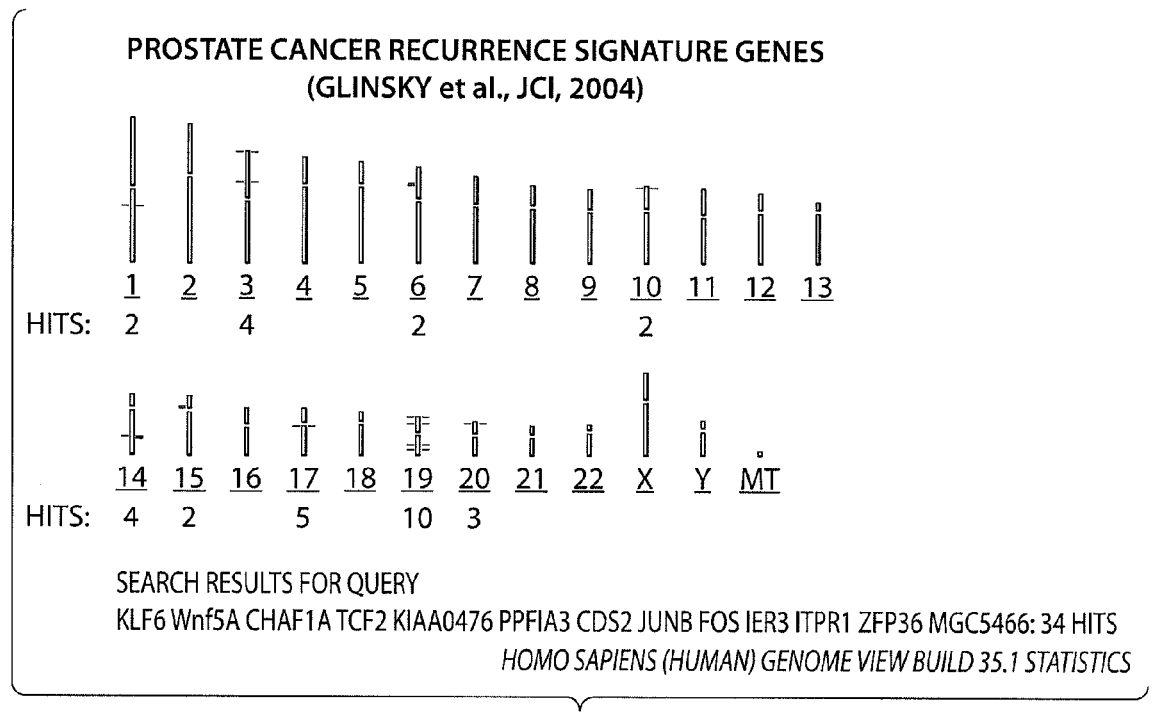
Figure 2B:
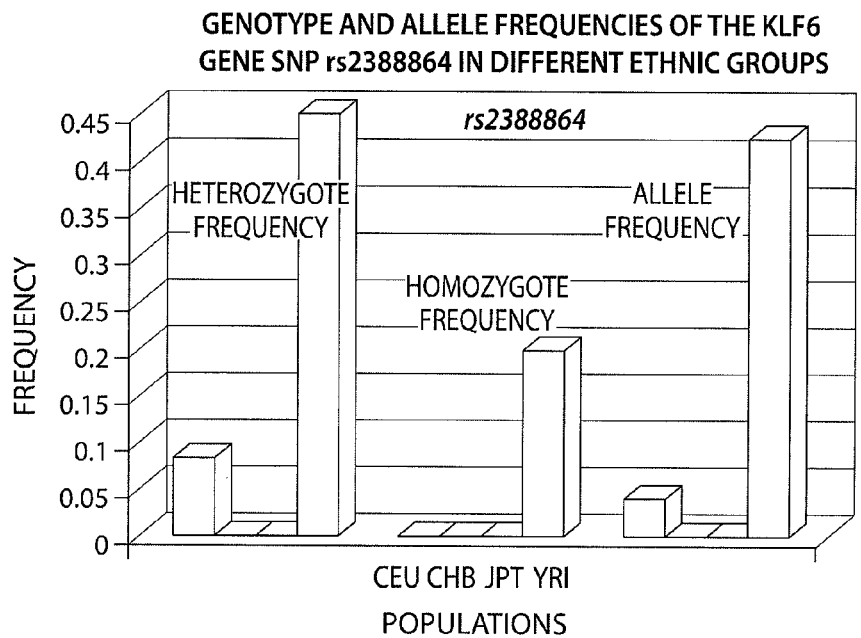
Figure 2C:
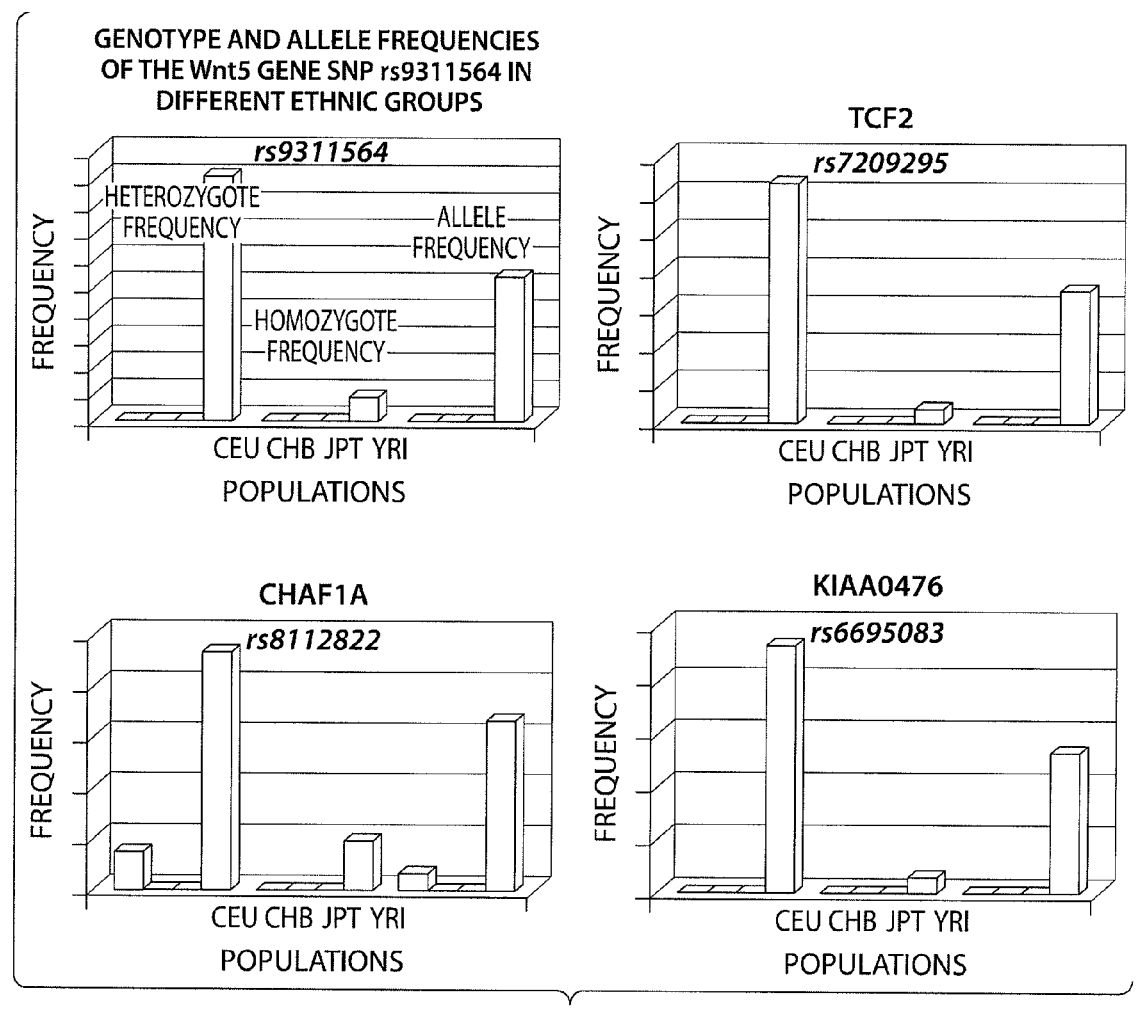
Figure 2D:
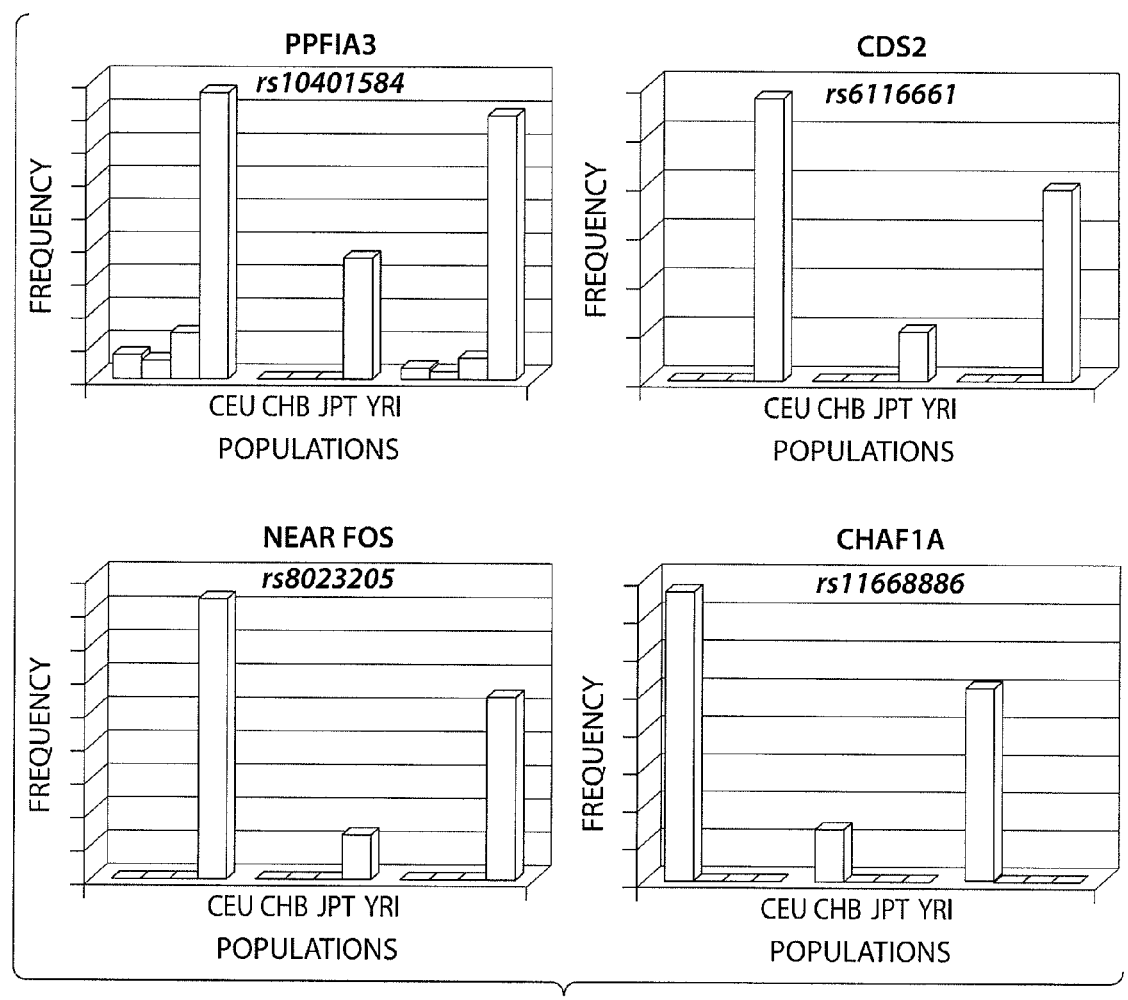

Genes considered to be in an "elite" group for use in predicting clinically relevant models are included in Table 1 below. These were generated by an analysis of the extensive genome-wide database of SNPs generated after the completion of the initial phase of the international HapMap project The initial effort was focused on 1) an analysis of the BMI1 oncogene, altered expression of which was functionally linked with the self-renewal state of normal and leukemic stem cells, and 2) a poor prognosis profile of an 11-gene death-from-cancer signature predicting therapy failure in patients with multiple types of cancer. A prominent feature of the BMI1-associated SNP pattern is YRI population-specific profiles of genotype and allele frequencies of multiple SNPs (FIG. 1). Intriguingly, similar population-specific SNP profiles are readily discernable for most of loci comprising the 11-gene CTOP signature (FIG. 1). Furthermore, this common SNP pattern is apparent for a majority of genetic loci expression profiles of which are predictive of therapy failure in prostate cancer patients after prostatectomy (FIG. 2). Finally, 86% of genetic loci comprising a proteomics-based 50-gene CTOP signature predicting therapy outcome in patients diagnosed with multiple types of cancer show population differentiation profiles of SNPs (FIG. 3).

Based on this analysis it is concluded that CTOP genes manifest a common feature of SNP patterns reflected in population-specific profiles of SNP genotype and allele frequencies. A majority of population-specific SNPs associated with CTOP genes represented by YRI population-differentiation SNPs, perhaps, reflecting a general trend of higher level of low-frequency alleles in the YRI population compared to CEU, CHB, and JPT populations due to bottlenecks in history of non-YRI populations. During the survey of the population-specific SNPs associated with CTOP genes, five non-synonymous coding SNPs (FIG. 4) were identified that represented good candidates for follow-up functional studies.

Oncogenes and tumor suppressor genes manifest population-specific profiles of SNP genotype and allele frequencies. Interestingly, in addition to CTOP genes, population-specific SNP patterns are readily discernable for genes with well-established causal role in cancer as oncogenes or tumor suppressor genes, implying that the genes are targets for geographically localized form of natural selection (FIG. 5). Taken together, the data suggests the presence of population differentiation-associated cancer-related patterns of SNPs spanning across multiple chromosomal loci and, perhaps, forming a genome-scale cancer haplotype pattern. The data suggest that a block-like structure and low haplotype diversity leading to substantial correlations of SNPs with many of their neighbors may span beyond small chromosomal regions and these "haplotype principles" may be extended to include multiple chromosomal loci, perhaps, on a genome-wide scale. Of note, gene expression signatures associated with deregulation of corresponding oncogenic pathways for most genes shown in FIG. 5 provide clinically relevant CTOP models.

Genes considered to be in an "elite" group for use in predicting clinically relevant CTOP models are included in Table 1 below.

TABLE 1

Elite set of genes and availability of antibodies for detection of corresponding protein products selected for development of diagnostic and prognostic applications.

| Gene name | UniGene | Company | Host | Signature |
|---|---|---|---|---|
| ADA | Hs.407135 | Santa Cruz Biotechnology, Inc. | rabbit IgG | M |
| AMACR + p63 | | Abcam | mouse IgG2a | PC marker |
| ANK3 | Hs.440478 | Santa Cruz Biotechnology, Inc. | mouse monoclonal IgG1 | DFC |
| BCL2L1 | Hs.305890 | Santa Cruz Biotechnology, Inc. | rabbit IgG | M |
| BIRC5 | Hs.1578 | Santa Cruz Biotechnology, Inc. | mouse IgG2a | DFC |
| BMI-1 | NM_005180 | Upstate | mouse monoclonal IgG1 | DFC |
| BMI-1 | NM_005180 | Santa Cruz Biotechnology, Inc. | rabbit polyclonal IgG | DFC |
| BUB1 | Hs.287472 | Chemicon | mouse monoclonal | DFC |
| CCNB1 | Hs.23960 | Santa Cruz Biotechnology, Inc. | mouse monoclonal IgG1 | DFC |
| CCND1 | Hs.523852 | Santa Cruz Biotechnology, Inc. | rabbit IgG | DFC |
| CES1 | Hs.499222 | Santa Cruz Biotechnology, Inc. | goat polyclonal | DFC |
| CHAF1A | Hs.79018 | Santa Cruz Biotechnology, Inc. | rabbit IgG polyclonal | R |
| CRIP1 | Hs.70327 | BD Biosciences Pharmingen | mouse monoclonal | M |
| CRYAB | Hs.408767 | Santa Cruz Biotechnology, Inc. | rabbit IgG | M |
| ESM1 | Hs.410668 | Santa Cruz Biotechnology, Inc. | goat IgG | M |
| EZH2 | Hs.444082 | Upstate | rabbit polyclonal | DFC |
| FGFR2 | Hs.404081 | Santa Cruz Biotechnology, Inc. | mouse IgG2b | DFC |
| FOS | Hs.25647 | Calbiochem | rabbit polyclonal | R |
| Gbx2 | Hs.184945 | Chemicon | rabbit polyclonal | DFC |
| HCFC1 | Hs.83634 | Santa Cruz Biotechnology, Inc. | goat polyclonal IgG | DFC |
| IER3 | Hs.76095 | Santa Cruz Biotechnology, Inc. | goat IgG polyclonal | R |
| ITPR1 | Hs.149900 | Abcam | rabbit polyclonal | R |
| JUNB | Hs.25292 | Santa Cruz Biotechnology, Inc. | rabbit IgG | R |
| KLF6 | Hs.285313 | Santa Cruz Biotechnology, Inc. | rabbit IgG | R |
| KI67 | Hs.80976 | Santa Cruz Biotechnology, Inc. | mouse monoclonal IgG1 | DFC |

TABLE 1-continued

Elite set of genes and availability of antibodies for detection of corresponding protein products selected for development of diagnostic and prognostic applications.

| Gene name | UniGene | Company | Host | Signature |
|---|---|---|---|---|
| KNTC2 | Hs.414407 | BD Biosciences Pharmingen | mouse monoclonal IgG1 | DFC |
| MGC5466 | Hs.370367 | Under development | | R |
| RNF2 | Hs.124186 | Under development | | DFC |
| Suz12 | Hs.462732 | Abcam | rabbit polyclonal IgG | DFC |
| TCF2 | Hs.408093 | Santa Cruz Biotechnology, Inc. | goat polyclonal | R |
| TRAP100 | Hs.23106 | Santa Cruz Biotechnology, Inc. | goat IgG polyclonal | M |
| USP22 | Hs.462492 | Under development | | DFC |
| Wnt5A | Hs.152213 | Santa Cruz Biotechnology, Inc. | goat polyclonal | R |
| ZFP36 | Hs.343586 | Santa Cruz Biotechnology, Inc. | rabbit polyclonal | R |

Legend:
PC, prostate carcinoma;
M, metastasis signature;
R, recurrence signature;
DFC, death-from-cancer signature. Differential expression of genes listed in the table was confirmed by the Q-RT-PCR method using LCM dissected samples of malignant and adjacent normal tissues from prostate tumor samples.

SNP-based gene expression signatures predict therapy outcome in prostate and breast cancer patients. Our analysis demonstrates that CTOP genes are distinguished by a common population specific SNP pattern and potential utility as molecular predictors of cancer treatment outcome based on distinct profiles of mRNA expression. All gene expression models designed to predict cancer therapy outcome were developed using phenotype-based signature discovery protocols, e.g., genetic loci comprising the predictive models were selected based on association of their expression profiles with clinically relevant phenotype of interest. One of the implications of our analysis is that heritable genetic variations driven by geographically localized form of natural selection determining population differentiations may have a significant impact on cancer treatment outcome by influencing the individual's gene expression profile. One of the predictions of this hypothesis is that genes, expression levels of which are known to be regulated by SNP variations, may provide good candidates for building gene expression-based CTOP models.

Consistent with this idea, we found that loci with genetically determined differences in mRNA expression levels among normal individuals (demonstrated by linkage analysis and by allelic associations of gene expression changes with SNP variations) generate statistically significant therapy outcome prediction models for breast and prostate cancer patients (FIGS. 6A-6D).

Figure 6A:
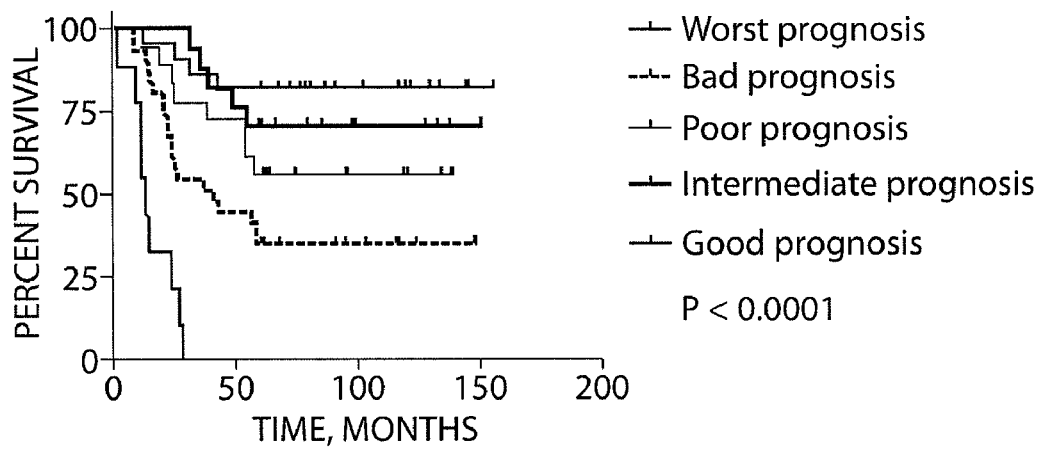
Figure 6B:
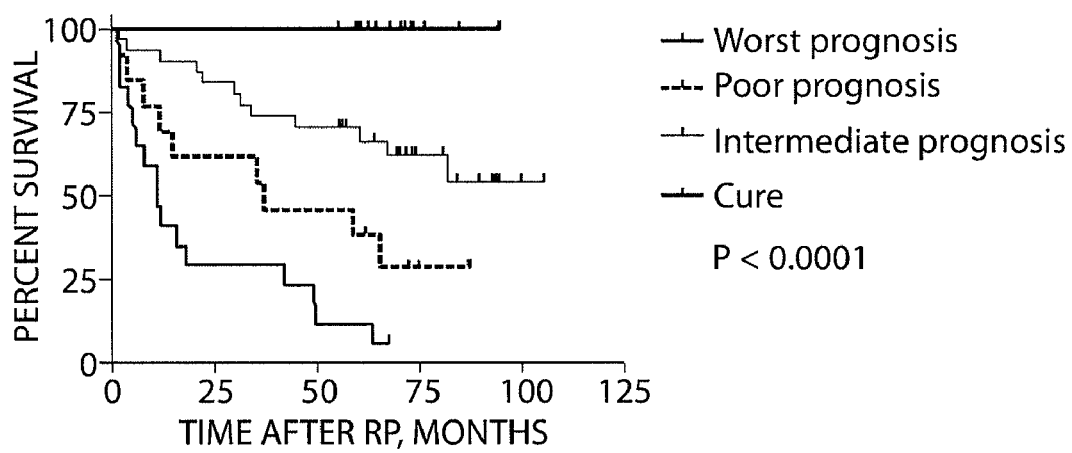
Figure 6C:
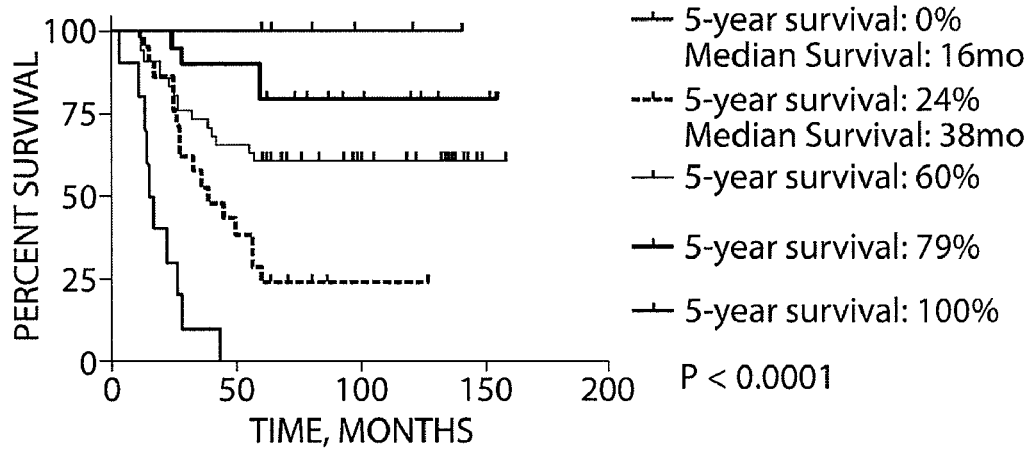
Figure 6D:
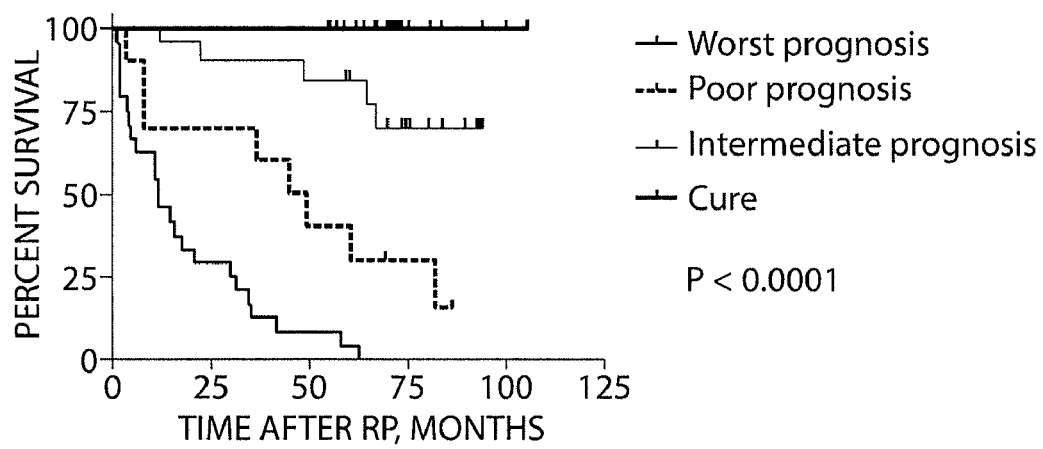
Figure 6E:
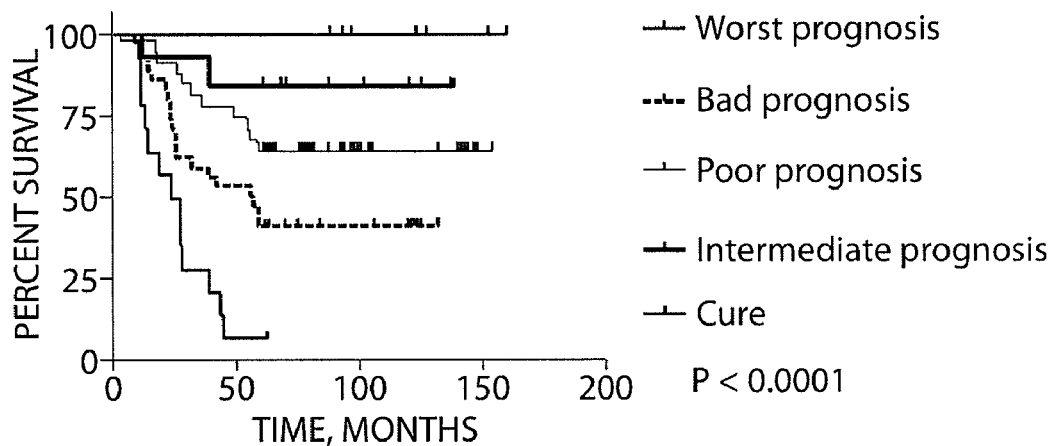
Figure 6F:
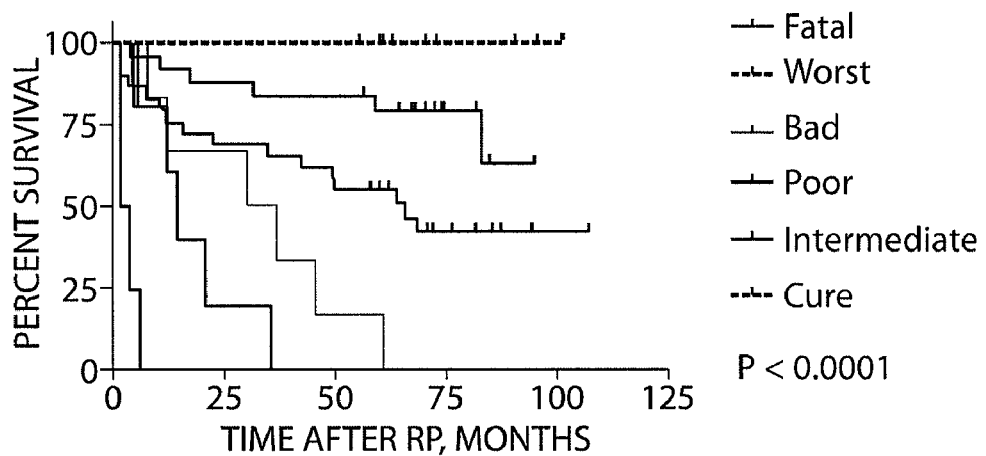
Figure 6G:
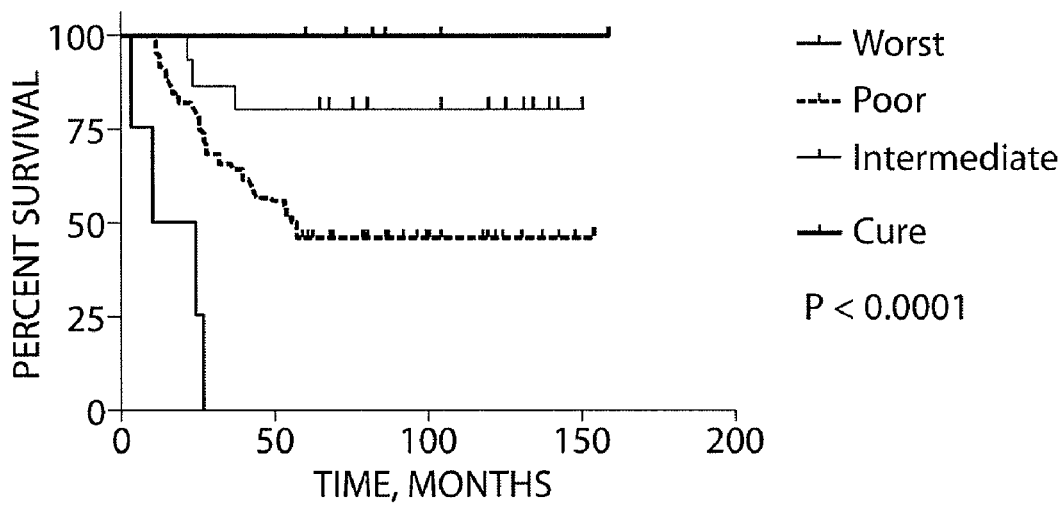
Figure 6H:
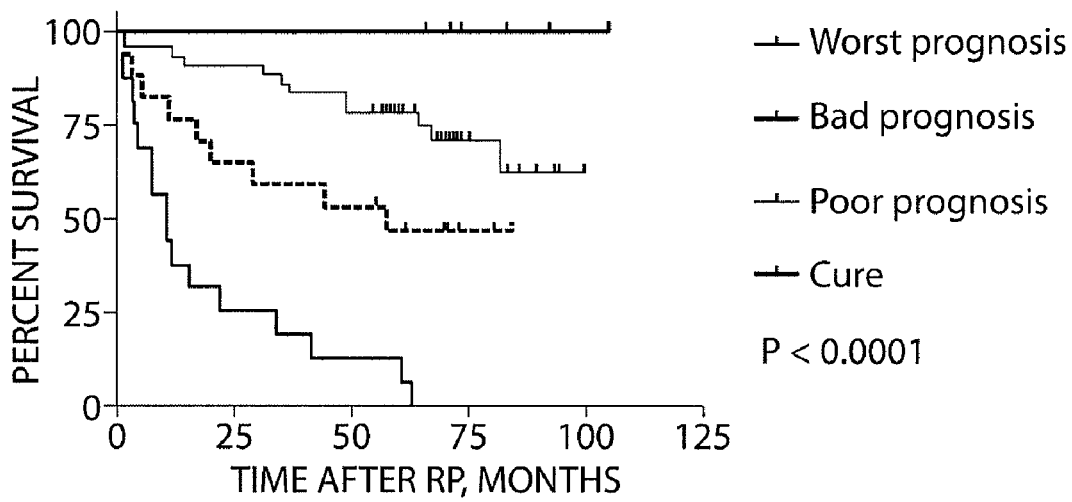
Figure 6I:
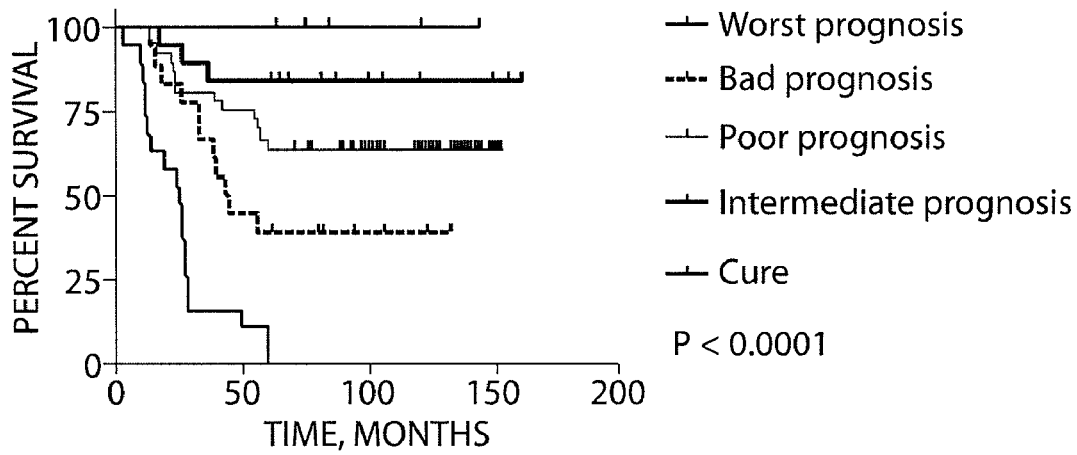
Figure 6J:
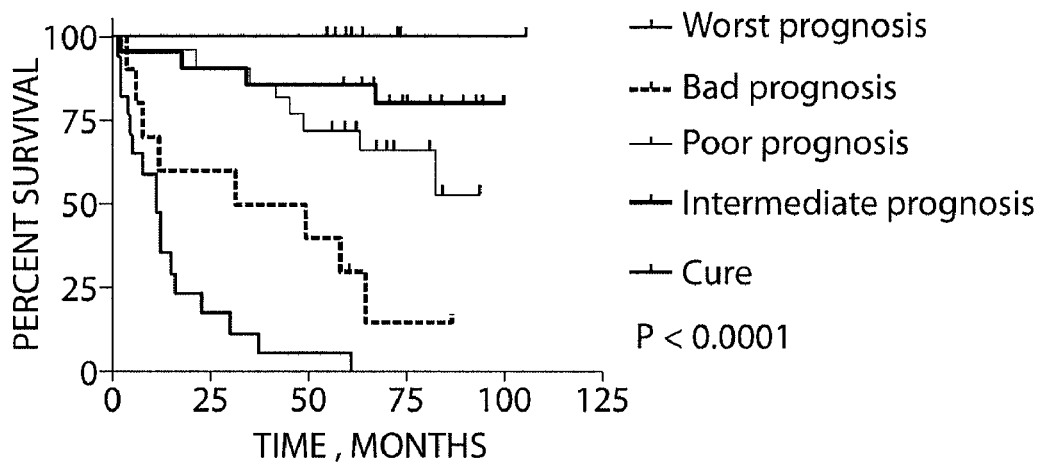
Figure 6K:
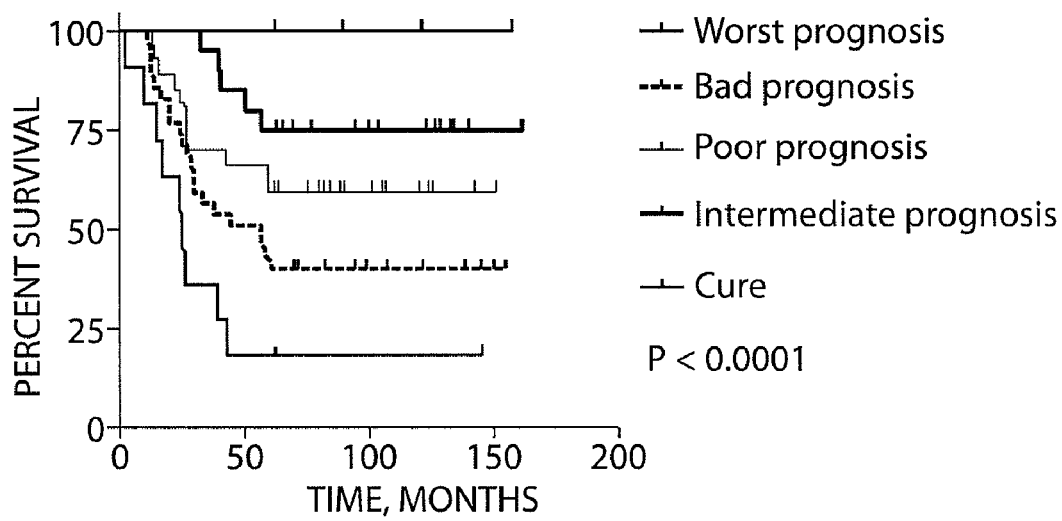
Figure 6L:
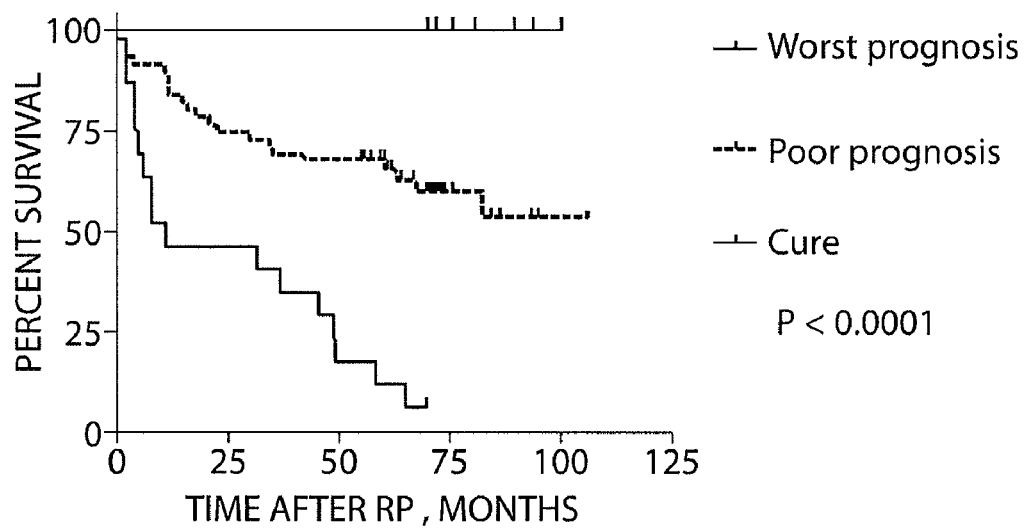
Figure 6M:
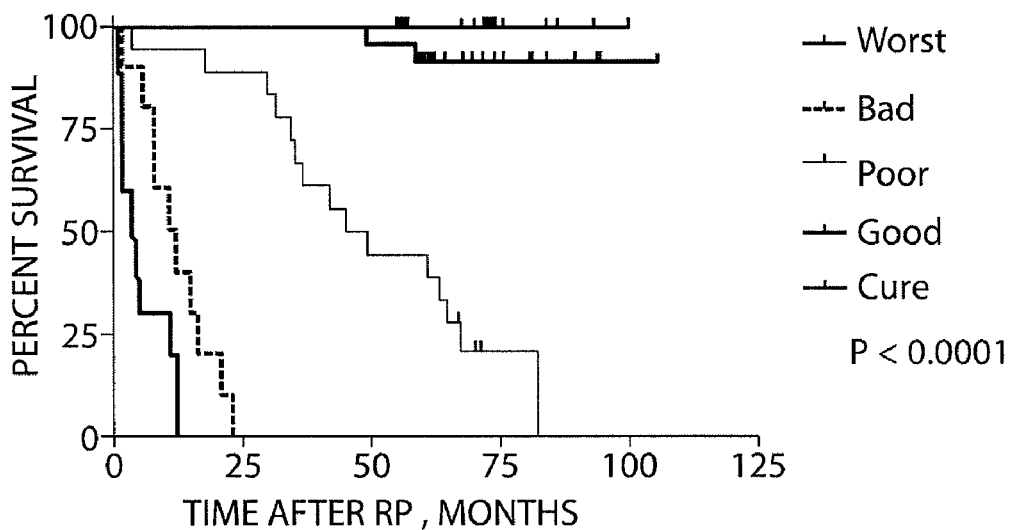
Figure 6N:
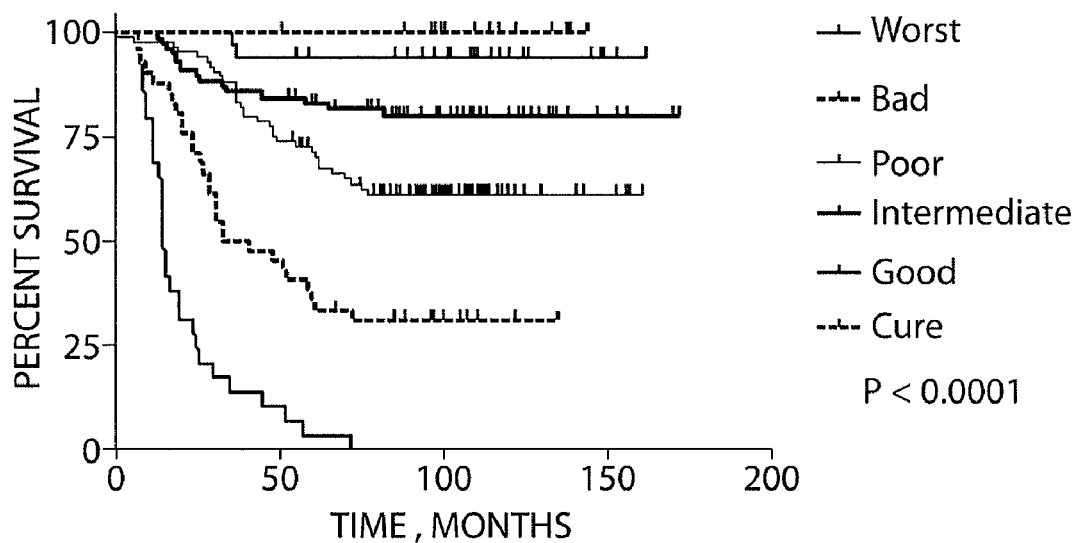
Figure 7A:
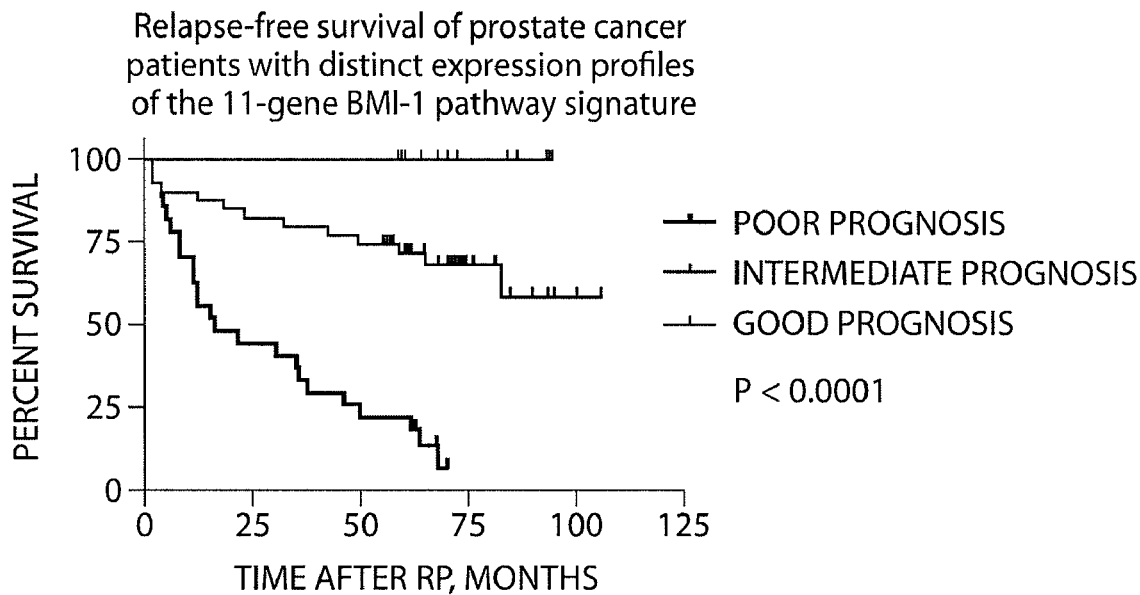
Figure 7B:
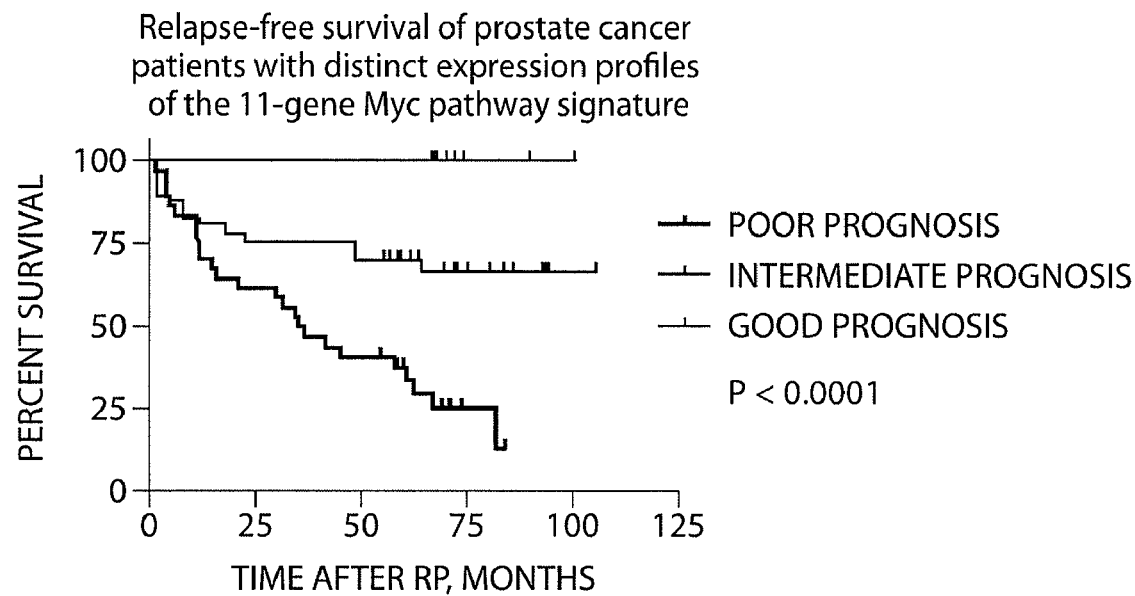
Figure 7C:
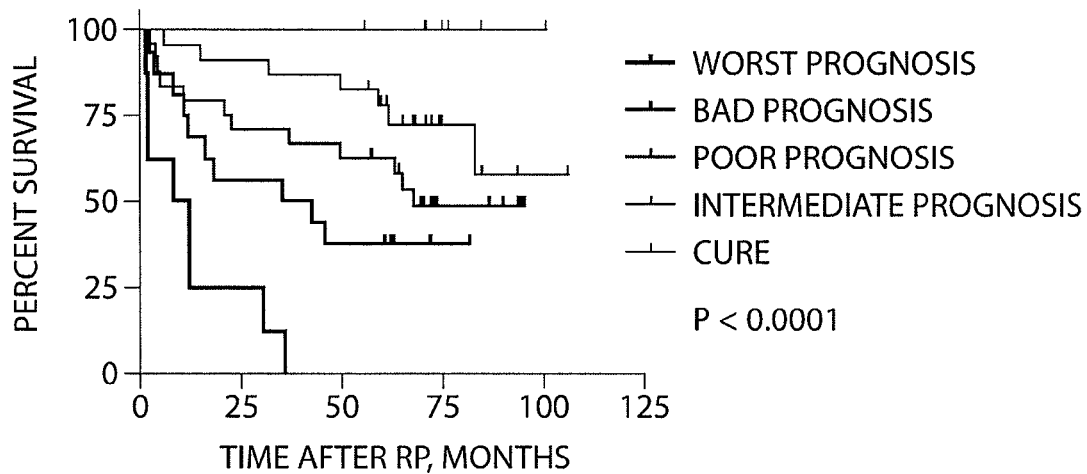
Figure 7D:
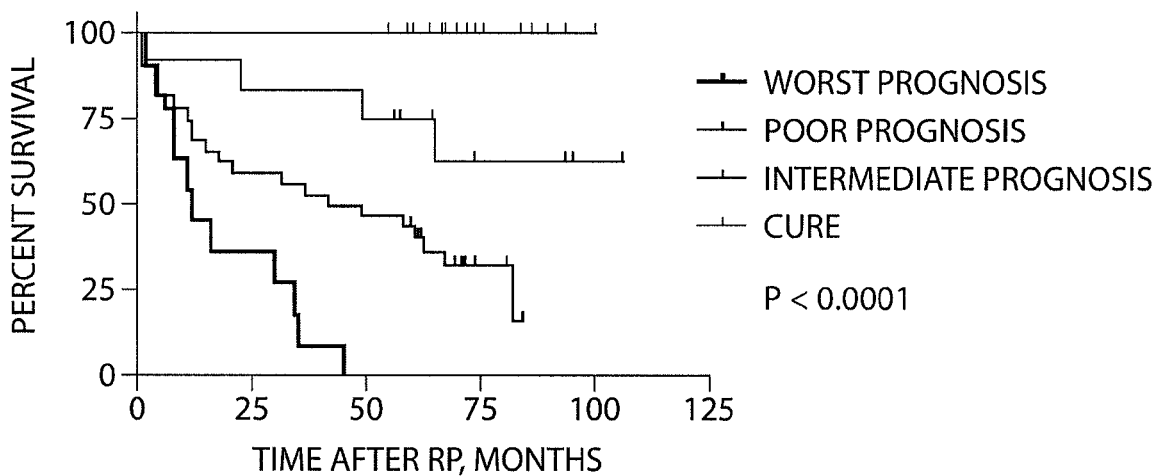
Figure 7E:
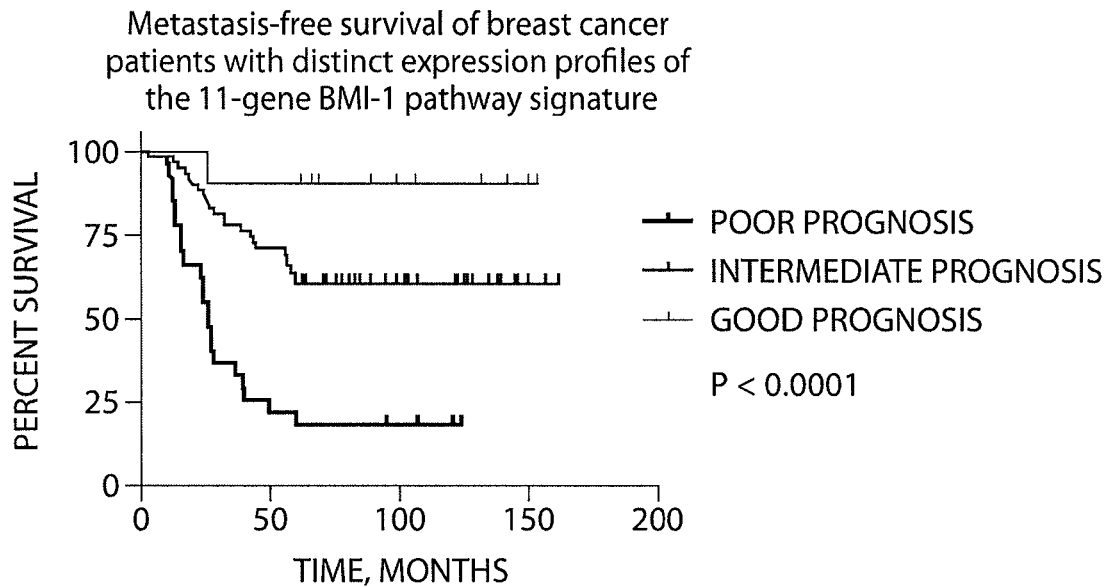
Figure 7F:
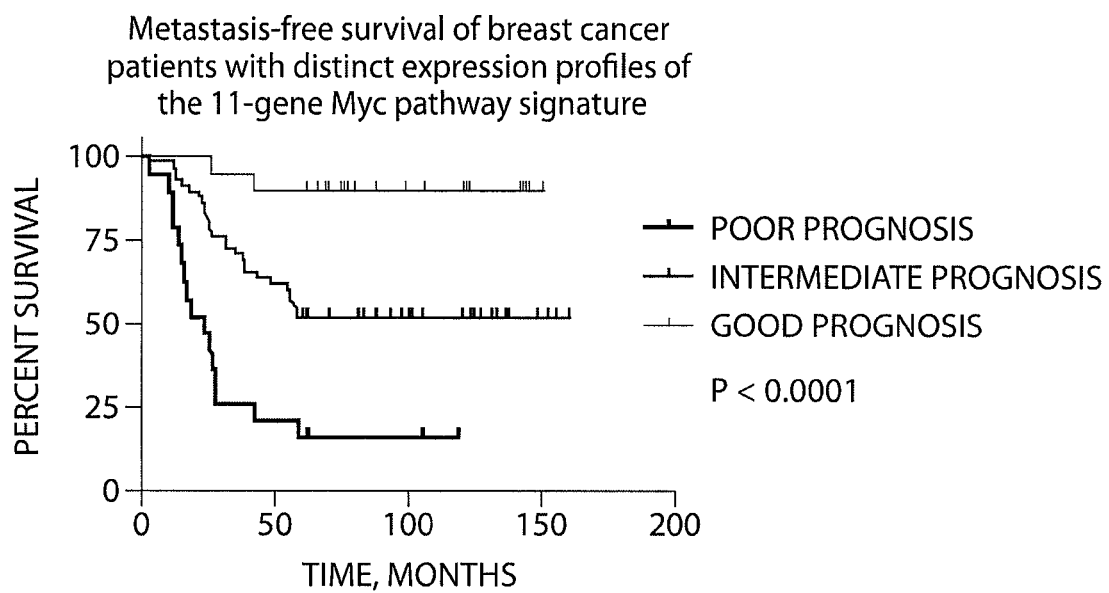
Figure 7G:
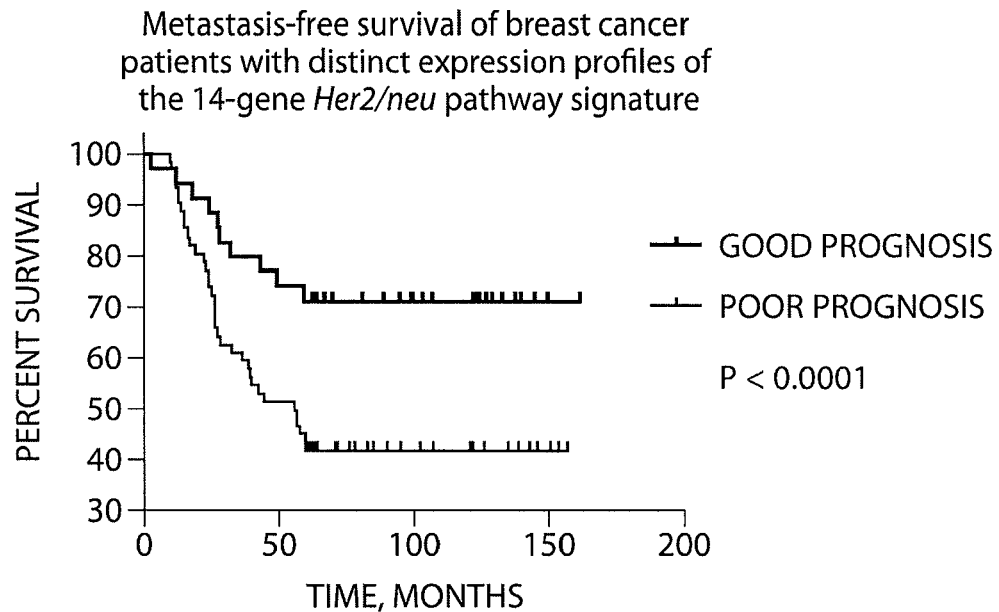
Figure 7H:
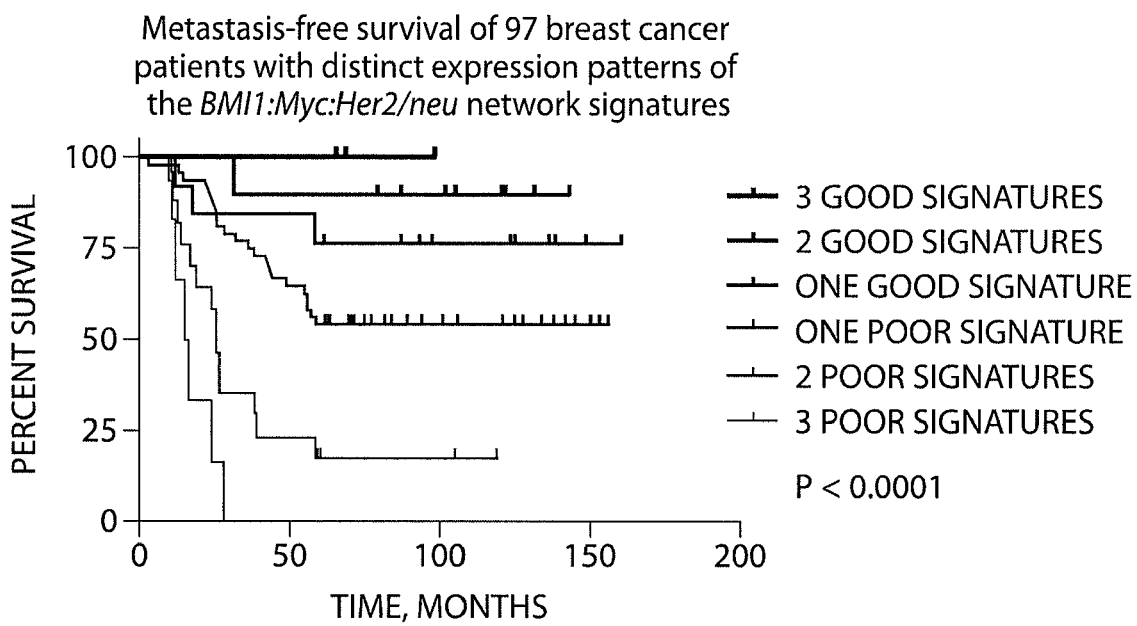
Figure 8A:
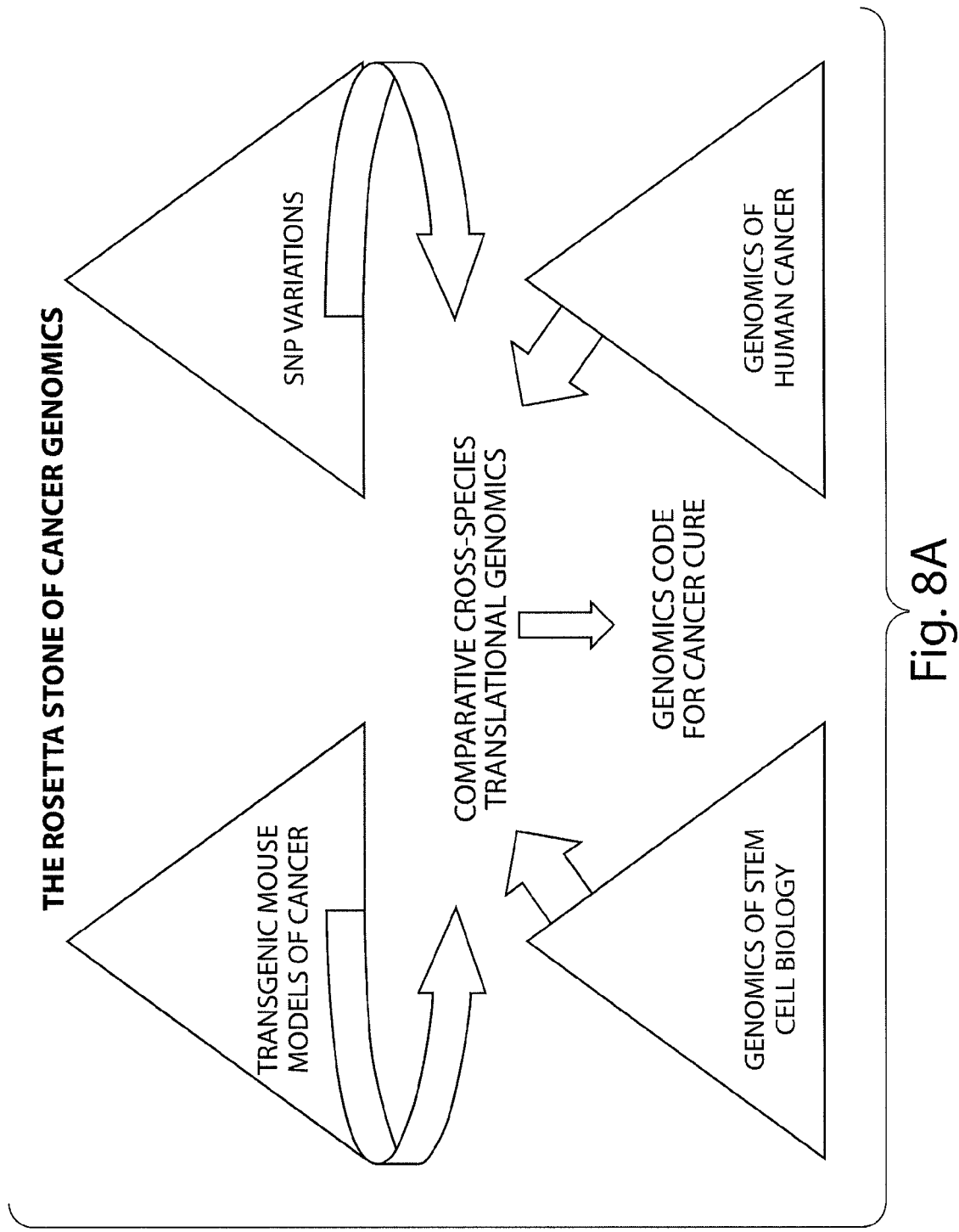
Figure 8B:
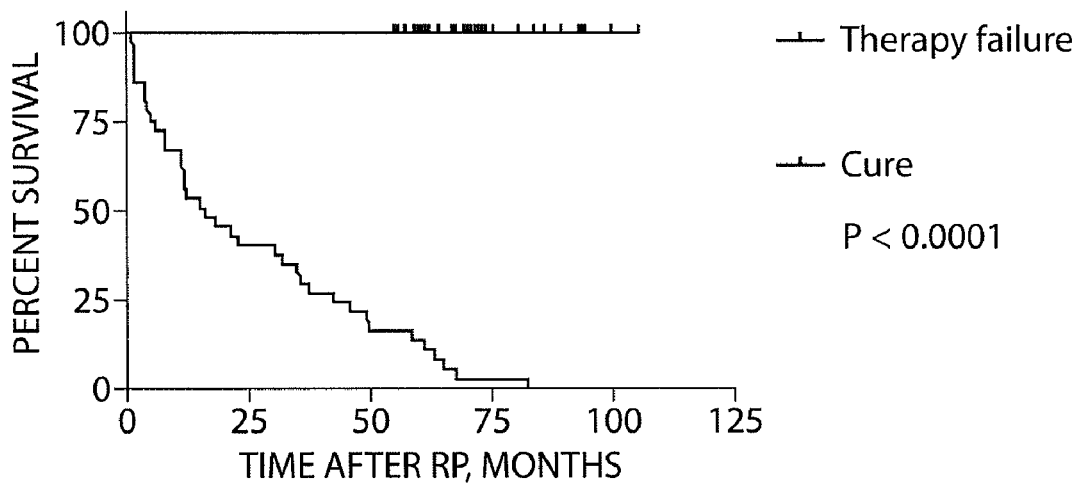
Figure 8C:
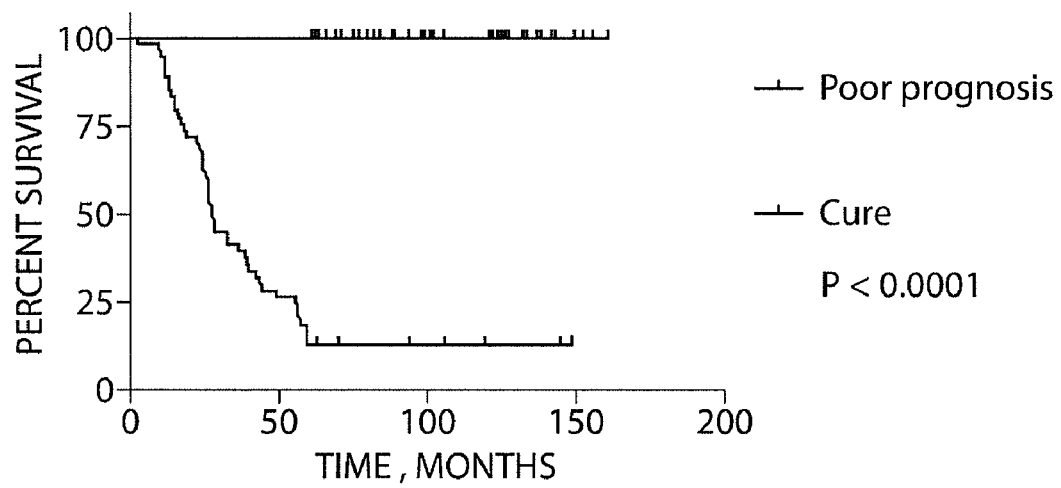

A hallmark feature of common SNP pattern of CTOP genes is population-specific profiles of SNP allele and genotype frequencies. Most CTOP genes have multiple SNPs with population-specific genotype and allele frequencies, suggesting that CTOP genes may be targets for geographically localized form of natural selection contributing to population differentiation. Consistent with this hypothesis, expression signatures of genes containing high-differentiation non-synonymous SNPs provide CTOP models for prostate and breast cancers (FIGS. 6E-6F). Similarly, expression signatures of genes representing loci in which natural selection most likely occurred appear highly informative in predicting therapy outcome in breast and prostate cancer patients (FIGS. 6G-6H). To further test the validity of this concept, we successfully used a common SNP pattern of CTOP genes to define novel gene expression models of cancer therapy outcome prediction without any input of mRNA expression data in the initial gene screening and selection process (FIGS. 6K-6L). Conversely, expression profiles of cancer-related genes with established SNP-based associations with incidence and severity of disease manifest therapy outcome prediction power (CYP3A4 for prostate cancer and SULT1A1 for breast cancer). Important end-point of this analysis with potential mechanistic implications is that patients with low expression levels of genes regulating catabolism of androgens (CYP3A4; prostate cancer), estrogens (SULT1A1; breast cancer) and thyroid hormones (DIO3; breast cancer) have significantly increased likelihood of therapy failure.

Microarray analysis identifies clinically relevant cooperating oncogenic pathways associated with cancer therapy outcome. Bild et al., Nature 439: 353-357 (2006) provides compelling evidence of the power of microarray gene expression analysis in identifying multiple clinically relevant oncogenic pathways activated in human cancers. It provides mechanistic explanation to mounting experimental data demonstrating that there are multiple gene expression signatures predicting cancer therapy outcome in a given set of patients diagnosed with a particular type of cancer: presence of multiple CTOP models is most likely reflect deregulation of multiple oncogenic pathways, perhaps, cooperating in development of an oncogenic state.

We tested this hypothesis by comparing the cancer therapy outcome prediction power of three gene expression signatures derived from corresponding transgenic mouse models associated with activation of oncogenic pathways driven by BMI1, Myc, and Her2/neu oncogenes during the prostate and mammary carcinogenesis. To evaluate the prognostic power of the BMI1-, Myc-, and Her2/neu-pathway signatures, we made use of two previously published gene expression datasets for prostate and breast cancers (Glinsky, G. V. et al., J. Clin. Invest. 113: 913-923 (2004); van 't Veer et al., Nature 415: 530-536 (2002)). As shown in FIG. 7, applications of three signatures clearly outperform individual signatures in patients' stratification into statistically distinct sub-groups based on likelihood of therapy failure. All cancer patients with evidence of activation of three pathways (3 poor prognosis signatures) failed therapy, whereas patients with no evidence of even single pathway activation remained disease-free (FIG. 7).

These data suggest that in a sub-group of prostate and breast cancer patients with therapy-resistant disease phenotype concomitant activation of pathways driven by BMI 1, Myc, and Her2/neu oncogenes may contribute to development of highly malignant clinically lethal oncogenic state. Taken together with data presented by Bild et al., supra, these results provides strong rationale for translational application of microarray analysis in assisting physicians and patients during rational evidence-based selection of individualized target-tailored cancer therapies with highest probability of cancer cure.

We tested a potential translational utility of this genome-wide approach to SNP analysis and gene expression profiling by building and retrospectively validating a CTOP algorithm integrating therapy outcome prediction calls of multiple phenotype-based and SNP-based molecular signatures of cancer treatment outcome. As shown in FIG. 8, this CTOP algorithm seems highly promising for identification at diagnosis prostate and breast cancer patients with 100% probability of a cure with existing therapy. It also allows selection of patients who would most likely benefit from more aggressive adjuvant systemic treatment protocols currently prescribed for patients with advanced metastatic cancers or disease relapse. If confirmed in prospective clinical validation studies, this approach should enable the practical implementation of a concept of individualized target-tailored cancer therapies allowing for rational evidence-based justification of prescription of such therapies for selected genetically defined group of patients at diagnosis. Finally, our analysis provides a strong rationale for development of genetic prognostic tests for prediction of cancer therapy outcome based on SNP analysis and expression profiling of individuals' normal cells such as blood cells.

In the human genome geographically localized form of natural selection causing population differentiation is reflected in population-specific signatures of a genome-wide SNP selection. Population differentiation is a generally accepted as a clue to past selection in one of the populations and 926 SNPs of this class have been described in the recent release of the HapMap project. Population-specific profiles of individual allele frequencies of the SNPs associated with CTOP genes suggest that cancer therapy outcome predictor genes can be found among genes carrying SNP-signatures of a genome-wide geographically localized form of natural selection causing population differentiation. Using these principles, we identified genes with SNP pattern similar to known CTO predictor genes among genetic loci with population differentiation SNP variants. Importantly, mRNA expression profiles of these genes generate statistically significant gene expression models of cancer therapy outcome prediction. These models were built without any input of mRNA expression data in the initial gene screening and selection process.

Analysis of a haplotype map of human genome indicates that vast majority of heterozygous sites in each person DNA will be explained by a limited set of common SNPs now contained (or captured through linkage disequilibrium, LD) in existing databases. Therefore, it is reasonable to assume that individual subjects within a population will likely carry unique combinations of population-differentiation SNPs identified in this study (or SNPs in LD with identified SNPs). We postulate that distinct patterns of population-differentiation SNPs associated with cancer-causing, cancer-associated, and CTOP genes would constitute important germ-line determinants of susceptibility, incidence, and severity of disease. Our analysis suggests that one of the main mechanisms of translation the SNP pattern diversity in disease phenotypes would be heritable SNP-driven variations in gene expression levels. Our analysis adds further support to recent data that SNP-driven effects on gene expression are seemingly spreading outside the boundaries of individual chromosomes and, perhaps, reaching a genome-wide scale. See FIG. 8 for description of analysis.

A majority of SNPs identified in this study is represented by intronic SNPs, suggesting that intronic SNPs may influence gene expression by yet unknown mechanism. Theoretically, intronic SNPs may influence gene expression by affecting a variety of processes such as chromatin silencing and remodeling, alternative splicing, transcription of microRNA genes, processivity of RNA polymerase, etc. Most likely mechanism of action would entail effect on stability and affinity of interactions between DNA molecule and corresponding multi-subunit complexes. Comparative genomics analysis has shown that about 5% of the human sequence is highly conserved across species, yet less than half of this sequence spans known functional elements such as exons. It is assumed that conserved non-genic sequences lack diversity because of selective constraint due to purifying selection; alternatively, such regions may be located in cold-spots for mutations. Most recent evidence shows that conserved non-genic sequences are not mutational cold-spots, and thus represent high interest for functional study. It would be of interest to determine whether population differentiation intronic SNPs overlap with such highly evolutionary conserved non-genic sequences.

Our analysis provides a possible clue with regard to mechanisms of genesis and evolution of disease-causing loci and translation of SNP variations in disease phenotypes. Geographically localized form of natural selection drives evolution of population differentiation SNP profiles which is translated in phenotypic diversity by determining individual gene expression variations. Until recently, this selection-driven evolution in human population was occurring within relatively restricted genetic pools due to travel and migration limitations in the demographic context of close alignment of populations' reproductive longevity and overall lifespan. During last century rapid and dramatic socio-economic and demographic changes (explosion in travel and migration; increasing length of individual's reproductive period; widening gap between reproductive longevity and life expectancy associated with a marked extension of continuous in vivo exposure of proliferating tissues to low levels of steroid hormones) altered the dynamic of these relationships in human population enhancing probability of emerging disease-enabling combinations of SNP profiles.

Markers from Polycomb Group (PcG) Pathway

Preferred markers within the context of the present invention include the double positive BMI1/Ezh2 from the PcG pathway. The Polycomb group (PcG) gene BMI1 is required for the proliferation and self-renewal of normal and leukemic stem cells. Over-expression of Bmi1 oncogene causes neoplastic transformation of lymphocytes and plays essential role in pathogenesis of myeloid leukemia. Another PcG protein, Ezh2, was implicated in metastatic prostate and breast cancers, suggesting that PcG pathway activation is relevant for epithelial malignancies. Whether an oncogenic role of the BMI1 and PcG pathway activation may be extended beyond the leukemia and may affect progression of solid tumors has previously remained unknown. Here it is demonstrated that activation of the BMI1 oncogene-associated PcG pathway plays an essential role in metastatic prostate cancer, thus mechanistically linking the pathogenesis of leukemia, self-renewal of stem cells, and prostate cancer metastasis.

To characterize the functional status of the PcG pathway in metastatic prostate cancer, advanced cell- and whole animal-imaging technologies, gene and protein expression profiling, stable siRNA-gene targeting, and tissue microarray (TMA) analysis in relevant experimental and clinical settings were utilized.

It was also demonstrated that in multiple experimental models of metastatic prostate cancer both BMI1 and Ezh2 genes are amplified and gene amplification is associated with increased expression of corresponding mRNAs and proteins. Images of human prostate carcinoma metastasis precursor cells isolated from blood were provided and shown to overexpress both BMI1 and Ezh2 oncoproteins. Consistent with the PcG pathway activation hypothesis, increased BMI1 and Ezh2 expression in metastatic cancer cells is associated with elevated levels of H2AubiK119 and H3metK27 histones.

Quantitative immunofluorescence co-localization analysis and expression profiling experiments documented increased BMI1 and Ezh2 expression in clinical prostate carcinoma samples and demonstrated that high levels of BMI1 and Ezh2 expression are associated with markedly increased likelihood of therapy failure and disease relapse after radical prostatectomy. Gene-silencing analysis reveals that activation of the PcG pathway is mechanistically linked with highly malignant behavior of human prostate carcinoma cells and is essential for in vivo growth and metastasis of human prostate cancer. It is concluded that the results of experimental and clinical analyses indicate the important biological role of the PcG pathway activation in metastatic prostate cancer. It is suggested that the PcG pathway activation is a common oncogenic event in pathogenesis of metastatic solid tumors and provides the basis for development of small molecule inhibitors of the PcG chromatin silencing pathway as a novel therapeutic modality for treatment of metastatic prostate cancer.

Activation of PcG Protein Chromatin Silencing Pathway in Human Prostate Carcinoma Metastasis Precursor Cells.

The PcG pathway activation hypothesis implies that individual cells with activated chromatin silencing pathway would exhibit a concomitant nuclear expression of both BMI1 and Ezh2 proteins. Furthermore, cells with activated PcG pathway would manifest the increased expression levels of protein substrates targeted by the activation of corresponding enzymes to catalyze the H2A-K119 ubiquitination (BMI1-containing PRC1 complex) and H3-K27 methylation (Ezh2-containing PRC2 complex). Observations that increased BMI1 expression is associated with metastatic prostate cancer suggest that the PcG pathway might be activated in metastatic human prostate carcinoma cells. Consistent with this idea, previous independent studies documented an association of the increased Ezh2 expression with metastatic disease in prostate cancer patients. Therefore, immunofluorescence analysis was applied to measure the expression of protein markers of the PcG pathway activation in prostate cancer metastasis precursor cells isolated from blood of nude mice bearing orthotopic human prostate carcinoma xenografts.

Immunofluorescence analysis reveals that expression of all four individual protein markers of PcG pathway activation is elevated in blood-borne human prostate carcinoma metastasis precursor cells compared to the parental cells comprising a bulk of primary tumors (FIGS. 20 & 21). In order to document the PcG pathway activation in individual cells, the quantitative immunofluorescence co-localization analysis allowing for a simultaneous detection and quantification of several markers in a single cell was carried out. The quantitative immunofluorescence co-localization analysis demonstrates a marked enrichment of the population of blood-borne human prostate carcinoma metastasis precursor cells with the dual positive high BMI1/Ezh2-expressing cells (FIG. 20A).

These results were confirmed using two different mouse/rabbit primary antibody combinations for BMI1 and Ezh2 protein detection as well as different secondary fluorescent antibodies. Similar enrichment for the PcG pathway activated cells in a pool of circulating metastasis precursor cells is evident for other two-marker combination panels as well (FIG. 21). In contrast to the protein markers of the PcG pathway activation, a significantly smaller fraction of cells expressing concomitantly high levels of the cytoplasmic AMACR/nuclear p63 proteins was detected in human prostate carcinoma metastasis precursor cells compared to the parental cell population. Therefore, the results of a quantitative immunofluorescence co-localization analysis indicate that measurements of several two-marker combinations demonstrate a significant enrichment of the population of prostate carcinoma metastasis precursor cells with the cells expressing high levels of the PcG pathway activation markers (FIGS. 20 & 21). Increased BMI1 and Ezh2 mRNA expression is associated with metastatic prostate cancer. Taken together these data support the hypothesis that PcG chromatin silencing pathway is activated in blood-borne human prostate carcinoma metastasis precursor cells and might contribute to the ability of metastatic cancer cells to survive and grow at distant sites.

Amplification of the BMI1 and Ezh2 Genes in Multiple Experimental Models of Human Prostate Cancer.

Increased expression of oncogenes is often associated with gene amplification. In agreement with proposed oncogenic role of the BMI1 and Ezh2 over-expression in human prostate carcinoma cells, it was documented that a significant amplification of both BMI1 and Ezh2 genes in human prostate carcinoma cell lines representing multiple experimental models of metastatic prostate cancer (FIG. 20E). Notably, the level of gene amplification as determined by the measurement of DNA copy number for both BMI1 and Ezh2 genes is higher in metastatic cancer cell variants compared to the non-metastatic or less malignant counterparts, suggesting that gene amplification may play a casual role in elevation of the BMI1 and Ezh2 oncoprotein expression levels and high BMI1/Ezh2-expressing cells may acquire a competitive survival advantage during tumor progression.

PcG Pathway Activation Renders Circulating Human Prostate Carcinoma Metastasis Precursor Cells Resistant to Anoikis.

To ascertain the biological role of the PcG pathway activation in prostate cancer metastasis, human prostate carcinoma metastasis precursor cells were isolated from the blood of nude mice bearing orthotopic human prostate carcinoma xenografts, transfected with BMI1, Ezh2, or control siRNAs, and continuously monitored for mRNA and protein expression levels of BMI1, Ezh2, and a set of additional genes and protein markers using immunofluorescence analysis, RT-PCR, and Q-RT-PCR methods. Q-RT-PCR and RT-PCR analyses showed that siRNA-mediated BMI1-silencing caused ~90% inhibition of the endogenous BMI1 mRNA expression. The effect of siRNA-mediated BMI1 silencing was validated at the protein expression level using immunofluorescence analysis (FIG. 22). The BMI1 silencing was specific since the expression levels of nine un-related transcripts were not altered (FIG. 22). Consistent with the hypothesis that expression of genes comprising the 11-gene death-from-cancer signature is associated with the expression of the BMI1 gene product, mRNA abundance levels of 8 of 11 interrogated BMI1-pathway target genes were altered in the human prostate carcinoma cells with siRNA-silenced BMI1 gene. For biological analysis we adopted the silencing protocol resulting in 80-100% reduction of the level of dual-positive BMI1/Ezh2 high-expressing metastasis precursor cells, thus yielding the cell population more closely resembling non-treated parental cells and markedly distinct from metastasis precursor cells treated with control siRNA (FIGS. 22 & 23).

Reduction of the BMI1 mRNA and protein expression in human prostate carcinoma metastasis precursor cells did not alter significantly the viability of adherent cultures grown at the optimal growth condition and in serum starvation experiments. siRNA treatment had only modest inhibitory effect on proliferation causing ~25% reduction in the number of cells. However, the ability of human prostate carcinoma cells to survive in non-adherent state was severely affected after siRNA-mediated reduction of the BMI1 expression (FIG. 22). FACS analysis revealed ~3-fold increase of apoptosis in the BMI1 siRNA-treated human prostate carcinoma cells cultured in non-adherent conditions (FIG. 22). These data suggest that human prostate carcinoma cells expressing high level of the BMI1 protein are more resistance to apoptosis induced in cells of epithelial origin in response to attachment deprivation (anoikis). It is likely that these anoikis-resistant cancer cells would survive better in blood or lymph during metastatic dissemination thus forming a pool of circulatory stress-surviving metastasis precursor cells. Similar results were obtained when Ezh2 silencing experiments were performed (FIG. 22), suggesting that targeting of either PRC1 or PRC2 complexes is sufficient for interference with the PcG pathway activity and inhibition of anoikis-resistance mechanisms in metastatic prostate carcinoma cells.

Targeted Depletion of Human Prostate Carcinoma Cells with Activated PcG Pathway Creates Population of Cancer Cells with Dramatically Diminished Malignant Potential In Vivo.

Results of the experiments demonstrate that a population of highly metastatic prostate carcinoma cells is markedly enriched for cancer cells expressing increased levels of multiple markers of the PcG pathway activation. These data suggest that carcinoma cells with activated PcG pathway may manifest a highly malignant behavior in vivo characteristic of cancer cell variants selected for increased metastatic potential. To test this hypothesis, blood-borne human prostate carcinoma metastasis precursor cells were treated with chemically modified stable siRNA targeting either BMI1 or Ezh2 mRNAs to generate a cancer cell population with diminished levels of dual positive high BMI1/Ezh2-expressing carcinoma cells. Stable siRNA-treated prostate carcinoma cells continue to grow in adherent culture in vitro for several weeks allowing for expansion of siRNA-treated cultures in quantities sufficient for in vivo analysis.

These observations also indicate that the treatment protocol was well-tolerated and was not detrimental for the general growth properties of a cancer cell population. Quantitative immunofluorescence co-localization analysis demonstrated that carcinoma cells after treatment with the BMI1- or Ezh2-targeting stable siRNA continue to express significantly lower levels of targeted proteins for extended period of time (~30-50% reduction at the 11 days post-treatment time point) compared to the cells treated with the control LUC siRNA (FIG. 23). Importantly, the siRNA-treated human prostate carcinoma cell populations were essentially depleted for dual positive high BMI1/Ezh2-expressing carcinoma cells (FIG. 23) thus setting up the stage for critical in vivo analysis using a fluorescent orthotopic model of human prostate cancer metastasis in nude mice.

Remarkably, highly malignant human prostate carcinoma cell populations depleted for dual positive high BMI1/Ezh2-expressing cells demonstrated markedly diminished tumorigenic and metastatic potential in vivo (FIG. 24). Within 3 weeks after inoculation of the $1.5 \times 10^6$ of tumor cells, 100% of control animals developed rapidly growing highly invasive and metastatic carcinomas in the mouse prostate and all animal died within 50 days of the experiment (FIG. 24). In contrast, only 20% of animals in both BMI1- and Ezh2-targeting therapy groups developed seemingly less malignant tumors causing death of hosts 78-87 days after tumor cell inoculation (FIG. 24). Significantly, 150 days after tumor cell inoculation 83% and 67% of animals remain alive and disease-free in the therapy groups targeting the BMI1 and Ezh2 proteins, respectively (FIG. 5; p=0.0007, Log rank test).

Increased Levels of Dual Positive High BMI/Ezh2-expressing Cells Indicate Activation of the PcG Pathway in a Majority of Human Prostate Adenocarcinomas.

To validate the significance of our findings for human disease, the quantitative immunofluorescence co-localization analysis was applied for measurements of the expression of BMI1 and Ezh2 proteins and detection of dual positive high BMI/Ezh2-expressing carcinoma cells in clinical samples obtained from patients diagnosed with prostate adenocarcinomas. The results of this analysis demonstrate that a majority (79%-91% in different cohorts of patients) of human prostate tumors contains dual positive high BMI1/Ezh2-expressing carcinoma cells exceeding the threshold expression level in prostate samples from normal individuals (FIG. 25). Interestingly, a panel of adenocarcinoma samples appears quite heterogeneous with respect to the relative levels of dual positive high BMI1/Ezh2-expressing cells (FIG. 25). While in 50%-74% of prostate tumors the level of high BMI1-, high Ezh2-, or dual positive high BMI1/Ezh2-expressing cells was only slightly elevated (<15% of positive cells), a significant fraction (17%-29%) of prostate adenocarcinomas demonstrates a marked enrichment for dual positive high BMI1/Ezh2-expressing cells (>15% of positive cells).

Increased BMI1 and Ezh2 Expression is Associated with High Likelihood of Therapy Failure in Prostate Cancer Patients after Radical Prostatectomy.

Figure 26A:
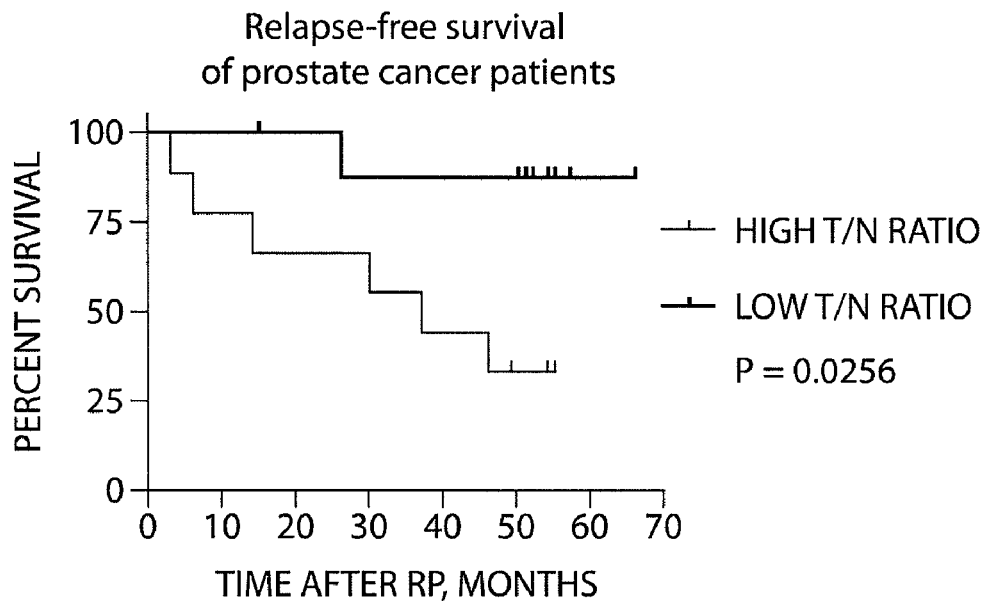
Figure 26B:
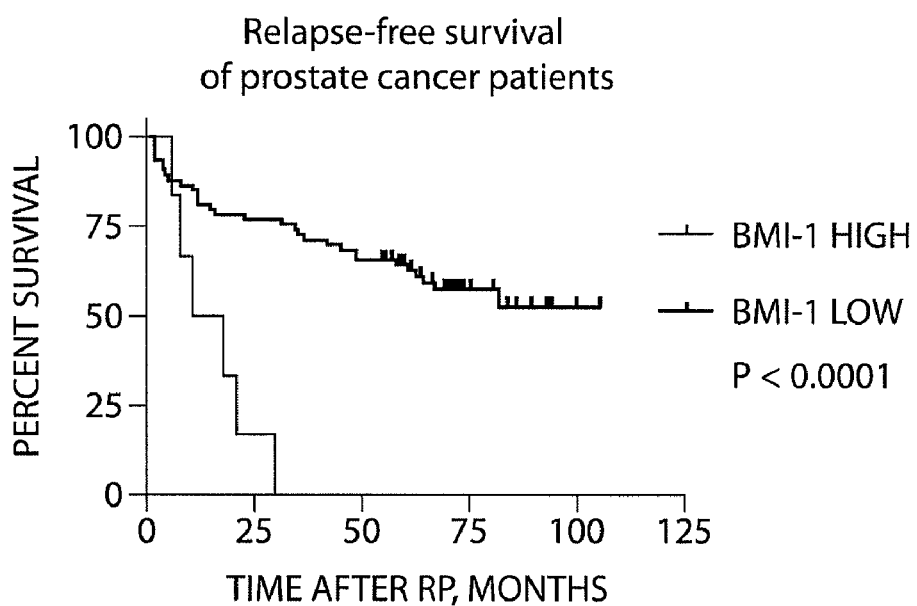
Figure 26C:
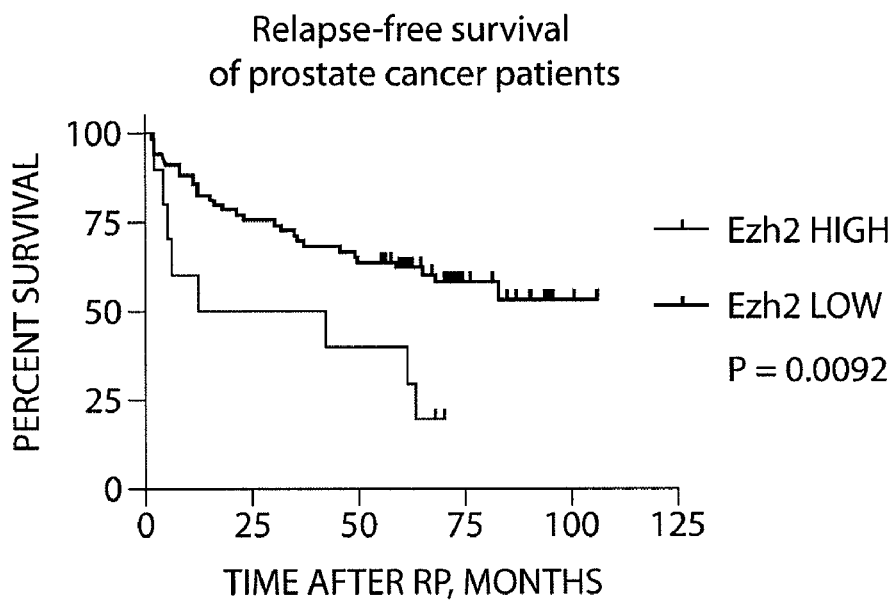
Figure 26D:
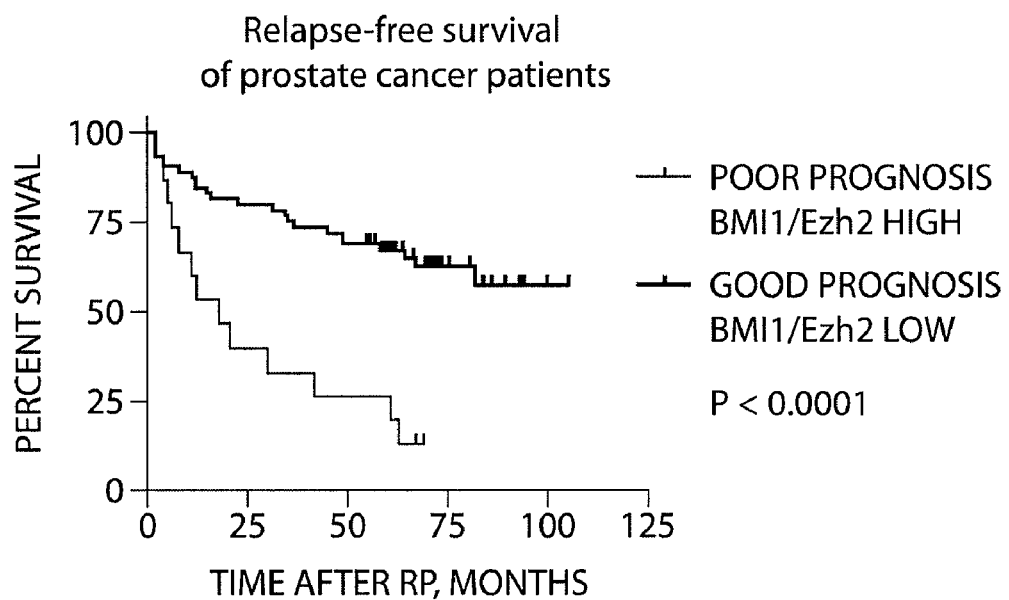
Figure 26E:
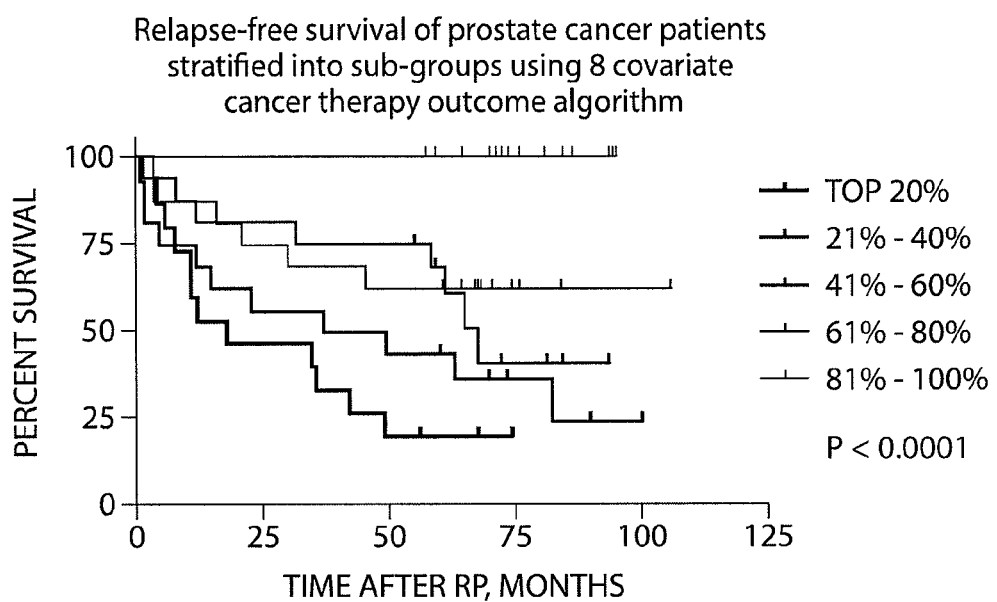

Microarray analysis demonstrates that cancer patients with high levels of BMI1 and Ezh2 mRNA expression in prostate tumors have a significantly worst relapse-free survival after radical prostatectomy (RP) compared with the patients having low levels of BMI1 and Ezh2 expression (FIG. 26), suggesting that more profound alterations of the PcG protein chromatin silencing pathway in carcinoma cells are associated with therapy resistant clinically lethal prostate cancer phenotype. FIG. 26E shows the Kaplan-Meier survival analysis of 79 prostate cancer patients stratified into five subgroups using eight-covariate cancer therapy outcome (CTO) algorithm (Table 2, below).

TABLE 2

8-covariate prostate cancer recurrence predictor model

| Covariate | Coefficient | SE | Significance, P | Confidence interval, low 95% | Confidence interval, high 95% |
| --- | --- | --- | --- | --- | --- |
| BMI1 | 4.7732 | 1.5179 | 0.0017 | 1.798 | 7.7483 |
| Ezh2 | 0.4345 | 0.8215 | 0.5969 | −1.1756 | 2.0446 |
| PRE RP PSA | 0.0236 | 0.023 | 0.3054 | −0.0215 | 0.0686 |
| RP GLSN SUM | 0.2809 | 0.1955 | 0.1508 | −0.1023 | 0.6642 |
| Capsular Inv | 1.4752 | 0.7593 | 0.052 | −0.0131 | 2.9634 |
| SM | 0.7786 | 0.4641 | 0.0934 | −0.1311 | 1.6883 |
| Sem Ves Inv | 0.5876 | 0.4419 | 0.1836 | −0.2785 | 1.4538 |
| AGE | 0.041 | 0.0335 | 0.2214 | −0.0247 | 0.1066 |

RP, radical prostatectomy;
PSA, prostate-specific antigen;
GLSN SUM, Gleason sum;
SM, surgical margins;
Sem Ves Inv, seminal vesicle invasion;
Capsular Inv, capsular invasion.
Overall model fit: Chi Square = 40.1250; df = 8; p < 0.0001.

The multivariate Cox proportional hazards survival analysis were carried out to ascertain the prognostic power of measurements of BMI1 and Ezh2 expression in combination with known clinical and pathological markers of prostate cancer therapy outcome such as Gleason score, surgical margins, extra-capsular invasion, seminal vesicle invasion, serum PSA levels, and age. Of note, BMI1 expression level remains a statistically significant prognostic marker in the multivariate analysis (Table 3). Application of the 8-covariate prostate cancer recurrence model combining the incremental statistical power of individual prognostic markers appears highly informative in stratification of prostate cancer patients into sub-groups with differing likelihood of therapy failure and disease relapse after radical prostatectomy (FIG. 26). One of the distinctive features of this model is that it identifies a sub-group of prostate cancer patients comprising bottom 20% of recurrence predictor score and manifesting no clinical or biochemical evidence of disease relapse (FIG. 26). In contrast, 80% of patients in a sub-group comprising top 20% of recurrence predictor score failed therapy within five year period after radical prostatectomy.

Increasing experimental evidence suggest that an oncogenic role of the BMI1 activation may be extended beyond the leukemia and, perhaps, play a key role in progression of the epithelial malignancies and other solid tumors as well. One of the compelling examples revealing an association of the activated BMI1 oncoprotein-driven pathway(s) with clinically lethal therapy-resistant malignant phenotype in patients diagnosed with multiple types of cancer is identification of a death-from-cancer gene expression signature. An 11-gene signature distinguishes stem cells with normal self-renewal function versus stem cells with drastically diminished self-renewal ability due to the loss of the BMI-1 oncogene and similarly expressed in metastatic prostate tumors. To date, the prognostic power of the 11-gene signature was validated in multiple independent therapy outcome sets of clinical samples obtained from more than 2,500 cancer patients diagnosed with 12 different types of cancer, including six epithelial (prostate; breast; lung; ovarian; gastric; and bladder cancers) and five non-epithelial (lymphoma; mesothelioma; medulloblastoma; glioma; and acute myeloid leukemia, AML) malignancies.

These data suggest the presence of a conserved BMI1 oncogene-driven pathway, which is similarly activated in both normal stem cells and a highly malignant subset of human cancers diagnosed in a wide range of organs and uniformly exhibiting a marked propensity toward metastatic dissemination as well as a therapy resistance phenotype. Taken together with the results of the present study these data support the hypothesis that activation of the PcG chromatin silencing pathway is one of the key regulatory factors determining a cellular phenotype captured by the expression of a death-from-cancer signature in therapy-resistant clinically lethal malignancies.

Cancer cells with activated PcG pathway would be expected to exhibit a concomitantly high expression of both BMI1 and Ezh2 proteins. Furthermore, cells with activated PcG pathway would manifest the increased expression levels of protein substrates targeted by the activation of corresponding enzymes to catalyze the H2A-K119 ubiquitination (BMI1-containing PRC1 complex) and H3-K27 methylation (Ezh2-containing PRC2 complex). In this study it was experimentally tested that the relevance of this concept for metastatic prostate cancer. A quantitative co-localization immunofluorescence analysis was applied to measure the expression of four distinct protein markers of the PcG pathway activation and demonstrated a concomitantly increased expression of all four markers in a sub-population of human prostate carcinoma metastasis precursor cells isolated from the blood of nude mice bearing orthotopic metastatic human prostate carcinoma xenografts. Presence of dual positive high BMI1/Ezh2-expressing cells appears essential for maintenance of tumorigenic and metastatic potential of human prostate carcinoma cells in vivo, since targeted depletion of dual positive high BMI1/Ezh2-expressing cells from a population of highly metastatic human prostate carcinoma cells treated with stable siRNAs generates a cancer cell population with dramatically diminished malignant potential in vivo.

Histone Markers within PcG Pathway

The BMI1 and Ezh2 proteins are members of the Polycomb group protein (PcG) chromatin silencing complexes conferring genome scale transcriptional repression via covalent modification of histones. The BMI1 PcG protein is a component hPRC1L complex (human Polycomb repressive complex 1-like) which was recently identified as the E3 ubiquitin ligase complex that is specific for histone H2A and plays a key role in Polycomb silencing. Ubiquitination/deubiquitination cycle of histones H2A and H2B is important in regulating chromatin dynamics and transcription mediated, in part, via 'cross-talk' between histone ubiquitination and methylation. Importantly, one of the up-regulated genes in the 11-gene death-from-cancer signature profile (Rnf2) plays a central role in the PRC1 complex formation and function thus complementing the BMI-1 function in the PRC1 complex. Rnf2 expression plays a crucial non-redundant role in development during a transient contact formation between PRC1 and PRC2 complexes via Rnf2 as described for *Drosophila*.

The Ezh2 protein is a member of the Polycomb PRC2 and PRC3 complexes with a histone lysine methyltransferase (HKMT) activity that is associated with transcriptional repression due to chromatin silencing. The HKMT-Ezh2 activity targets lysine residues on histones H1 and H3 (H3-K27 or H1-K26). H3-K27 methylation conferred by an active HKMT-Ezh2-containing complex is one of the key molecular events essential for chromatin silencing in vivo. Collectively, these data imply that in vivo Polycomb chromatin silencing pathway in distinct cell types would require a coordinate activation of multiple distinct PRC complexes. For example, Ezh2 associates with different EED isoforms thereby determining the specificity of histone methyltransferase activity toward histone H3-K27 or histone H1-K26. Collectively, these results suggest that coherent function of the PcG chromatin silencing pathway would require a concomitant coordinated activation of multiple protein components of PRC1, PRC2, and PRC3 complexes implying a coordinate regulation of expression of their essential components such as BMI1 and Ezh2 oncoproteins. It follows that dual positive high BMI1/Ezh2-expressing carcinoma cells with elevated expression of the H2AubiK119 and H3metK27 histones should be regarded as cells with activated PcG protein chromatin silencing pathway.

In human cells the BMI1-containing PcG complex forms a unique discrete nuclear structure that was termed the PcG bodies, the size and number of which in nuclei significantly varied in different cell types. Of note, the nuclei of dual positive high BMI1/Ezh2-expressing cells almost uniformly contain six prominent discrete PcG bodies, perhaps, reflecting the high level of the BMI1 expression and indicating the active state of the PcG protein chromatin silencing pathway. It has been shown recently that in cancer cells expressing high level of the Ezh2 protein the new type of the PcG chromatin silencing complex is formed containing the Sirt1 protein. This suggests that in high Ezh2-expressing carcinoma cells a distinct set of genetic loci could be repressed due to activation of the Ezh2/Sirt1-containing PcG chromatin silencing complex.

One of the notable features of dual positive high BMI1/Ezh2-expressing carcinoma cells is a prominent cytosolic expression of the Ezh2 oncoprotein (FIG. 20). Recent evidence revealed the existence of the cytosolic Ezh2-containing methyltransferase complex regulating actin polymerization and extra-nuclear signaling processes in various cell types. It is possible that both nuclear and extra-nuclear functions of the Ezh2-containing methyltransferase complex may play an important role in determining the malignant behavior of metastatic human prostate carcinoma cells. Recent observations directly demonstrated that the PcG repressive complexes PRC1 and PRC2 co-occupied a large set of genes in human and murine genomes, many of which are transcriptional developmental regulators. This suggests that repression of multiple developmental and differentiation pathways by Polycomb complexes may be required for maintaining stem cell pluripotency and add further support to the idea that repression of critical developmental regulators by PcG proteins may play a crucial role in tumor progression and metastasis.

The results of our experiments indicate that PcG pathway is frequently activated in human prostate tumors and is mechanistically linked to the highly malignant behavior of human prostate carcinoma cells in a xenograft model of prostate cancer metastasis. It remains to be elucidated whether similarly to the xenograft model of human prostate cancer metastasis in nude mice the PcG pathway activation is mechanistically associated with metastatic disease in prostate cancer patients as well. Whether the level of enrichment of primary prostate tumors with dual positive high BMI1/Ezh2-expressing cancer cells would correlate with a degree of PcG pathway activation and would be informative in predicting the clinical behavior of prostate cancer in patients. Follow-up studies are expected to determine whether human prostate tumors manifesting markedly increased levels of dual positive high BMI1/Ezh2-expressing cells represent a therapy resistant clinically lethal type of prostate adenocarcinomas. This technology provides the basis for development of small molecule inhibitors of the PcG protein chromatin silencing pathway as a novel therapeutic modality for treatment of metastatic prostate cancer.

Stemness Pathway

Another pathway implicated in cancer progression is the "stemness" pathway. A cancer stem cell hypothesis proposes that the presence of rare stem cell-resembling tumor cells among the heterogeneous mix of cells comprising a tumor is essential for tumor progression and metastasis of epithelial malignancies. One of the implications of a cancer stem cell hypothesis is that similar genetic regulatory pathways might define critical stem cell-like functions in both normal and tumor stem cells.

Recent experimental and clinical observations identified the BMI1 oncogene-driven pathway(s) as one of the key regulatory mechanisms of "stemness" functions in both normal and cancer stem cells. The Polycomb group (PcG) gene BMI1 influences the proliferative potential of normal and leukemic stem cells and is required for the self-renewal of hematopoietic and neural stem cells. Self-renewal ability is one of the essential defining properties of a pluripotent stem cell phenotype. BMI1 oncogene is expressed in all primary myeloid leukemia and leukemic cell lines analyzed so far and over-expression of BMI1 causes neoplastic transformation of lymphocytes. Recent experimental observations documented an increased BMI1 expression in human non-small-cell lung cancer, human breast carcinomas and breast cancer cell lines, human medulloblastomas, prostate carcinomas, and gastrointestinal cancers, supporting the idea that an oncogenic role of the BMI1 activation may affect progression of the epithelial malignancies and other solid tumors as well.

Recent clinical genomics data provide a powerful evidence supporting a cancer stem cell hypothesis and suggest that gene expression signatures associated with the "stemness" state of a cell (defined as phenotypes of self-renewal, asymmetrical division, and pluripotency) might be informative as molecular predictors of cancer therapy outcome. A mouse/human comparative cross-species translational genomics approach was utilized to identify an 11-gene signature that distinguishes stem cells with normal self-renewal function from stem cells with drastically diminished self-renewal ability due to the loss of the BMI1 oncogene as well as consistently displays a normal stem cell-like expression profile in distant metastatic lesions as revealed by the analysis of metastases and primary tumors in both a transgenic mouse model of prostate cancer and cancer patients.

Kaplan-Meier analysis confirmed that a stem cell-like expression profile of the 11-gene signature in primary tumors is a consistent powerful predictor of a short interval to disease recurrence, distant metastasis, and death after therapy in cancer patients diagnosed with twelve distinct types of cancer.

These data suggest the presence of a conserved BMI1 oncogene-driven pathway, which is similarly activated in both normal stem cells and a clinically lethal therapy-resistant subset of human tumors diagnosed in a wide range of organs and uniformly exhibiting a marked propensity toward metastatic dissemination. Consistent with this idea, the essential role of the BMI1 oncogene activation in prostate cancer metastasis as well as in the maintenance of a self-renewal ability and high malignant potential of human breast cancer stem cells has been demonstrated. Cancer stem cells may indeed constitute metastasis precursor cells since most of the early disseminated carcinoma cells detected in the bone marrow of breast cancer patients manifest a breast cancer stem cell phenotype.

Recent genome-scale chromatin immunoprecipitation (ChIP) experiments and RNA interference analysis identified multiple critical pathways comprising an essential genetic regulatory circuitry of mouse and human embryonic stem cells (ESC). Similarly to the BMI1 knockout studies, in these experiments the self-renewal and proliferation functions of the normal stem cells appeared successfully uncoupled, thus allowing to dissect the critical regulatory pathways essential for maintenance of the self-renewal state of ESC and providing reliable models to study the relevance of the ESC-defined "stemness"/differentiation pathways to human cancer.

These advances were used to identify gene expression signatures of embryonic stem cells (ESC) during transition from self-renewing, pluripotent state to differentiated phenotypes in several experimental models of differentiation of human and mouse ESC. This analysis reveals multiple gene expression signatures of the ESC regulatory circuitry which appear highly informative in stratification of the early-stage breast, lung, and prostate cancer patients into sub-groups with dramatically distinct likelihood of therapy failure.

Genetic Signatures of Regulatory Circuitry of Embryonic Stem Cells (ESC) Identify Therapy-resistant Phenotypes in Cancer Patients Diagnosed with Multiple Types of Epithelial Malignancies.

Recent discovery of death-from-cancer signature genes implies that genetic signatures associated with a "stemness" state (defined as phenotypes of asymmetrical division, pluripotency, and self-renewal) might be informative as molecular predictors of cancer therapy outcome (Glinsky et al., J. Clin. Invest. 115: 1503-1521 (2005)). The validity of this concept was tested while exploring the results of genome-wide microarray and chromatin immunoprecipitation analyses of several experimental models of differentiation of human and mouse ESC (Boyer et al, Cell 122 947-956 (2005; Lee et al., Cell 125: 301-313 (2006); Bernstein et al., Cell 125: 315-326 (2006); Boyer et al., Nature 441: 349-353 (2006).

Applying signature discovery principles to analysis of gene expression profiles during transition of ESC from self-renewing, pluripotent state to differentiated phenotypes, it was identified that seven gene expression signatures associated with a "stemness" epigenetic program of ESC that appear highly informative in stratification of the early-stage breast, prostate, and lung cancer patients into sub-groups with dramatically distinct likelihood of therapy failure. Cancer therapy outcome predictor (CTOP) algorithm employing a panel of "stemness" signatures [signatures of Nanog/Sox2/Oct4-, EED-, and Suz12-patways; transposon exclusion zones (TEZ) and bivalent chromatin domains (BCD) signatures] and a Myc-driven "wound signature" demonstrates nearly 100% specificity and sensitivity of CTOP power in retrospective analysis of large independent cohorts of breast, prostate, lung, and ovarian cancer patients. To date, the retrospective analysis of the prognostic power of individual "stemness" signatures is being extended to more than 3,100 patients diagnosed with 12 distinct types of cancer (Table 3)

TABLE 3

Cancer types and number of cancer patients in clinical cohorts utilized for analysis of therapy outcome correlations with distinct expression profiles of the 11-gene BMI1-pathway signature

| Cancer Type | Number of patients in the outcome sets | References |
| --- | --- | --- |
| Prostate Cancer | 220 | J. Clin. Invest., 113: 913 (2004); Cancer Cell, 1: 203 (2002); PNAS, 101: 614 (2004); PNAS, 101: 811 (2004); JCO, 22: 2790 (2004); J. Clin. Invest., 115: 1503 (2005) |
| Breast Cancer | 1171 | Nature, 415: 530 (2002); NEJM, 347: 1999 (2002); PNAS, 100: 10393 (2003); Cancer Cell, 5: 607 (2004); PNAS, 100: 8418 (2003); Lancet, 361: 1590 (2003); Lancet, 365: 671 (2005); JCI, 115: 44 (2005); Nature, 439: 353 (2006) |
| Lung Cancer | 340 | PNAS, 98: 13790 (2001); Nature Medicine, 8: 816 (2002); Nature, 439: 353 (2006) |
| Gastric Cancer | 89 | PNAS, 99: 15203 (2002) |
| Ovarian Cancer | 216 | Clin. Cancer Res. 10: 3291 (2004); J. Soc. Gynecol. Investig. 11: 51 (2004); Nature, 439: 353 (2006) |
| Bladder Cancer | 31 | Nature Genetics, 33: 90 (2003) |
| Follicular Lymphoma | 191 | NEJM, 351: 2159 (2004) |
| Lymphoma (DLBCL) | 298 | NEJM, 346: 1937 (2002); Nature Medicine, 8: 68 (2002) |
| Mesothelioma | 17 | J. National Cancer Inst., 95: 598 (2003) |
| Medulloblastoma | 60 | Nature, 415: 436 (2002) |
| Glioma | 50 | Cancer Res., 63: 1602 (2003) |
| Lymphoma (MCL) | 92 | Cancer Cell, 3: 185 (2003) |
| AML | 401 | NEJM, 350: 1605 (2004); NEJM, 350: 1617 (2004) |
| Total | 3176 | |

The analysis demonstrates that therapy-resistant and therapy-responsive cancer phenotypes manifest distinct patterns of association with "stemness"/differentiation pathways, suggesting that therapy-resistant and therapy-responsive tumors develop within genetically distinct "stemness"/differentiation programs. These differences can be exploited for development of prognostic and therapy selection genetic tests utilizing microarray-based CTOP algorithm. One of the major regulatory pathways manifesting distinct patterns of association with therapy-resistant and therapy-responsive cancer phenotypes is the Polycomb group (PcG) proteins chromatin silencing pathway. RNAi-mediated targeting of the critical regulatory components of the PcG pathway in metastatic cancer cells eradicates disease in 67-83% of animals in a fluorescent orthotopic model of human prostate cancer metastasis in nude mice. To further validate the clinical relevance of these findings, the quantitative co-localization immunofluorescence analysis of the selected PcG proteins was carried out using TMA of more than 300 prostate tumors obtained from patients with known long-term clinical outcome after therapy. The analysis demonstrates that "stemness" pattern of the PcG pathway activation in prostate tumors is associated with the increased likelihood of therapy failure. Genetic signatures of "stemness" state identify therapy-resistant phenotypes in cancer patients diagnosed with multiple types of epithelial malignancies. These results provide powerful clinical evidence supporting the validity of the concept of cancer stem cells for human solid tumors.

Multiple Gene Expression Signatures of the ESC Regulatory Circuitry Predict Therapy Failure in Prostate Cancer Patients Translational genomics data suggest that gene expression signatures associated with the "stemness" state of a cell might be informative as molecular predictors of cancer therapy outcome. Recent ChIP and RNA interference experiments identified multiple genetic pathways comprising an essential genetic regulatory circuitry of mouse and human embryonic stem cells. Similarly to the BMI1 knockout studies, in these experiments the self-renewal and proliferation functions of the normal stem cells were successfully uncoupled, thus providing reliable model systems dissecting the critical regulatory pathways essential for maintenance of the self-renewal state of ESC. These advances were used to study the relevance to human cancer of the multiple ESC-associated "stemness"/differentiation pathways defined in several experimental models of differentiation of human and mouse ESC.

Six large parent gene sets representing major genetic pathways associated with the essential regulatory circuitry of mouse and human ESC were selected for the initial analysis (Table 4).

TABLE 4

Classification performance of individual Polycomb pathway "stemness" signatures and CTOP "stemness" algorithms in predicting clinical outcome of prostate cancer

| Affymetrix Microarray Platform CTOP "stemness" signatures | Number of Transcripts Parent Gene Sets | Number of Transcripts Prostate Cancer | Detection of failures, % | P value | Chi square | Log-rank test Hazard Ratio | 95% CI of ratio | Parent Gene Sets Data Source |
|---|---|---|---|---|---|---|---|---|
| TEZ | 236 | 32 | 33/37 (89%) | <0.0001 | 54.03 | 16.12 | 6.925 to 28.29 | FIG. 35 |
| EED-pathway | 117 | 36 | 33/37 (89%) | <0.0001 | 52.73 | 15.7 | 6.691 to 27.28 | FIG. 39 |
| Suz12/POLII | 79 | 22 | 33/37 (89%) | <0.0001 | 52.44 | 15.86 | 6.559 to 26.49 | FIG. 40 |
| Suz12 | 142 | 26 | 35/37 (95%) | <0.0001 | 66.58 | 34.87 | 9.343 to 38.38 | FIG. 40 |
| Nanog/Sox2/Oct4 | 164 | 28 | 33/37 (89%) | <0.0001 | 54.37 | 16.04 | 7.052 to 29.01 | FIG. 35 |
| PcG-TF | 176 | 21 | 33/37 (89%) | <0.0001 | 48.49 | 14.96 | 5.787 to 22.89 | FIG. 34 |
| BCD-TF | 73 | 31 | 33/37 (89%) | <0.0001 | 50.53 | 15.4 | 6.180 to 24.73 | FIG. 33 |
| ESC pattern 3 | 158 | 37 | 35/37 (95%) | <0.0001 | 72.9 | 37.19 | 11.30 to 47.95 | |
| BMI1 pathway | 199 | 11 | 28/37 (76%) | <0.0001 | 18.81 | 4.454 | 2.240 to 8.471 | FIG. 32 |
| PcG methylation | 98 | 35 | 33/37 (89%) | <0.0001 | 55.71 | 16.57 | 7.275 to 29.90 | FIG. 34 |
| Histone H3 | 20 | 20 | 29/37 (78%) | <0.0001 | 26.7 | 5.903 | 3.036 to 11.80 | This work |
| Histone H2A | 24 | 24 | 32/37 (86%) | <0.0001 | 41.44 | 11.08 | 4.767 to 18.71 | This work |
| Histones H3/H2A | 44 | 27 | 34/37 (92%) | <0.0001 | 59.97 | 21.97 | 8.103 to 33.46 | This work |
| Six ESC signatures | 914 | 165 | 37/37 (100%) | <0.0001 | 83.12 | Und | Undefined | This work |
| Eight ESC signatures | 1145 | 233 | 37/37 (100%) | <0.0001 | 83.12 | Und | Undefined | This work |
| Nine "stemness" signatures | 1344 | 244 | 37/37 (100%) | <0.0001 | 83.12 | Und | Undefined | This work |
| Ten "stemness" signatures | 1442 | 279 | 37/37 (100%) | <0.0001 | 81.18 | Und | Undefined | This work |
| Eleven "stemness" signatures | 1486 | 306 | 37/37 (100%) | <0.0001 | 81.18 | Und | Undefined | This work |

Legend:

Seventy-nine prostate cancer patients, thirty-seven of which failed therapy within five years after radical prostatectomy and forty-two remain disease-free for at least five years, were stratified into poor prognosis (top 50% scores) and good prognosis (bottom 50% scores) groups based on the values of either individual CTOP scores (determined using weighted algorithm scores of the corresponding "stemness" signatures) or cumulative CTOP scores comprising the sum of the multipleindividual signatures:

Six ESC signatures (TEZ; EED; Suz12/POLII; Suz12; Nanog/Sox2/Oct4; PcG-TF signatures);

Eight ESC signatures (six ESC signatures plus BCD-TF and ESC pattern3 signatures);

Nine "stemness" signatures (eight ESC signatures plus BMI-pathway signature);

Ten "stemness" signatures (nine "stemness" signatures plus PcG methylation signature);

Eleven "stemness" signatures (ten "stemness" signatures plus Histones H3/H2A signature).

Detection of failures (the number and percentage) was calculated as the number of cases that actually failed therapy and were classified by the CTOP algorithm into poor prognosis groups (top 50% scores) with relation to the total number of therapy failure cases in the data set. Microarray data sets and associated clinical information were reported elsewhere (5).

Und, undefined due to the 100% cure rate in the good prognosis group.

These pathways were independently defined by different groups using distinct experimental approaches and protocols. Using multivariate Cox regression analysis, the prognostic power of these gene sets were interrogated and it was found that all six gene sets provide highly informative signatures for stratification of prostate cancer patients into sub-groups with distinct likelihood of therapy failure (FIG. 41 and Table 4). To assess the comparative prognostic performance of the signatures, we evaluated the individual Kaplan-Meier survival curves using the same 50% cut-off level in dividing the patients into poor prognosis (top 50% scores) and good prognosis (bottom 50% scores) sub-groups. It was found that all six signatures perform with similar accuracy in stratification of prostate cancer patients into sub-groups with statistically distinct probability of relapse after radical prostatectomy (FIG. 41). When the prognostic powers of the ESC-derived signatures were combined into six-signature cancer therapy outcome predictor (CTOP) algorithm by adding the values of individual CTOP scores, the resulting prognostic performance appears significantly improved reaching nearly 100% accuracy (FIG. 41 and Table 4).

Gene Expression Signatures of the ESC Regulatory Circuitry Predict Therapy Failure in Multiple Independent Data Sets of Breast Cancer Patients.

At the next step of the analysis it was sought to determine whether this approach would be applicable for evaluation of therapy outcome in breast cancer patients as well. Similarly to the prostate cancer data set, all six gene sets of the ESC regulatory circuitry generate gene expression-based predictors of the likelihood of treatment failure in breast cancer patients (FIG. 42 and Table 5).

TABLE 5

Classification performance of individual Polycomb pathway "stemness" signatures and CTOP "stemness" algorithms in predicting clinical outcome of the early-stage LN negative breast cancer (Affymetrix Microarray Platform)

| Affymetrix Microarray Platform CTOP "stemness" signatures | Number of Transcripts Parent Gene Sets | Number of Transcripts Breast Cancer | Detection of failures, % | P value | Chi square | Log-rank test Hazard Ratio | 95% CI of ratio | Parent Gene Sets Data Source |
|---|---|---|---|---|---|---|---|---|
| TEZ | 236 | 36 | 85/107 (79%) | <0.0001 | 60.1 | 5.191 | 3.131 to 6.778 | FIG. 35 |
| EED-pathway | 117 | 20 | 79/107 (74%) | <0.0001 | 41.46 | 3.704 | 2.413 to 5.217 | FIG. 39 |
| Suz12/POLII | 79 | 20 | 82/107 (77%) | <0.0001 | 51.63 | 4.427 | 2.800 to 6.064 | FIG. 40 |
| Suz12 | 142 | 25 | 81/107 (76%) | <0.0001 | 46.63 | 4.092 | 2.603 to 5.623 | FIG. 40 |
| Nanog/Sox2/Oct4 | 164 | 41 | 87/107 (81%) | <0.0001 | 73.64 | 6.282 | 3.724 to 8.110 | FIG. 35 |
| PcG-TF | 176 | 30 | 81/107 (76%) | <0.0001 | 48.47 | 4.182 | 2.680 to 5.804 | FIG. 38 |
| BCD-TF | 73 | 26 | 82/107 (77%) | <0.0001 | 51.42 | 4.413 | 2.793 to 6.048 | FIG. 35 |
| ESC pattern 3 | 158 | 35 | 87/107 (81%) | <0.0001 | 72.67 | 6.218 | 3.679 to 8.009 | |
| BMI1 pathway | 199 | 11 | 67/107 (63%) | 0.0005 | 12.11 | 1.972 | 1.345 to 2.886 | FIG. 32 |
| PcG methylation | 98 | 22 | 87/107 (81%) | <0.0001 | 73.94 | 6.301 | 3.737 to 8.139 | FIG. 34 |
| Histone H3 | 20 | 13 | 72/107 (67%) | <0.0001 | 22.23 | 2.54 | 1.713 to 3.687 | This work |
| Histone H2A | 24 | 24 | 70/107 (65%) | <0.0001 | 19.53 | 2.378 | 1.618 to 3.482 | This work |
| Histones H3/H2A | 44 | 44 | 76/107 (71%) | <0.0001 | 31.98 | 3.113 | 2.063 to 4.447 | This work |
| Six ESC signatures | 914 | 172 | 94/107 (88%) | <0.0001 | 107.4 | 11.09 | 5.381 to 11.79 | This work |
| Eight ESC signatures | 1145 | 233 | 95/107 (89%) | <0.0001 | 112.3 | 12.17 | 5.651 to 12.40 | This work |
| Nine "stemness" signatures | 1344 | 244 | 97/107 (91%) | <0.0001 | 124.3 | 15.25 | 6.351 to 13.98 | This work |
| Ten "stemness" signatures | 1442 | 266 | 98/107 (92%) | <0.0001 | 127.7 | 17.01 | 6.538 to 14.37 | This work |
| Eleven "stemness" signatures | 1486 | 310 | 99/107 (93%) | <0.0001 | 132.1 | 19.31 | 6.793 to 14.93 | This work |

Legend:

Two-hundred-eighty-six early-stage LN-negative breast cancer patients, one-hundred-seven of which failed therapy within five years after surgery and one-hundred-seventy-nine remain disease-free for at least five years, were stratified into poor prognosis (top 50% scores) and good prognosis (bottom 50% scores) groups based on the values of either individual CTOP scores (determined using weighted algorithm scores of the corresponding "stemness" signatures) or cumulative CTOP scorescomprising the sum of the multiple individual signatures:

Six ESC signatures (TEZ; EED; Suz12/POLII; Suz12; Nanog/Sox2/Oct4; PcG-TF signatures);

Eight ESC signatures (six ESC signatures plus BCD-TF and ESC pattern3 signatures);

Nine "stemness" signatures (eight ESC signatures plus BMI-pathway signature);

Ten "stemness" signatures (nine "stemness" signatures plus PcG methylation signature);

Eleven "stemness" signatures (ten "stemness" signatures plus Histones H3/H2A signature).

Detection of failures (the number and percentage) was calculated as the number of cases that actually failed therapy and were classified by the CTOP algorithm into poor prognosis groups (top 50% scores) with relation to the total number of therapy failure cases in the data set.

Microarray data sets and associated clinical information were reported elsewhere.

The individual predictors perform with similar prognostic classification accuracy and six-signature CTOP algorithm demonstrates significantly improved patients' stratification performance compared to the individual signatures (FIG. 42 and Table 5). To validate the findings, the analysis is extended by using four additional breast cancer therapy outcome data sets which were previously developed and analyzed in three independent institutions. As shown in FIG. 42, this analysis confirmed that ESC-based CTOP algorithm is informative in multiple independent breast cancer therapy outcome data sets comprising altogether more than 900 breast cancer patients (FIG. 42 and Tables 5-7).

TABLE 6

Classification performance of individual Polycomb pathway "stemness" signatures and CTOP "stemness" algorithms in predicting clinical outcome of the early-stage LN negative breast cancer (Agilent Microarray Platform; clinical end-point: metastasis-free survival)

| Agilent Microarray Platform "Stemness" CTOP signatures | Number of Transcripts Breast Cancer | Detection of failures, % | Log-rank test P values | Chi square | Hazard Ratio | 95% CI of ratio |
|---|---|---|---|---|---|---|
| TEZ signature | 17 | 37/46 (80%) | <0.0001 | 37 | 6.797 | 3.580 to 12.04 |
| EED-pathway | 22 | 36/46 (78%) | <0.0001 | 33.98 | 6.045 | 3.313 to 11.15 |
| Suz12/POLII | 21 | 39/46 (85%) | <0.0001 | 47.16 | 9.493 | 4.631 to 15.76 |
| Suz12 | 27 | 37/46 (80%) | <0.0001 | 36.59 | 6.724 | 3.545 to 11.93 |
| Nanog/Sox2/Oct4 | 38 | 39/46 (85%) | <0.0001 | 52.78 | 10.36 | 5.378 to 18.64 |
| PcG-TF signature | 28 | 33/46 (72%) | <0.0001 | 16.55 | 3.445 | 1.888 to 6.161 |
| BCD-TF | 26 | 39/46 (85%) | <0.0001 | 52.6 | 10.37 | 5.338 to 18.45 |
| BMI1 pathway | 11 | 31/36 (67%) | 0.0003 | 13.23 | 2.946 | 1.660 to 5.428 |
| PcG methylation | 29 | 43/46 (93%) | <0.0001 | 73.54 | 26.55 | 8.258 to 28.85 |
| Histone H3 | 14 | 31/46 (67%) | 0.0002 | 14.15 | 3.041 | 1.728 to 5.681 |
| Histone H2A | 15 | 33/46 (72%) | <0.0001 | 15.72 | 3.357 | 1.827 to 5.935 |
| Histones H3/H2A | 29 | 36/46 (78%) | <0.0001 | 29.23 | 5.451 | 2.865 to 9.484 |
| Six ESC signatures | 153 | 43/46 (93%) | <0.0001 | 75.11 | 27.11 | 8.547 to 29.95 |
| Ten "stemness" signatures | 248 | 44/46 (96%) | <0.0001 | 88.05 | 44.81 | 11.18 to 40.00 |

Legend:

Ninety-seven early-stage LN-negative breast cancer patients, forty-six of which failed therapy within five years after surgery and fifty-one remain disease-free for at least five years, were stratified into poor prognosis (top 50% scores) and good prognosis (bottom 50% scores) groups based on the values of either individual CTOP scores (determined using weighted algorithm scores of the corresponding "stemness" signatures) or cumulative CTOP scores comprising the sum of themultiple individual signatures:

Six ESC signatures (TEZ; EED; Suz12/POLII; Suz12; Nanog/Sox2/Oct4; PcG-TF signatures);

Ten "stemness" signatures (six ESC signatures plus BCD-TF, BMI1-pathway, PcG methylation, and Histones H3/H2A signatures).

Detection of failures (the number and percentage) was calculated as the number of cases that actually failed therapy and were classified by the CTOP algorithm into poor prognosis groups (top 50% scores) with relation to the total number of therapy failure cases in the data set.

Microarray data sets and associated clinical information were reported elsewhere.

TABLE 7

Classification performance of individual Polycomb pathway "stemness" signatures and CTOP "stemness" algorithms in predicting clinical outcome of breast cancer (Agilent Microarray Platform; clinical end-point: death after therapy)

| Agilent Microarray Platform "Stemness" CTOP signatures | Number of Transcripts Breast Cancer | Detection of failures, % | Log-rank test P values | Chi square | Hazard Ratio | 95% CI of ratio |
|---|---|---|---|---|---|---|
| TEZ signature | 17 | 63/79 (80%) | <0.0001 | 42.45 | 5.116 | 2.819 to 6.876 |
| EED-pathway | 22 | 66/79 (84%) | <0.0001 | 50.08 | 6.419 | 3.202 to 7.810 |
| Suz12/POLII | 21 | 62/79 (78%) | <0.0001 | 34.11 | 4.321 | 2.404 to 5.829 |
| Suz12 | 27 | 63/79 (80%) | <0.0001 | 41.40 | 5.021 | 2.768 to 6.753 |
| Nanog/Sox2/Oct4 | 38 | 66/79 (84%) | <0.0001 | 57.62 | 7.071 | 3.654 to 9.007 |
| PcG-TF signature | 28 | 62/79 (78%) | <0.0001 | 38.07 | 4.621 | 2.603 to 6.343 |
| BCD-TF | 26 | 57/79 (72%) | <0.0001 | 23.00 | 3.122 | 1.901 to 4.620 |
| BMI1 pathway | 11 | 60/79 (76%) | <0.0001 | 30.95 | 3.877 | 2.264 to 5.505 |
| PcG methylation | 29 | 65/79 (82%) | <0.0001 | 42.31 | 5.483 | 2.793 to 6.775 |
| Histone H3 | 14 | 51/79 (65%) | 0.0008 | 11.18 | 2.148 | 1.369 to 3.328 |
| Histone H2A | 15 | 60/79 (76%) | <0.0001 | 32.50 | 3.984 | 2.341 to 5.709 |
| Histones H3/H2A | 9 | 61/79 (77%) | <0.0001 | 36.30 | 4.348 | 2.529 to 6.186 |
| Six ESC signatures | 153 | 72/79 (91%) | <0.0001 | 80.42 | 14.33 | 5.010 to 12.34 |
| Nine "stemness' signatures | 219 | 72/79 (91%) | <0.0001 | 80.05 | 14.26 | 4.987 to 12.29 |

TABLE 7-continued

Classification performance of individual Polycomb pathway "stemness" signatures and CTOP "stemness" algorithms in predicting clinical outcome of breast cancer (Agilent Microarray Platform; clinical end-point: death after therapy)

| Agilent Microarray Platform "Stemness" CTOP signatures | Number of Transcripts Breast Cancer | Detection of failures, % | Log-rank test P values | Chi square | Hazard Ratio | 95% CI of ratio |
|---|---|---|---|---|---|---|
| Ten "stemness" signatures | 238 | 73/79 (92%) | <0.0001 | 85.38 | 17.07 | 5.347 to 13.19 |

Legend:
Two-hundred-ninety-five breast cancer patients, seventy-nine of which died within five years after therapy and two-hundred-sixteen remain alive for at least five years, were stratified into poor prognosis (top 50% scores) and good prognosis (bottom 50% scores) groups based on the values of either individual CTOP scores (determined using weighted algorithm scores of the corresponding "stemness" signatures) or cumulative CTOP scores comprising the sum of the multiple individual signatures:
Six ESC signatures (TEZ; EED; Suz12/POLII; Suz12; Nanog/Sox2/Oct4; PcG-TF signatures);
Nine "stemness" signatures (six ESC signatures plus BCD-TF, BMI1-pathway, and PcG methylation signatures).
Ten "stemness" signatures (six ESC signatures plus BCD-TF, BMI1-pathway, PcG methylation, and Histones H3/H2A signatures).
Detection of failures (the number and percentage) was calculated as the number of cases that actually failed therapy and were classified by the CTOP algorithm into poor prognosis groups (top 50% scores) with relation to the total number of therapy failure cases in the data set.
Microarray data sets and associated clinical information were reported elsewhere.

Transcription Factors as Markers within Oncogenic Pathways

The present invention can also be used to analyze the level of transcription factors as either an indicator of the presence of cancer or as a predictor of cancer therapy outcome. Details of transcription factor analysis are below.

Distinct Gene Expression Profiles of the Bivalent Chromatin Domain Transcription Factor Genes (BCD-TF) are Associated with Therapy-resistant and Therapy-sensitive Phenotypes of Human Prostate and Breast Cancers.

In genomes of somatic cells nucleosomal compositions of histones harboring specific modifications of the histone tails defines mutually exclusive transcriptionally active or silent states of the chromatin. Transcriptional status of corresponding genetic loci in genomes of most cells is governed by the nucleosome-defined chromatin patterns and strictly follows activation/repression rules. In contrast to somatic cells, in ESC multiple chromosomal regions were identified simultaneously harboring both "silent" (H3K27met3) and "active" (H3K4) histone marks and ~100 transcription factor (TF) encoding genes are residing within these bivalent chromatin domain-containing chromosomal regions. Many of the bivalent chromatin domain (BCD)—containing genes were previously identified as the Polycomb Group (PcG) protein-target genes in both human and mouse ESC and are repressed or transcribed at low levels in ESC.

These observations form the basis for a hypothesis that transcriptional repression of BCD genes is essential for maintenance of the "stemness" state of ESC and the unique BCD status of these genes make them poised for rapid transcriptional activation during transition from pluripotent self-renewing state of ESC to differentiated phenotypes.

Consistent with this idea, in differentiated cells the BCD pattern of these genes is resolved in either transcriptionally active or repressed chromatin domains and activated or repressed transcription of corresponding genes. It is noted that many BCD genes were also identified earlier as members of the core transcriptional regulatory circuitry of ESC manifesting the co-occupancy of their promoters by major "stemness" transcription factors. Furthermore, careful review of the available gene expression data sets of ESC in pluripotent self-renewing state reveals that several BCD-TF genes of this category are maintained in a transcriptionally active state.

This analysis suggests that expression of selected TF encoding genes in ESC, including bivalent chromatin domain-containing TF genes (BCD-TF), maintenance of a "stemness" state, and transition to differentiated phenotypes may be regulated by the balance of the "stemness" TFs such as Nanog, Sox2, Oct4, and PcG proteins bound to the promoters of target genes. If this is true, the "stemness" state of ESC should be associated with the unique profile of the BCD-TF expression comprising both up- and down-regulated transcripts that may be defined as the "stemness" BCD-TF signature (FIG. 43). It would be of interest to determine whether human tumors manifest a common pattern of the BCD-TF expression resembling a "stemness" profile of the BCD-TF signature.

Gene expression profiles of BCD-TF in clinical samples were independently generated for therapy-resistant breast and prostate tumors using multivariate Cox regression analysis of microarrays of tumor samples from 286 breast cancer and 79 prostate cancer patients with known log-term clinical outcome after therapy and tested for concordant pattern. This analysis identified the thirteen-gene BCD-TF signature manifesting highly concordant gene expression profiles (r=0.853; P<0.001; FIG. 43) in breast and prostate tumors from patients with therapy-resistant disease phenotypes. Next, "stemness" gene expression profiles of BCD-TF in mouse ESC were derived by comparing microarray analyses of pluripotent self-renewing ESC (control ESC cultures treated with HP siRNA) versus ESC treated with Esrrb siRNA (day 6). At this time point, Esrrb siRNA-treated ESC does not manifest "stemness" phenotype and form colonies of differentiated cells. Mouse genes comprising the "stemness" BCD-TF signature were translated into set of human orthologs and BCD-TF gene expression profiles of therapy-resistant clinical samples and ESC were tested for concordant pattern. This analysis identifies the eight-gene BCD-TF signature manifesting highly concordant expression profiles (r=0.716; p<0.001; FIG. 43) in ESC and therapy-resistant breast and prostate tumors. Kaplan-Meier analysis demonstrates that prostate and breast cancer patients with tumors harboring ESC-like expression profiles of the eight-gene BCD-TF signature are more likely to fail therapy (bottom two panels), suggesting that a sub-set of BCD-TF genes defined here as the eight gene BCD-TF signature manifests "stemness" expression profiles in therapy-resistant prostate and breast tumors (FIG. 43).

Therapy-resistant and Therapy-sensitive Tumors Manifest Distinct Gene Expression Profiles of the ESC "Stemness"/differentiation Program.

The analysis suggests that therapy-resistant and therapy-sensitive tumors manifest distinct pattern of association with "stemness"/differentiation pathways engaged in ESC during transition from pluripotent self-renewing state to differentiated phenotypes. One of the major implications of this hypothesis is the prediction that therapy-resistant and therapy-sensitive tumors develop within genetically distinct "stemness"/differentiation programs. This prediction was tested by interrogating the prognostic power of genes comprising the ESC pattern 3 "stemness"/differentiation program recently identified by a combination of the RNA interference and gene expression analyses. It was found that similarly to the BCD-TF signatures the gene set comprising the ESC pattern 3 "stemness"/differentiation pathway generates gene expression signatures discriminating therapy-resistant and therapy-sensitive prostate and breast tumors (FIG. 44). These results support the hypothesis that therapy-resistant and therapy-sensitive cancers may develop within genetically distinct "stemness"/differentiation programs triggered by the altered balance of "stemness" TF and immediate downstream changes in expression of the BCD-TF genes.

DNA Promoter Methylation Patterns as Markers within Oncogenic Pathways

The present invention can also be used to analyze the DNA promoter methylation patterns of genes within oncogenic pathways as either an indicator of the presence of cancer or as a predictor of cancer therapy outcome. Details of the analysis of DNA promoter methylation patterns of genes within oncogenic pathways are below.

Is Therapy-resistant Phenotype of Human Epithelial Malignancies Associated with Distinct Methylation Patterns of the Polycomb Target Genes?

Recent experimental observations indicate that promoters of genes identified as the PcG targets in ESC are preferentially targeted for cancer-associated DNA hypermethylation and stable transcriptional repression in multiple types of human cancers. DNA promoter methylation patterns of the PcG target genes appear significantly distinct in different types of tumors, suggesting the presence of cancer type-specific profiles of DNA promoter hypermethylation, transcriptional repression, and mRNA expression of the PcG target genes. To determine whether gene expression profiles of the PcG target genes promoters of which are hypermethylated in human cancers would be associated with distinct likelihood of therapy failure in prostate and breast cancer patients was analyzed. The analysis utilized a set of 88 PcG target genes previously reported to be hypermethylated in cancer (FIG. 32). Multivariate Cox regression analysis demonstrates that PcG target genes with promoters frequently hypermethylated in cancer manifest distinct expression profiles associated with therapy-resistant and therapy-sensitive prostate and breast cancers (FIG. 45), implying that differences in gene expression between tumors with distinct outcome after therapy may be driven, in part, by the distinct promoter hypermethylation patterns of the PcG target genes. These differences can be exploited to generate highly informative gene expression signatures of the PcG target genes hypermethylated in cancer for stratification of prostate and breast cancer patients into sub-groups with statistically distinct likelihood of therapy failure (FIG. 45). This analysis suggests that therapy-resistant and therapy-sensitive tumors are likely to manifest different profiles of the promoter hypermethylation of PcG target genes and these differences can be utilized for development of DNA-based diagnostic, prognostic, and individualized therapy selection tests.

Post-translational modifications of the histones H3 and H2A, in particular, trimethylation of the lysine 27 residue (H3met3K27) by the Ezh2-containing PRC2 complex and ubiquitination of the histone H2A by the BMI 1-containing PRC 1 complex, are consistently linked to the transcriptional silencing mediated by the PcG proteins and a cross-talk between Polycomb targeting and DNA promoter hypermethylation. It was therefore tested whether therapy-resistant and therapy-sensitive tumors would manifest distinct expression profiles of the histones H3 and H2A variants. Multivariate Cox regression analysis demonstrates that activation and inhibition of expression of distinct variants of the H3 and H2A histones are associated with tumors manifesting different outcome after therapy. Strikingly, gene expression signatures capturing expression profiles of the limited number of variants of a single protein (either histone H3 or histone H2A) appear informative in distinguishing prostate and breast cancer patients with statistically distinct probabilities of therapy failure (FIG. 45). Interestingly, cumulative CTOP scores comprising a sum of the individual CTOP scores of the H3, H2A, and PcG methylation signatures demonstrate improved patients' stratification performance compared to individual signatures (FIG. 45).

"Stemness" CTOP Algorithm Identifies Therapy-Resistant Phenotypes and Predicts the Likelihood of Treatment Failure in Prostate, Breast, Ovarian, and Lung Cancer Patients.

The analysis indicates that genetic components of the PcG chromatin silencing complexes as well as genes identified as either direct or immediate down-stream targets of the Polycomb pathway in ESC manifest distinct patterns of association with therapy-resistant and therapy-sensitive phenotypes of human prostate and breast cancers. To investigate the status of the Polycomb pathway in human tumors with distinct clinical outcome after therapy, we divided PcG pathway-associated genes into several functionally and/or structurally linked groups (Tables 4-8) and interrogated each gene set for gene expression pattern association with therapy-resistant phenotypes using multivariate Cox regression analysis.

TABLE 8

Classification performance of the CTOP algorithm comprising six Polycomb pathway ESC "stemness" signatures in predicting clinical outcome of breast cancer in multiple independent cohorts of patients

| Affimetrix and Agilent Microarray Platform Data Sets | Breast cancer Number of patients | Detection of failures, % | Log-rank test P values | Chi square | Hazard Ratio | 95% CI of ratio |
| --- | --- | --- | --- | --- | --- | --- |
| Netherlands-286 | 286 (107) | 94/107 (88%) | <0.0001 | 107.4 | 11.09 | 5.381 to 11.79 |
| MSKCC-95 | 95 (33) | 31/33 (94%) | <0.0001 | 48.22 | 25.64 | 6.450 to 27.94 |
| DUKE-169 | 169 (52) | 47/52 (90%) | <0.0001 | 55.42 | 14.01 | 4.775 to 14.60 |

TABLE 8-continued

Classification performance of the CTOP algorithm comprising six Polycomb pathway ESC "stemness" signatures in predicting clinical outcome of breast cancer in multiple independent cohorts of patients

| Affimetrix and Agilent Microarray Platform Data Sets | Breast cancer Number of patients | Detection of failures, % | Log-rank test P values | Chi square | Hazard Ratio | 95% CI of ratio |
|---|---|---|---|---|---|---|
| Netherlands-97 | 97 (46) | 43/46 (93%) | <0.0001 | 75.11 | 27.11 | 8.547 to 29.95 |
| Netherlands-295 | 295 (79) | 65/79 (82%) | <0.0001 | 51.20 | 6.242 | 3.279 to 8.034 |
| Netherlands-295 | 295 (79) | 72/79 (91%) | <0.0001 | 80.42 | 14.33 | 5.010 to 12.34 |

Legend:
The Affimetrix-based CTOP algorithms were developed using the Netherlaqnds-286 data set and tested using the MSKCC-95 and Duke-169 data sets.
The Agilent-based CTOP algorithms were developed using the Netherlads-97 data set and tested using the Netherlands-295 data set.
The CTOP algorithms based on the cancer-specific death after therapy were developed using the Netherlands-295 data set (last row).
In the Duke-169, MSKCC-95, and Netherlands-295 data sets the end-points are the overall survival and cancer-specific death.
In the Netherlands-286 data set the end-points are the relapse-free survival.
In the Netherlands-97 data set the end-points are metastasis-free survival.

This approach generates multiple gene expression signatures that are highly informative in stratification of cancer patients into sub-groups with statistically distinct likelihood of therapy failure (FIGS. 41-45). However, all of the signatures appear informative as therapy outcome predictors only for a fraction of patients and none of the signatures seems sufficiently accurate and robust to serve as a prototype for diagnostic, prognostic, or therapy-selection applications. Therefore, whether CTOP algorithm combining the prognostic power of individual gene expression signatures would be more informative as a molecular predictor cancer treatment outcome (FIGS. 44 and 45). For each patient a cumulative CTOP score was calculated comprising a sum of nine individual CTOP scores derived from analysis of nine gene expression signatures (Tables 4-7). Next, the patients were ranked within data set in descending order based on the values of the cumulative CTOP scores, divided each data set into five sub-groups at 20% increment of the cumulative CTOP score values, and carried out the Kaplan-Meier survival analysis (FIG. 46). This approach generates highly informative CTOP algorithm stratifying cancer patients into five sub-groups with statistically distinct probabilities of therapy failure (FIG. 46). One of the striking features revealed by our analysis is the apparent applicability of this approach for development of gene expression-based CTOP algorithms for lung and ovarian cancer patients as well (FIG. 46).

TABLE 9

Classification performance of the CTOP algorithm comprising nine "stemness" signatures in predicting clinical outcome in prostate, breast, lung, and ovarian cancer patients

| Affimetrix and Agilent Microarray Platform Data Sets | Breast cancer Number of patients | Detection of failures, % | Log-rank test P values | Chi square | Hazard Ratio | 95% CI of ratio |
|---|---|---|---|---|---|---|
| Breast Cancer | 286 (107) | 97/107 (91%) | <0.0001 | 124.3 | 15.25 | 6.351 to 13.98 |
| Prostate Cancer | 79 (37) | 37/37 (100%) | <0.0001 | 83.12 | Und | Und |
| Lung Cancer | 91 (45) | 41/45 (91%) | <0.0001 | 84.64 | 22.92 | 11.69 to 44.23 |
| Ovarian Cancer | 133 (72) | 56/72 (78%) | <0.0001 | 78.47 | 7.592 | 6.272 to 17.81 |

Legend:
The Affimetrix-based CTOP algorithms were developed separately for breast cancer and prostate cancer data sets.
CTOP algorithm identified using breast cancer data set was applied to the lung cancer data set and ovarian cancer data set.
In the ovarian cancer and lung cancer data sets the end-points are the overall survival and cancer-specific death.
In the breast cancer data set the end-points are the disease-free survival.
In the prostate cancer data set the end point is the relapse-free survival.
In all data sets poor prognosis groups include patients with top 50% values of the cumulative CTOP scores in a given data set.
Und, undefined due to the 100% cure rate in the good prognosis group. See text for details.

TABLE 10

Classification performance of the CTOP algorithm comprising nine "stemness" signatures in predicting clinical outcome in prostate, breast, lung, and ovarian cancer patients

| Affimetrix and Agilent Microarray Platform Data Sets | Breast cancer Number of patients | Detection of failures, % | Log-rank test P values | Chi square | Hazard Ratio | 95% CI of ratio |
|---|---|---|---|---|---|---|
| Breast Cancer | 286 (107) | 104/107 (97%) | <0.0001 | 96.59 | 34.31 | 4.663 to 10.04 |
| Prostate Cancer | 79 (37) | 37/37 (100%) | <0.0001 | 43.72 | Und | Und |
| Lung Cancer | 91 (45) | 44/45 (98%) | <0.0001 | 65.05 | 62.87 | 6.910 to 23.90 |
| Ovarian Cancer | 133 (72) | 71/72 (99%) | <0.0001 | 28.19 | 29.19 | 2.436 to 6.904 |

Legend:
The Affimetrix-based CTOP algorithms were developed separately for breast cancer and prostate cancer data sets.
CTOP algorithm identified using breast cancer data set was applied to the lung cancer data set and ovarian cancer data set.
In the ovarian cancer and lung cancer data sets the end-points are the overall survival and cancer-specific death.
In the breast cancer data set the end-points are the disease-free survival.
In the prostate cancer data set the end point is the relapse-free survival.
In all data sets, except ovarian cancer, poor prognosis groups include patients with top 60% values of the cumulative CTOP scores in a given data set.
In ovarian cancer data set the poor prognosis group includes patients with top 80% cumulative CTOP score values.
Und, undefined due to the 100% cure rate in the good prognosis group. See FIG. 6 and text for details.

TABLE 11

Classification performance of the CTOP algorithm comprising nine "stemness" signatures in predicting clinical outcome in prostate, breast, lung, and ovarian cancer patients

| Affimetrix and Agilent Microarray Platform Data Sets | Breast cancer Number of patients | Detection of failures, % | Log-rank test P values | Chi square | Hazard Ratio | 95% CI of ratio |
|---|---|---|---|---|---|---|
| Breast Cancer | 286 (107) | 104/107 (97%) | <0.0001 | 96.59 | 34.31 | 4.663 to 10.04 |
| Prostate Cancer | 79 (37) | 37/37 (100%) | <0.0001 | 43.72 | Und | Und |
| Lung Cancer | 91 (45) | 44/45 (98%) | <0.0001 | 65.05 | 62.87 | 6.910 to 23.90 |
| Ovarian Cancer | 133 (72) | 62/72 (86%) | <0.0001 | 57.15 | 7.890 | 4.040 to 10.74 |

Legend:
The Affimetrix-based CTOP algorithms were developed separately for breast cancer and prostate cancer data sets.
CTOP algorithm identified using breast cancer data set was applied to the lung cancer data set and ovarian cancer data set.
In the ovarian cancer and lung cancer data sets the end-points are the overall survival and cancer-specific death.
In the breast cancer data set the end-points are the disease-free survival.
In the prostate cancer data set the end point is the relapse-free survival.
In all data sets poor prognosis groups include patients with top 60% values of the cumulative CTOP scores in a given data set.
Und, undefined due to the 100% cure rate in the good prognosis group. See text for details.

Validation of the PcG Proteins Chromatin Silencing Pathway Involvement in Development of Therapy-resistant Prostate Cancer.

The association of the PcG protein chromatin silencing pathway activation with therapy-resistant cancer using alternative analytical approaches were investigated. Consistent with this idea, a quantitative immunofluorescent co-localization analysis demonstrates that a cancer stem cell-like CD44+/CD34− population isolated by sterile FACS sorting from the blood-borne PC3-32 human prostate carcinoma metastasis precursor cells is markedly enriched for dual-positive BMI1/Ezh2 high expressing cancer cells compared to the CD44+/CD24− population isolated from the maintained in culture parental PC3 cell line (FIG. 47). Furthermore, a multi-color FISH analysis reveals that blood-borne human prostate carcinoma metastasis precursor cell population contains a large proportion of cancer cells with the high level co-amplification of both BMI1 and Ezh2 genes (FIG. 47 and Table 12), suggesting that increased co-expression in these cells of the BMI1 and Ezh2 oncoproteins is driven by the co-amplification of two oncogenes, BMI1 and Ezh2.

tive tumors develop within genetically distinct "stemness"/differentiation programs driven by engagement of the PcG proteins chromatin silencing pathway. The signatures of the PcG pathway appear highly informative in stratification of the early-stage breast, lung, and prostate cancer patients into sub-groups with dramatically distinct likelihood of therapy failure. The findings and conclusions were validated by applying alternatives analytical techniques and methodologies of the PcG pathway analysis in cell culture experiments, animal models of cancer metastasis, and clinical tumor samples, including a variety of protein expression assays using combinations of immunofluorescence, FACS, and tissue microarray techniques. Taking together, the analysis indicates that epigenetic landscape of therapy-resistant human cancers is defined to a significant extent by the activation of the PcG protein chromatin silencing pathway and heritable imprinting of a stem cell-like epigenetic program via cross-talk between PcG pathway and DNA promoter hypermethylation.

Clinical genomics data suggest that gene expression signatures associated with the "stemness" state of a cell might be

TABLE 12

FISH analysis of DNA copy numbers of the Polycomb Group BMI1 and Ezh2 genes in human prostate carcinoma cell lines (parental PC-3 cells and blood-borne PC-3-32 metastasis precursor cells) and diploid hTERT-immortalized human fibroblasts.

| | N | | BMI1-Cy3 | Ezh2-Cy5 | Dual-positive, N (%) | N | BMI1-Cy5 | Ezh2-Cy3 | Dual-positive, N (%) |
|---|---|---|---|---|---|---|---|---|---|
| BJ-1 | 52 | Average | 2.333333 | 2 | 0 | 45 | 2.386364 | 2.533333 | 0 |
| | | STDEV | 0.905388 | 0.709768 | | | 1.125103 | 1.013545 | |
| PC-3 | 74 | Average | 2.125 | 4.125 | 1 (1.4%) | 59 | 2.192308 | 4.482143 | 2 (3%) |
| | | STDEV | 1.090475 | 1.470492 | | | 1.00738 | 2.071031 | |
| | | T-test* | 0.941271 | 5.13E−13 | | | 0.393451 | 1.38E−08 | |
| PC-3-32 | 99 | Average | 3.597561 | 5.185185 | 33 (33%) | 102 | 3.540816 | 5.490196 | 34 (33%) |
| | | STDEV | 1.638481 | 1.743298 | | | 1.486492 | 1.733451 | |
| | | T-test** | 8.43E−09 | 7.24E−31 | | | 1.49E−06 | 2.55E−25 | |
| | | T-test*** | 7.49E−09 | 3.19E−08 | | | 6.38E−10 | 0.002259 | |

Dual-positive, N (%), nuclei with 5 or more copies of the Ezh2 gene and 4 or more copies of the BMI1 gene
T-test*, BJ-1 vs PC-3
T-test**, BJ-1 vs PC-3-32
T-test***, PC-3 vs PC-3-32

Finally, a multi-color quantitative immunofluorescent co-localization TMA analysis of 71 prostate carcinomas indicates that patients with tumors having increased levels (>1%) of dual-positive BMI1/Ezh2 high expressing cells manifest clinically aggressive disease phenotypes and significantly more likely to relapse and develop disease recurrence after radical prostatectomy (FIG. 47). Taken together with the previously reported experimental evidence of the essential role of PcG pathway activation in metastatic prostate cancer, these data strongly support the hypothesis of the causal association of the Polycomb pathway activation and manifestation of the clinically lethal therapy-resistant prostate cancer phenotypes.

The analysis generated a "stemness" cancer therapy outcome predictor (CTOP) algorithm comprising a combination of nine signatures [signatures of BMI1-, Nanog/Sox2/Oct4-, EED-, and Suz12-patways; transposon exclusion zones (TEZ) and ESC pattern 3 signatures; signatures of polycomb-bound transcription factors (PcG-TF) and bivalent chromatin domain transcription factors (BCD-TF)]. A "stemness" CTOP algorithm demonstrates nearly 100% prognostic accuracy for a majority of patients in retrospective analysis of large cohorts of breast, prostate, lung, and ovarian cancer patients, suggesting that therapy-resistant and therapy-sensiinformative as molecular predictors of cancer therapy outcome. This hypothesis was tested by applying the signature discovery principles to genomic analysis of human and mouse ESC during transition from self-renewing, pluripotent state to differentiated phenotypes in several experimental models of ESC differentiation. Collectively, the data suggest that therapy-resistant and therapy-sensitive tumors develop within genetically distinct "stemness"/differentiation programs. To date, the retrospective analysis of the prognostic power of individual "stemness" signatures is being extended to more than 3,100 patients diagnosed with 13 distinct types of cancer supporting the conclusion that therapy-resistant and therapy-responsive cancer phenotypes manifest distinct patterns of association with "stemness"/differentiation pathways.

Taken together, the analysis further supports the existence of transcriptionally discernable type of human cancer detectable in a sub-group of early-stage cancer patients diagnosed with distinct epithelial malignancies appearing in multiple organs. These early-stage carcinomas of seemingly various origins appear to exhibit a poor therapy outcome gene expression profile, which is uniformly associated with increased propensity to develop metastasis, high likelihood of treatment failure, and increased probability of death from cancer after therapy. Cancer patients who fit this transcriptional profile might represent a genetically, biologically, and clinically distinct type of cancer exhibiting highly malignant clinical behavior and therapy resistance phenotype even at the early stage of tumor progression. It has been suggested that one of the characteristic features of this early-stage, therapy-resistant metastatic cancer is the transcriptional (and, perhaps, biological) resemblance to the normal stem cells. A stem cell cancer hypothesis has been proposed to explain a possible mechanistic contribution of the normal stem cells to the pathogenesis of this type of human cancer. According to this hypothesis, a genetically defined sub-set of transformed cells (perhaps, arising with higher probability in a genetically defined human sub-population) form tumors with high tropism toward normal stem cells (NSCs) mediated by molecules collectively defined as "presence of wound" and/or "hypoxia" signals. Enrichment of primary tumors with NSCs increases likelihood of horizontal genomic transfer (large-scale transfer of DNA and chromatin) between NSCs and tumor cells via cell fusion and/or uptake of apoptotic bodies. Reprogrammed somatic hybrids of tumor cells and NSCs acquire transformed phenotype and epigenetic self-renewal program. Postulated progeny of hybrid cells contains a sub-population of self-renewing cancer stem cells with epigenetic and transcriptional markers of NSCs and high propensity toward metastatic dissemination. Recent experimental observations demonstrate direct involvement of the bone marrow-derived cells in development of breast and colon cancers in transgenic mouse cancer models suggesting that cancer stem cells can originate from the bone marrow-derived cells.

The analysis highlights the significant challenges associated with a prospect of practical implementation of the concept of personalized medicine in clinical oncology settings. Many of these challenges are based on a fundamental reality of a biological context defined by the multigenic nature of human cancers and its implications for diagnostic, prognostic (inter-patients and intra-tumor heterogeneities; requirements for multi-signatures diagnostic, prognostic, and therapy selection algorithms), and therapeutic applications (the eventual necessity for highly individualized combinations of cancer therapeutics for simultaneous targeting of relevant oncogenic and stemness pathways to alleviate the probability of selection of therapy-resistant phenotypes). One of such non-anticipated near-term health care management and regulatory implications for successful clinical implementation of the concept of personalized cancer therapies revealed by the analysis is the unrestricted physicians' ability to prescribe and exercise in a routine clinical setting an off-label use of the FDA approved drugs.

One of the important end-points of our work is development of a concise catalog of gene expression changes comprising ~300 human genes divided into nine signatures and reflecting a transcriptional pathology of "stemness"/differentiation pathways associated with therapy-resistant phenotypes of human solid tumors. One of the significant advantages of having such a "stemness" catalog available is the potential to exploit this information for a therapeutic gain in the effort to target clinically lethal states of malignant phenotypes. Therefore, evaluating a potential therapeutic utility of the association of "stemness" and therapy-resistant cancer phenotypes was attempted by exploring the connectivity map (CMAP) of "stemness" pathways in human solid tumors with distinct clinical outcome after therapy. CMAP-based search for cancer therapeutics targeting "stemness" pathways in solid tumors reveals drug combinations causing transcriptional reversal of "stemness" signatures associated with therapy-resistant phenotypes of epithelial cancers. CMAP analysis demonstrates that a combination of the PI3K pathway inhibitor, estrogen receptor (ER) antagonist, and mTOR inhibitor causes transcriptional reversal of "stemness" signatures in 35 of 37 (95%) patients diagnosed with therapy-resistant prostate cancer. CMAP-based design of target-tailored individualized breast cancer therapies reveals drug combinations causing transcriptional reversal of "stemness" signatures in 91 of 107 (85%) of the early-stage breast cancer patients with therapy-resistant disease phenotypes. A combination of PI3K pathway inhibitor, ER antagonist, and HDAC inhibitor causes transcriptional reversal of "stemness" pathways in 53 of 107 (49.5%) patients diagnosed with the early-stage therapy-resistant breast cancer. Similarly, CMAP-based analysis of target-tailored individualized therapies for lung cancer reveals drug combinations causing transcriptional reversal of "stemness" signatures in 39 of 45 (87%) of the early-stage lung cancer patients with therapy-resistant tumor phenotypes. Outlined in this work the connectivity map-based approach to discovery of small molecule drugs targeting clinical phenotype-associated gene expression signatures may be useful for multiple therapeutic applications beyond therapy-resistant human malignancies.

The analysis seems to indicate that several individual drugs and/or their analogs which are already either FDA approved for clinical use or in the late-stage clinical trials may have a promising therapeutic potential against therapy-resistant clinically lethal forms of human cancers. Therefore, the findings may have a significant near-term impact on design and conduct of clinical trials for evaluation of the efficacy of novel personalized target-tailored combinations of cancer therapeutics designed to target therapy-resistant phenotypes of human solid tumors by applying the evidence-based rational selection principles during the design stage of drug combinations. These findings will likely have a near-term impact on protocols of design and execution of the clinical trials for novel cancer therapeutics, including the regulatory guidelines for patients' eligibility requirements at the enrollment stage. It should allow the execution of such protocols in most cost-efficient way and with the maximum potential benefits for patients by facilitating the selection for a trial the populations at the high-risk of failure of existing therapy. Another conclusion from our analysis with major health care management and regulatory implications is that a near-term progress in practical implementation of the concept of personalized cancer therapies would depend on physicians' ability to select, prescribe, and exercise in a routine clinical setting an off-label use of the FDA approved drugs. In this context the issues of timely delivery to the practicing physicians of relevant scientific information and the dynamic evolution of the supporting regulatory environment adherent to the state of the art scientific evidence would be of paramount importance.

The following examples are intended to further illustrate certain embodiments of the invention and are not intended to limit the scope of the invention.

EXAMPLE 1

Preparation of Clinical Samples

Two clinical outcome sets comprising 21 (outcome set 1) and 79 (outcome set 2) samples were utilized for analysis of the association of the therapy outcome with expression levels of the BMI1 and Ezh2 genes and other clinico-pathological parameters. Expression profiling data of primary tumor samples obtained from 1243 microarray analyses of eight independent therapy outcome cohorts of cancer patients diagnosed with four types of human cancer were analyzed in this study. Microarray analysis and associated clinical information for clinical samples analyzed in this work were previously published and are publicly available.

Prostate tumor tissues comprising clinical outcome data set were obtained from 79 prostate cancer patients undergoing therapeutic or diagnostic procedures performed as part of routine clinical management at the Memorial Sloan-Kettering Cancer Center (MSKCC). Clinical and pathological features of 79 prostate cancer cases comprising validation outcome set are presented elsewhere. Median follow-up after therapy in this cohort of patients was 70 months. Samples were snap-frozen in liquid nitrogen and stored at −80° C. Each sample was examined histologically using H&E-stained cryostat sections. Care was taken to remove normeoplastic tissues from tumor samples. Cells of interest were manually dissected from the frozen block, trimming away other tissues. Overall, 146 human prostate tissue samples were analyzed in this study, including forty-six samples in a tissue microarray (TMA) format. TMA samples analyzed in this study were exempt according to the NIH guidelines.

In addition, we carried out the analysis of gene expression profiling data from 942 microarray experiments derived from five different breast cancer therapy outcome data sets. Expression profiling data for tumor samples obtained from 91 lung adenocarcinoma patients, 169 breast cancer patients, and 133 ovarian cancer patients were analyzed in this study. The original microarray analyses as well as associated clinical information for these samples were reported elsewhere. Primary gene expression data files of clinical samples as well as associated clinical information can be found in corresponding papers. To date the cancer therapy outcome database includes 3,176 therapy outcome samples from patients diagnosed with thirteen distinct types of cancers (Table 3): prostate cancer (220 patients); breast cancer (1171 patients); lung adenocarcinoma (340 patients); ovarian cancer (216 patients); gastric cancer (89 patients); bladder cancer (31 patients); follicular lymphoma (191 patients); diffuse large B-cell lymphoma (DLBCL, 298 patients); mantle cell lymphoma (MCL, 92 patients); mesothelioma (17 patients); medulloblastoma (60 patients); glioma (50 patients); acute myeloid leukemia (AML, 401 patients).

EXAMPLE 2

Cell Culture

Cell lines used in this study were previously described in Glinsky et al., *Cancer Lett.*, 201: 67-77 (2003). The LNCap- and PC-3-derived cell lines were developed by consecutive serial orthotopic implantation, either from metastases to the lymph node (for the LN series), or reimplanted from the prostate (Pro series). This procedure generated cell variants with differing tumorigenicity, frequency and latency of regional lymph node metastasis. Except where noted, cell lines were grown in RPMI1640 supplemented with 10% FBS and gentamycin (Gibco BRL) to 70-80% confluence and subjected to serum starvation as described, or maintained in fresh complete media, supplemented with 10% FBS. Growth inhibitory experiments were carried out in the 96-well format based on Hoechst staining for the estimate of live cell counts using high-through put robotics of the Target and Drug Discovery Facility (TDDF) of the Ordway Research Institute Cancer Center. Chemicals, reagents, and drugs were purchased from Sigma, except were indicated otherwise.

EXAMPLE 3

Anoikis Assay

Cells were harvested by 5-min digestion with 0.25% trypsin/0.02% EDTA (Irvine Scientific, Santa Ana, Calif., USA), washed and resuspended in serum free medium. Cells at concentration $1.7 \times 10^5$ cells/well in 1 ml of serum free medium were plated in 24-well ultra low attachment polystyrene plates (Corning Inc., Corning, N.Y., USA) and incubated at 37° C. and 5% $CO_2$ overnight. Viability of cell cultures subjected to anoikis assays were >95% in Trypan blue dye exclusion test.

EXAMPLE 4

Apoptosis Assay

Apoptotic cells were identified and quantified using the Annexin V-FITC kit (BD Biosciences Pharmingen) per manufacturer instructions. The following controls were used to set up compensation and quadrants: 1) Unstained cells; 2) Cells stained with Annexin V-FITC (no PI); 3) Cells stained with PI (no Annexin V-FITC). Each measurements were carried out in quadruplicate and each experiments were repeated at least twice. Annexin V-FITC positive cells were scored as early apoptotic cells; both Annexin V-FITC and PI positive cells were scored as late apoptotic cells; unstained Annexin V-FITC and PI negative cells were scored as viable or surviving cells. In selected experiments apoptotic cell death was documented using the TUNEL assay.

EXAMPLE 5

Flow Cytometry

Cells were washed in cold PBS phosphate-buffered saline and stained according to manufacturer's instructions using the Annexin V-FITC Apoptosis Detection Kit (BD Biosciences, San Jose, Calif., USA) or appropriate antibodies for cell surface markers. Flow analysis was performed by a FACS Calibur instrument (BD Biosciences, San Jose, Calif., USA). Cell Quest Software was used for data acquisition and analysis. All measurements were performed under the same instrument setting, analyzing $10^3$-$10^4$ cells per sample.

EXAMPLE 6

Tissue Processing for mRNA and RNA Isolation

Fresh frozen orthotopic and transgenic primary tumors, metastases, and mouse prostates were examined by use of hematoxylin and eosin stained frozen sections as described previously. Orthotopic tumors of all sublines exhibited similar morphology consisting of sheets of monotonous closely packed tumor cells with little evidence of differentiation interrupted by only occasional zones of largely stromal components, vascular lakes, or lymphocytic infiltrates. Fragments of tumor judged free of these non-epithelial clusters were used for mRNA preparation. Frozen tissue (1-3 mm×1-3 mm) was submerged in liquid nitrogen in a ceramic mortar and ground to powder. The frozen tissue powder was dissolved and immediately processed for mRNA isolation using a Fast Tract kit for mRNA extraction (Invitrogen, Carlsbad, Calif., see above) according to the manufacturers instructions.

RNA and mRNA extraction: For gene expression analysis, cells were harvested in lysis buffer 2 hrs after the last media change at 70-80% confluence and total RNA or mRNA was extracted using the RNeasy (Qiagen, Chatsworth, Calif.) or FastTract kits (Invitrogen, Carlsbad, Calif.). Cell lines were not split more than 5 times prior to RNA extraction, except where noted. Detailed protocols were described elsewhere.

Affymetrix arrays: The protocol for mRNA quality control and gene expression analysis was that recommended by Affymetrix. In brief, approximately one microgram of mRNA was reverse transcribed with an oligo(dT) primer that has a T7 RNA polymerase promoter at the 5' end. Second strand synthesis was followed by cRNA production incorporating a biotinylated base. Hybridization to Affymetrix U95Av2 arrays representing 12,625 transcripts overnight for 16 h was followed by washing and labeling using a fluorescently labeled antibody. The arrays were read and data processed using Affymetrix equipment and software as reported previously.

Data analysis: Detailed protocols for data analysis and documentation of the sensitivity, reproducibility and other aspects of the quantitative statistical microarray analysis using Affymetrix technology have been reported. 40-50% of the surveyed genes were called present by the Affymetrix Microarray Suite 5.0 software in these experiments. The concordance analysis of differential gene expression across the data sets was performed using Affymetrix MicroDB v. 3.0 and DMT v.3.0 software as described earlier. The microarray data was processed using the Affymetrix Microarray Suite v.5.0 software and performed statistical analysis of expression data set using the Affymetrix MicroDB and Affymetrix DMT software. The Pearson correlation coefficient for individual test samples and appropriate reference standard was determined using the Microsoft Excel and the GraphPad Prism version 4.00 software. The significance of the overlap between the lists of stem cell-associated and prostate cancer-associated genes was calculated by using the hypergeometric distribution test. The Multiple Experiments Viewer (MEV) software version 3.0.3 of the Institute for Genomic Research (TIGR) was used for clustering algorithm data analysis and visualization.

Polycomb pathway "stemness" signatures: The initial analysis was performed using two cancer therapy outcome data sets: 79-patients prostate cancer data set and 286-patients breast cancer data set. For each parent signature (Table 4), the multivariate Cox regression analysis was carried out. Consistent with the concept that therapy resistant and therapy sensitive tumors develop within distinct Polycomb-driven "stemness"/differentiation programs, all signatures generate statistically significant models of cancer therapy outcome were found. The number of predictors in each signature, we removed from further analysis all probe sets with low independent predictive values were removed from further analysis to eliminate redundancy (typically, with the p>0.1 in multivariate Cox regression analysis). These steps generate nine cancer therapy outcome signatures listed in the Table 4 all of which provide statistically significant therapy outcome models in multivariate Cox regression analysis in multiple cancer therapy outcome data sets. For each patient, the expression values of all genes comprising a signature into a single numerical value were calculated using either Pearson correlation coefficient approach or weighted coefficient method as described previously. These numerical values provide the cancer therapy outcome predictor (CTOP) scores for each signature for every individual patient. The log 10transformed fold change expression values or individual weighted coefficients obtained from the multivariate Cox regression analysis were used as multidimensional numerical vectors in Pearson and weighted methods, respectively. The Kaplan-Meier survival analysis was performed to assess the patients' stratification performance of each signature. Patients were sorted in descending order based on the numerical values of the CTOP scores and survival curves were generated by designating the patients with top 50% scores and bottom 50% scores into poor prognosis and good prognosis groups, respectively. These analytical protocols were independently carried out for 79-patients prostate cancer data set and 286-patients breast cancer data set. Gene expression signatures generated using 286-patients breast cancer data set were utilized in subsequent analyses of four additional independent breast cancer data sets as well as lung cancer and ovarian cancer data sets (Table 3).

EXAMPLE 7

Random Co-occurrence Test 10,000 permutations test were performed to check how likely small gene signatures derived from the large signature would display high discrimination power to assess the significance at the 0.1% level as described earlier. It was found that 10,000 permutations generated 7 random 11-gene signatures performing at sample classification level of the 11-gene MTTS/PNS signature.

EXAMPLE 8

Weighted Survival Predictor Score Algorithm

The weighted survival score analysis was implemented to reflect the incremental statistical power of the individual covariates as predictors of therapy outcome based on a multi-component prognostic model. The microarray-based or Q-RT-PCR-derived gene expression values were normalized and log-transformed on a base 10 scale. The log-transformed normalized expression values for each data set were analyzed in a multivariate Cox proportional hazards regression model, with overall survival or event-free survival as the dependent variable. To calculate the survival/prognosis predictor score for each patient, the log-transformed normalized gene expression value measured for each gene by a coefficient derived from the multivariate Cox proportional hazard regression analysis was multiplied. Final survival predictor score comprises a sum of scores for individual genes and reflects the relative contribution of each of the eleven genes in the multivariate analysis. The negative weighting values indicate that higher expression correlates with longer survival and favorable prognosis, whereas the positive score values indicate that higher expression correlates with poor outcome and shorter survival. Thus, the weighted survival predictor model is based on a cumulative score of the weighted expression values of eleven genes. For example, the following equation is describing the relapse-free survival predictor score for prostate cancer patients (Table 4): CTOP score=$(-0.403 \times Gbx2)+(1.2494 \times KI67)+(-0.3105 \times Cyclin\ B1)+(-0.1226 \times BUB1)+(0.0077 \times HEC)+(0.0369 \times KIAA1063)+(-1.7493 \times HCFC1)+1.1853 \times RNF2)+(1.5242 \times ANK3)+(-0.5628 \times FGFR2)+(-0.4333 \times CES1)$.

EXAMPLE 9

Immunofluorescence Microscopy

Cells fixed with 3.7% paraformaldehyde in phosphate-buffered saline (PFA/PBS) for 15 minutes were permeabilized with 0.5% Triton-X100 (Sigma, St. Louis, Mo., USA)/

PBS for 5 min. After washing in PBS, cells were incubated in PBS containing 100 mM glycine for 10 min. Primary antibodies were diluted in 0.5% BSA/0.05% gelatin cold water fish skin/PBS, and cells were incubated in this buffer for 10 min before antibodies were applied for 16 hrs at room temperature. After washing in PBS buffer, cells were incubated with secondary antibodies at 1:500 dilution. Coverslips were mounted in Prolong (Molecular Probes, Inc.). Images were collected on an inverted microscope (OlympusIX70) equipped with a DeltaVision imaging system using a ×40 objective. Images were processed by softWoRx v.2.5 software (Applied Precision Inc., Issaquah, Wash.) and images were quantified with using ImageJ 1.29× software.

Quantitative immunofluorescence analysis of the PcG protein expression was performed using human prostate cancer tissue microarrays (TMAs) representing 46 prostate tissue samples (thirty-nine cases of prostate cancer and seven cases of normal prostate). Analysis was carried-out on the prostate cancer TMAs from Chemicon (Temecula, Calif.; TMA #3202-4; four cancer cases and two cases of normal tissue; and TMA #1202-4; twenty five cases of cancer and five cases of normal tissue) and TMA of 10 cases of prostate cancer from the SKCC tumor bank (San Diego, Calif.). TMAs contain two 2.0 mm cores of each case and haematoxylin-and-eosin (H&E) sections which were used for visual selection of the pathological tissues, histological diagnosis, and grading by the pathologists of TMA providers.

Four- or five-micrometer paraffin-embedded sections were baked at 56° C. for 1 hour, allowed to cool for about 5 minutes, dewaxed in xylene, and rehydrated in a series of graded alcohols. Antigen retrieval was achieved by boiling slides in 10 mM sodium citrate buffer, 0.05% Tween 20, pH 6.0 in a water bath for 30 minutes. The sections were washed with PBS, incubated in 100 mM glycine/PBS for 10 minutes, blocked in 0.5% BSA/0.05% gelatine cold water fish skin/PBS and incubated with primary antibody overnight.

Primary antibodies were EZH2 rabbit polyclonal antibody (1:50), BMI1 mouse monoclonal IgG1 antibody (1:50), ubiH2A mouse IgM (1:100), 3metK27 rabbit polyclonal antibody (1:100) (Upstate, Lake Placid, N.Y.). Suz12 rabbit (1:50), AMACR rabbit (1:50) antibodies and Dicer mouse IgG1 (1:20) were purchased from Abcam (Cambridge, Mass.). BMI1 rabbit (1:50) and TRAP100 (1:50) goat antibodies were from Santa Cruz Biotechnology (Santa Cruz, Calif.). Cyclin D1 rabbit polyclonal antibody (1:50) were from Biocare Medical (Concord, Calif.). EZH2 mouse monoclonal antibodies were kindly provided by Dr. A. P. Otte.

The primary antibodies were rinsed off with PBS and slides were incubated with secondary antibodies at 1:300 dilutions for 1 hour at room temperature. Secondary antibodies (chicken antirabbit Alexa 594, goat antimouse Alexa 488, goat antimouse IgG1 Alexa 350, and donkey antigoat Alexa 488 conjugates) were from Molecular Probes (Eugene, Oreg.). The slides were washed four times in PBS for five minutes each wash, rinsed in distilled water and the specimen were coversliped with Prolong Gold Antifade Reagent (Molecular Probes, Eugene, Oreg.) containing DAPI. For negative controls, the primary antibodies were omitted. Three samples were excluded from analysis because one of the following reasons: core loss, unrepresentative sample, or suboptimal DNA and antigen preservation.

Images were collected on an inverted fluorescent microscope (LEICA DMIRE 2 or Olympus IX70) using an ×40 objective. Images were processed by Leica FW4000 software and images were quantified with using ImageJ 1.29× software (http://rsb.info.nih.gov/ij). Expression values were measured in at least 200 nuclei from two microscopic fields for each case.

The measurements were carried out in the nuclei of individual cells defined by DAPI staining both in experimental and clinical samples. For experimental samples, the comparison thresholds for each marker combination were defined at the 90-95% exclusion levels for dual positive cells in corresponding control samples (parental low metastatic cells). For clinical samples, the comparison thresholds for each marker combination were defined at the 99% or greater exclusion levels for dual positive cells in corresponding control samples (normal epithelial cells in TMA experiments). All individual immunofluorescent assay experiments (defined as the experiments in which the corresponding comparisons were made) were carried out simultaneously using the same reagents and included all experimental samples and controls utilized for a quantitative analysis. Statistical significance of the measurements was ascertained and consistency of the findings was confirmed in multiple independent experiments, including several independent sources of the prostate cancer TMA samples.

EXAMPLE 10

Orthotopic Xenografts

Orthotopic xenografts of human prostate PC-3 cells and prostate cancer metastasis precursor sublines used in this study were developed by surgical orthotopic implantation as previously described in Glinsky et al (2003), supra. Briefly, $2 \times 10^6$ cultured PC-3 cells or sublines were injected subcutaneously into male athymic mice, and allowed to develop into firm palpable and visible tumors over the course of 2-4 weeks. Intact tissue was harvested from a single subcutaneous tumor and surgically implanted in the ventral lateral lobes of the prostate gland in a series of ten athymic mice per cell line subtype as described in Glinsky et al (2003), supra. During orthotopic cell inoculation experiments, a single-cell suspension of $1.5 \times 10^6$ cells was injected into mouse prostate gland in a series of ten athymic mice per therapy group.

EXAMPLE 11

Fluorescence in Situ Hybridization (FISH)

PC3 human prostate adenocarcinoma cell line, derived subline PC3-32 and diploid human fibroblast BJ1-hTERT cells were used for the assessment of gene amplification status. The cyanine-3 or cyanine-5 labeled BAC clone RP11-28C14 was used for the EZH2 locus (7q35-q36), the BAC clone RP11-232K21 was used for the BMI1 locus (10p11.23), the BAC clone RP11-440N18 was used for the Myc locus (8q24.12-q24.13), the BAC clone RP11-1112H21 was used for the LPL locus (8p22). FISH analysis was done accordingly protocol as described previously.

Methanol/glacial acetic acid cell fixation: Cell cultures were synchronized with 4 ug/ml aphidicolin (Sigma Chemical Co.) for 17 hour at 37° C. Synchronized cells were subjected to hypotonic treatment in 0.56% KCl for 20 minute at 37° C., followed by fixation in Carnoy's fixative (3:1 methanol:glacial acetic acid). Cell suspension was dropped onto glass slides, air dried. The slides are treated for 30 minutes with 0.005% pepsin in 0.01N HCl at room temperature and then are dehydrated through a series washes in 70%, 85%, and 100% ethanol. Denaturation of DNA is performed by plunging the slide in a coplin jar containing 70% formamide/2×

SSC (pH 7.0) for 30 min at 75° C. The slide immediately are plunged into ice-cold 2×SSC and then dehydrated as earlier.

Fluorescence in situ hybridization (FISH): All BAC clones were obtained from the Rosewell Park Cancer Institute (RPCI, Buffalo, N.Y.). The BAC DNA was labeled with Cy3-dCTP or Cy5-dCTP (Perkin Elmer Life Sciences, Inc.) using BioPrime DNA Labeling System (Invitrogen). The resultant probes are purified with QIAquick PCR Purification Kit (Qiagen). DNA recovery and the amount of incorporated Cy3 or Cy5 are verified by Nanodrop spectrophotometry.

Prior to hybridization the probe is precipitated with 20 ug competitor human Cot-1 DNA (per 18×18 mm coverslip) and washed in 70% ethanol. The dried pellet is thoroughly resuspended in 10 ul hybridization buffer (2×SSC, 20% dextran sulfate, 1 mg/ml BSA; NEB Inc.). The denatured probe solution is deposited onto cells on slide. Hybridization was carried out overnight at 42° C. in a dark humidified chamber. After three washes in 50% formamide/2×SSC (adjusted to pH 7.0) and three washes in 2×SSC at 42° C., slides were counterstained and mounted in Prolong Gold Antifade Reagent with 4',6-diamino-2-phenylindole (Invitrogen). Slides were examined using a Leica DMIRE2 fluorescence microscope (Leica, Deerfield, Ill.). Gene amplification status was determined by scoring 60-100 nuclei.

EXAMPLE 12 siRNA Experiments

The target siRNA SMART pools and chemically modified degradation-resistant variants of the siRNAs (stable siRNAs) for BMI1, Ezh2, and control luciferase siRNAs were purchased from Dharmacon Research, Inc. siRNAs were transfected into human prostate carcinoma cells according to the manufacturer's protocols. Cell cultures were continuously monitored for growth and viability and assayed for mRNA expression levels of BMI1, Ezh2, and selected set of genes using RT-PCR and Q-RT-PCR methods. Eight individual siRNA sequences comprising the SMART pools (four sequences for each gene, BMI1 and Ezh2) were tested and a single most effective siRNA sequence was selected for synthesis in the chemically modified stable siRNA form for each gene. The siRNA treatment protocol [two consecutive treatments of cells in adherent cultures with 100 nM (final concentration) of Dharmacon degradation-resistant siRNAs at day 1 and 4 after plating], as designed, caused only moderate reduction in the average BMI1 and Ezh2 protein expression levels (20-50% maximal effect) and having no or only marginal effect on cell proliferation in the adherent cultures (at most ~25% reduction in cell proliferation).

EXAMPLE 13

Quantitative RT-PCR Analysis

The real time PCR methods measures the accumulation of PCR products by a fluorescence detector system and allows for quantification of the amount of amplified PCR products in the log phase of the reaction. Total RNA was extracted using RNeasy mini-kit (Qiagen, Valencia, Calif., USA) following the manufacturer's instructions. A measure of 1 µg (tumor samples), or 2 µg and 4 µg (independent preparations of reference cDNA and DNA samples from cell culture experiments) of total RNA was used then as a template for cDNA synthesis with SuperScript II (Invitrogen, Carlsbad, Calif., USA). cDNA synthesis step was omitted in the DNA copy number analysis (32). Q-PCR primer sequences were selected for each cDNA and DNA with the aid of Primer Express™ software (Applied Biosystems, Foster City, Calif., USA). PCR amplification was performed with the gene-specific primers.

Q-PCR reactions and measurements were performed with the SYBR-Green and ROX as a passive reference, using the ABI 7900 HT Sequence Detection System (Applied Biosystems, Foster City, Calif., USA). Conditions for the PCR were as follows: one cycle of 10 min at 95° C.; 40 cycles of 0.20 min at 94° C., 0.20 min at 60° C. and 0.30 min at 72° C. The results were normalized to the relative amount of expression of an endogenous control gene GAPDH.

Expression of messenger RNA (mRNA) and DNA copy number for target genes and an endogenous control gene (GAPDH) was measured by real-time PCR method on an ABI PRISM 7900 HT Sequence Detection System (Applied Biosystems). For each gene at least two sets of primers were tested and the set-up with highest amplification efficiency was selected for the assay used in this study. Specificity of the assay for mRNA measurements was confirmed by the absence of the expected PCR products when genomic DNA was used as a template. Glyceraldehyde-3-phosphate dehydrogenase (GAPDH: 5'-CCCTCAACGACCACTTTGTCA-3' (SEQ ID NO: 1) and 5'-TTCCTCTTGTGCTCTTGCTGG-3' (SEQ ID NO: 2) was used as the endogenous RNA and cDNA quantity normalization control. For calibration and generation of standard curves, several reference cDNAs were prepared: cDNA prepared from primary in vitro cultures of normal human prostate epithelial cells, cDNA derived from the PC-3M human prostate carcinoma cell line, and cDNA prepared from normal human prostate. For DNA copy number analysis, human placental DNA was used as a normalization control. Expression and DNA copy number analysis of all genes was assessed at least in two independent experiments using reference cDNAs to control for variations among different Q-RT-PCR experiments. Prior to statistical analysis, the normalized gene expression values were log-transformed (on a base 10 scale) similarly to the transformation of the array-based gene expression data.

EXAMPLE 14

Survival Analysis

The Kaplan-Meier survival analysis was carried out using the GraphPad Prism version 4.00 software (GraphPad Software, San Diego, Calif.). The end point for survival analysis in prostate cancer was the biochemical recurrence defined by the serum PSA increase after therapy. Disease-free interval (DFI) was defined as the time period between the date of radical prostatectomy (RP) and the date of PSA relapse (recurrence group) or date of last follow-up (non-recurrence group). Statistical significance of the difference between the survival curves for different groups of patients was assessed using Chi square and Log-rank tests. To evaluate the incremental statistical power of the individual covariates as predictors of therapy outcome and unfavorable prognosis, both univariate and multivariate Cox proportional hazard survival analyses were performed. Clinico-pathological covariates included in this analysis were preoperative PSA, Gleason score, surgical margins, extra-capsular invasion, seminal vesicle invasion, and age.

I claim:

1. A method for diagnosing prostate cancer or predicting prostate cancer-therapy outcome in a subject, said method comprising the step of measuring the expression of two or more markers in a tumor sample from the subject wherein the two or more markers are selected from the group consisting of:
   (1) the histone H3 protein methylated at lysine residue 27 (H3metK27);
   (2) the histone H2A protein ubiquinated at lysine residue 119 (H2AubiK119)
   (3) BMI1 and H2AubiK 119; and
   (4) EZH2 and H3metK27,
wherein high expression of the two or more markers in the tumor sample indicates an aggressive form of cancer and a poor prognosis.

2. The method of claim 1, wherein the aberrant expression level of two or more markers is detected by subjecting the cells to an analysis selected from the group consisting of multicolor quantitative immunofluorescence co-localization analysis, fluorescence in situ hybridization, and quantitative RT-PCR analysis.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 1
ccctcaacga ccactttgtc a                                    21

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
ttcctcttgt gctcttgctg g                                    21